US012697455B2

(12) United States Patent
Eves et al.

(10) Patent No.: US 12,697,455 B2
(45) Date of Patent: Aug. 4, 2026

(54) TEXTILE SEAL-FORMING STRUCTURE WITH MULTIPLE CURVATURES

(71) Applicant: ResMed Pty Ltd, Bella Vista (AU)

(72) Inventors: Matthew Eves, Sydney (AU); Rupert Christian Scheiner, Sydney (AU); Callum Tyler De Vries, Sydney (AU); Memduh Guney, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 60 days.

(21) Appl. No.: 18/459,790

(22) Filed: Sep. 1, 2023

(65) Prior Publication Data

US 2023/0414891 A1     Dec. 28, 2023

Related U.S. Application Data

(63) Continuation of application No. 18/187,761, filed on Mar. 22, 2023, now Pat. No. 11,844,887, which is a
(Continued)

(30) Foreign Application Priority Data

Jul. 9, 2020    (AU) ................................ 2020902371

(51) Int. Cl.
     *A61M 16/06*        (2006.01)
     *A61M 16/08*        (2006.01)
     *A61M 16/16*        (2006.01)
(52) U.S. Cl.
     CPC ........ *A61M 16/0622* (2014.02); *A61M 16/06* (2013.01); *A61M 16/0611* (2014.02);
     (Continued)

(58) Field of Classification Search
     None
     See application file for complete search history.

(56) References Cited

U.S. PATENT DOCUMENTS 3,799,164 A     3/1974  Rollins
4,540,617 A     9/1985  Kawanishi
                (Continued)

FOREIGN PATENT DOCUMENTS

CN        101495170 A       7/2009
CN        107683160 A       2/2018
                (Continued)

OTHER PUBLICATIONS

Office Action dated Mar. 4, 2024 issued in Japanese Application No. 2021-521046 with English translation (9 pages).
(Continued)

*Primary Examiner* — Valerie L Woodward
(74) *Attorney, Agent, or Firm* — Nixon & Vanderhye P.C.

(57)                ABSTRACT

A patient interface including a seal-forming structure with a textile membrane that has at least one hole such that the flow of air at a therapeutic pressure is delivered to at least an entrance to the patient's nares and/or an entrance to the patient's mouth. The seal-forming structure is constructed and arranged to maintain the therapeutic pressure in a cavity of a plenum chamber throughout the patient's respiratory cycle, in use. The textile membrane includes a first portion that is held in a relaxed state and a second portion that is held in a taut state. The taut state of the second portion is configured to allow the seal-forming structure to include a three-dimensional shape that has multiple curvatures.

22 Claims, 59 Drawing Sheets

Related U.S. Application Data continuation of application No. 17/769,685, filed as application No. PCT/AU2020/051109 on Oct. 15, 2020, now Pat. No. 11,648,364, which is a continuation-in-part of application No. 16/850,803, filed on Apr. 16, 2020, now Pat. No. 12,059,528, which is a continuation-in-part of application No. PCT/IB2019/058832, filed on Oct. 16, 2019.

(52) U.S. Cl.
CPC .... *A61M 16/0616* (2014.02); *A61M 16/0666* (2013.01); *A61M 16/0683* (2013.01); *A61M 16/0875* (2013.01); *A61M 2016/0661* (2013.01); *A61M 16/16* (2013.01); *A61M 2205/02* (2013.01); *A61M 2205/0216* (2013.01); *A61M 2207/00* (2013.01); *A61M 2207/10* (2013.01); *A61M 2210/0618* (2013.01); *A61M 2210/0625* (2013.01)

(56) References Cited

U.S. PATENT DOCUMENTS

| | | | |
|---|---|---|---|
| 4,782,832 | A | 11/1988 | Trimble et al. |
| 4,944,310 | A | 7/1990 | Sullivan |
| 6,354,296 | B1 | 3/2002 | Baumann |
| 6,532,959 | B1 | 3/2003 | Berthon-Jones |
| 6,561,191 | B1 | 5/2003 | Kwok |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 9,731,090 | B2 | 8/2017 | Ovzinsky et al. |
| 9,981,104 | B1 | 5/2018 | Groll |
| 10,357,626 | B1 | 7/2019 | Baker |
| 10,888,681 | B2 | 1/2021 | Baigent et al. |
| 11,648,364 | B2 | 5/2023 | Eves et al. |
| 2002/0059935 | A1 | 5/2002 | Wood |
| 2008/0047560 | A1* | 2/2008 | Veliss ............... A61M 16/0694 |
| | | | 128/207.11 |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2010/0229868 | A1 | 9/2010 | Rummery |
| 2011/0088699 | A1* | 4/2011 | Skipper ................. A61M 16/06 |
| | | | 128/206.26 |
| 2011/0247628 | A1 | 10/2011 | Ho |
| 2011/0253144 | A1 | 10/2011 | Groll |
| 2012/0080035 | A1* | 4/2012 | Guney .............. A61M 16/0616 |
| | | | 128/205.25 |
| 2012/0204881 | A1 | 8/2012 | Davidson et al. |
| 2012/0285469 | A1 | 11/2012 | Ho et al. |
| 2013/0213400 | A1 | 8/2013 | Barlow et al. |
| 2014/0102456 | A1* | 4/2014 | Ovizinsky ......... A61M 16/0066 |
| | | | 128/205.25 |
| 2014/0109911 | A1 | 4/2014 | Asvadi et al. |
| 2014/0158136 | A1* | 6/2014 | Romagnoli ........ A61M 16/0611 |
| | | | 128/206.24 |
| 2014/0251338 | A1 | 9/2014 | Asvadi et al. |
| 2015/0040909 | A1 | 2/2015 | Willard |
| 2015/0182719 | A1 | 7/2015 | Grashow et al. |
| 2015/0352306 | A1 | 12/2015 | Scheiner et al. |
| 2015/0352308 | A1 | 12/2015 | Cullen et al. |
| 2016/0022944 | A1 | 1/2016 | Chodkowski et al. |
| 2016/0082214 | A1* | 3/2016 | Barlow ............. A61M 16/0622 |
| | | | 128/206.24 |
| 2017/0049983 | A1 | 2/2017 | Ellis |
| 2017/0049984 | A1 | 2/2017 | Biener et al. |
| 2017/0319806 | A1 | 11/2017 | Teller et al. |
| 2017/0326320 | A1 | 11/2017 | Baigent |
| 2017/0326321 | A1 | 11/2017 | Grashow et al. |
| 2018/0043120 | A1 | 2/2018 | Hunley et al. |
| 2018/0056023 | A1 | 3/2018 | Han |
| 2019/0009045 | A1 | 1/2019 | Bernard |
| 2019/0070379 | A1 | 3/2019 | Lockhart |
| 2019/0143152 | A1 | 5/2019 | Lee |
| 2019/0240436 | A1 | 8/2019 | Romagnoli et al. |
| 2020/0016356 | A1 | 1/2020 | Patel et al. |
| 2020/0016358 | A1* | 1/2020 | Bornholdt ......... A61M 16/0069 |
| 2020/0246572 | A1 | 8/2020 | Scheiner |
| 2022/0395658 | A1 | 12/2022 | Eves et al. |

FOREIGN PATENT DOCUMENTS

| | | | |
|---|---|---|---|
| CN | 108463264 | A | 8/2018 |
| DE | 10 2008039645 | | 3/2010 |
| JP | 2007-538356 | A | 12/2007 |
| JP | 2009-233375 | A | 10/2009 |
| JP | 2014-524801 | A | 9/2014 |
| JP | 2017-535370 | A | 11/2017 |
| JP | 2019-501734 | A | 1/2019 |
| WO | WO 98/004310 | A1 | 2/1998 |
| WO | WO 98/034665 | A1 | 8/1998 |
| WO | WO 2000/078381 | A1 | 12/2000 |
| WO | WO 2004/073778 | A1 | 9/2004 |
| WO | WO 2005/063328 | A1 | 7/2005 |
| WO | WO 2006/074513 | A1 | 7/2006 |
| WO | WO 2006/130903 | A1 | 12/2006 |
| WO | 2008/011682 | A1 | 1/2008 |
| WO | 2008/011683 | A1 | 1/2008 |
| WO | WO 2009/052560 | A1 | 4/2009 |
| WO | WO 2010/135785 | A1 | 12/2010 |
| WO | 2012/167327 | A1 | 12/2012 |
| WO | WO 2012/171072 | A1 | 12/2012 |
| WO | 2013/006913 | A1 | 1/2013 |
| WO | 2013/026091 | A1 | 2/2013 |
| WO | WO 2013/020167 | A1 | 2/2013 |
| WO | 2014/077708 | A1 | 5/2014 |
| WO | 2014/183167 | A1 | 11/2014 |
| WO | 2015/161345 | A1 | 10/2015 |
| WO | 2016/030381 | | 3/2016 |
| WO | 2016/082001 | A1 | 6/2016 |
| WO | 2017/049360 | A1 | 3/2017 |
| WO | WO-2017120643 | A1 * | 7/2017 ............. A61B 5/256 |
| WO | 2017/158471 | A1 | 9/2017 |
| WO | 2017/185140 | A1 | 11/2017 |
| WO | 2018/124889 | A1 | 7/2018 |
| WO | 2018/160077 | A1 | 9/2018 |
| WO | 2019/183680 | A1 | 10/2019 |
| WO | 2019/183681 | A1 | 10/2019 |
| WO | 2020/009589 | A1 | 1/2020 |
| WO | 2020/079617 | A1 | 4/2020 |
| WO | 2020/165761 | A1 | 8/2020 |
| WO | 2021/019312 | | 2/2021 |

OTHER PUBLICATIONS

Office Action dated Mar. 15, 2024 issued in Chinese Application No. 2021-521046 with English translation (16 pages).

Extended European Search Report dated Nov. 14, 2023 issued in European Application No. 20877830.8 (16 pages).

Office Action dated Jan. 26, 2023 issued in U.S. Appl. No. 17/669,719 (23 pages).

Extended European Search Report dated Jul. 21, 2022 issued in European Application No. 19874097.9 (12 pages).

Office Action dated Oct. 7, 2022 issued in U.S. Appl. No. 17/669,719 (19 pages).

International Preliminary Report on Patentability dated Apr. 19, 2022 issued in International Application No. PCT/AU2020/051109 (10 pages).

"*Respiratory Physiology*", by John B. West, Lippincott Williams & Wilkins, 9th edition published 2012 (8 pages).

Written Opinion of the International Preliminary Examining Authority dated Sep. 9, 2020 issued in corresponding PCT Application No. PCT/IB2019/058832 (5 pages).

International Search Report mailed Jan. 6, 2020 in corresponding PCT Application PCT/IB2019/058832 (8 pages).

Written Opinion mailed Jan. 6, 2020 in corresponding PCT Application PCT/IB2019/058832 (5 pages).

(56)　　　　　References Cited

OTHER PUBLICATIONS

International Search Report mailed May 29, 2020 in related PCT Application PCT/IB2020/053324 (7 pages).
Written Opinion mailed May 29, 2020 in related PCT Application PCT/IB2020/053324 (4 pages).
Written Opinion dated Dec. 15, 2020 issued in International Application No. PCT/IB2019/058832 (4 pages).
International Search Report dated Jan. 19, 2021 issued in International Application No. PCT/AU2020/051109 (5 pages).
Written Opinion dated Jan. 19, 2021 issued in International Application No. PCT/AU2020/051109 (9 pages).
Office Action dated Jun. 30, 2021 issued in U.S. Appl. No. 16/654,778 (26 pages).
Office Action dated Jul. 27, 2021 issued in U.S. Appl. No. 17/285,279 (23 pages).
First Examination Report dated Mar. 2, 2022 issued in Australia Application No. 2020323962 (3 pages).
Office Action dated May 17, 2024 issued in Chinese Application No. 202180032514.3 with English translation (9 pages).
Office Action dated May 17, 2024 issued in Chinese Application No. 202180040875.2 with English translation (29 pages).
Office Action dated Jun. 17, 2024 issued in Japanese Application No. 2022-523001 with English translation (8 pages).
Decision of Rejection and the Decision to Dismiss Amendment with English Translation issued in related JP Application No. 2021-521046, 10 pages, dated Mar. 11, 2025.
Office Action issued in related U.S. Appl. No. 18/476,704, 19 pages, dated Mar. 27, 2025.
Extended European Search Report in related European Application No. 25191980.9 issued Jan. 28, 2026 (10 pages).
Extended European Search Report in related European Application No. 25197845.8 issued Jan. 28, 2026 (14 pages).
First Examination Report issued in corresponding Australian Application No. 2025203195, 3 pages, dated Feb. 17, 2026.

* cited by examiner

Nasal cavity

Oral cavity

Larynx

Vocal folds

Oesophagus

Trachea

Bronchus

Lung

Heart

Diaphragm

Alveolar sacs

Nasal cavity

Nasal bone

Lateral nasal cartilage

Greater alar cartilage

Nostril

Lip superior

Lip inferior

Hard palate

Soft palate

Oropharynx

Tongue

Epiglottis

Vocal folds

Larynx

Esophagus

Trachea

Frontal sinus

Nasal bone

Septum cartilage

Medial crus of greater alar cartilage

Anterior nasal spine

Frontal process of maxilla

Lesser alar cartilage

Fibrofatty tissue

Epidermis

Adipose tissue

Nasal bone

Lateral cartilage

Septum cartilage

Greater alar cartilage

Parietal bone

Temporal bone

Occipital bone

Trapezius m.

Frontal bone

Sphenoid bone

Nasal bone

Zygomatic bone

Maxilla

Masseter m.

Mandible

Mental protuberance

Digastricus m.

Sternocleidomastoid m.

Concha

Frontal bone

Supraorbital foramen

Nasal bones

Septal cartilage

Lateral cartilage

Sesamoid cartilage

Greater alar cartilage

Medial crus of greater alar cartilage

Anterior nasal spine

Infraorbital foramen

Lesser nasal cartilage

Alar fibrofatty tissue

Septal cartilage

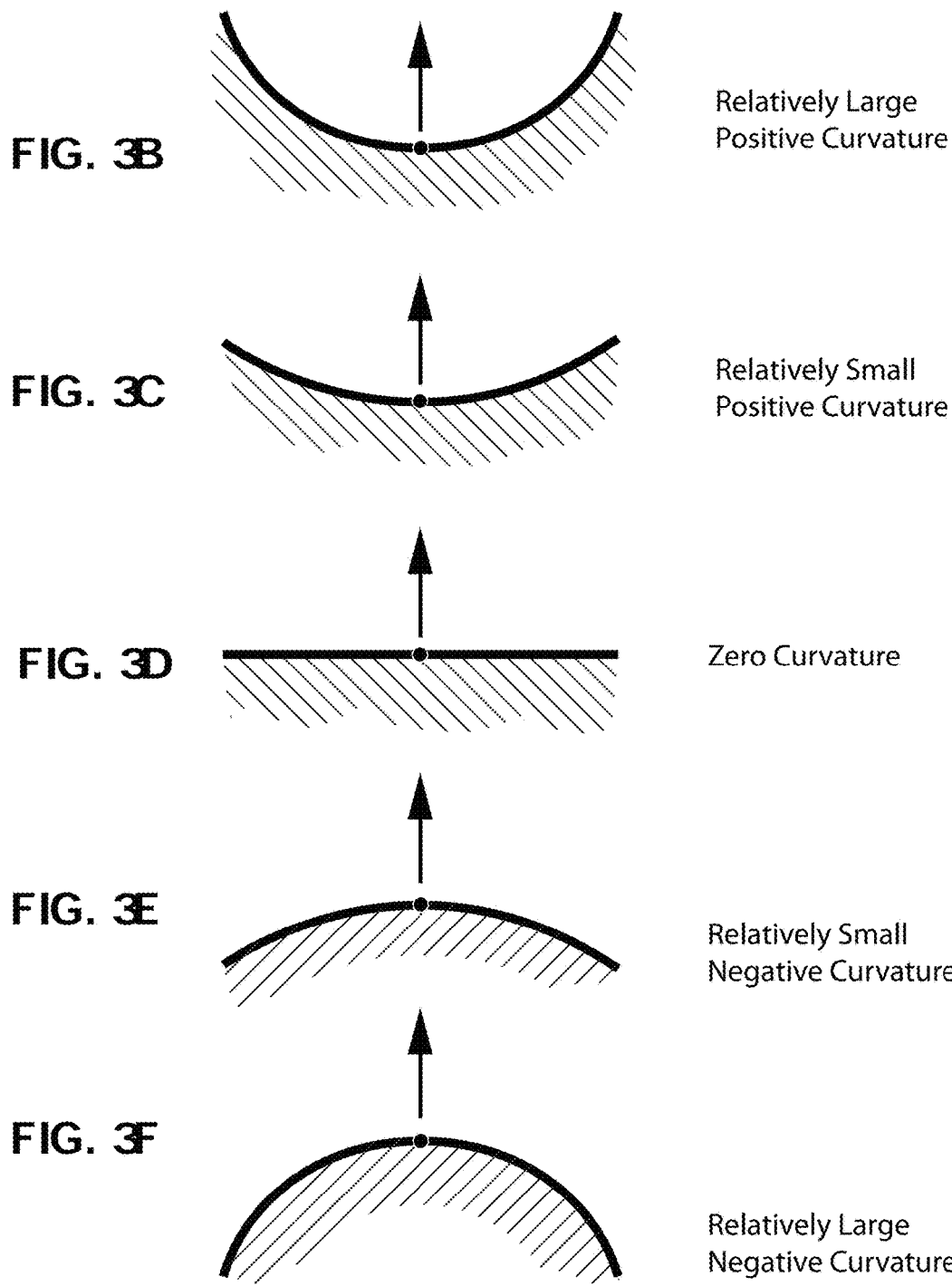
FIG. 3B     Relatively Large Positive Curvature
FIG. 3C     Relatively Small Positive Curvature
FIG. 3D     Zero Curvature
FIG. 3E     Relatively Small Negative Curvature
FIG. 3F     Relatively Large Negative Curvature

Left-hand rule
Right-hand rule
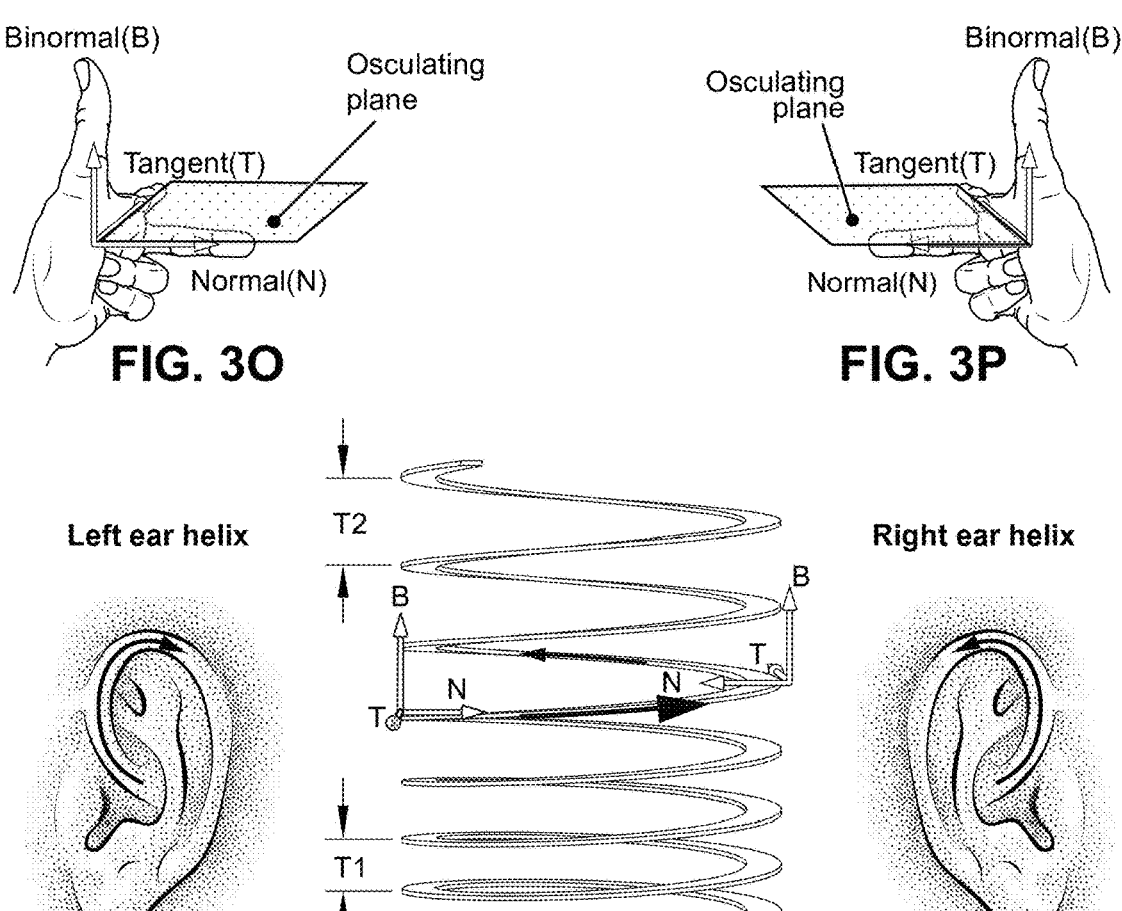
FIG. 3O
FIG. 3P
Left ear helix
Right ear helix
FIG. 3Q
**Right-hand helix
Right-hand positive**
FIG. 3R
FIG. 3S
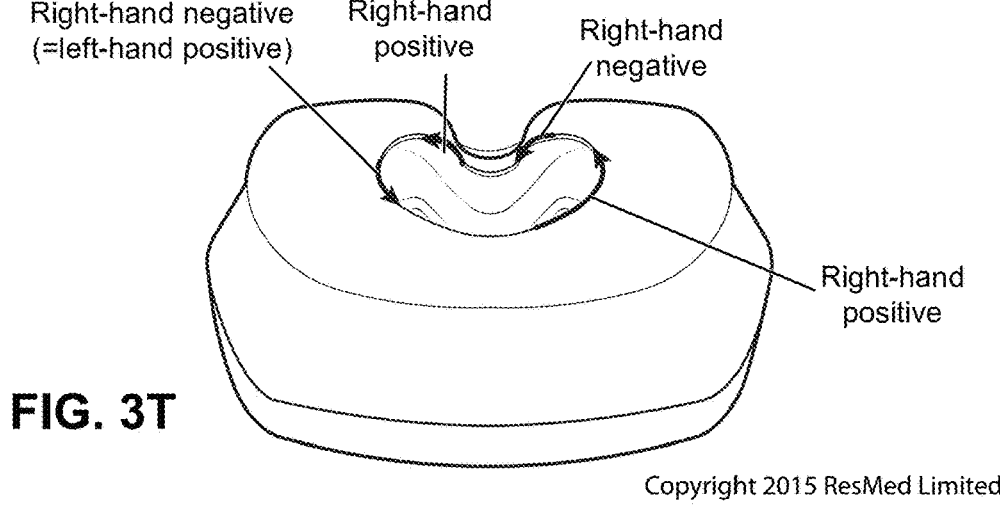
FIG. 3T

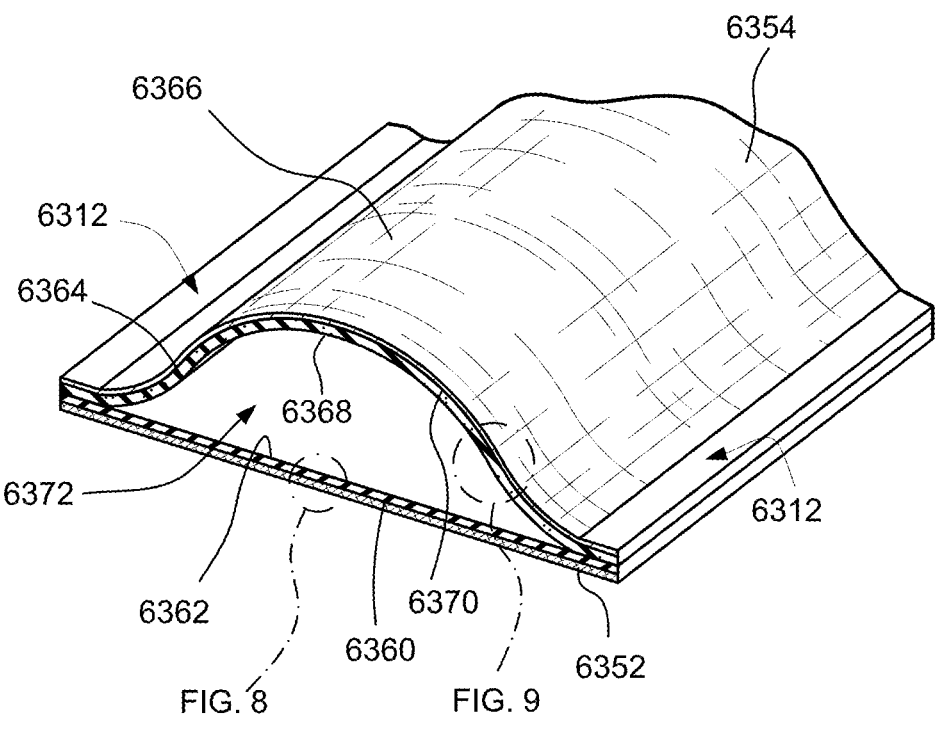
FIG. 8
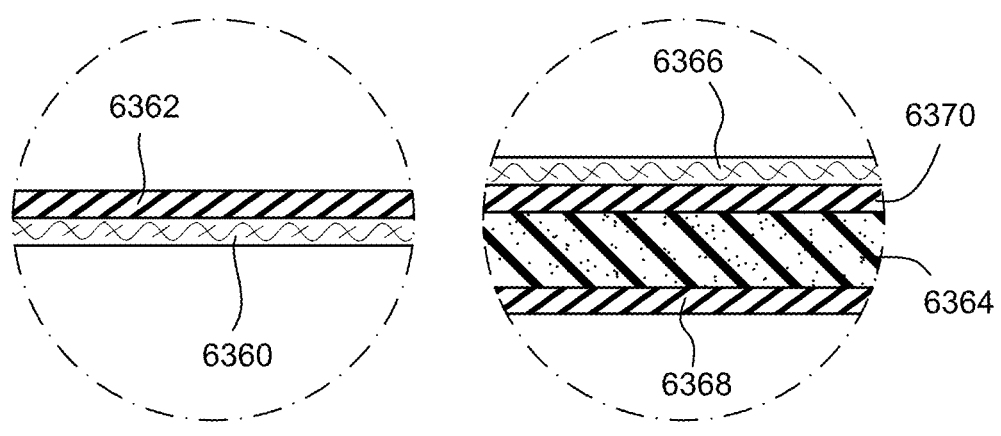
FIG. 9                    FIG. 10

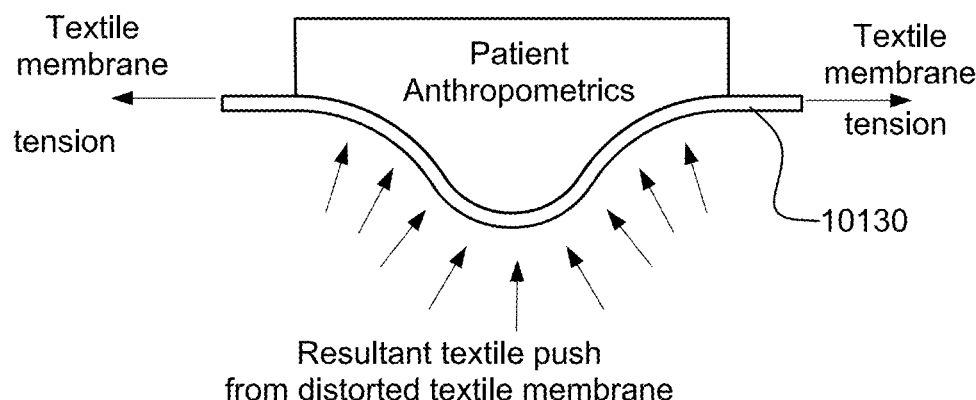
FIG. 42
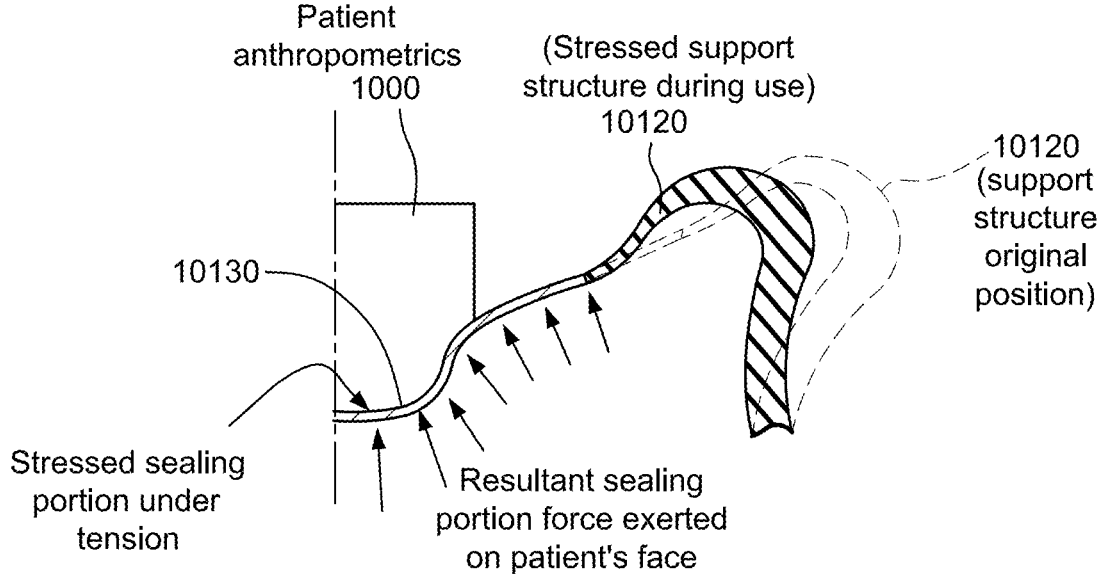
FIG. 43
FIG. 44

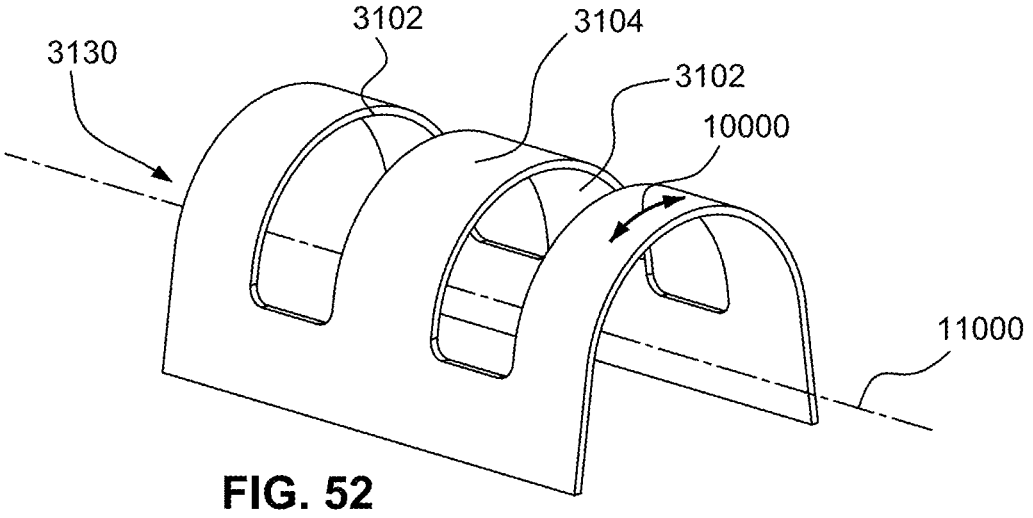
FIG. 52
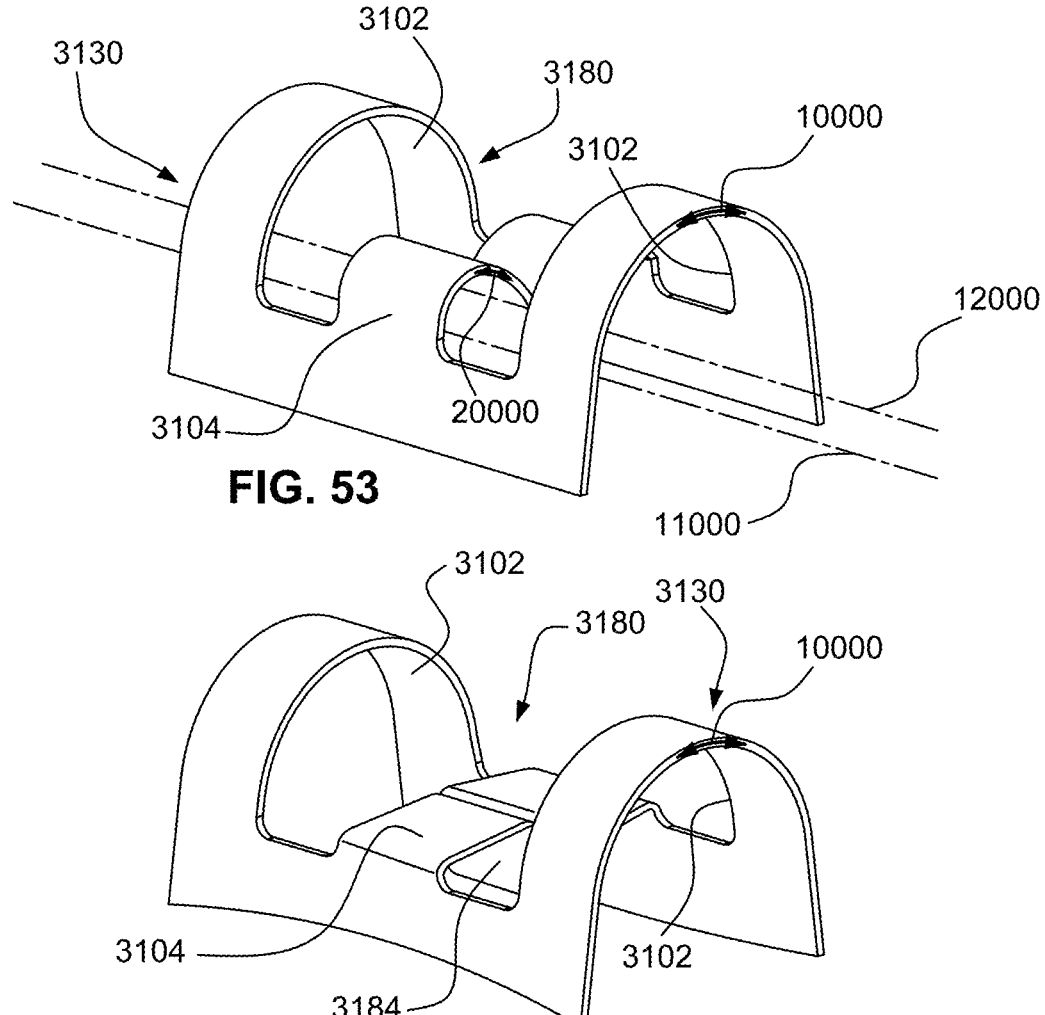
FIG. 53
FIG. 54

TEXTILE SEAL-FORMING STRUCTURE WITH MULTIPLE CURVATURES

1 CROSS-REFERENCE TO RELATED APPLICATIONS

This a continuation of U.S. application Ser. No. 18/187,761, filed Mar. 22, 2023, which is a continuation of U.S. application Ser. No. 17/769,685, filed Apr. 15, 2022, now U.S. Pat. No. 11,648,364, which is the U.S. national phase of International Application No. PCT/AU2020/051109 filed Jul. 9, 2020 which designated the U.S. and claims priority to AU 2020902371 filed Jul. 9, 2020, and is a continuation-in-part of U.S. application Ser. No. 16/850,803, filed Apr. 16, 2020, which is a continuation-in-part of International Application No. PCT/IB2019/058832, the entire contents of each of which are hereby incorporated by reference.

International Application No. PCT/IB2019/058832 claims the benefit of U.S. Provisional Application No. 62/805,147, filed Feb. 13, 2019, and also claims the benefit of Australian Provisional Application Nos. AU2018904886, filed Dec. 21, 2018, and AU2018903752, filed Oct. 16, 2018, each of which is also hereby incorporated herein by reference in their entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea to a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH₂O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ M Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the lower jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.7 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology is a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and a seal-forming structure.

One form of the present technology comprises a textile seal-forming structure with a bridge portion between a first hole and a second hole, the bridge portion is crimped so as to be held in greater tension than a remainder of the textile membrane.

Another aspect of one form of the present technology is a seal-forming structure having a textile membrane coupled to a flexible support structure in a relaxed state, and a bridge portion of the textile membrane is crimped so as to be held in greater tension than a remainder of the textile membrane.

Another aspect of the present technology is a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and a seal-forming structure having:

a textile membrane constructed and arranged to form a pressure-assisted seal with a region of the patient's face surrounding an entrance to the patient's airways inferior to a nasal bridge region of the patient's face, said textile membrane having a portion, the seal-forming structure constructed and arranged to maintain said therapeutic pressure in the cavity throughout the patient's respiratory cycle in use, wherein:

the textile membrane is held in a relaxed state, and the portion is held in greater tension than a remainder of the textile membrane, e.g., selectively tensioned.

In some aspects, the textile membrane has at least one hole or two holes formed such that the flow of air at said therapeutic pressure is delivered to at least an entrance to the patient's airways.

In some aspects, the portion is tensioned via various techniques, including crimping at one or more portions of the textile membrane, e.g., a central portion and/or a bridge portion. Instead of or in addition to the central or bridge portion, one or more other portions of the textile membrane may be tensioned, e.g., crimping or other techniques. The textile membrane may be supported by a flexible support that may be subject to selective tensioning, as an alternative or in addition to selective tensioning of one or more portions of the textile membrane.

Another aspect of the present technology is a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and a seal-forming structure having:

a textile membrane constructed and arranged to form a pressure-assisted seal with a region of the patient's face surrounding an entrance to the patient's airways inferior to a nasal bridge region of the patient's face, said textile membrane having at least one hole such that the flow of air at said therapeutic pressure is delivered to at least an entrance to the patient's nares, the seal-forming structure constructed and arranged to maintain said therapeutic pressure in the cavity throughout the patient's respiratory cycle in use, wherein:

the textile membrane includes a first portion held in a relaxed state and a second portion held in a taut state, the taut state of the second portion configured to allow the seal-forming structure to include a three-dimensional shape having multiple curvatures.

In some aspects, a) an area of the first portion is greater than an area of the second portion; b) the at least one hole includes a first hole and a second hole, each configured to be positioned adjacent one of the patient's nares in use, and wherein a bridge portion is disposed between the first hole and the second hole; c) the bridge portion is the second portion and is held in a taut state; d) the bridge portion is crimped so as to be held in greater tension than the first portion of the textile membrane; e) the bridge portion includes a first section and a second section, the first section being substantially flat and configured to contact the patient in use, and the second section extending into the plenum chamber; f) the bridge portion is crimped using ultrasonic welding and/or an adhesive; and/or g) ultrasonic welding and/or adhesives are applied to the second section.

In some aspects a) the seal-forming structure further includes a flexible support structure for holding the textile membrane in the three-dimensional shape; b) the seal-forming structure includes a single wall, and wherein an end of the flexible support structure contacts the textile membrane; c) the seal-forming structure includes a pair of walls, wherein the flexible support structure includes a free end, and the textile membrane is coupled to the flexible support structure distal to the free end, and wherein the free end is spaced apart from the textile membrane so that the textile membrane is arranged radially outside of the free end; d) the flexible support structure is coupled to the textile membrane using injection molding; and/or e) the bridge portion is a locating spigot after being crimped.

In some aspects a) the textile membrane includes a first curvature about a first axis intersecting the first hole and the second hole, and wherein before being crimped, the bridge portion includes a bridge curvature about the first axis in an opposite direction from a remainder of the textile membrane; b) a second axis extends transverse to the first axis and along the bridge portion, the textile membrane including a secondary curvature about the second axis; c) the secondary curvature has one of a domed region and a saddle region, and the first curvature has the other of a domed region and a saddle region; d) the secondary curvature is configured to contact the patient's subnasale, in use; e) a third axis extends transverse to the second axis and skewed with respect to the first axis, the textile membrane including a tertiary curvature about the third axis; f) the tertiary curvature is configured to contact the patient's lip superior, in use; g) a fourth axis extends transverse to the second axis and to the third axis, and parallel to the first axis, the textile membrane including a quaternary curvature about the fourth axis; h) the quaternary curvature includes a variable radius of curvature; and/or i) the quaternary curvature extends into the primary curvature proximate to an edge of the textile membrane.

In some aspects a) a portion of the first hole distal to the bridge portion is movable between a first position and a second position; b) the first position is a natural state, and the textile membrane moves to the second position as a result of an external force; c) the portion of the first hole extends into the plenum chamber in the second position; d) the first hole includes a substantially tear-drop shape in the second position; e) in the second position, the first hole is configured to contact a periphery of the entrance to one of the patient's nares proximate to an alar rim; and/or f) a portion of the second hole distal to the bridge portion is movable between the first position and the second position.

In some aspects a) the textile membrane includes a textile layer and a silicone layer coupled to the textile layer, the silicone layer having impermeable properties; b) the silicone layer is approximately 0.5 mm thick.; c) the silicone layer is disposed within the cavity and is configured to not touch the patient's skin, in use; and/or d) the silicone layer has a low durometer characteristic, and the textile membrane includes a high stretch capability when coupled to the flexible support structure.

In some aspects a) a length of the bridge portion is directly related to a size of the first hole and to a size of the second hole; b) the textile membrane is configured to be curved about at least two non-parallel axes as a result of taut state of the second portion in order to form the three-dimensional shape; c) the textile membrane includes a multi-layered textile material and silicone layer coupled to the multi-layered textile material; d) the multi-layered textile material includes a first layer, a second layer, and a third layer, the silicone layer contacting only the first layer, and wherein the third layer is configured to contact the patient's face, in use; e) the first layer and the third layer are constructed from nylon, and wherein the second layer is constructed from spandex; f) the textile membrane is approximately 0.35 mm to approximately 0.45 mm thick; and/or g) the patient's nose and lip superior are configured to contact only the textile membrane, in use.

Another aspect of the present technology is a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and a seal-forming structure having:

a textile membrane constructed and arranged to form a pressure-assisted seal with a region of the patient's face surrounding an entrance to the patient's airways inferior to a nasal bridge region of the patient's face, said textile membrane having a first hole and a second hole and a bridge portion disposed between the first hole and the second hole, the first hole and the second hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use, and a flexible support structure for holding the textile membrane in a predefined shape;

wherein:

the textile membrane is coupled to the flexible support structure in a relaxed state, and the bridge portion is crimped so as to be held in greater tension than a remainder of the textile membrane.

Another aspect of the present technology is a patient interface for sealed delivery of a flow of air at a continuously positive pressure with respect to ambient air pressure to an entrance of a patient's nares and to an entrance of the patient's mouth, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and a seal-forming structure comprising a textile membrane constructed and arranged to form a pressure-assisted seal with a region of the patient's face surrounding the entrance to the patient's nares and the entrance to the patient's mouth, the seal-forming structure comprising:

a nasal portion configured to at least partially surround the entrance to the patient's nares, and an oral portion configured to at least partially surround the entrance to the patient's mouth, wherein said textile membrane having at least one hole such that the flow of air at said therapeutic pressure is delivered to at least the entrance to the patient's nares and/or to the entrance of the patient's mouth, the seal-forming structure constructed and arranged to maintain said therapeutic pressure in the cavity throughout the patient's respiratory cycle in use, wherein the textile membrane includes a first portion held in a relaxed state and a second portion held in a taut state, the taut state of the second portion configured to allow the seal-forming structure to include a three-dimensional shape having multiple curvatures.

In some aspects a) the at least one hole includes a naris opening configured to be positioned adjacent to the patient's nares, and an oral portion hole configured to be positioned adjacent the patient's mouth in use; b) a bridge portion extends across the naris opening and divides the naris opening into a first hole and a second hole, each of the first hole and the second hole configured to be positioned adjacent to one of the patients nares in use; c) the bridge portion is the second portion and is held in a taut state; and/or d) the bridge portion is crimped using ultrasonic welding and/or an adhesive.

In some aspects a) the first portion is at least partially comprised of the oral portion; b) the first portion includes the oral portion and a section of the nasal portion; c) the seal-forming structure further includes a flexible support structure for holding the textile membrane in the three-dimensional shape; d) the flexible support structure includes at least one support rib that engages the oral portion within the cavity of the plenum chamber; e) the flexible support structure further comprises a secondary rib disposed within the cavity, the support rib extending between the secondary rib and the oral portion; f) the textile membrane of the seal-forming structure is curved about at least two non-parallel axes as a result of taut state of the second portion in order to form the three-dimensional shape; g) the oral portion is curved about the at least two non-parallel axes; and/or h) the textile membrane includes a textile layer and a silicone layer coupled to the textile layer, the silicone layer having impermeable properties. In some aspects a) the seal-forming structure is constructed from a textile membrane having a first sub-section and a second sub-section that is spaced apart from the first sub-section; b) the seal-forming structure further comprises a flexible support portion constructed from a material other than the textile membrane, the flexible support portion disposed between the first sub-section and the second sub-section; c) the second sub-section is positioned superior to the first sub-section in use; d) the second sub-section is disposed at least partially between ends of the first sub-section; e) the at least one hole includes a naris opening configured to be positioned adjacent to the patient's nares, and an oral portion hole configured to be positioned adjacent the patient's mouth, wherein, the first sub-section completely forms a perimeter of the oral portion hole; and the second sub-section completely forms a perimeter of the naris opening; f) the at least one hole includes a naris opening configured to be positioned adjacent to the patient's nares, and an oral portion hole configured to be positioned adjacent the patient's mouth, wherein, a perimeter of the naris opening is completely formed by the second sub-section; and a perimeter of the oral portion hole is at least partially formed by a combination of the first sub-section the second sub-section; g) the first sub-section forms at least part of the oral portion and includes an annular shape; and/or h) the second sub-section forms at least part of the oral portion and includes a U-shape.

In some aspects a) a single, continuous piece of the textile membrane is used to construct the oral portion and the nasal portion; b) the patient's nose and lip superior are configured to contact only the textile membrane, in use; and/or c) foam inserts coupled to the seal-forming structure and configured to contact the patient's nasal ala in use.

In some aspects, the textile membrane is configured to include be curved about at least two non-parallel axes as a result of the bridge portion being crimped.

In some aspects, the bridge portion is crimped using ultrasonic welding and/or an adhesive.

In some aspects, a length of the bridge portion is directly related to a size of the first hole and to a size of the second hole.

In some aspects, the bridge portion includes a first section and a second section, the first section being substantially flat and configured to contact the patient in use, and the second section extending into the plenum chamber.

In some aspects, ultrasonic welding and/or adhesives are applied to the second section.

In some aspects, the seal-forming structure includes a single wall, and wherein an end of the flexible support structure contacts the textile membrane.

In some aspects, the seal-forming structure includes a pair of walls, wherein the flexible support structure includes a free end, and the textile membrane is coupled to the flexible support structure distal to the free end, and wherein the free end is spaced apart from the textile membrane so that the textile membrane is arranged radially outside of the free end.

In some aspects, the flexible support structure is coupled to the textile membrane using injection molding.

In some aspects, the bridge portion is a locating spigot after being crimped.

In some aspects, the textile membrane includes a textile layer and a silicone layer coupled to the textile layer, the silicone layer having impermeable properties.

In some aspects, the silicone layer is approximately 0.5 mm thick.

In some aspects, the textile membrane includes a multi-layered textile material and silicone layer coupled to the multi-layered textile material.

In some aspects, the multi-layered textile material includes a first layer, a second layer, and a third layer, the silicone layer contacting only the first layer, and the third layer configured to contact the patient's face, in use.

In some aspects, the first layer and the third layer are constructed from nylon, and wherein the second layer is constructed from spandex.

In some aspects, the silicone layer is disposed within the cavity and is configured to not touch the patient's skin, in use.

In some aspects, the silicone layer has a low durometer characteristic, and the textile membrane includes a high stretch capability when coupled to the flexible support structure.

In some aspects, the textile membrane is approximately 0.35 mm to approximately 0.45 mm thick.

In some aspects, the textile membrane includes a first curvature about a first axis intersecting the first opening and the second opening, and wherein before being crimped, the bridge portion includes a bridge curvature about the first axis in an opposite direction from a remainder of the textile membrane.

In some aspects, a second axis extends transverse to the first axis and along the bridge portion, the textile membrane including a secondary curvature about the second axis.

In some aspects, the secondary curvature has an opposite concavity than the first curvature.

In some aspects, the secondary curvature is configured to contact the patient's subnasale, in use.

In some aspects, a third axis extends transverse to the second axis and skewed with respect to the first axis, the textile membrane including a tertiary curvature about the third axis.

In some aspects, the tertiary curvature is configured to contact the patient's lip superior, in use.

In some aspects, a fourth axis extends transverse to the second axis and to the third axis, and parallel to the first axis, the textile membrane including a quaternary curvature about the fourth axis.

In some aspects, the quaternary curvature includes a variable radius of curvature.

In some aspects, the quaternary curvature extends into the primary curvature proximate to an edge of the textile membrane.

In some aspects, a portion of the first hole distal to the bridge portion is movable between a first position and a second position.

In some aspects, the first position is a natural state, and the textile membrane moves to the second position as a result of an external force.

In some aspects, the portion of the first hole extends into the plenum chamber in the second position.

In some aspects, the first hole includes a substantially tear-drop shape in the second position.

In some aspects, in the second position, the first hole is configured to contact a periphery of the entrance to one of the patient's nares proximate to an alar rim.

In some aspects, a portion of the second hole distal to the bridge portion is movable between the first position and the second position.

In some aspects, the patient's nose and lip superior are configured to contact only the textile membrane, in use.

In some aspects, the patient interface is a nasal cushion, nasal cradle, oronasal cushion, ultra-compact full-face mask, or full-face mask.

In another aspect of the present invention, a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and a seal-forming structure having a textile membrane constructed and arranged to form a pressure-assisted seal with a region of the patient's face surrounding an entrance to the patient's airways inferior to a nasal bridge region of the patient's face, said textile membrane having a first hole and a second hole and a bridge portion disposed between the first hole and the second hole, the first hole and the second hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use, wherein:

the seal-forming structure includes a flexible support structure to hold the textile membrane in a predefined curved shape, the textile membrane includes a first curvature about a first axis and a second curvature about a second axis generally transverse to the first axis, the first axis configured to be generally transverse to a sagittal plane of the patient's head so that the first curvature includes a vertex in a posterior direction so that the first curvature passes around the nasolabial sulcus of the patient's nose, and the second axis configured to be generally parallel with the sagittal plane so that the second curvature includes a vertex in an inferior direction so that the second curvature is a saddle region and has a generally a positive curvature with respect to the patient's lip superior in use, the bridge portion has a third curvature opposite of the first curvature, the third curvature of the bridge portion limiting creasing along the surface of the textile membrane, the textile membrane is coupled to the flexible support structure in a relaxed state, in use, the textile membrane is configured to press against the patient's face such that the patient's nose is not received in the cavity, and the textile membrane is attached to the flexible support structure along an outer perimeter of the textile membrane such that textile membrane extends radially inwardly beyond the support structure.

In some aspects, the bridge portion is crimped in order to maintain the third curvature and limit flipping to the first curvature.

In some aspects, the bridge portion is crimped using ultrasonic welding and/or an adhesive.

In some aspects, the textile membrane is substantially impermeable to air.

In some aspects, the textile membrane includes a textile layer and a silicone layer coupled to the textile layer, the silicone layer having impermeable properties.

In some aspects, the silicone layer is approximately 0.5 mm thick.

In some aspects, the silicone layer is disposed within the cavity and is configured to not touch the patient's skin, in use.

In some aspects, the silicone layer has a low durometer characteristic, and the textile layer includes a high stretch capability when coupled to the support structure.

In some aspects, the textile membrane is approximately 0.35 mm to approximately 0.45 mm thick.

In some aspects, the seal-forming structure includes a single wall, and wherein an end of the flexible support structure contacts the textile membrane.

In some aspects, the seal-forming includes a pair of walls, wherein the flexible support structure includes a free end, and the textile membrane is coupled to the flexible support structure distal to the free end, and wherein the free end is spaced apart from the textile membrane so that the textile membrane is arranged radially outside of the free end.

In some aspects, the first hole includes a first arched portion, the first arched portion having generally the first curvature, and the first arched portion is configured to be positioned within a first naris of the patient.

In some aspects, the first arched portion is configured to flip from having generally the first curvature to having generally the third curvature after being positioned within the first naris of the patient, the arched portion configured to wrap around a periphery of an entrance to the first naris.

In some aspects, the second hole includes a second arched portion, the second arched portion having generally the first curvature, and the second arched portion configured to be positioned within a second naris of the patient.

In some aspects, the first hole includes a substantially circular shape, and is configured to include a substantially tear-drop shape after contacting the patient's face.

In some aspects, the textile membrane is configured to contact only the patient's lip superior, subnasale, and pronasale, in use.

In some aspects, the flexible support is coupled to the textile membrane using injection molding.

In some aspects, the textile membrane includes a fourth curvature about a fourth axis, the fourth curvature being generally a saddle region with a positive curvature with respect to the patient's subnasale in use, and the fourth axis being generally transverse to the first axis and to the second axis.

In some aspects, an area influenced by the second curvature is formed by a generally rectangular region encompassing the first hole and the second hole, the generally rectangular region having a generally tangential relationship with respect to the first hole and to the second hole, wherein the generally tangential relationship limits creasing in the textile membrane.

In another aspect of the present technology, a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and a seal-forming structure having a textile membrane constructed and arranged to form a pressure-assisted seal with a region of the patient's face surrounding an entrance to the patient's airways inferior to a nasal bridge region of the patient's face, said textile membrane having a first hole and a second hole and a bridge portion disposed between the first hole and the second hole, the first hole and the second hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use, wherein:

the seal-forming structure includes a flexible support structure to hold the textile membrane in a predefined curved shape, the textile membrane includes a first curvature about a first axis and a second curvature about a second axis generally transverse to the first axis, the first axis is configured to be generally transverse to a sagittal plane of the patient's head so that the first curvature includes a vertex in a posterior direction so that the first curvature is generally a negative dome curvature with respect to the patient's lip superior in use, and the second axis is configured to be generally parallel with the sagittal plane so that the second curvature includes a vertex in an inferior direction so that the second curvature is generally a saddle region and a positive curvature with respect to the patient's pronasale in use, the bridge portion has a third curvature opposite of the first curvature, the third curvature of the bridge portion limiting creasing along the surface of the textile membrane, the textile membrane is coupled to the flexible support structure in a relaxed state, in use, the textile membrane is configured to press against the patient's face such that the patient's nose is not received in the cavity, and the textile membrane is attached to the flexible support structure along an outer perimeter of the textile membrane such that textile membrane extends radially inwardly beyond the support structure.

In some aspects, the textile membrane includes a fourth curvature about a fourth axis configured to be generally parallel to the first axis so that the fourth curvature includes a vertex in the posterior direction so that the fourth curvature passes around the nasolabial sulcus of the patient's nose.

In some aspects, the bridge portion is crimped in order to maintain the third curvature and limit flipping to the first curvature.

In some aspects, the bridge portion is crimped using ultrasonic welding and/or an adhesive.

In some aspects, the textile membrane is substantially impermeable to air.

In some aspects, the textile membrane includes a textile layer and a silicone layer coupled to the textile layer, the silicone layer having impermeable properties.

In some aspects, the silicone layer is approximately 0.5 mm thick.

In some aspects, the silicone layer is disposed within the cavity and is configured to not touch the patient's skin, in use.

In some aspects, the silicone layer has a low durometer characteristic, and the textile layer includes a high stretch capability when coupled to the support structure.

In some aspects, the textile membrane is approximately 0.35 mm to approximately 0.45 mm thick.

In some aspects, the seal-forming structure includes a single wall, and wherein an end of the flexible support structure contacts the textile membrane.

In some aspects, the seal-forming includes a pair of walls, wherein the flexible support structure includes a free end, and the textile membrane is coupled to the flexible support structure distal to the free end, and wherein the free end is spaced apart from the textile membrane so that the textile membrane is arranged radially outside of the free end.

In some aspects, the first hole includes a first arched portion, the first arched portion having generally the first curvature, and the first arched portion is configured to be positioned within a first naris of the patient.

In another aspect of the present technology, a seal-forming structure has:

a textile membrane constructed and arranged to form a pressure-assisted seal with a region of the patient's face surrounding an entrance to the patient's airways inferior to a nasal bridge region of the patient's face, said textile membrane having a first hole and a second hole and a bridge portion disposed between the first hole and the second hole, the first hole and the second hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use, and a flexible support structure for holding the textile membrane in a predefined shape;

wherein:

the textile membrane is coupled to the flexible support structure in a relaxed state, and the bridge portion is crimped so as to be held in greater tension than a remainder of the textile membrane.

Another aspect of the present technology is a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and a seal-forming structure having:

a textile membrane constructed and arranged to form a pressure-assisted seal with a region of the patient's face surrounding an entrance to the patient's airways inferior to a nasal bridge region of the patient's face, said textile membrane having a portion, the seal-forming structure constructed and arranged to maintain said therapeutic pressure in the cavity throughout the patient's respiratory cycle in use, wherein the textile membrane is held in a taut state.

One form of the present technology comprises a textile seal-forming structure with a bridge portion between a first hole and a second hole, the entire textile seal-forming structure being held in a taut state.

Another aspect of one form of the present technology is a seal-forming structure having a textile membrane coupled to a flexible support structure in a taut state, and a bridge portion of the textile membrane is substantially flat as a result of the tension.

Another aspect of one form of the present technology is a seal-forming structure having a textile membrane coupled to a flexible support structure in a taut state prior to use, the textile membrane having a substantially flat surface in at least one direction in the taut state prior to use.

In some aspects, the textile membrane is tensioned via various techniques, including without crimping at one or more portions of the textile membrane, e.g., a central portion and/or a bridge portion. The central portion and/or a bridge portion may be taut and substantially flat prior to use by a patient. The textile membrane may be supported by a flexible support and may be stretched, or otherwise tensioned, prior to connecting to flexible support.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
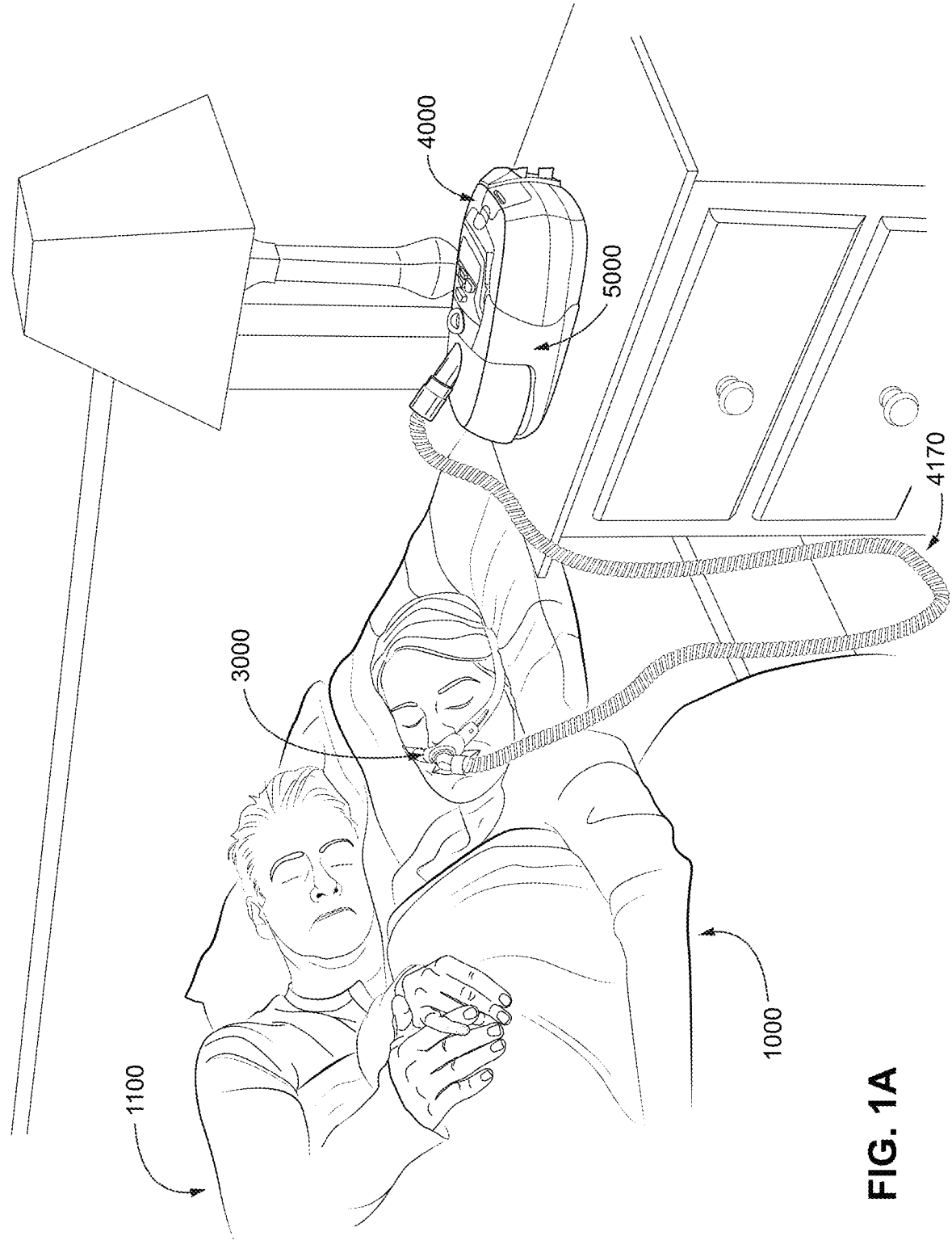
Figure 1B:
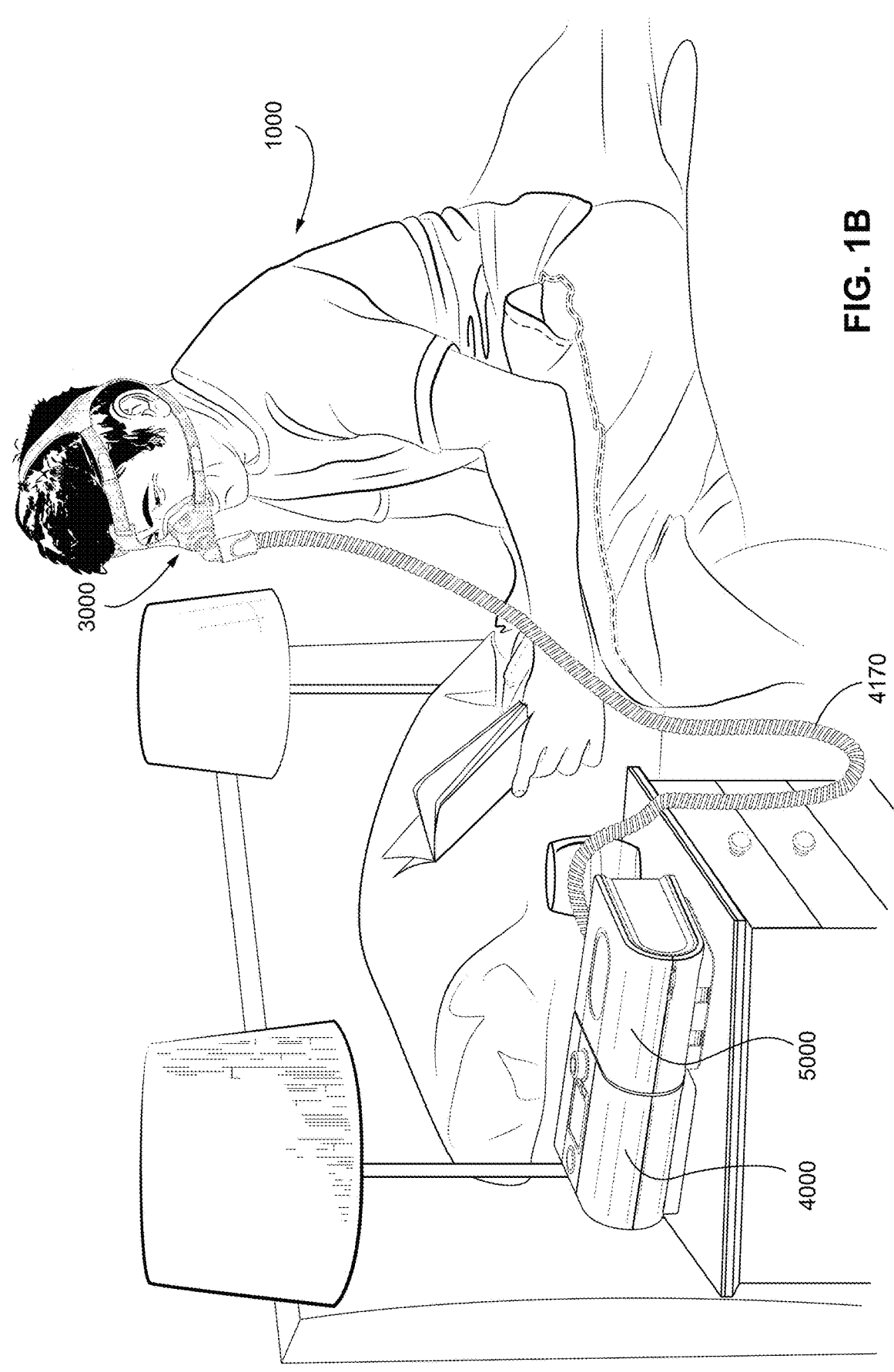
Figure 1C:
Figure 2A:
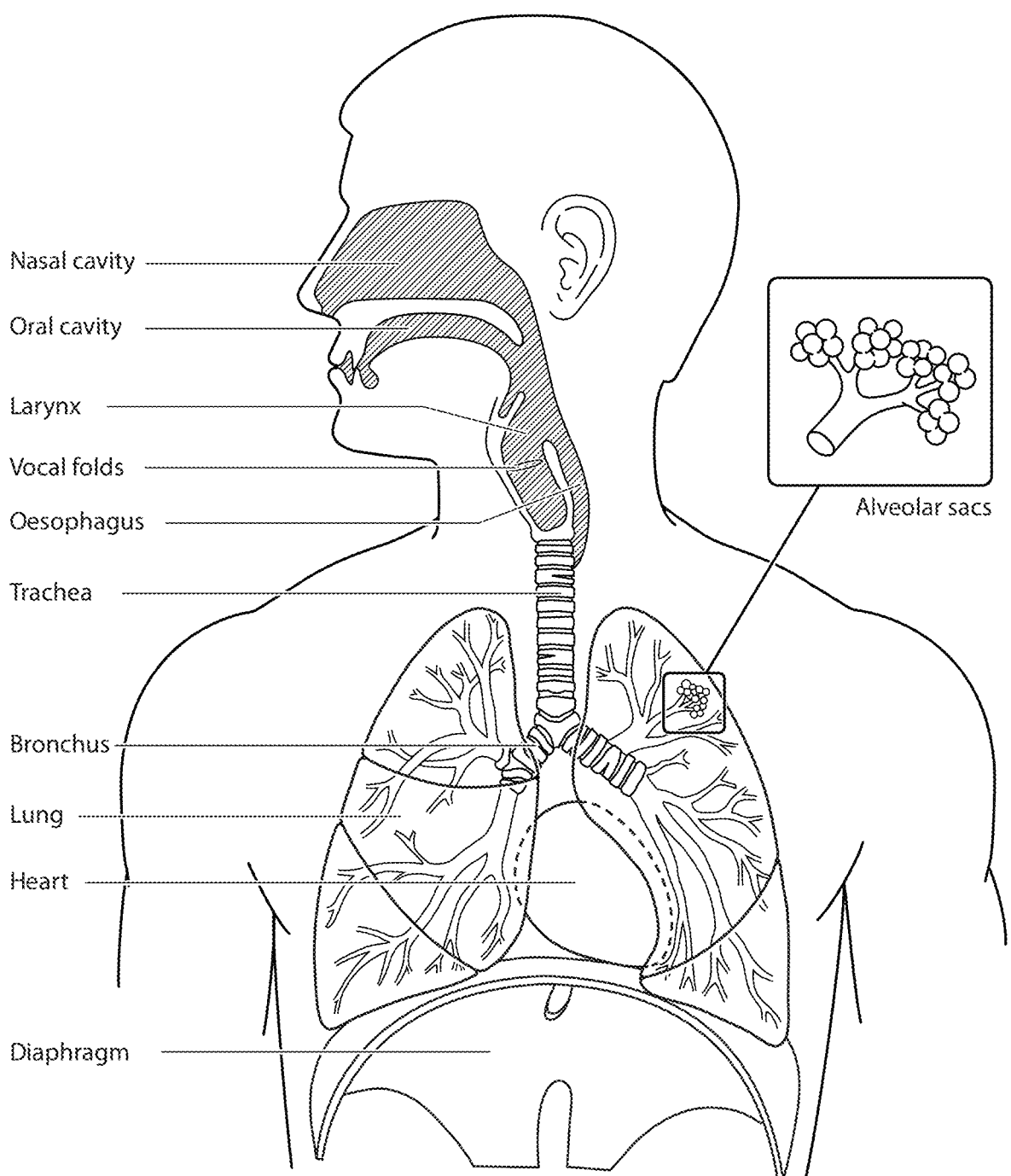
FIG. 2A shows an overview of a human respiratory system including the nasal and oral cavities, the larynx, vocal folds, oesophagus, trachea, bronchus, lung, alveolar sacs, heart and diaphragm.
Figure 2B:
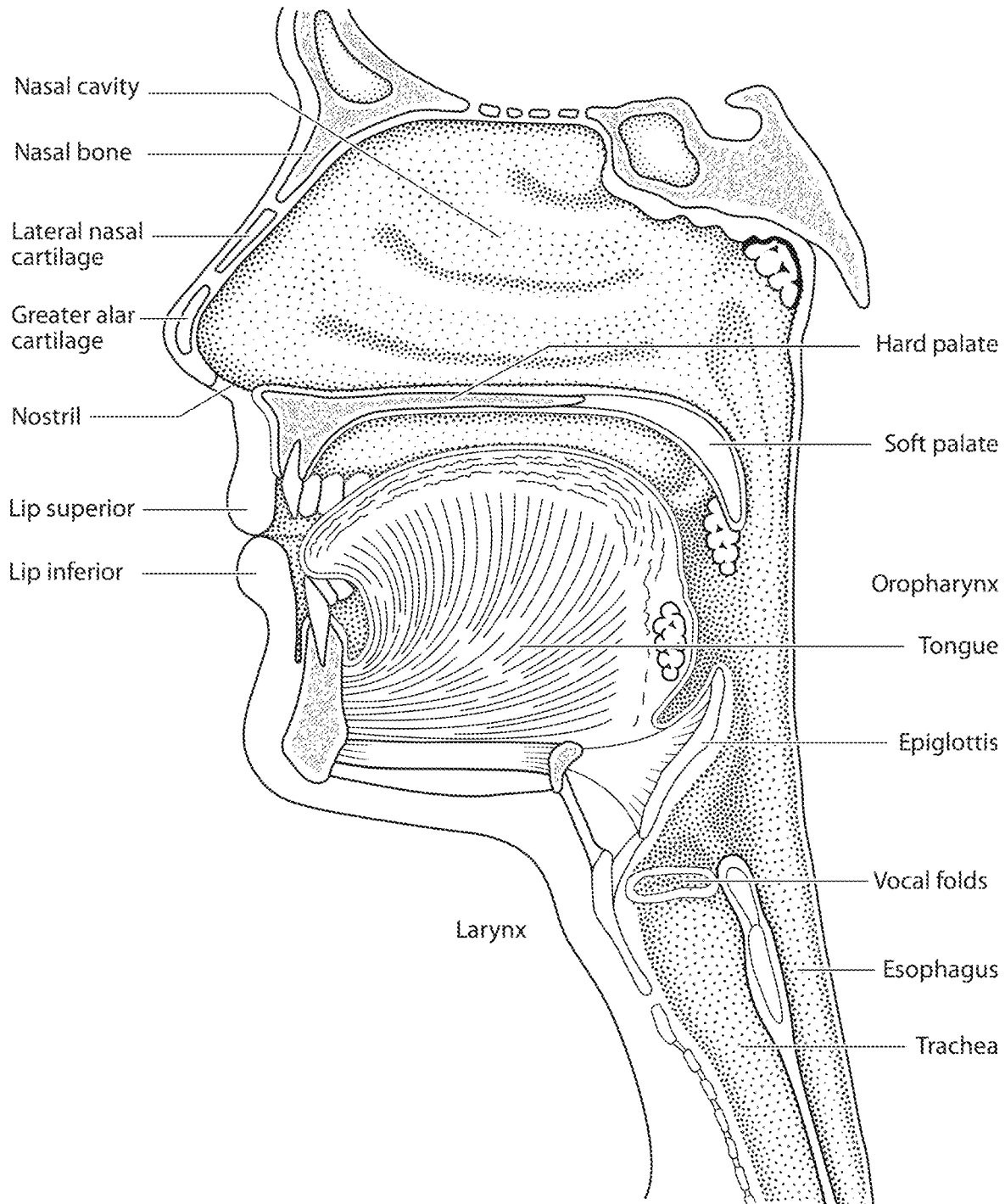
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
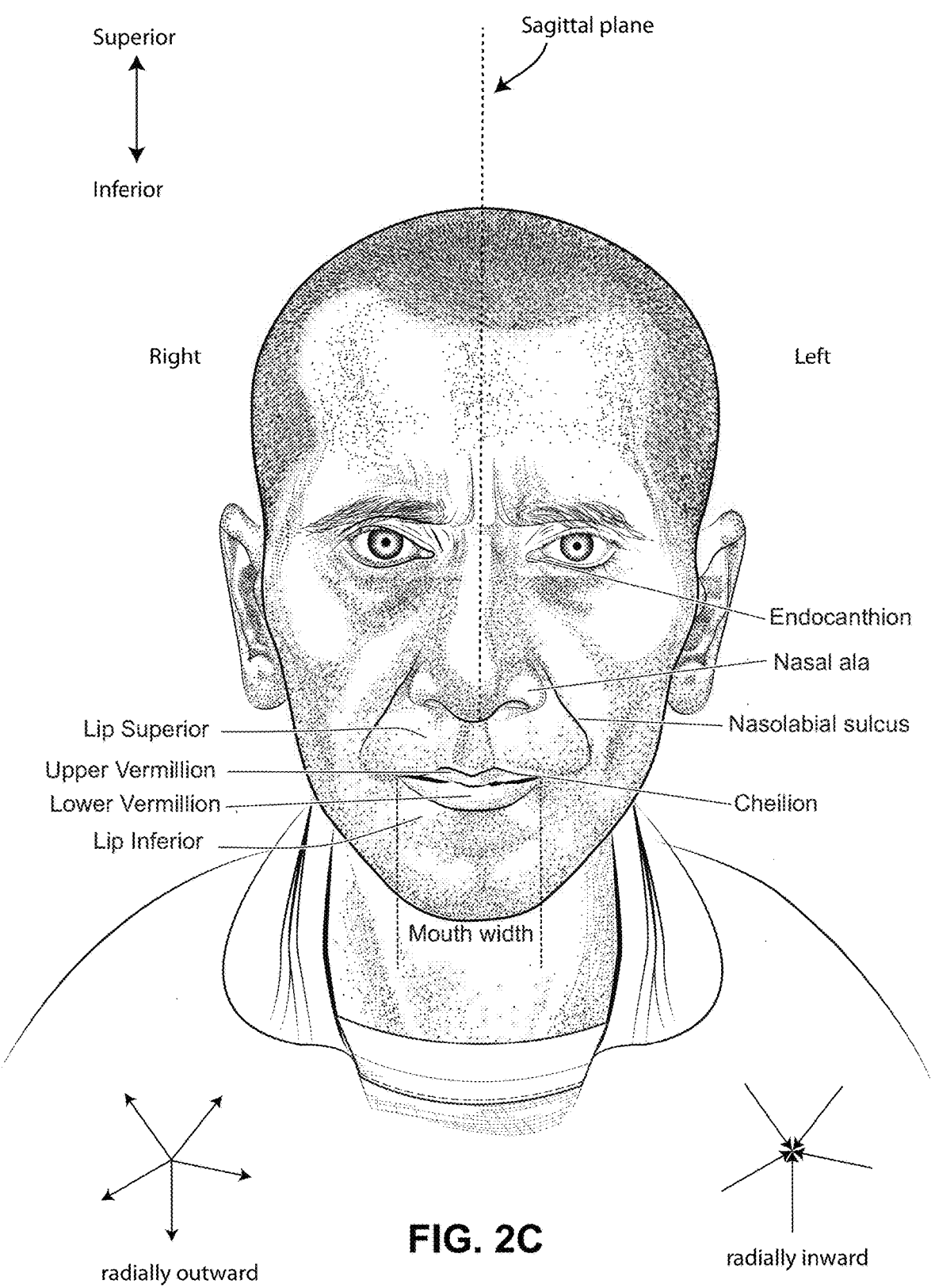
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
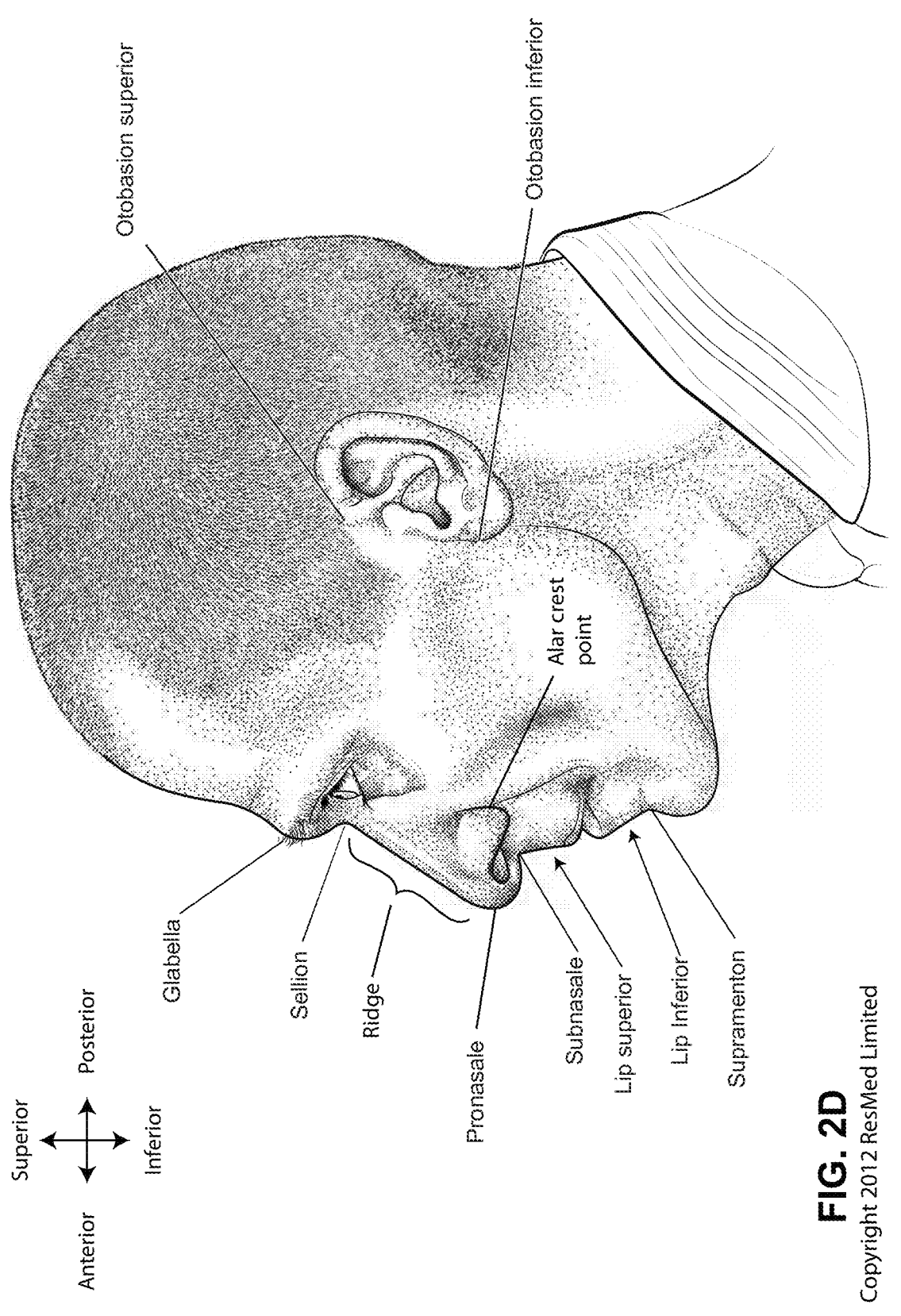
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
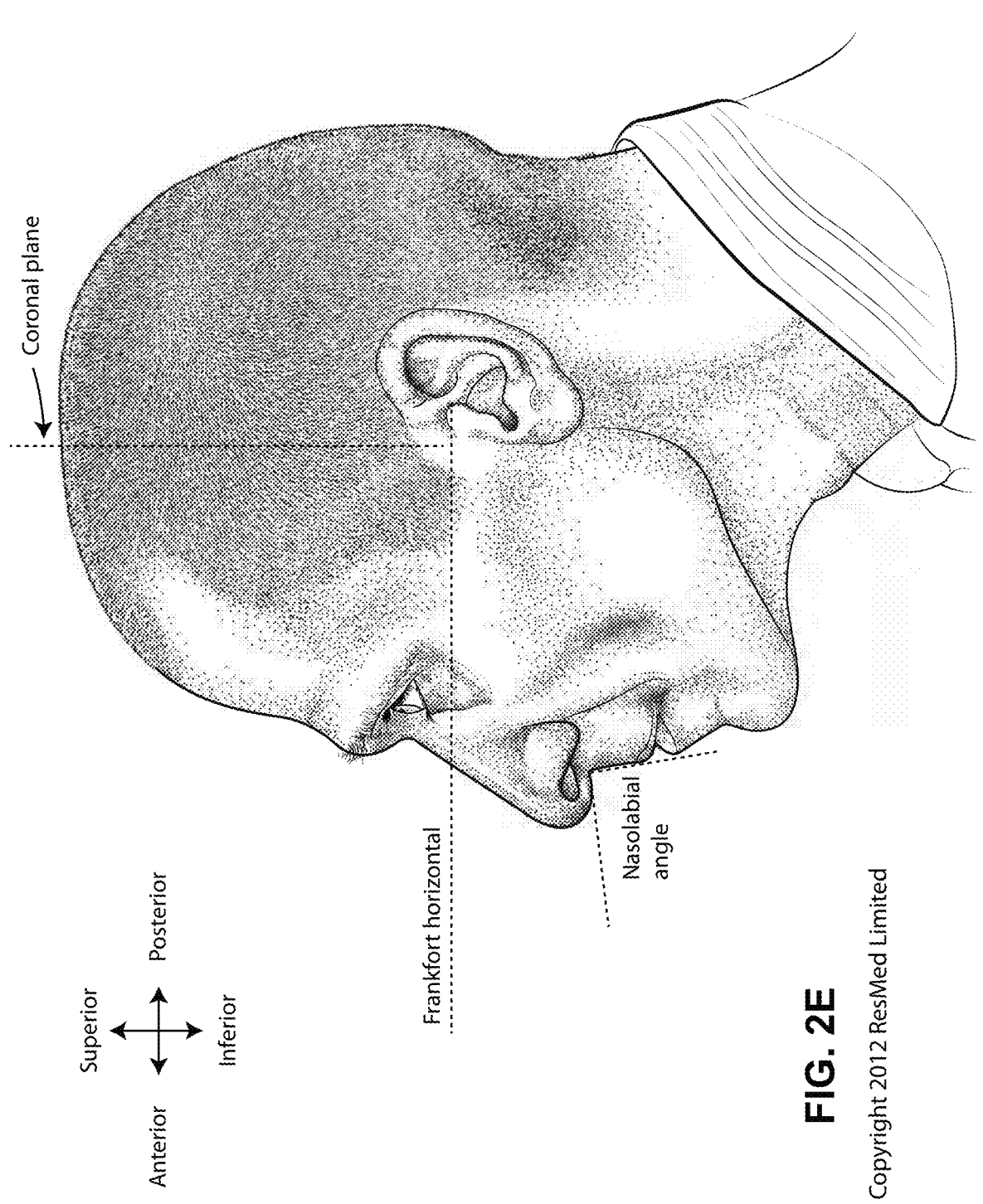

FIG. 2E is a further side view of a head. The approximate locations of the Frankfort horizontal and nasolabial angle are indicated. The coronal plane is also indicated.

Figure 2F:
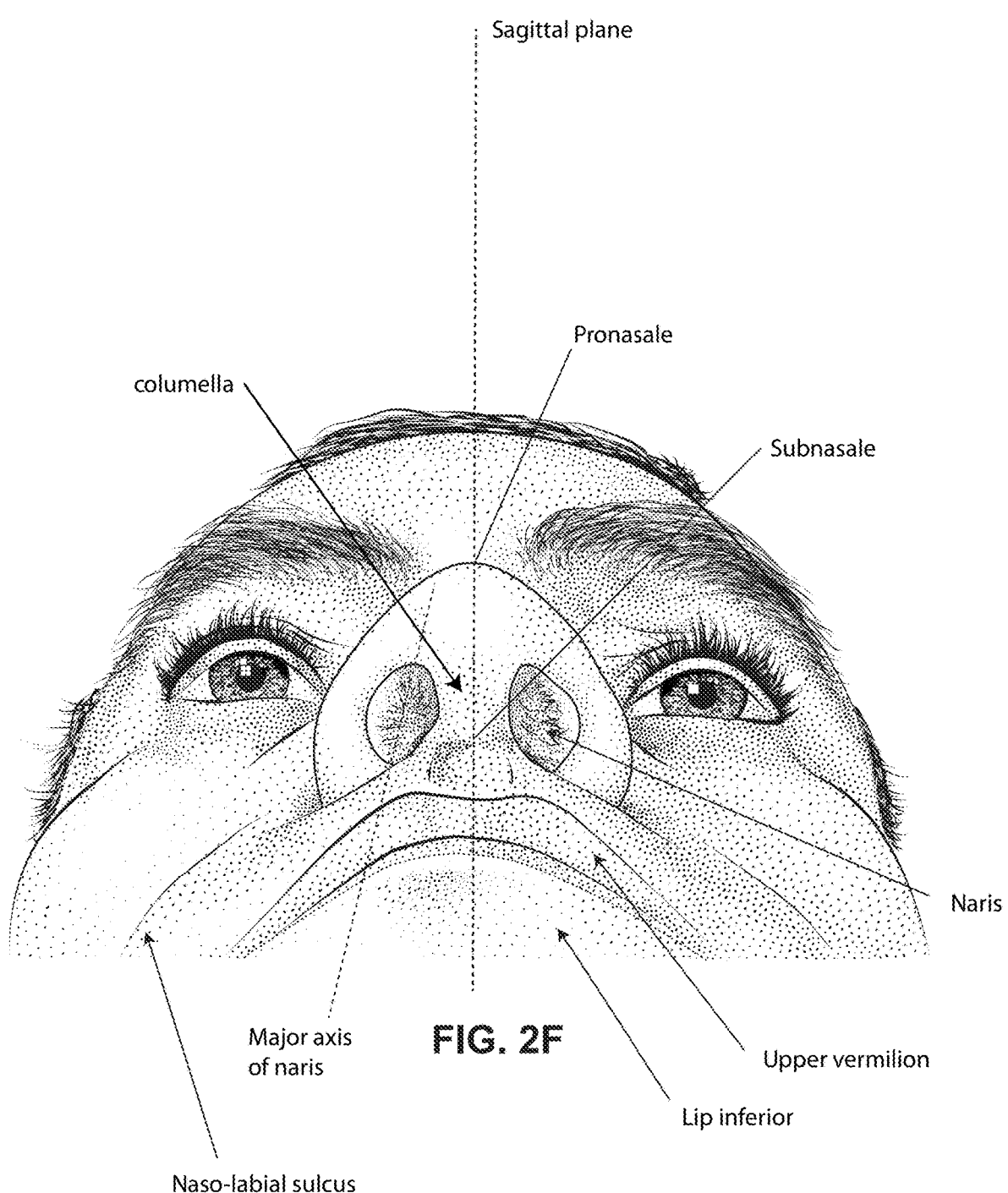

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
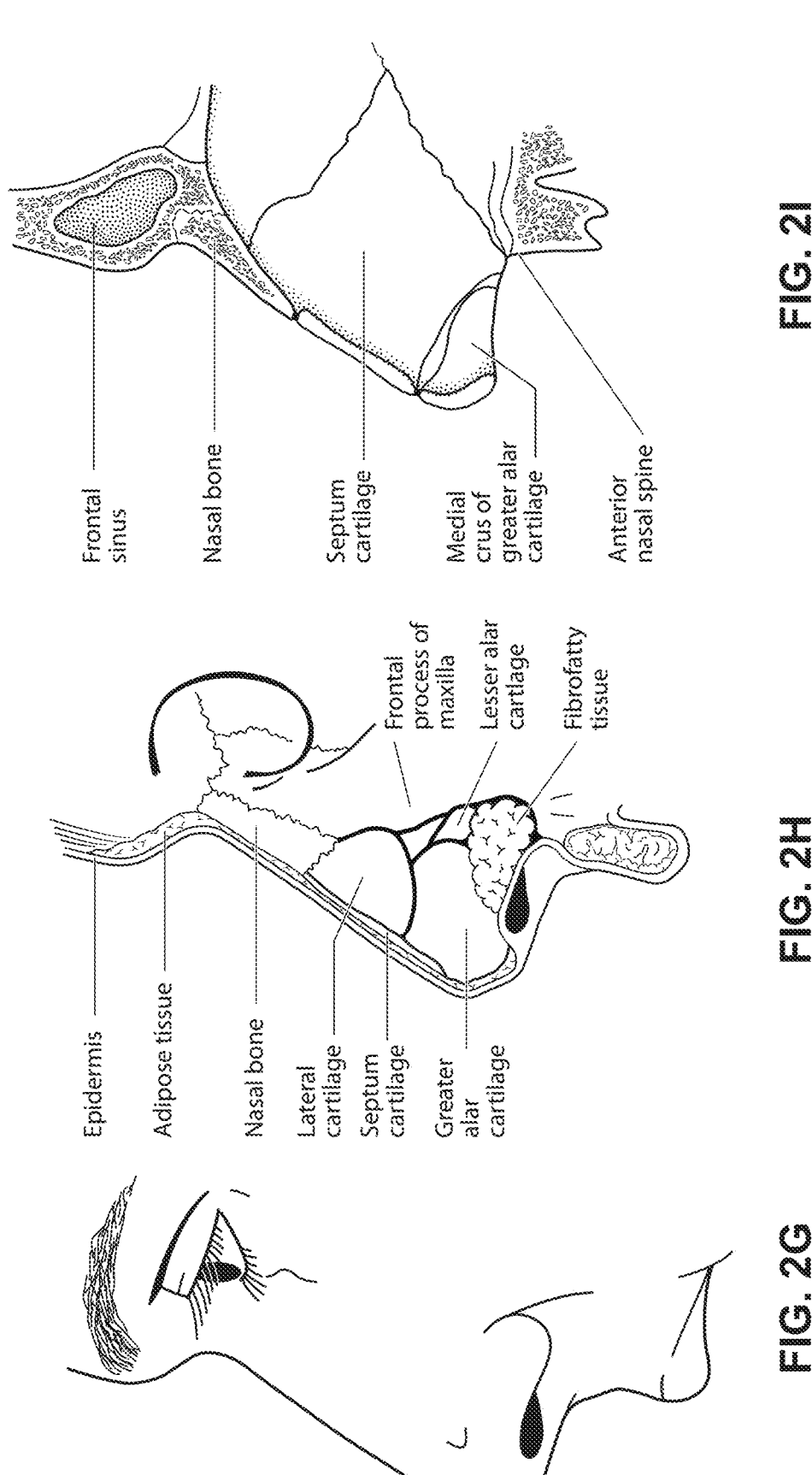

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
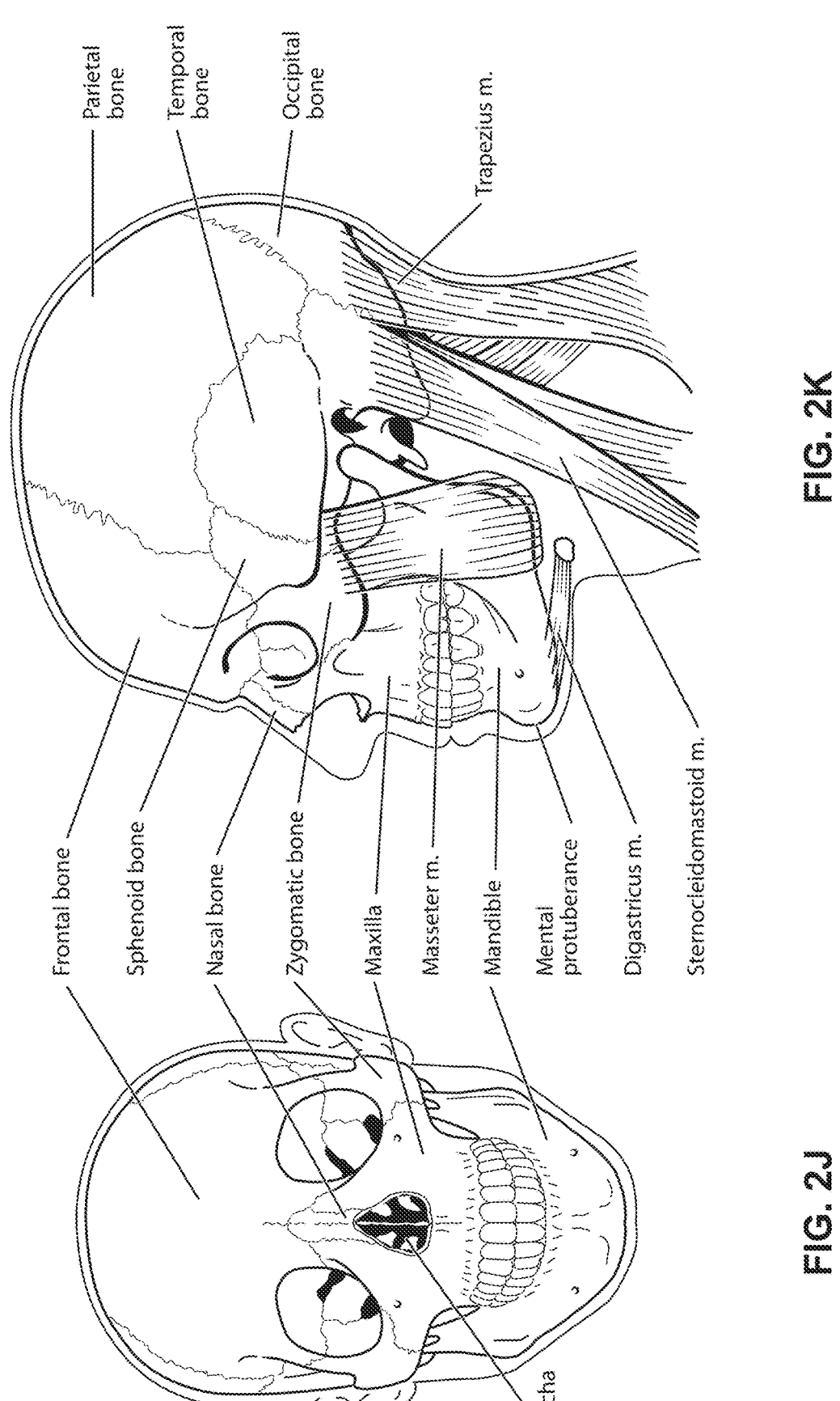

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
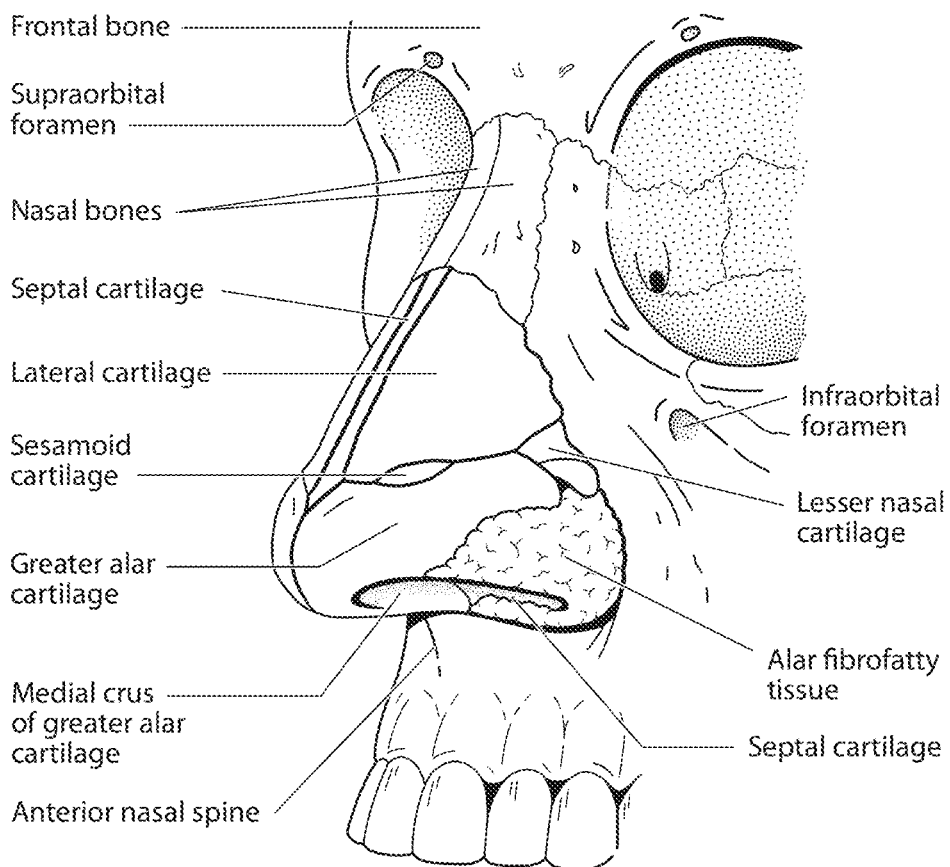

FIG. 2L shows an anterolateral view of a nose.

4.3 Patient Interface

Figure 3A:
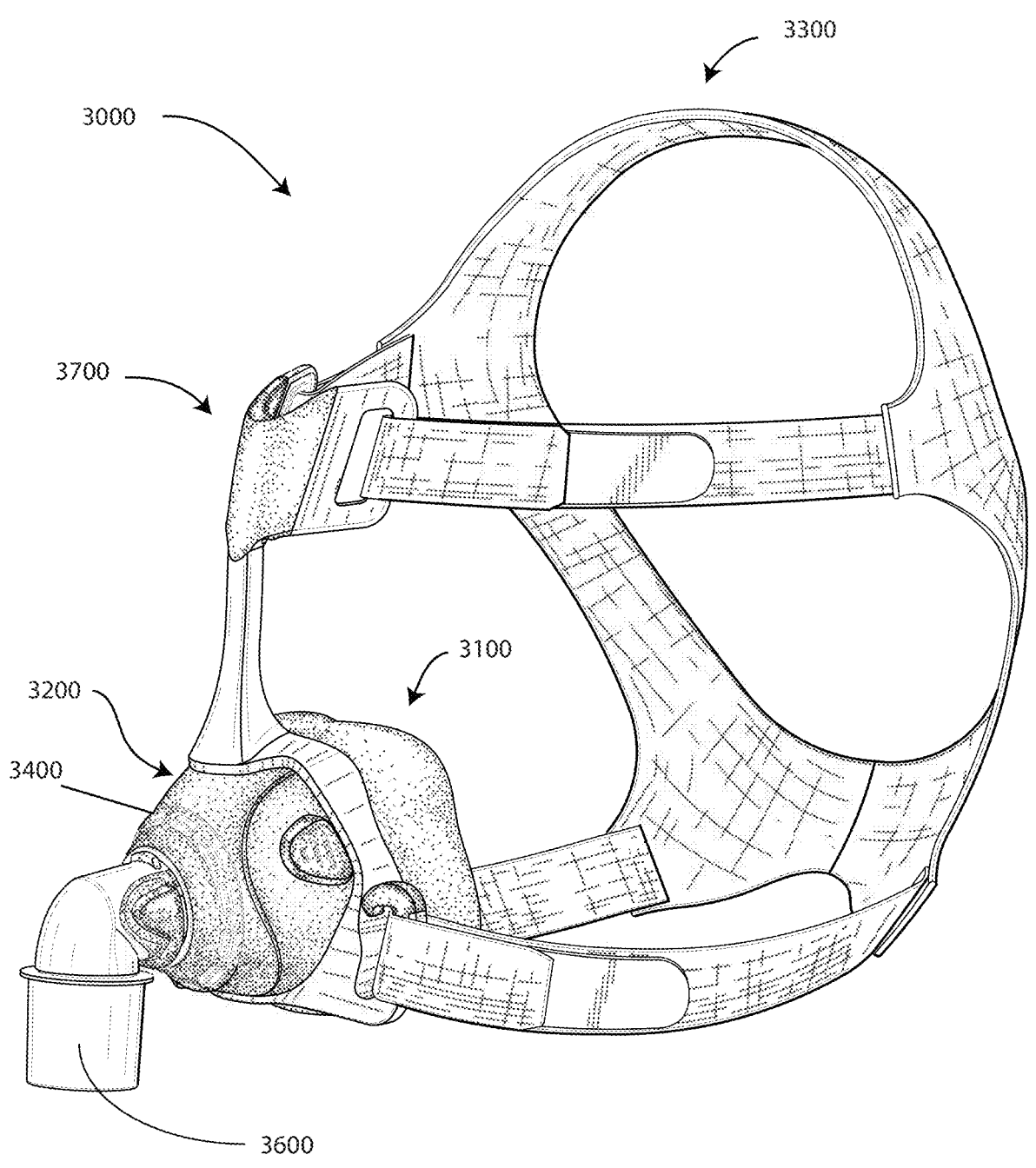

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
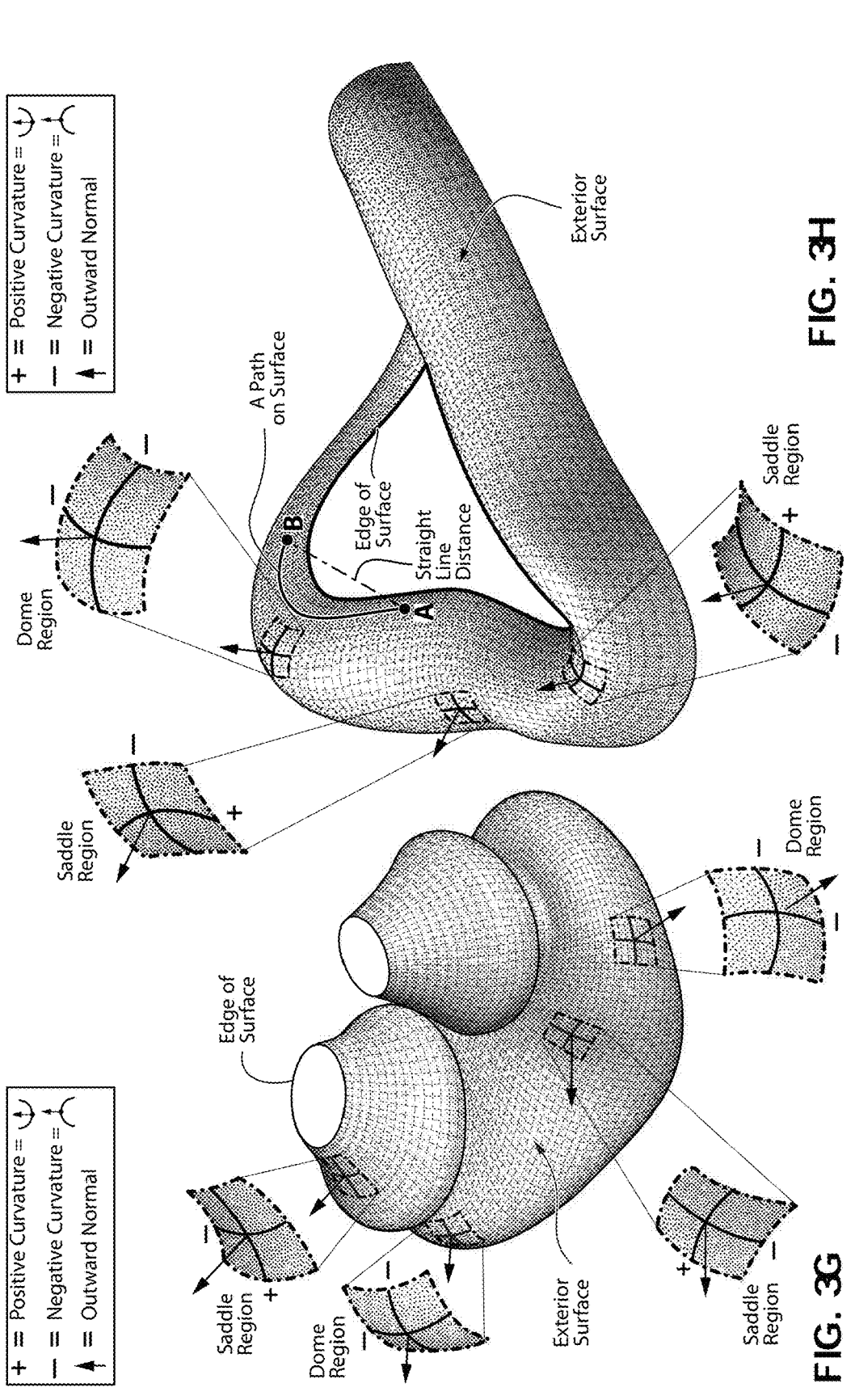

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figures 3I, 3J, 3K, 3L, 3M, 3N:
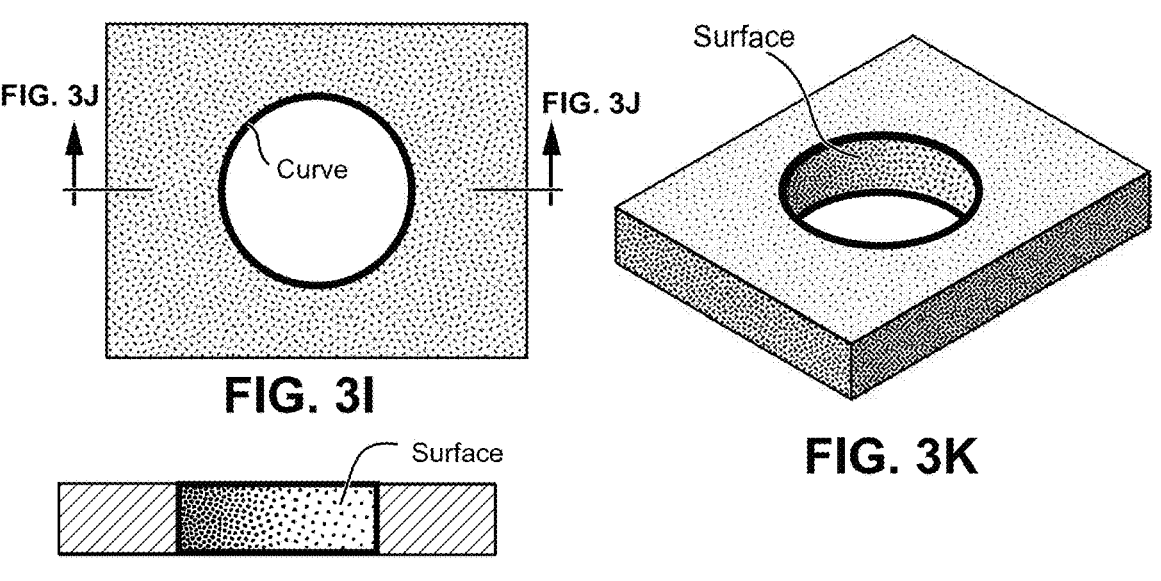

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figures 3U, 3V, 3W, 3X:
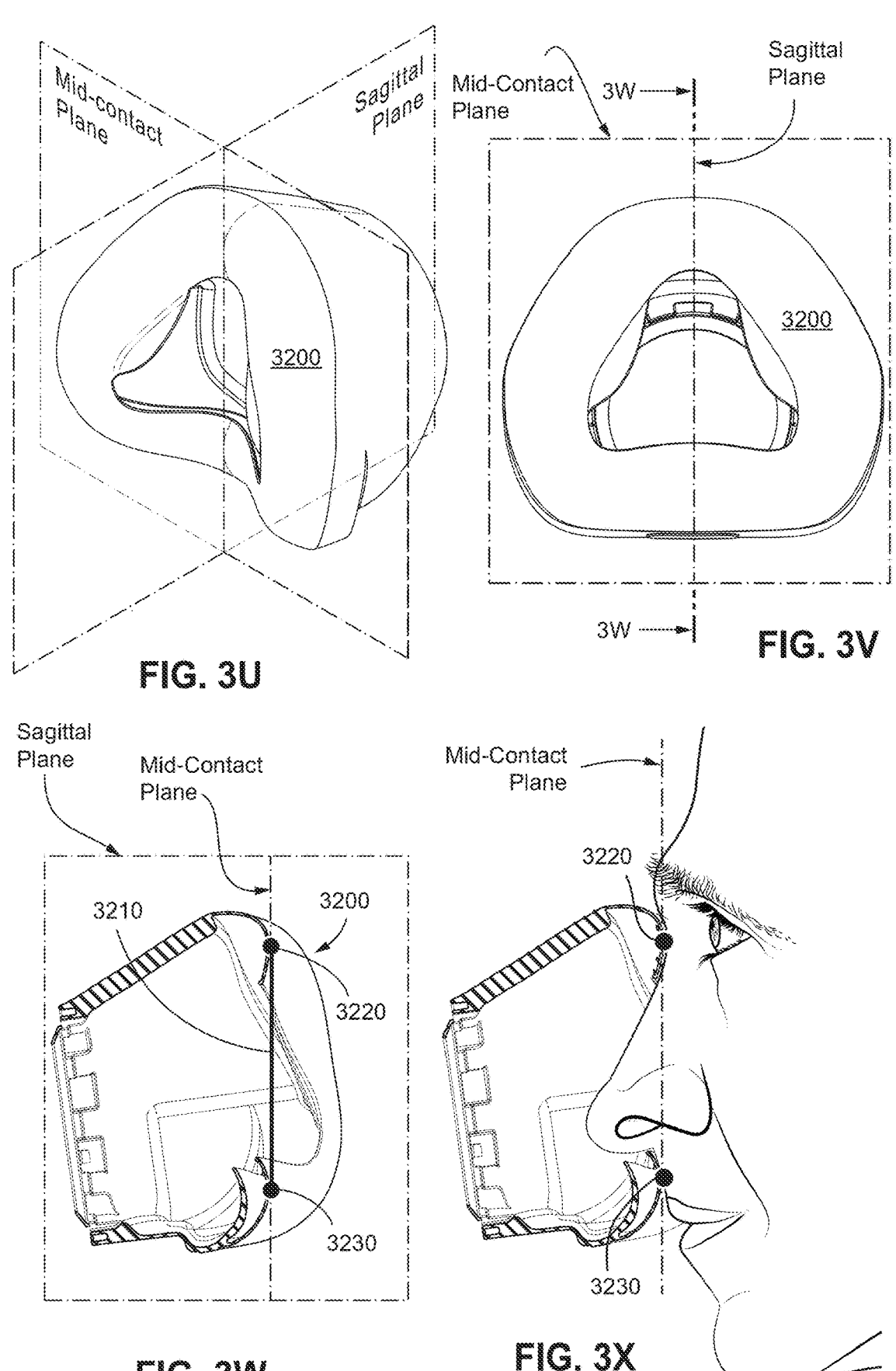

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
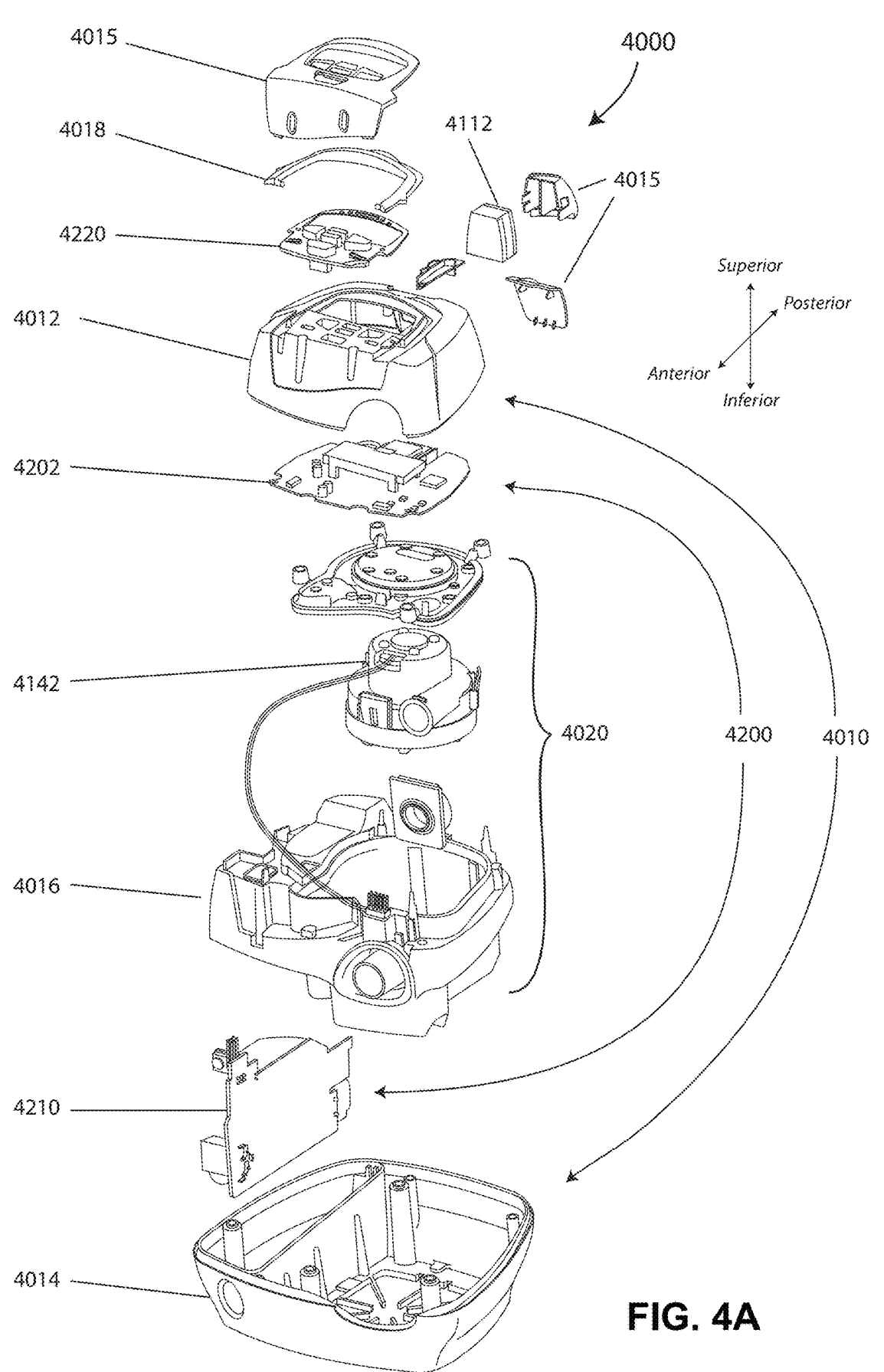

FIG. 4A shows an RPT device in accordance with one form of the present technology.

Figure 4B:
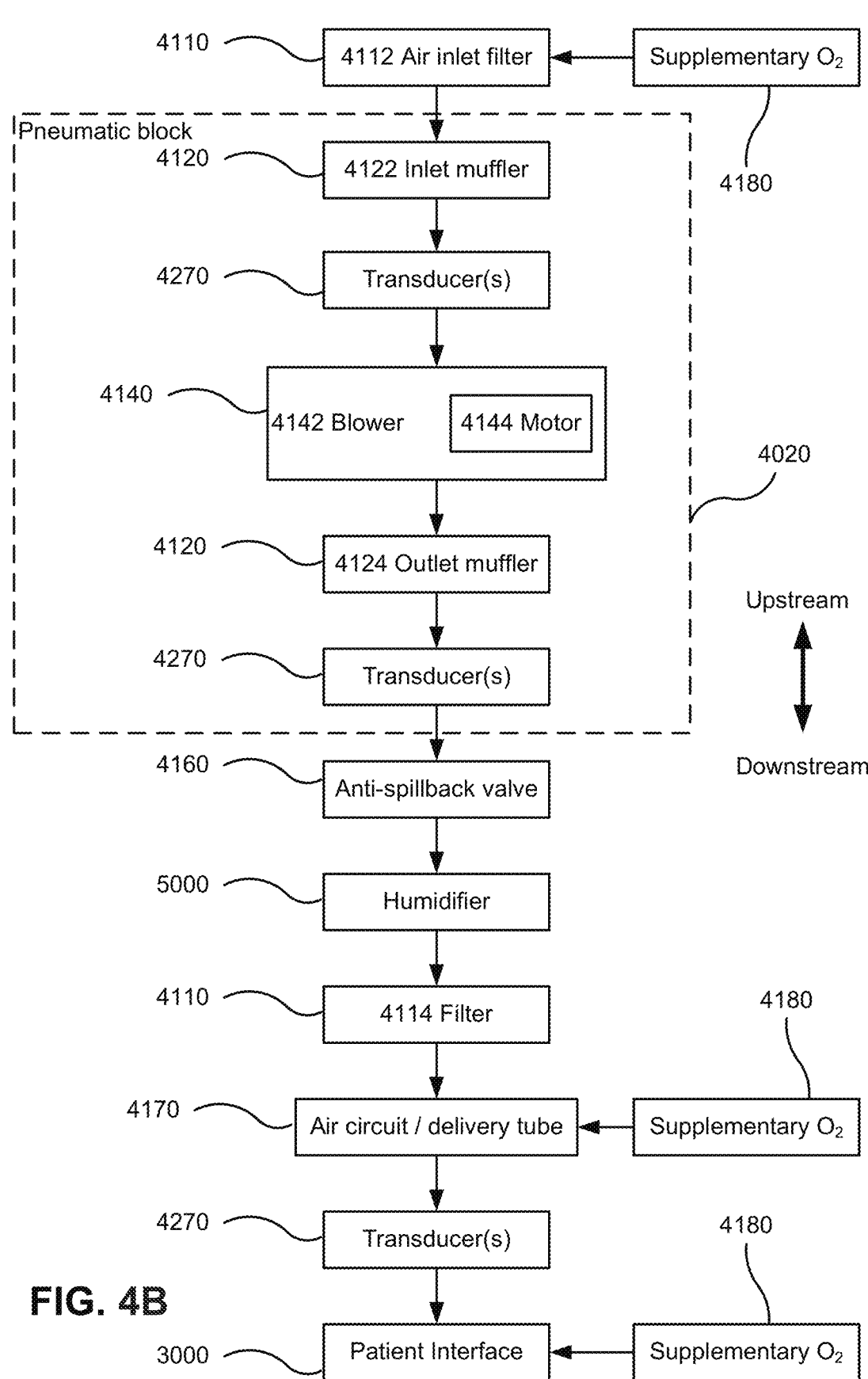

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Breathing Waveforms

Figure 5:
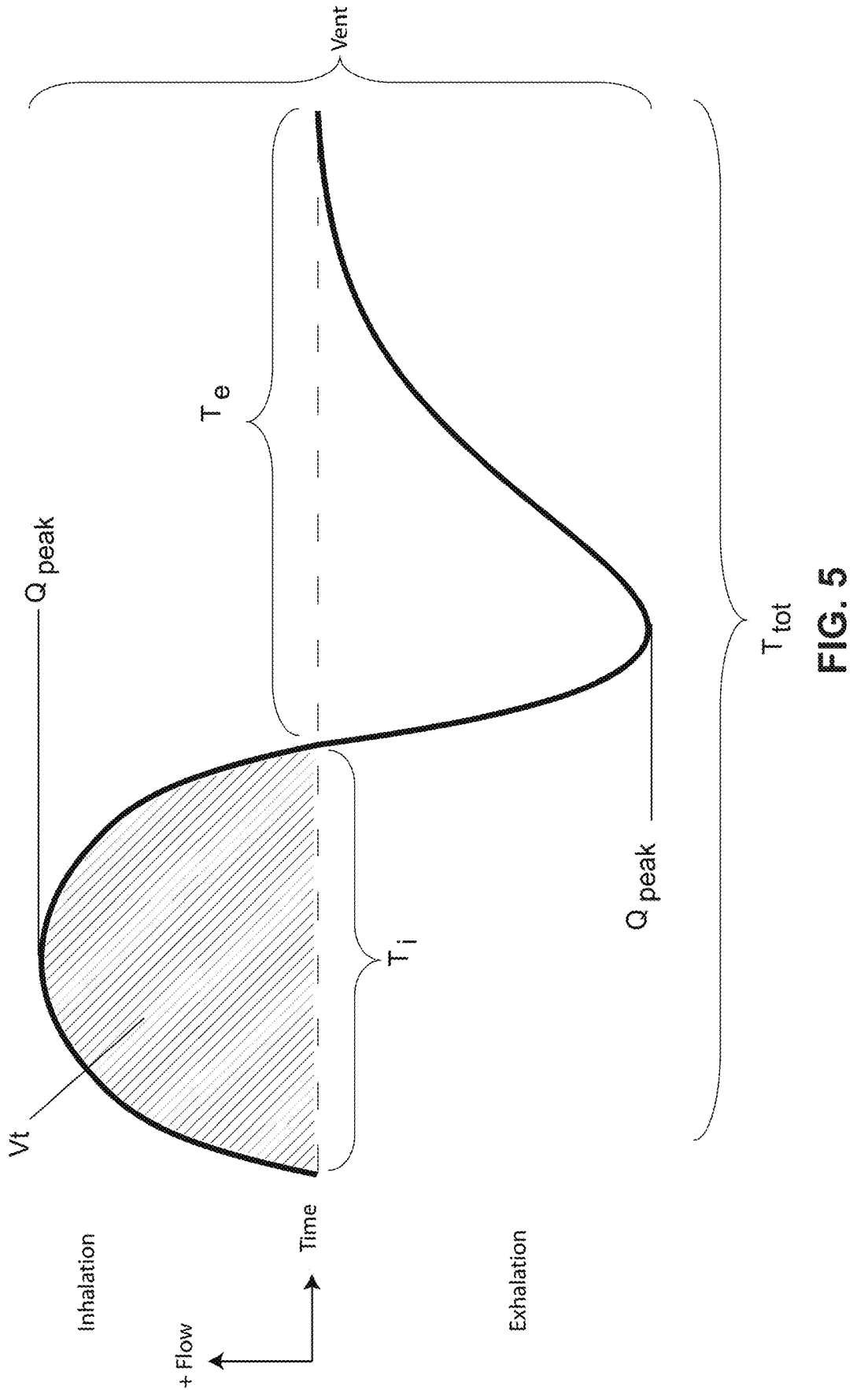

FIG. 5 shows a model typical breath waveform of a person while sleeping.

4.6 Patient Interface According to the Present Technology

Figure 6:
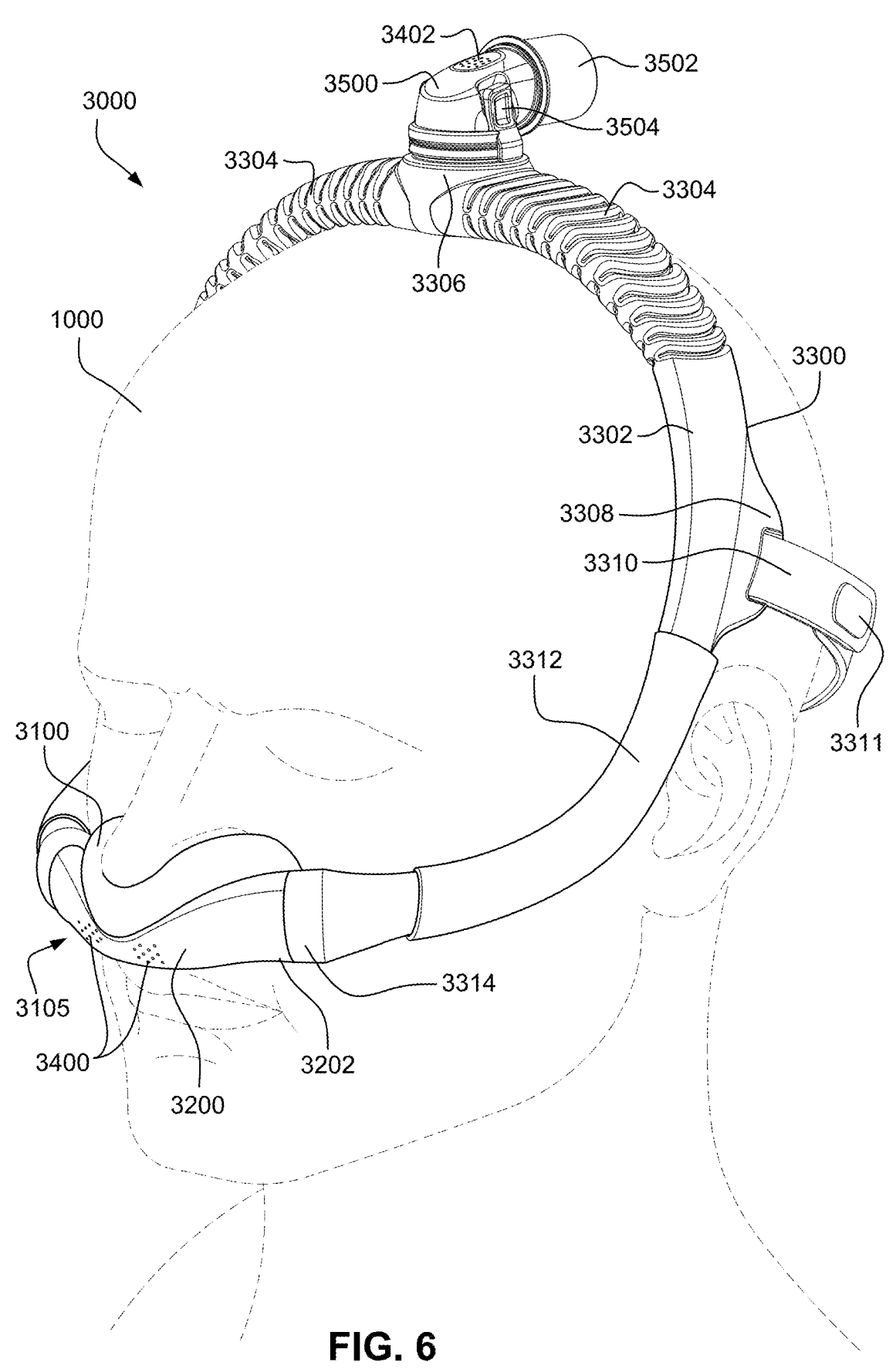

FIG. 6 is a perspective view of a patient interface according to an example of the present technology worn by a patient.

Figure 7:
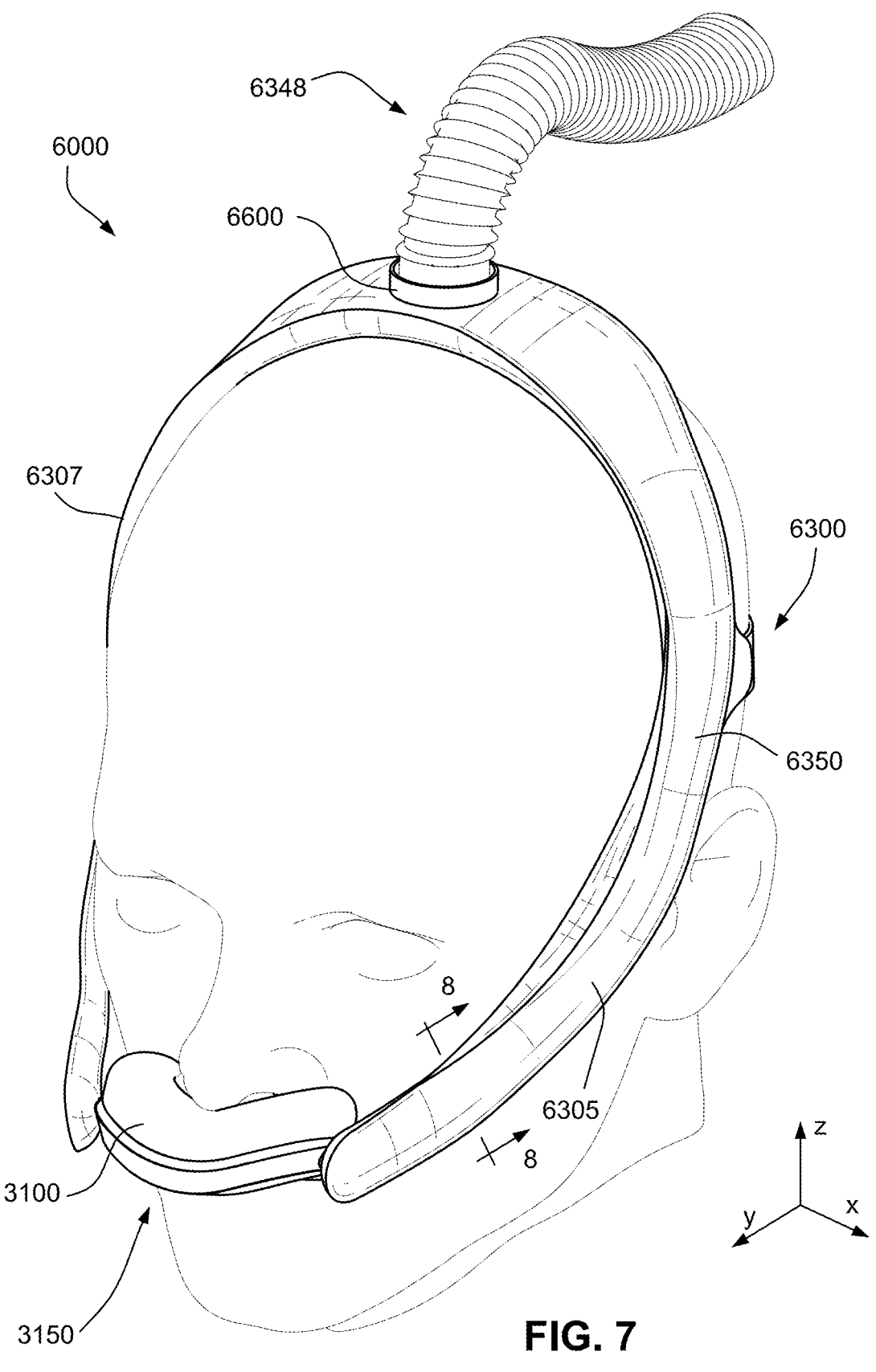

FIG. 7 is a perspective view of a patient interface according to another example of the present technology worn by a patient.

Figure 33:
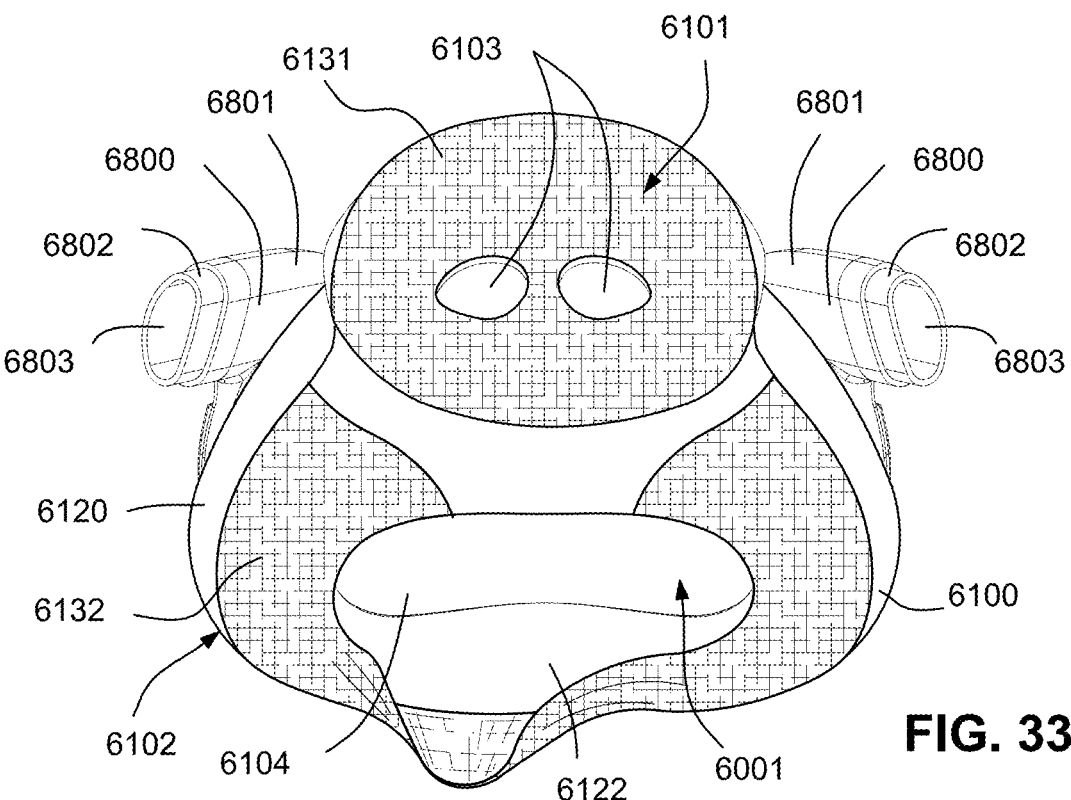
Figures 1, 33:
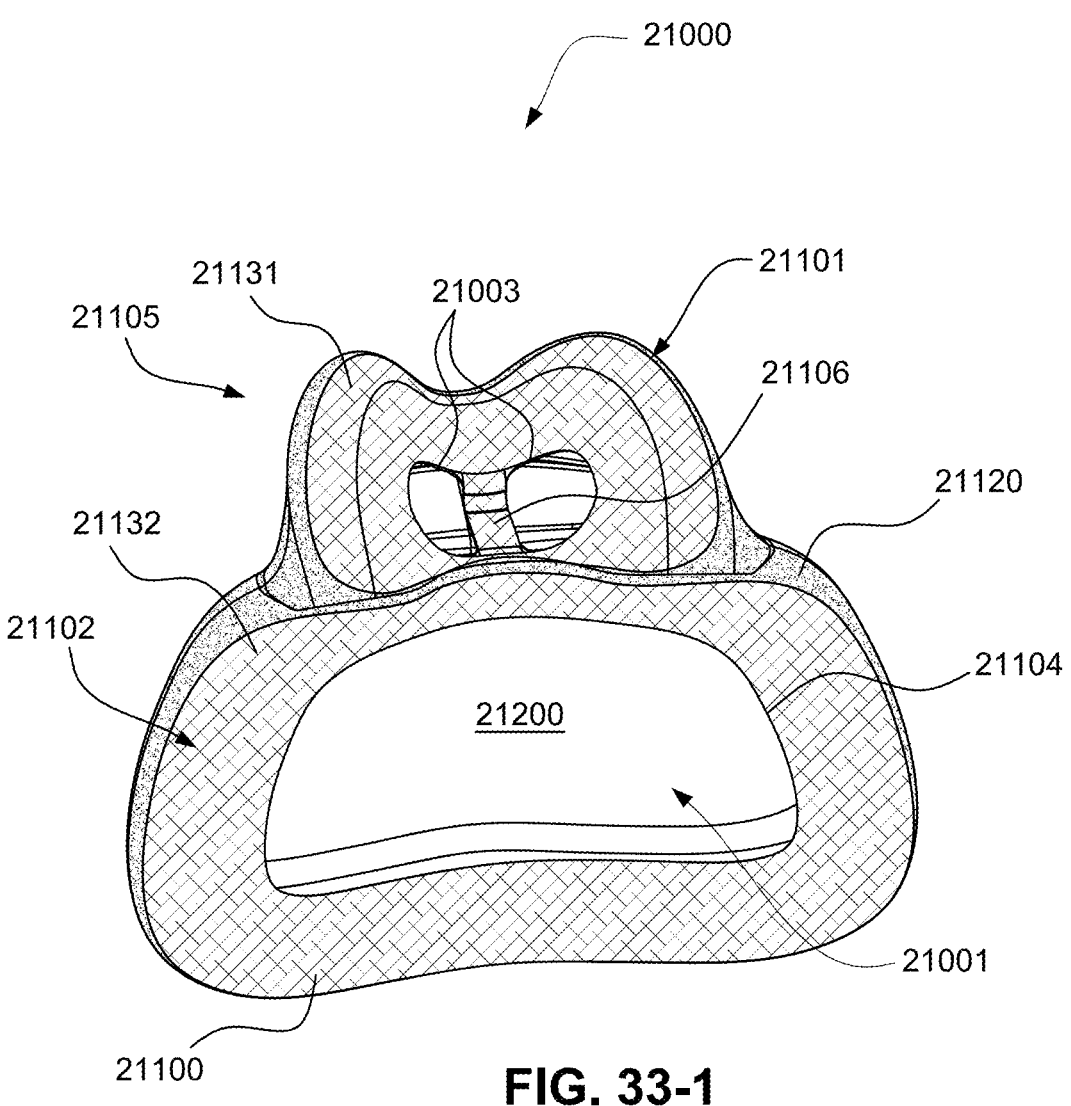
Figures 2, 3, 33:
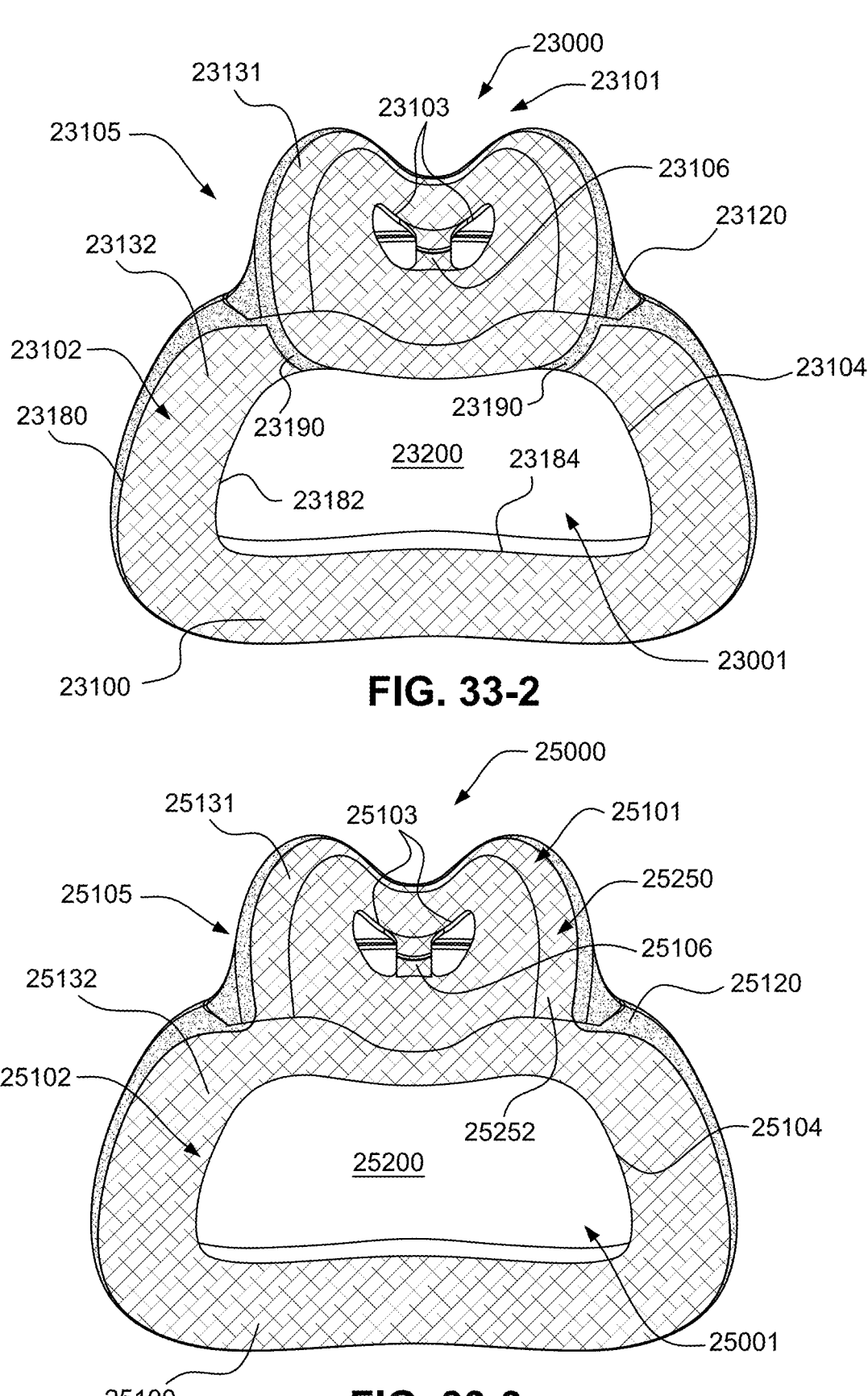
Figures 4, 33:
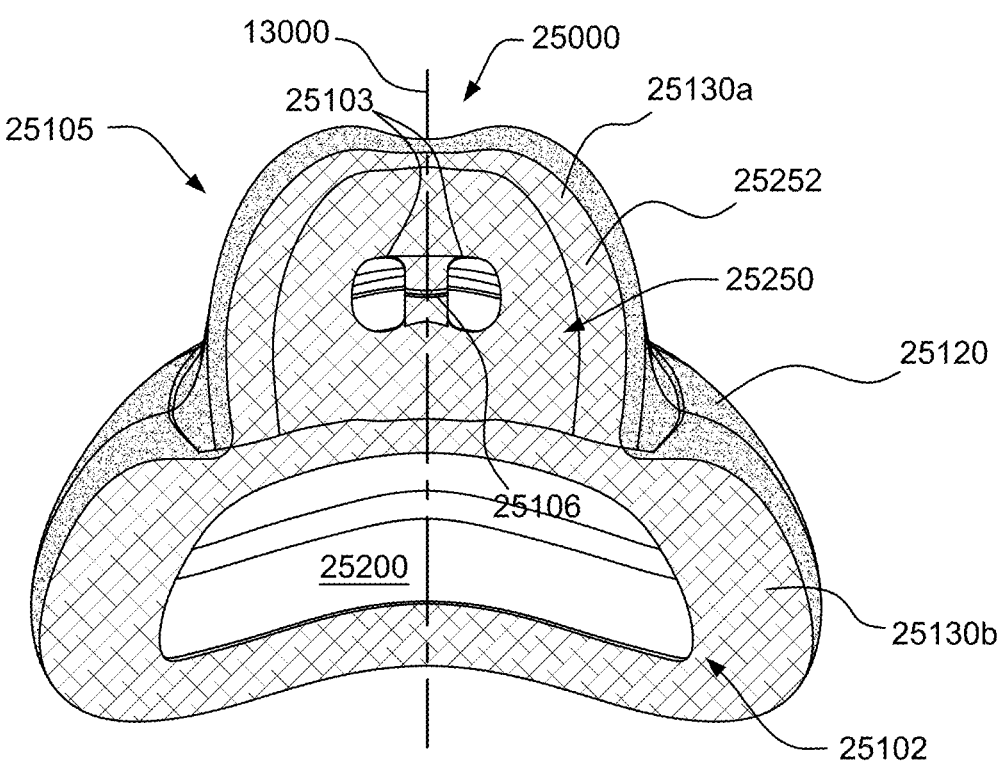
Figures 5, 33:
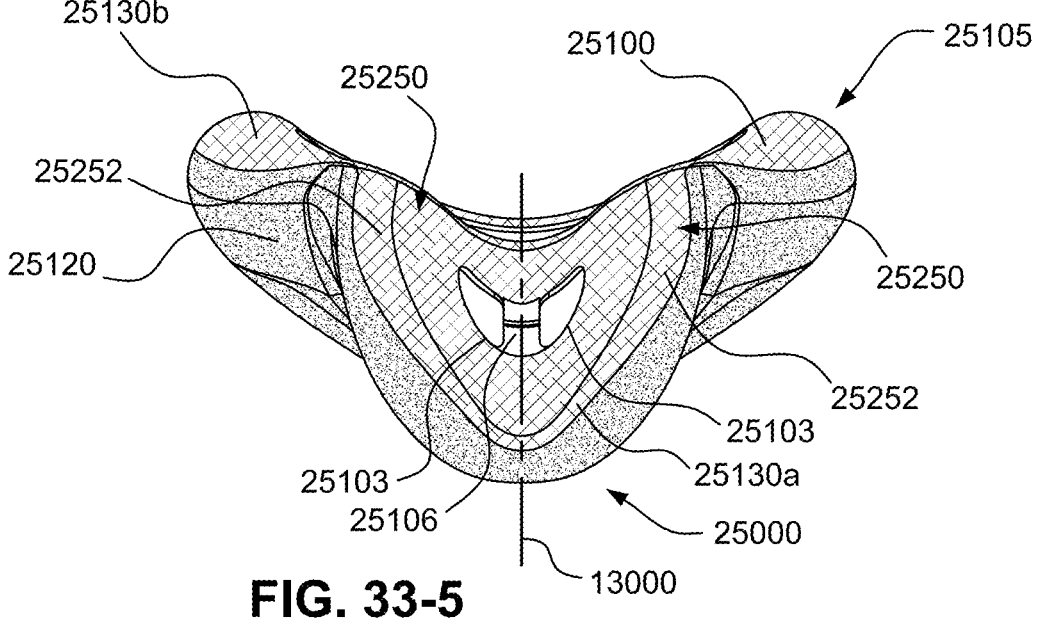
Figures 6, 33:
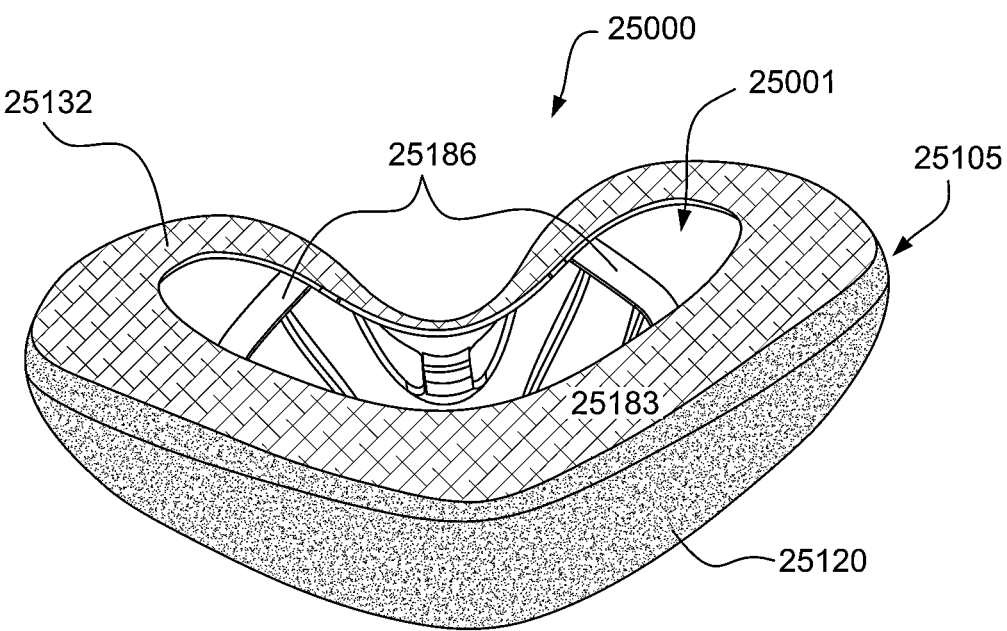
Figures 7, 33:
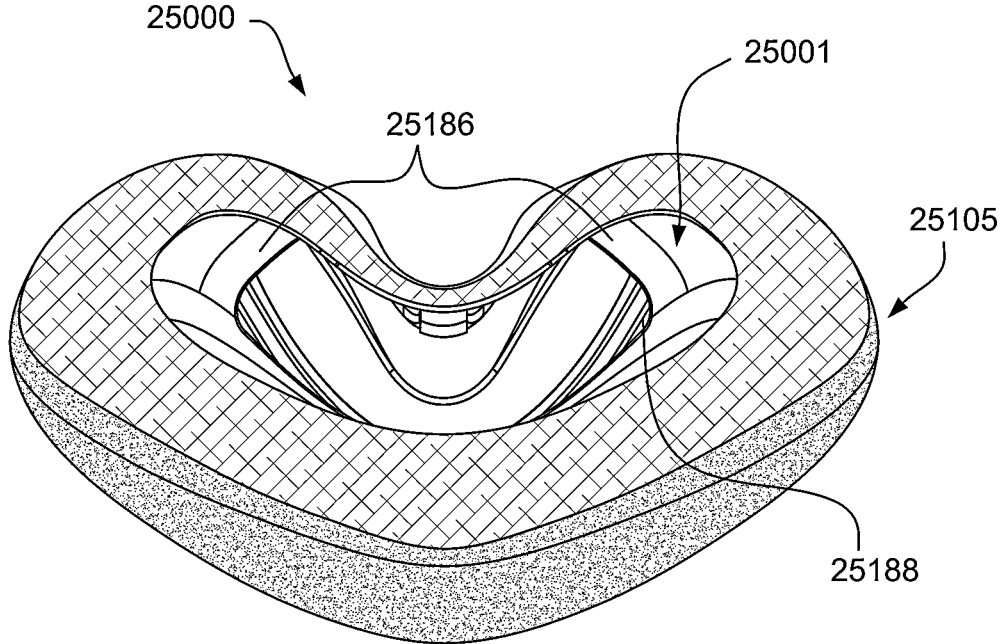
Figures 8, 33:
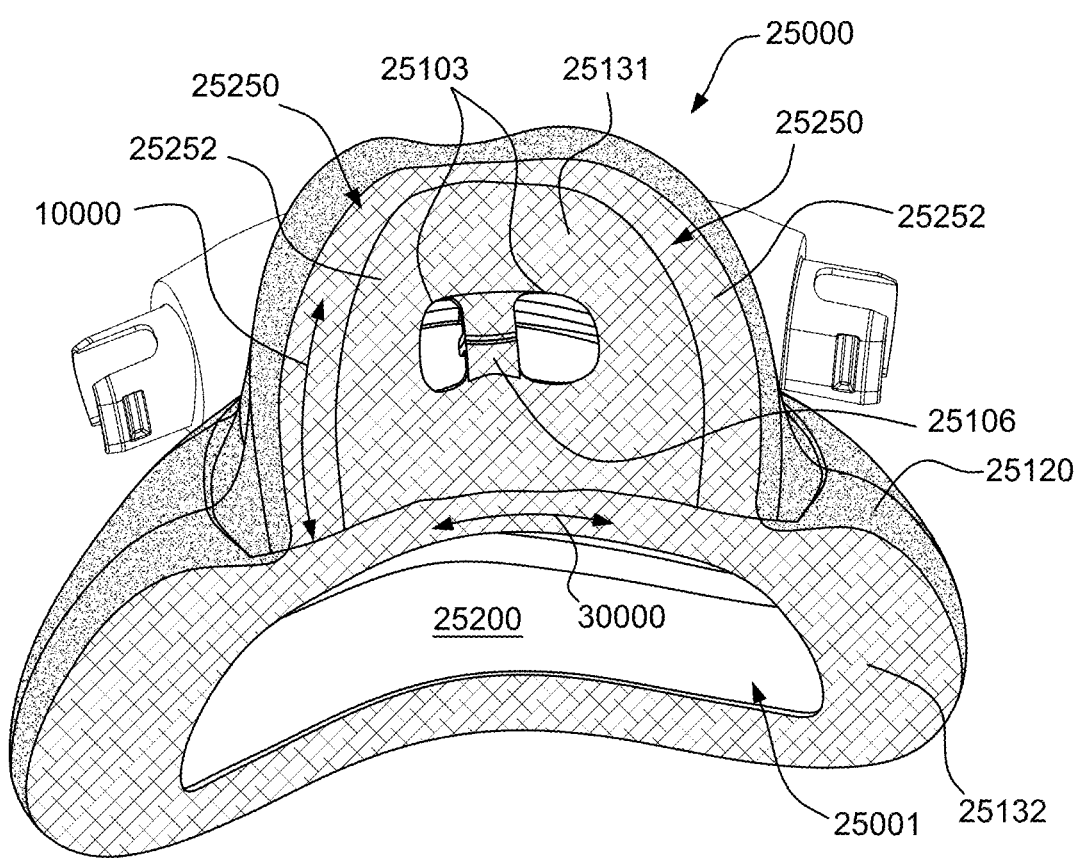

FIG. 8 is a cross-sectional view of the positioning and stabilising structure along the line 8-8 in FIG. 7.

Figures 9, 33:
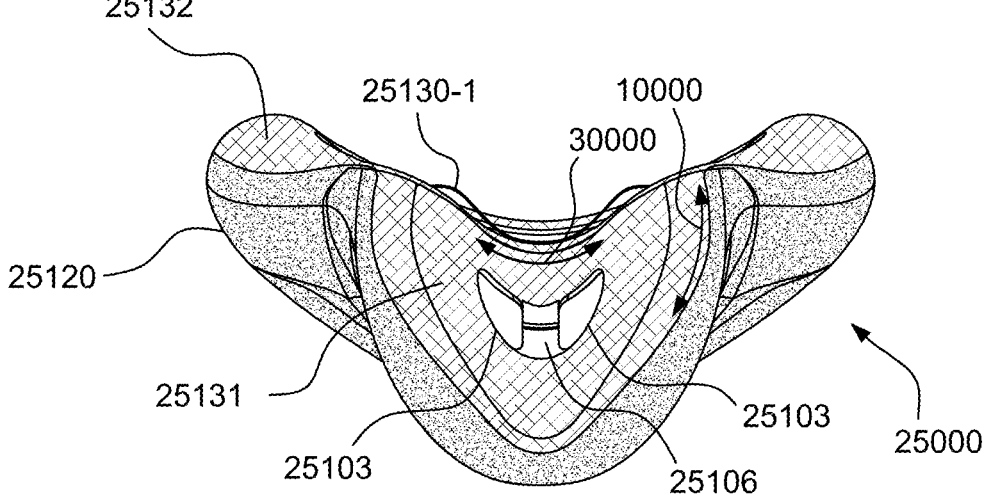

FIG. 9 is an enlarged view of a portion of the positioning and stabilising structure of FIG. 8.

Figures 10, 33:
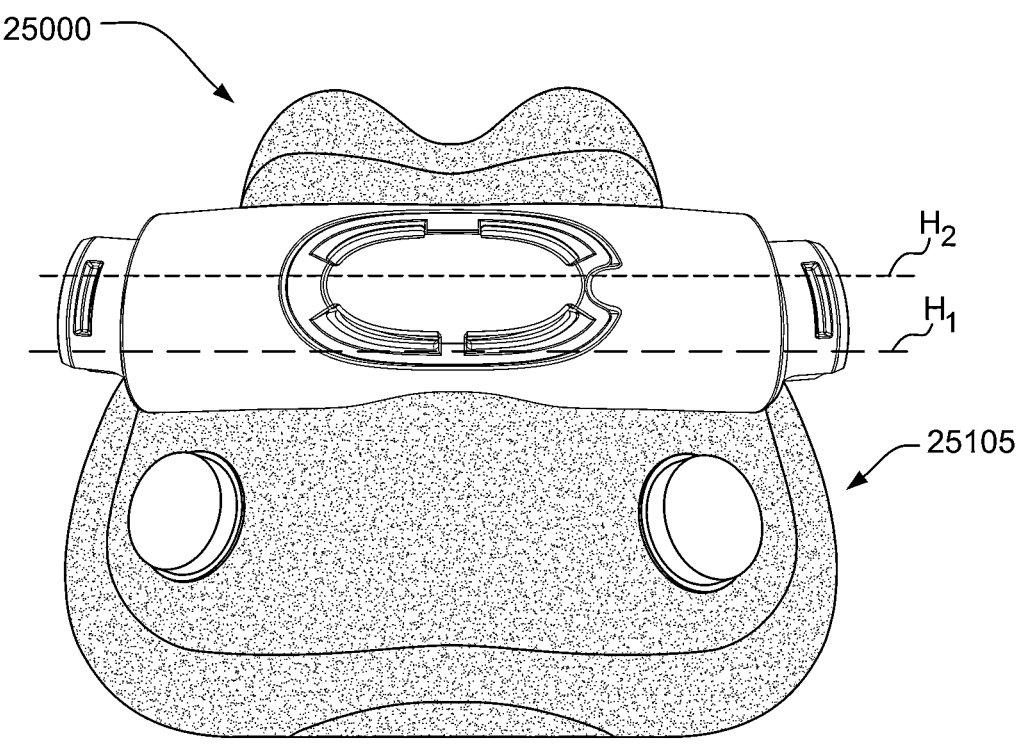
Figures 11, 33:
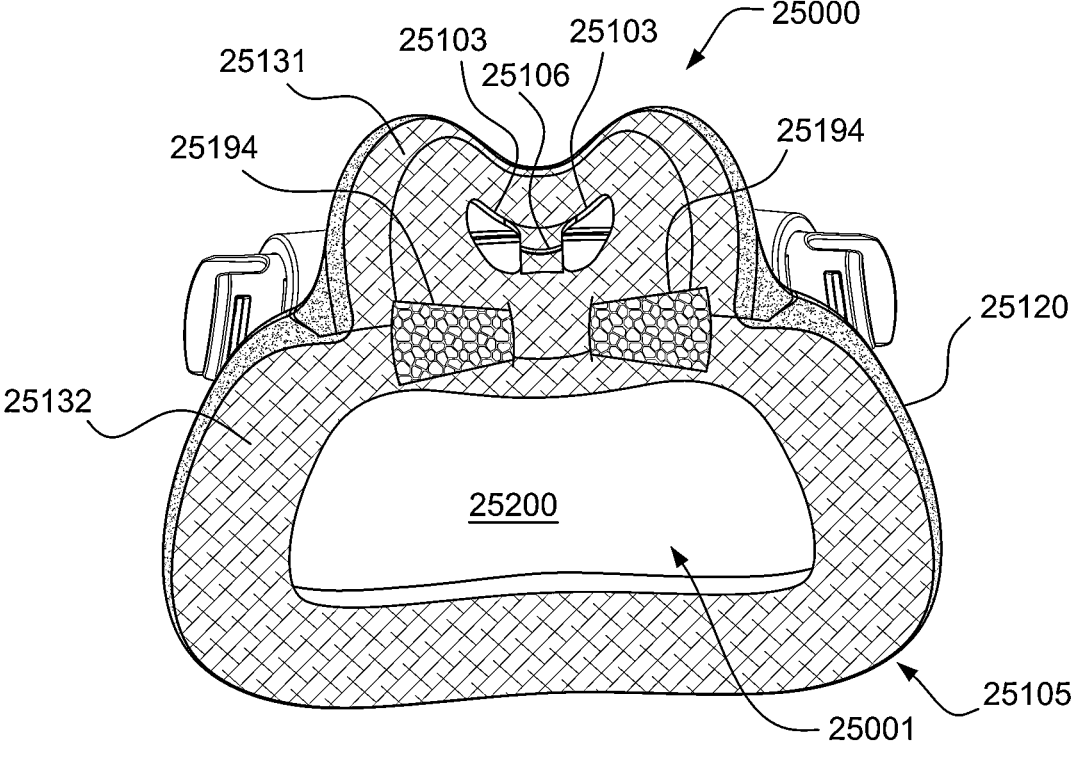

FIG. 10 is an enlarged view of a portion of the positioning and stabilising structure of FIG. 8.

Figure 11:
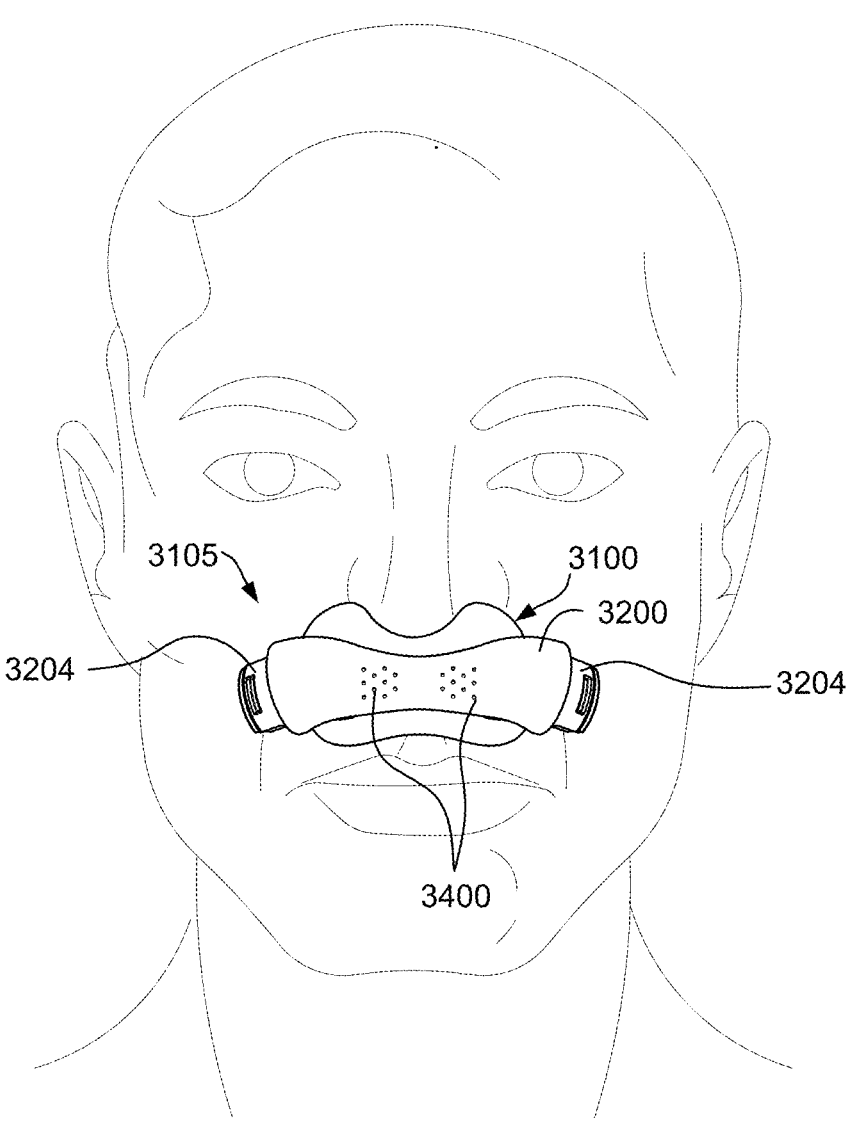

FIG. 11 is a front view of the cushion assembly of FIG. 6 positioned on a patient's face.

Figure 12:
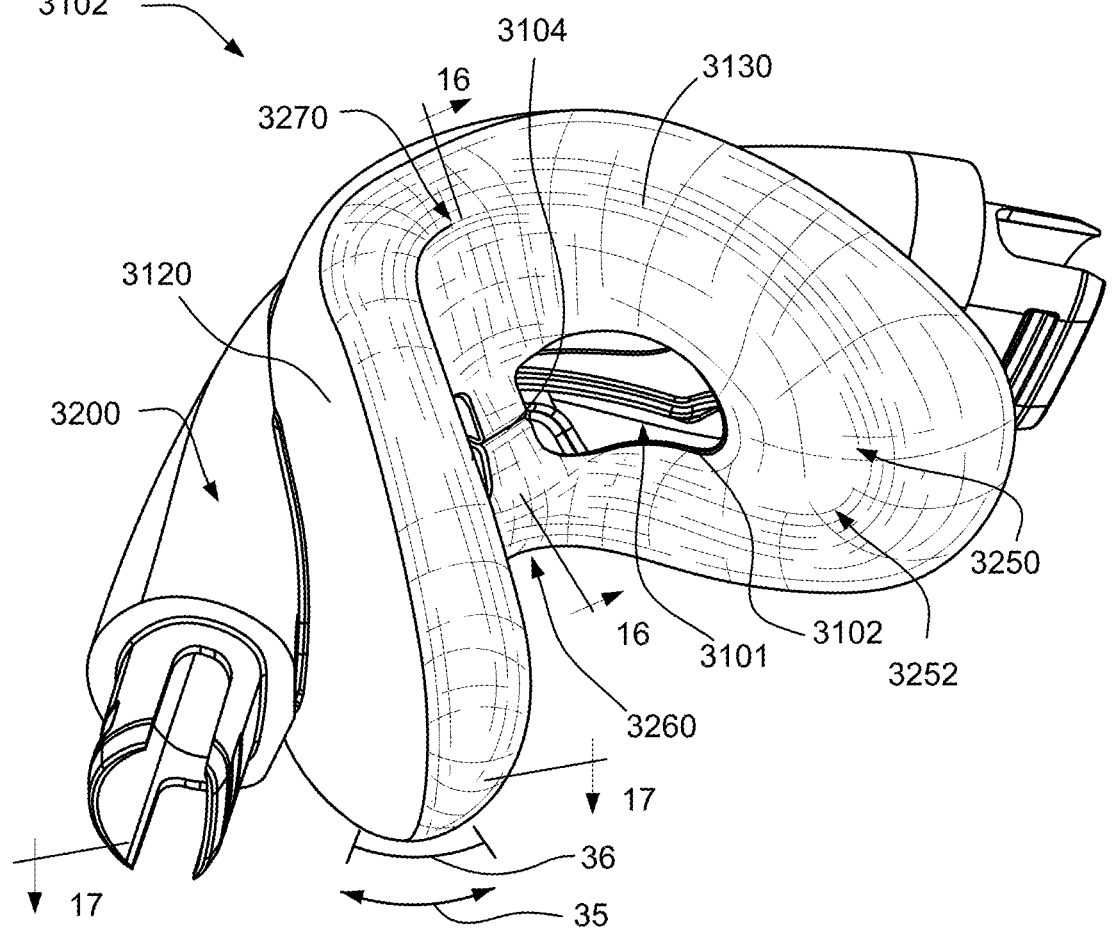

FIG. 12 is a front perspective view of a cushion assembly according to an example of the present technology.

Figure 13:
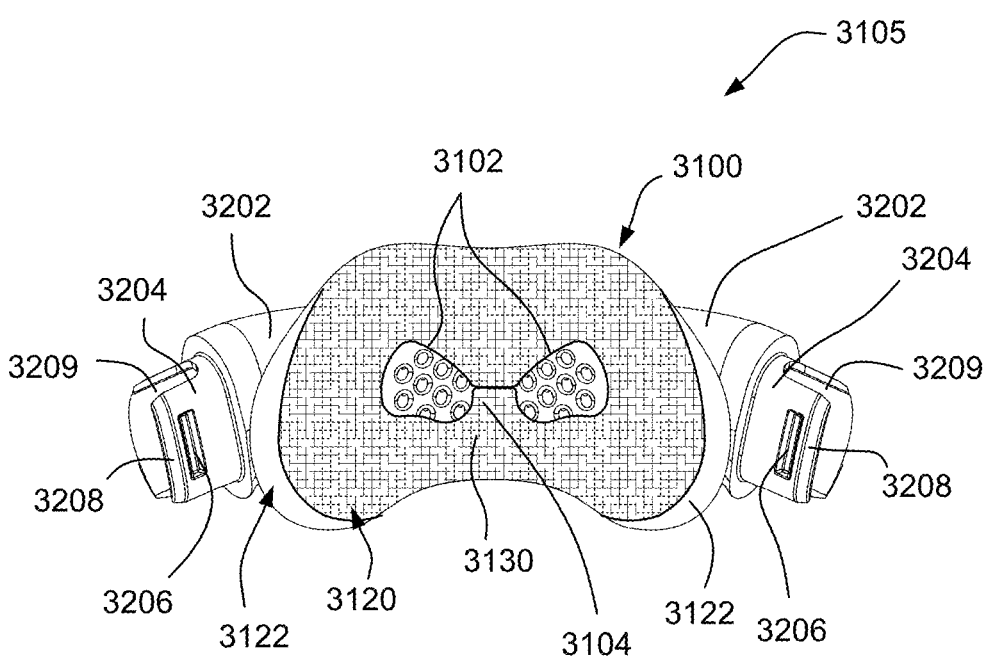

FIG. 13 is a front view of the cushion assembly of FIG. 12.

Figure 14:
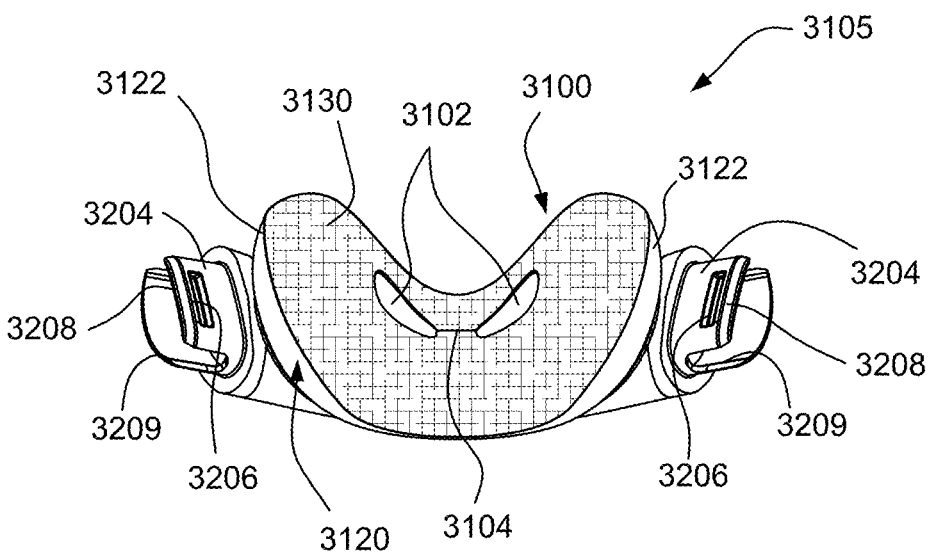

FIG. 14 is a top perspective view of the cushion assembly of FIG. 12.

Figure 15:
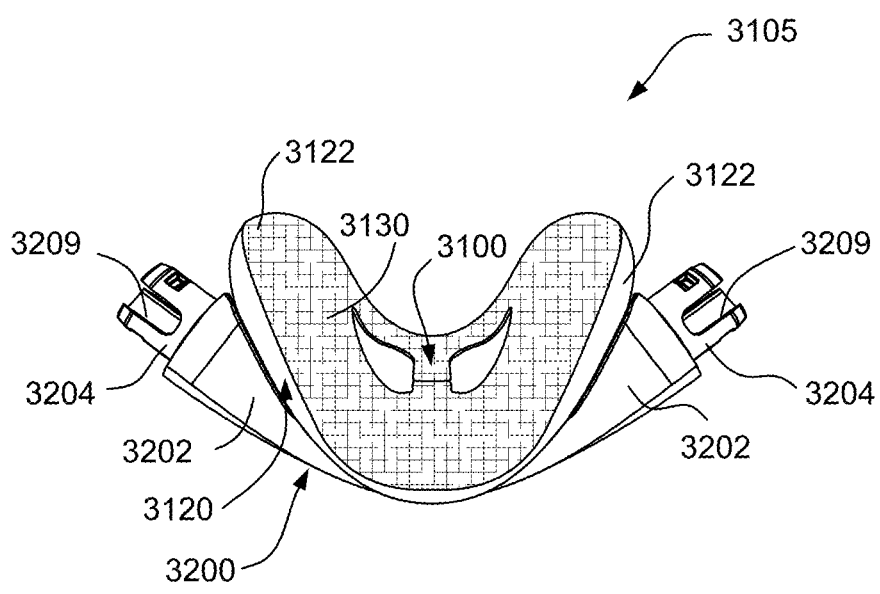

FIG. 15 is a top view of the cushion assembly of FIG. 12.

Figure 16:
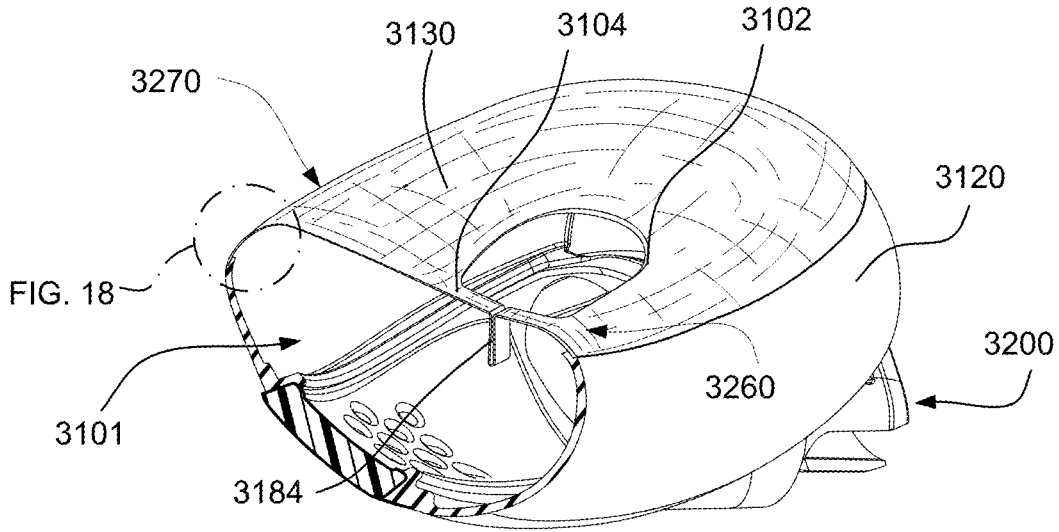

FIG. 16 is a cross-sectional view along the line 16-16 in FIG. 12.

Figure 17:
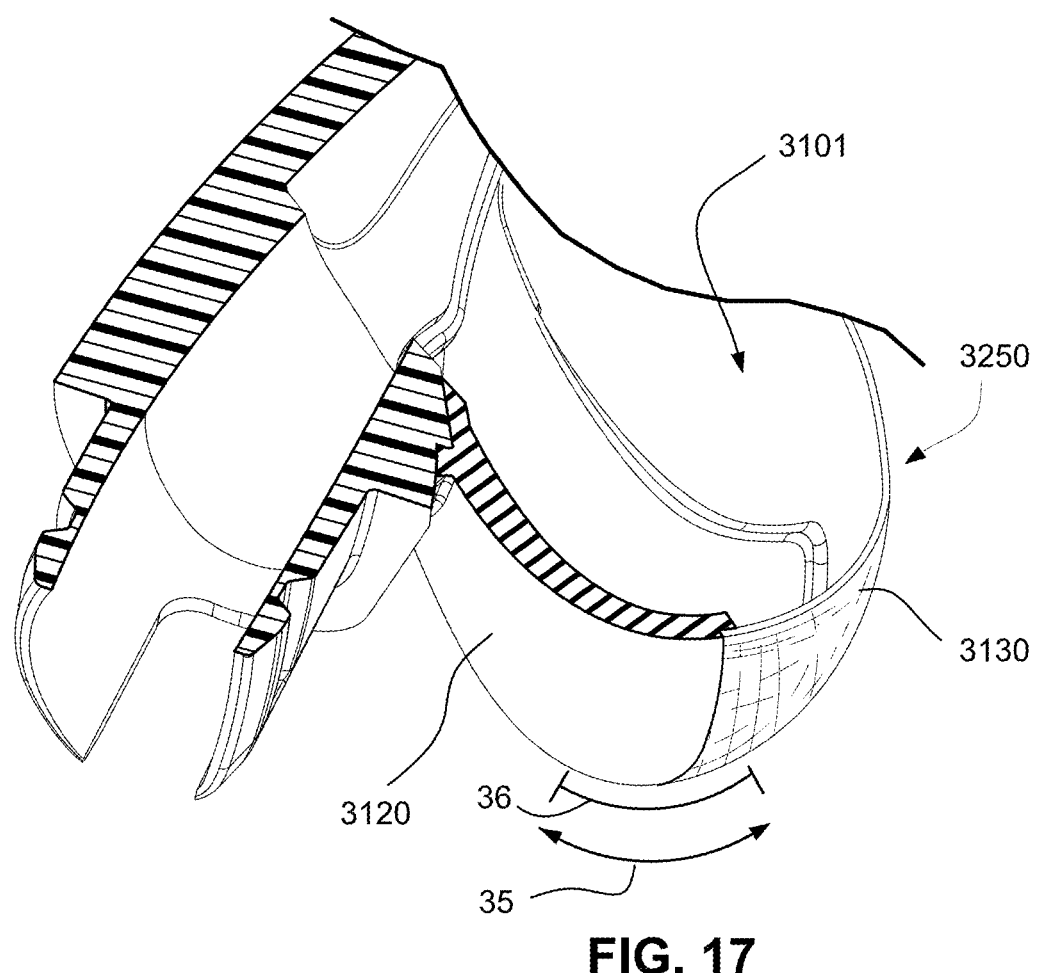

FIG. 17 is a cross-sectional view along the line 17-17 in FIG. 12.

Figure 18:
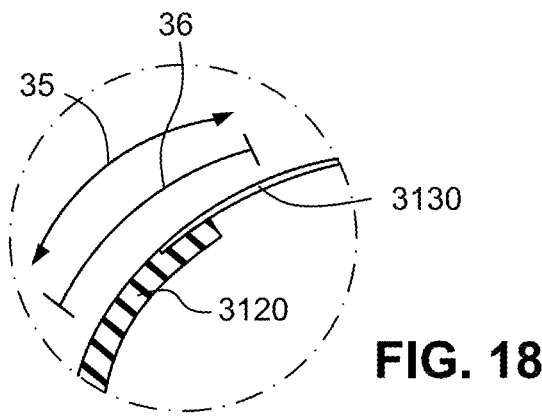

FIG. 18 is an enlarged detail taken from FIG. 16.

Figures 19, 20, 21:
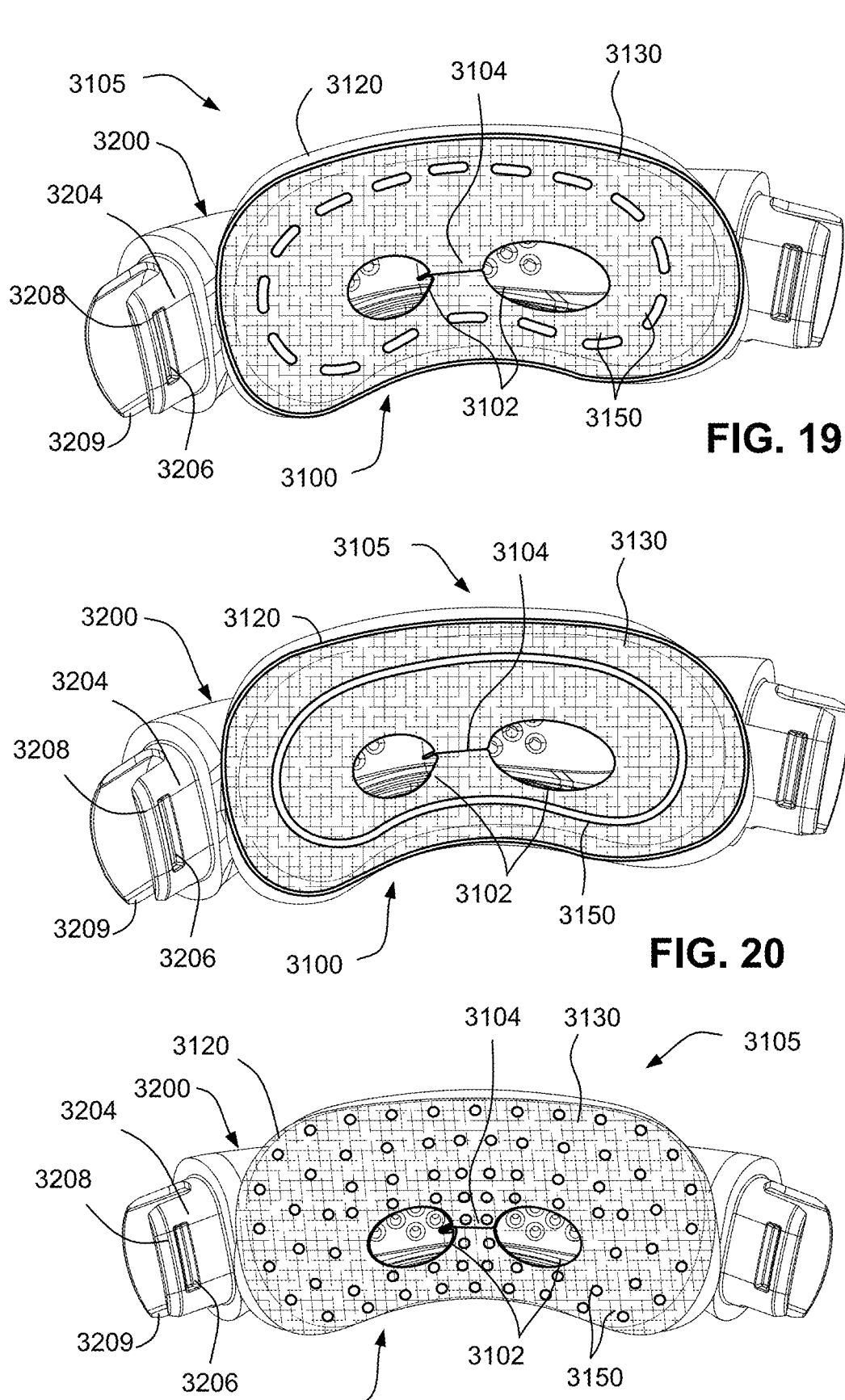

FIGS. 19-21 are front perspective views of cushion assemblies having grip pads disposed on the textile membrane according examples of the present technology.

Figure 22:
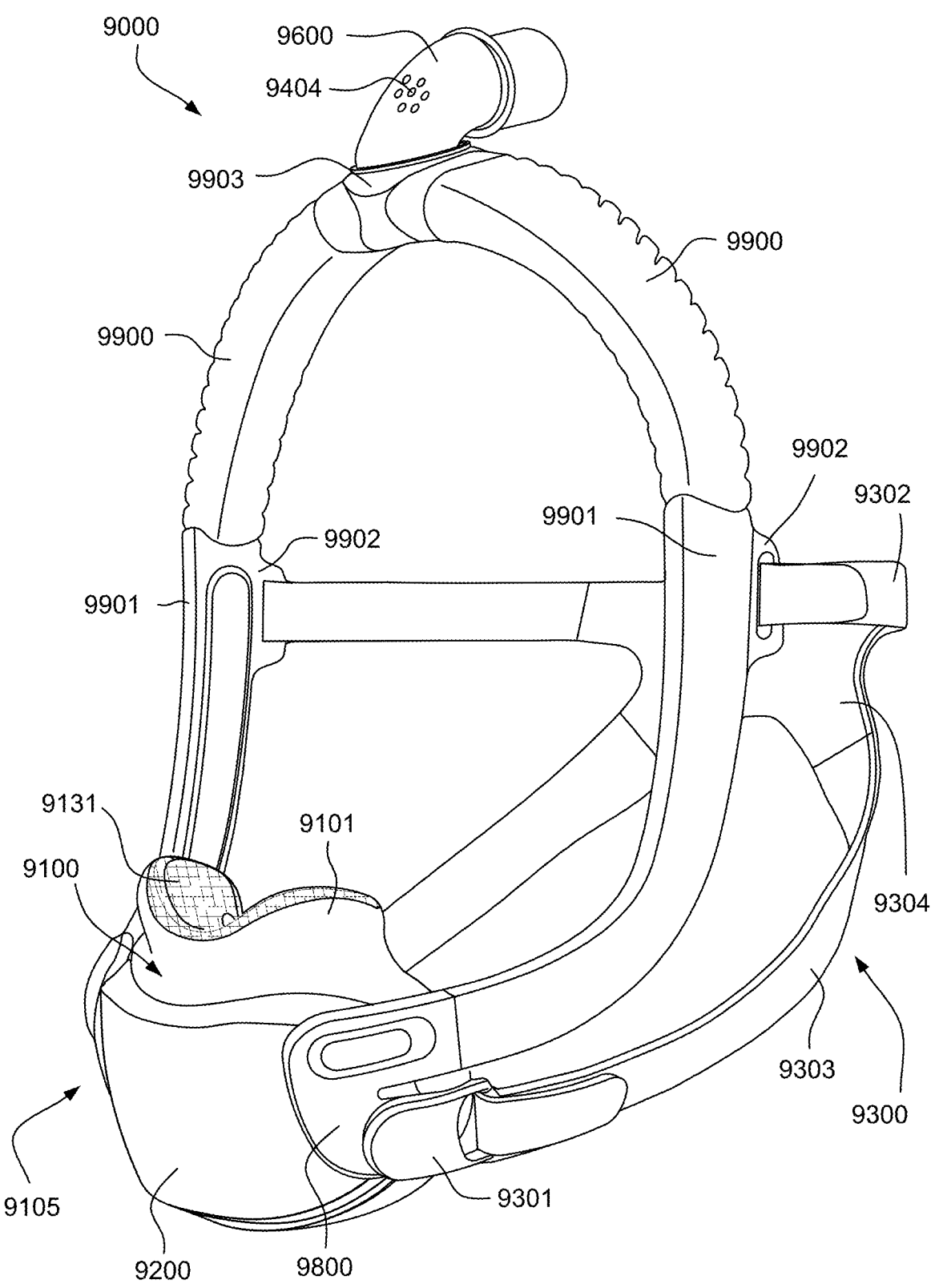

FIG. 22 is a perspective view of a patient interface according to another example of the present technology.

Figure 23:
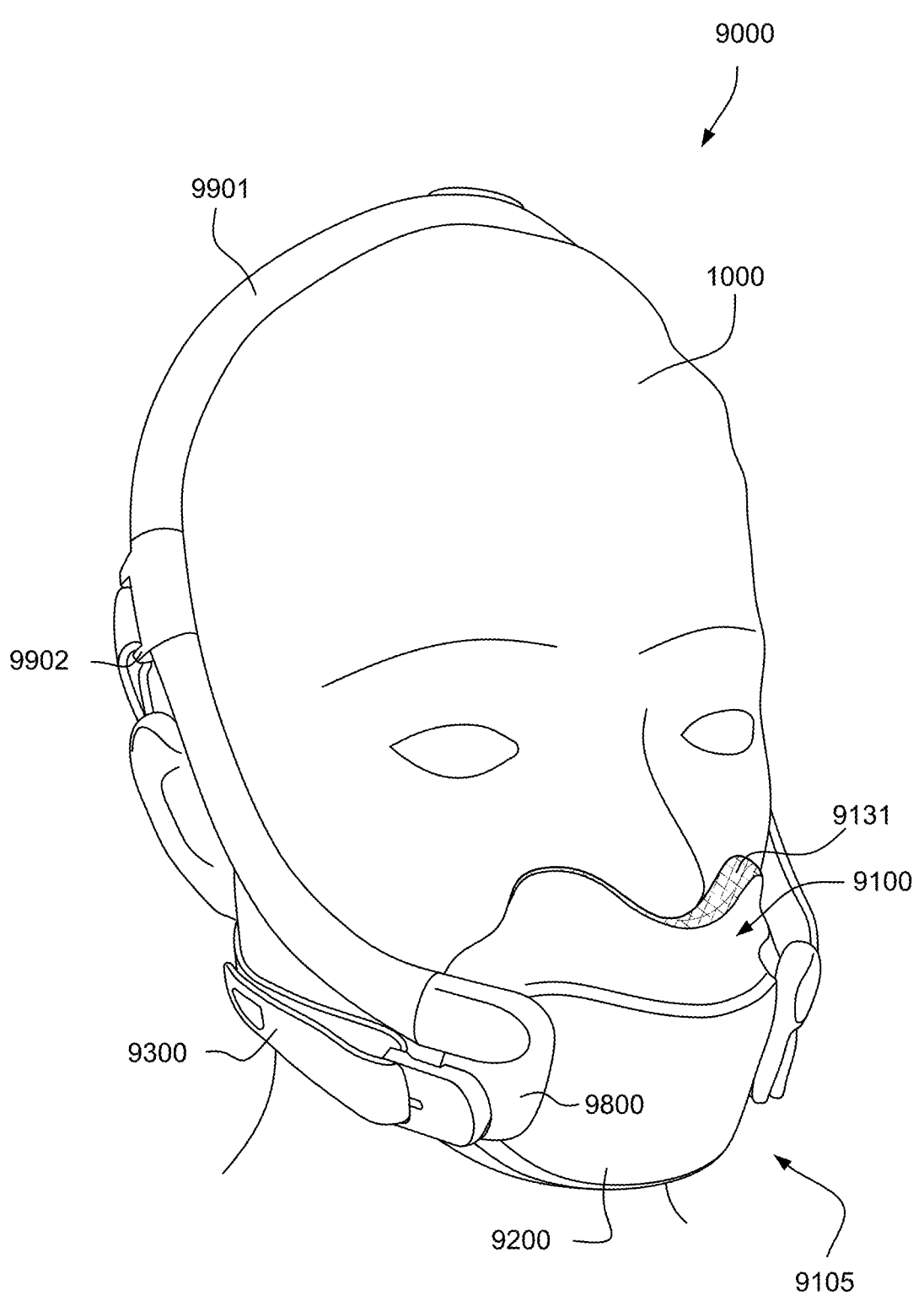

FIG. 23 is a perspective view of the patient interface of FIG. 22 worn by a patient.

Figure 24:
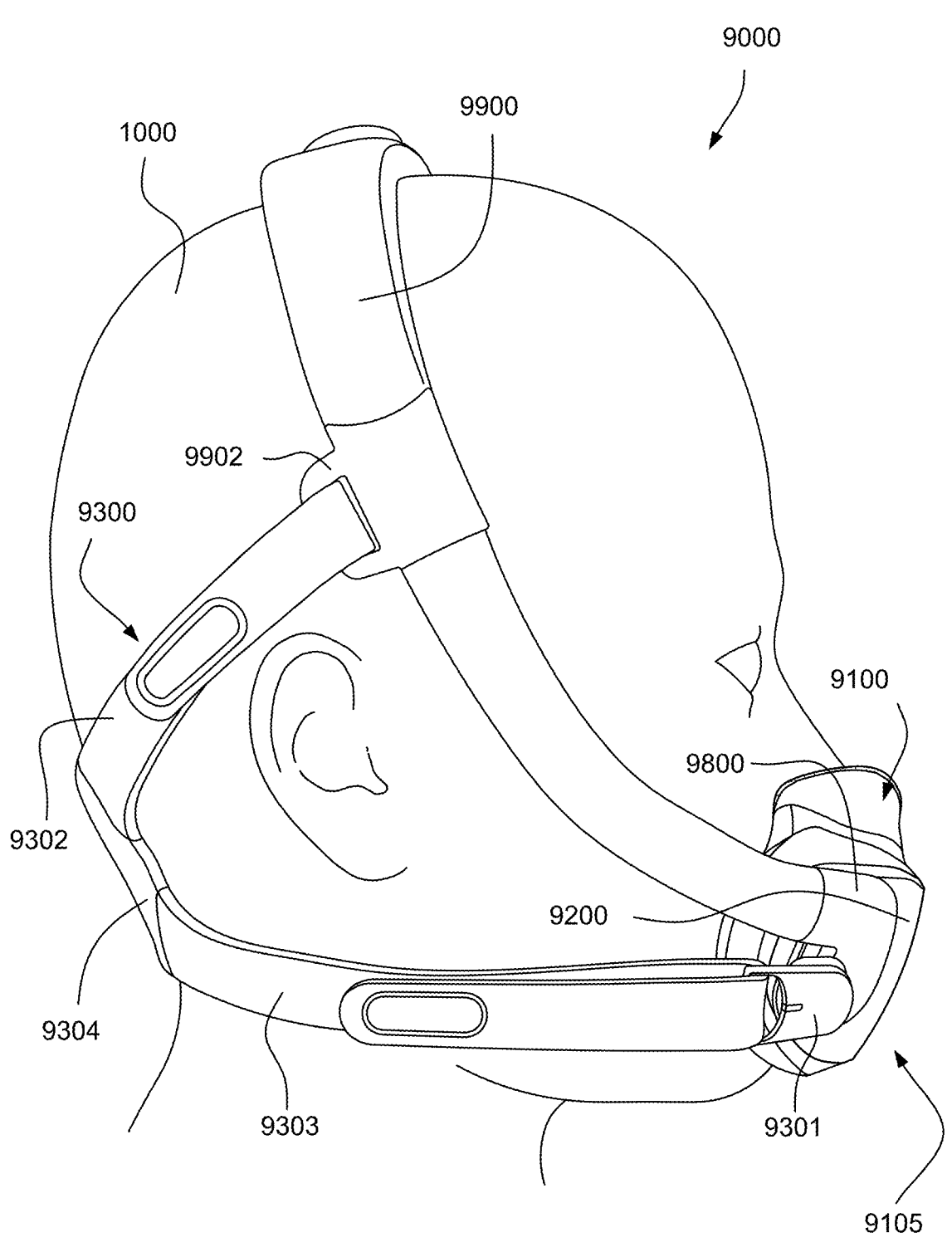

FIG. 24 is a side view of the patient interface of FIG. 23.

Figure 25:
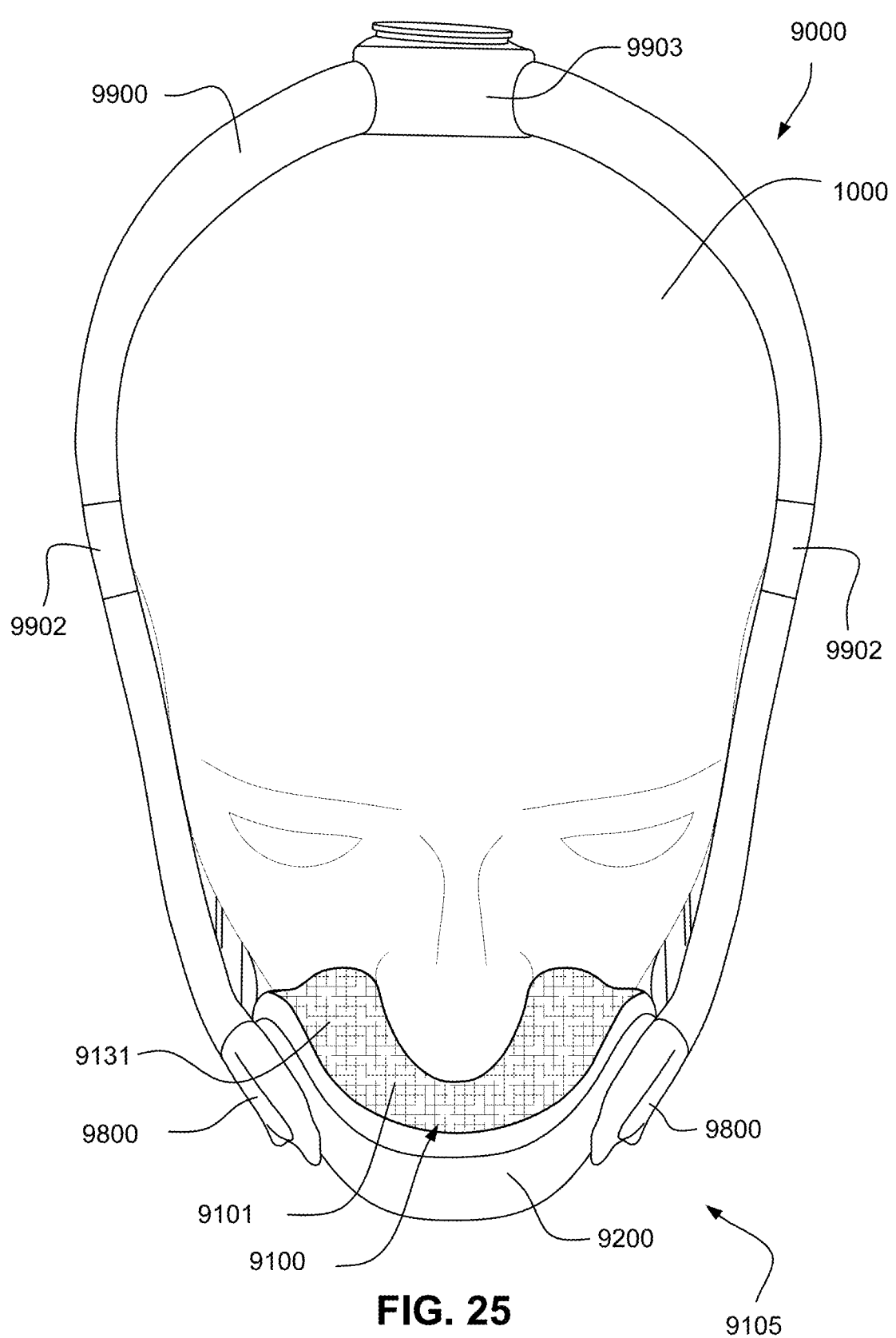

FIG. 25 is a front perspective view of the patient interface of FIG. 23.

Figure 26:
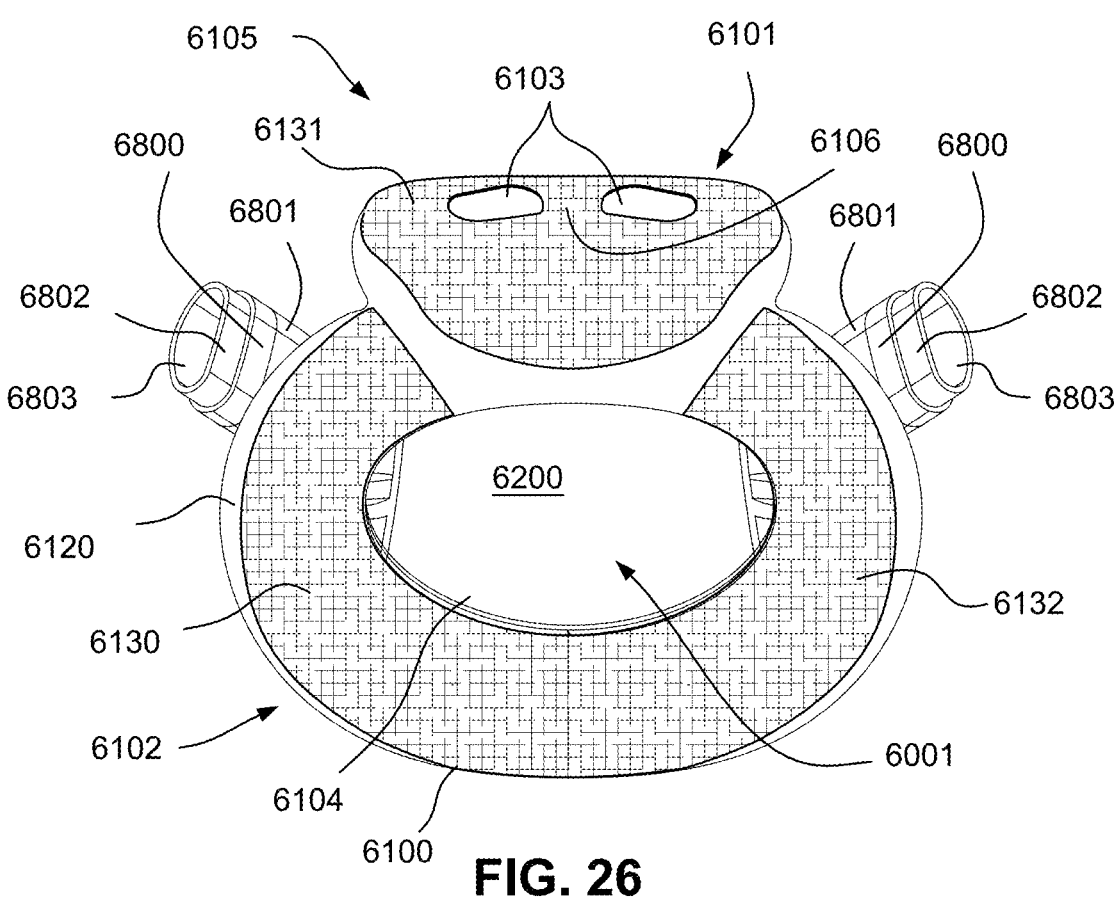

FIG. 26 is a front view of a cushion assembly of a patient interface in accordance to an example of the present technology.

Figure 27:
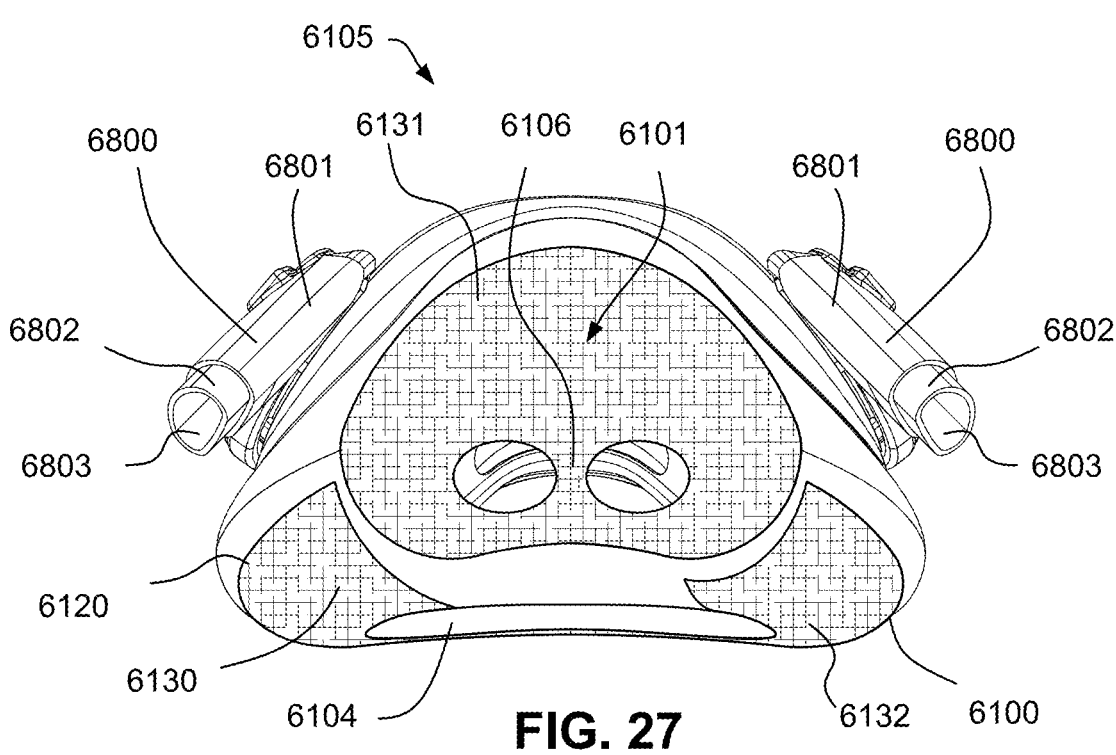

FIG. 27 is a top view of the cushion assembly of FIG. 26.

Figure 28:
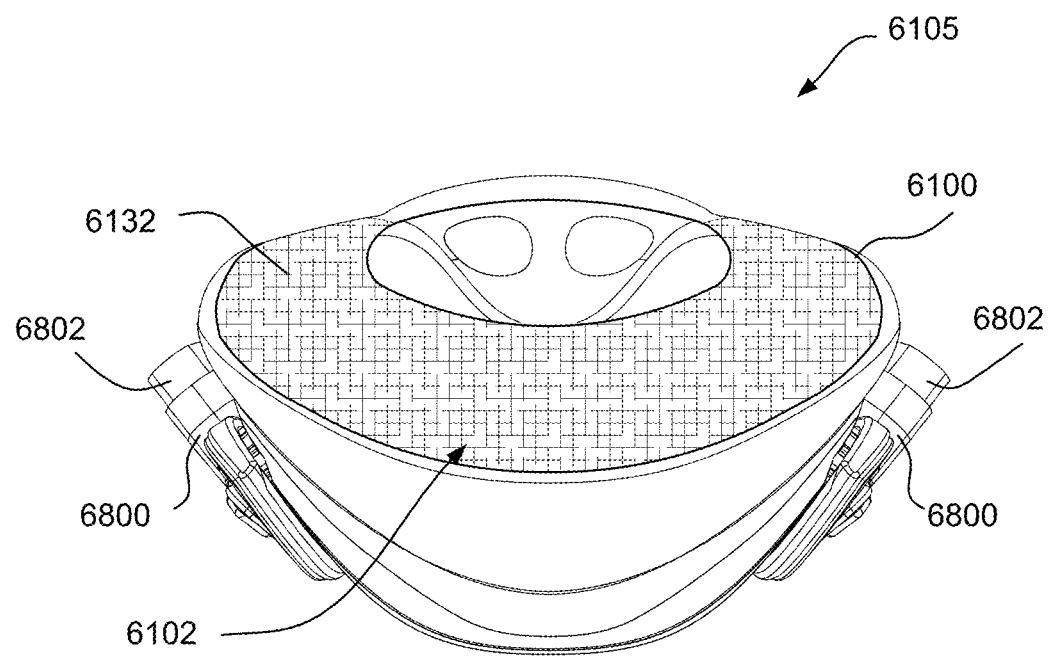

FIG. 28 is a bottom view of the cushion assembly of FIG. 26.

Figure 29:
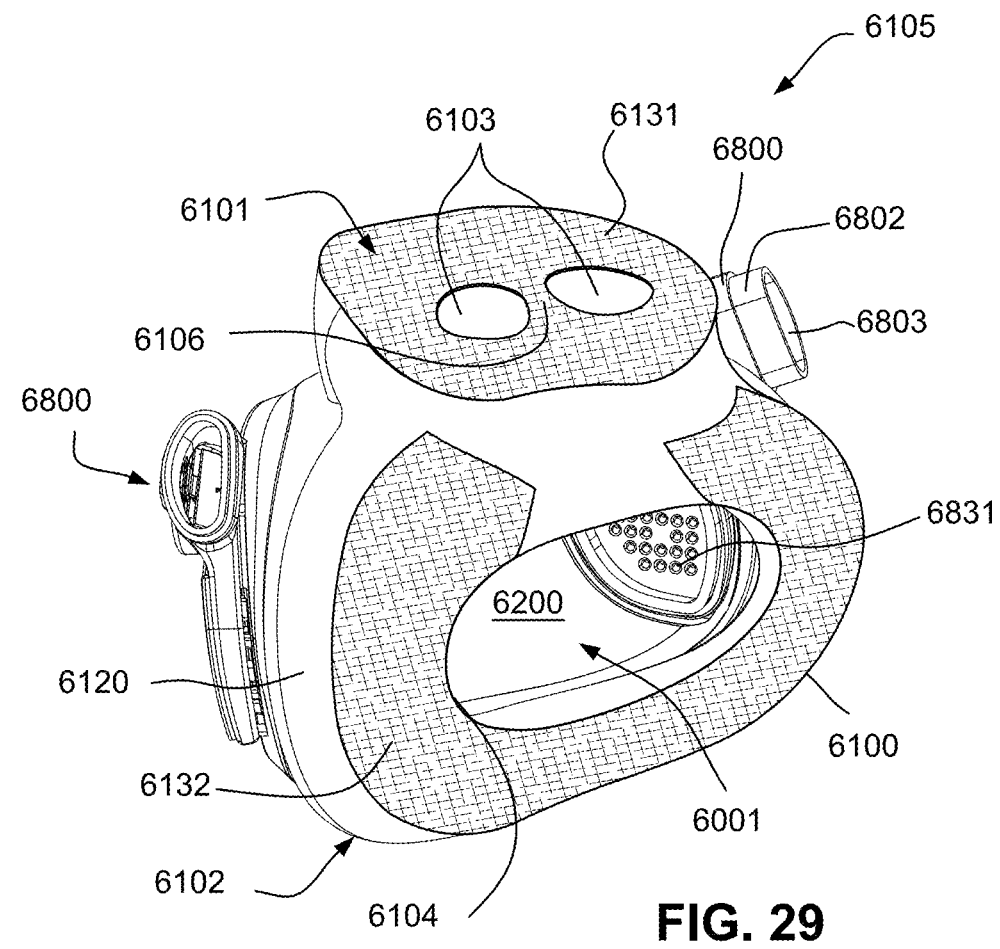

FIG. 29 is a front perspective view of the cushion assembly of FIG. 26.

Figure 30:
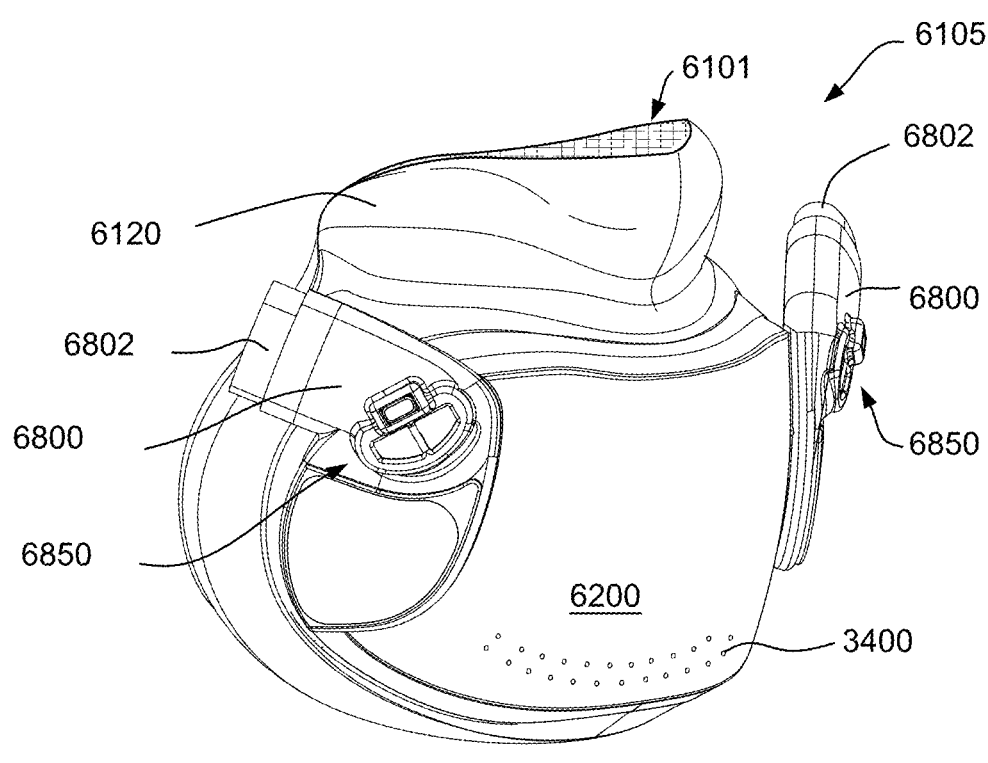

FIG. 30 is a rear perspective view of the cushion assembly of FIG. 26.

Figure 31:
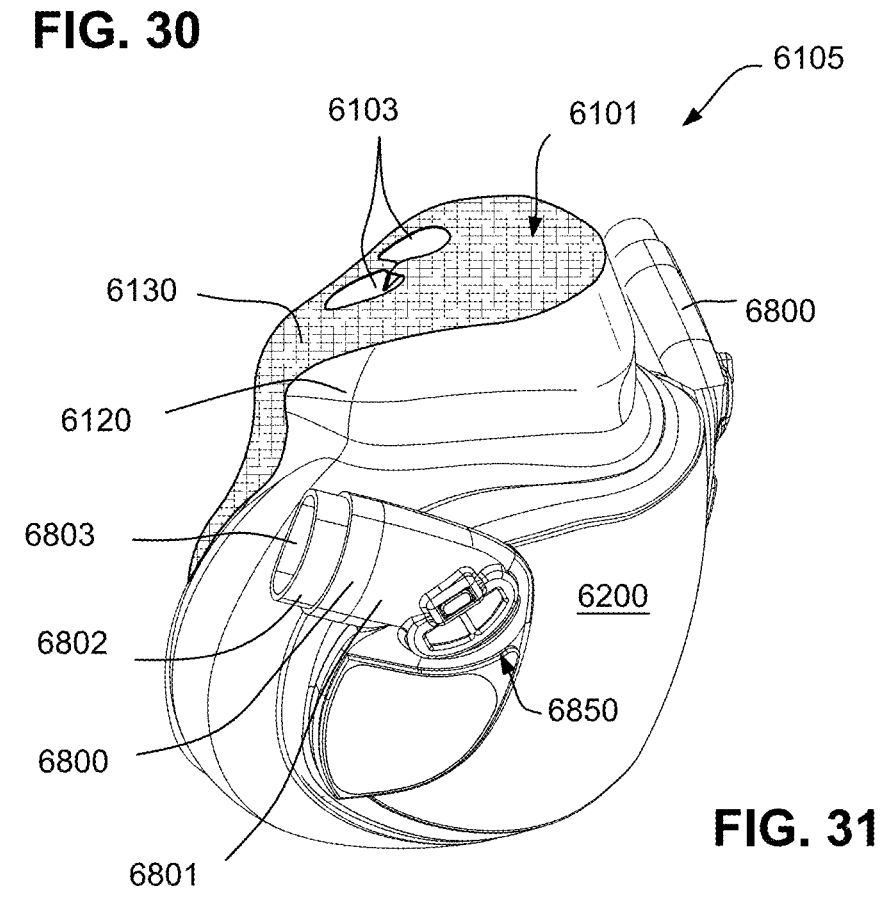

FIG. 31 is a side perspective view of the cushion assembly of FIG. 26.

Figure 32:
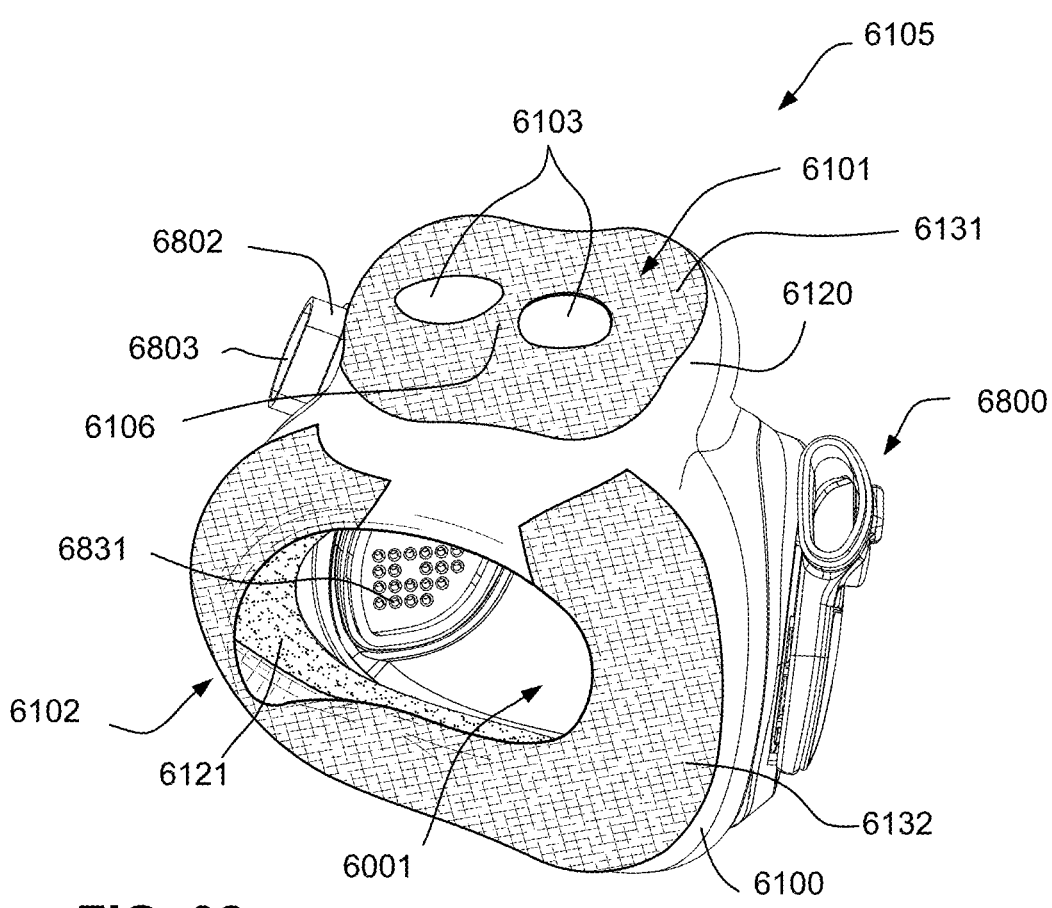

FIG. 32 is a front perspective view of the cushion assembly of FIG. 26 showing an interior portion of the cushion assembly.

FIG. 33 is a front view of the cushion assembly of FIG. 26 showing an interior portion of the cushion assembly.

FIG. 33-1 is a rear perspective view of a cushion assembly according to an example of the present technology.

FIG. 33-2 is a rear perspective view of a cushion assembly according to an example of the present technology.

FIG. 33-3 is a rear perspective view of a cushion assembly according to an example of the present technology, where a sealing portion is constructed from a single piece of textile material.

FIG. 33-4 is a rear perspective view of the cushion assembly of FIG. 33-3, illustrating a more positively domed curvature of the sealing portion at a location configured to contact the patient's lip superior.

FIG. 33-5 is a top view of the cushion assembly of FIG. 33-4.

FIG. 33-6 is a side perspective view of the cushion assembly of FIG. 33-3, illustrating support ribs.

FIG. 33-7 is a side perspective view of the cushion assembly of FIG. 33-3, illustrating larger support ribs as compared to FIG. 33-6.

FIG. 33-8 is a rear perspective view of the cushion assembly of FIG. 33-3 having a thicker corner of nose region in order to provide a narrower space to receive a patient's nose.

FIG. 33-9 is a top view of the cushion assembly of FIG. 33-8.

FIG. 33-10 is a front view of the cushion assembly of FIG. 33-3, illustrating raising a conduit connector portion as compared to the patient interface of FIG. 24.

FIG. 33-11 is a rear perspective view of the cushion assembly of FIG. 33-3, illustrating foam inserts configured to contact a patient's corner of nose region.

Figure 34:
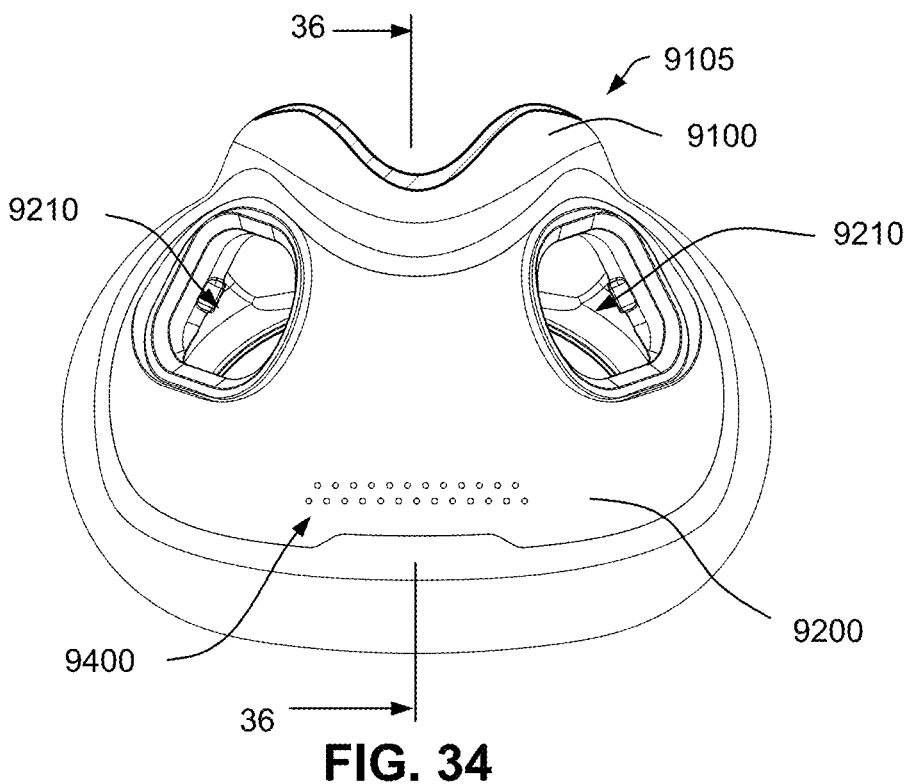

FIG. 34 is a rear view of a cushion assembly used with the patient interface of FIG. 22.

Figure 35:
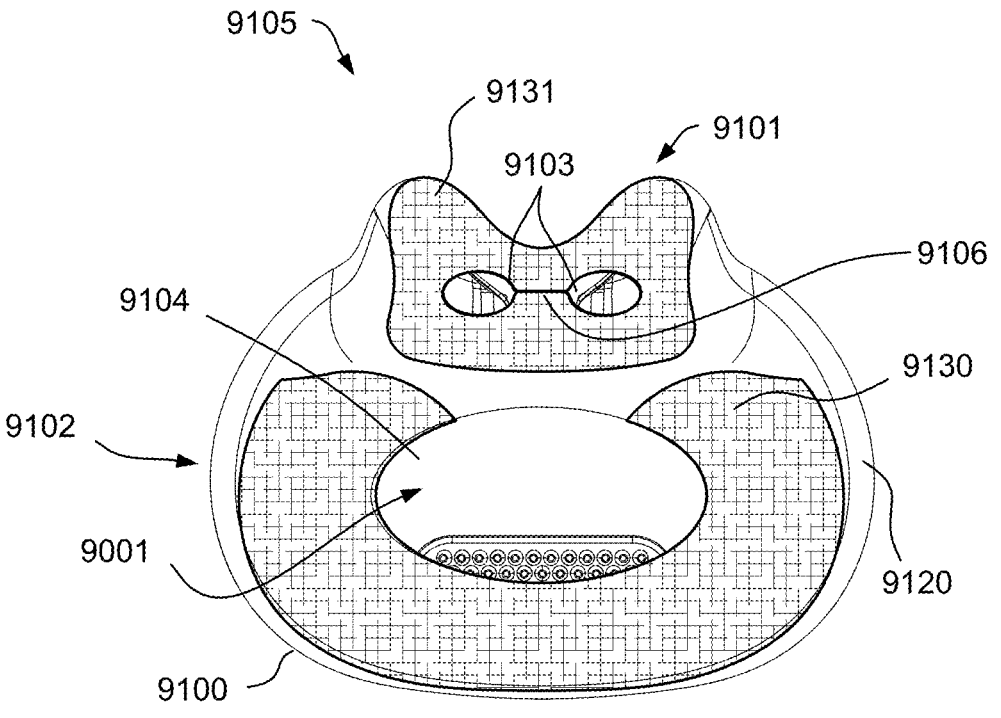

FIG. 35 is a front view of the cushion assembly of FIG. 34.

Figure 36:
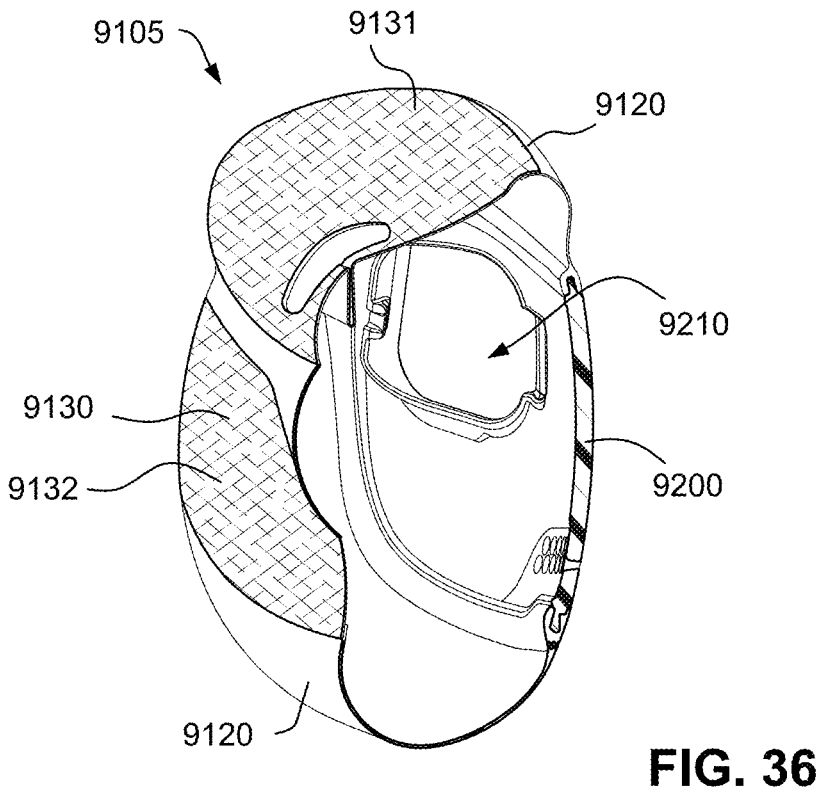

FIG. 36 is a cross-sectional view of the cushion assembly of FIG. 34, viewed along line 36-36.

Figure 37:
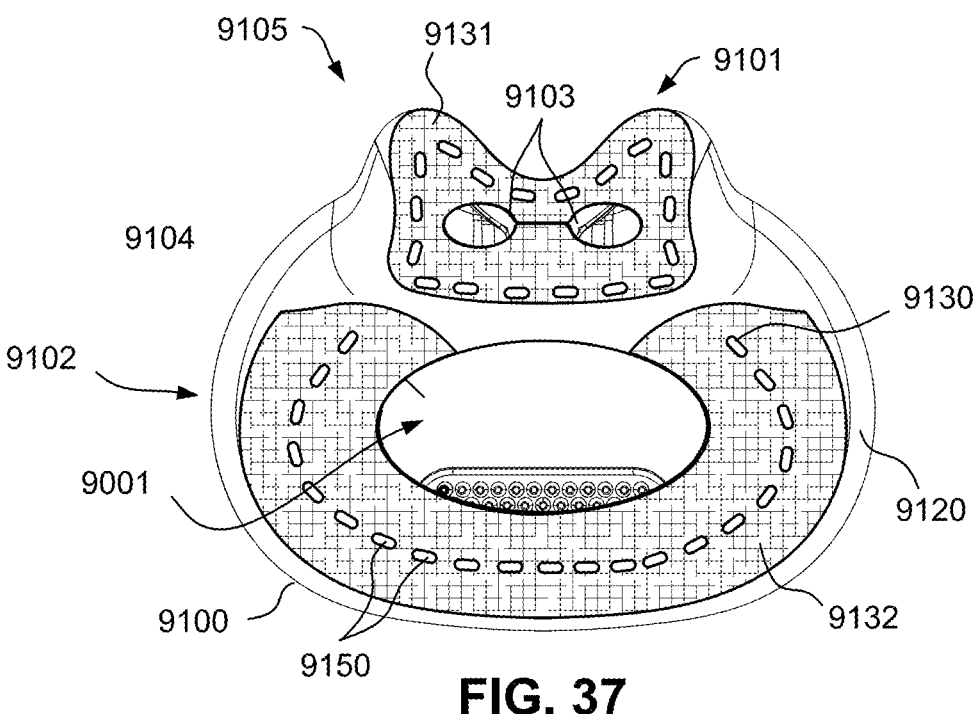
Figure 38:
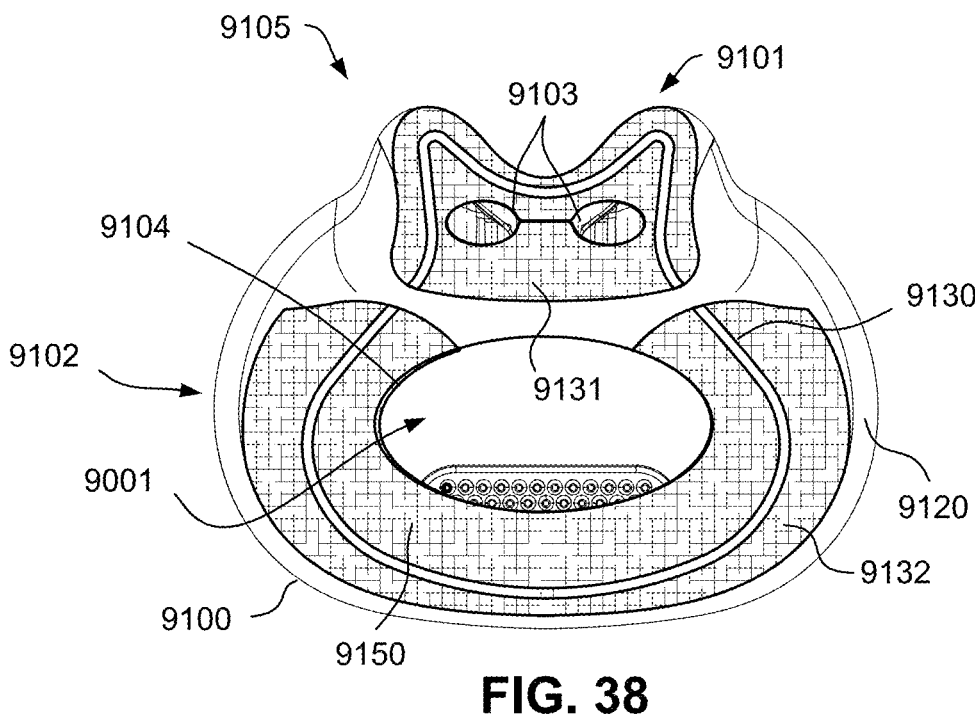
Figure 39:
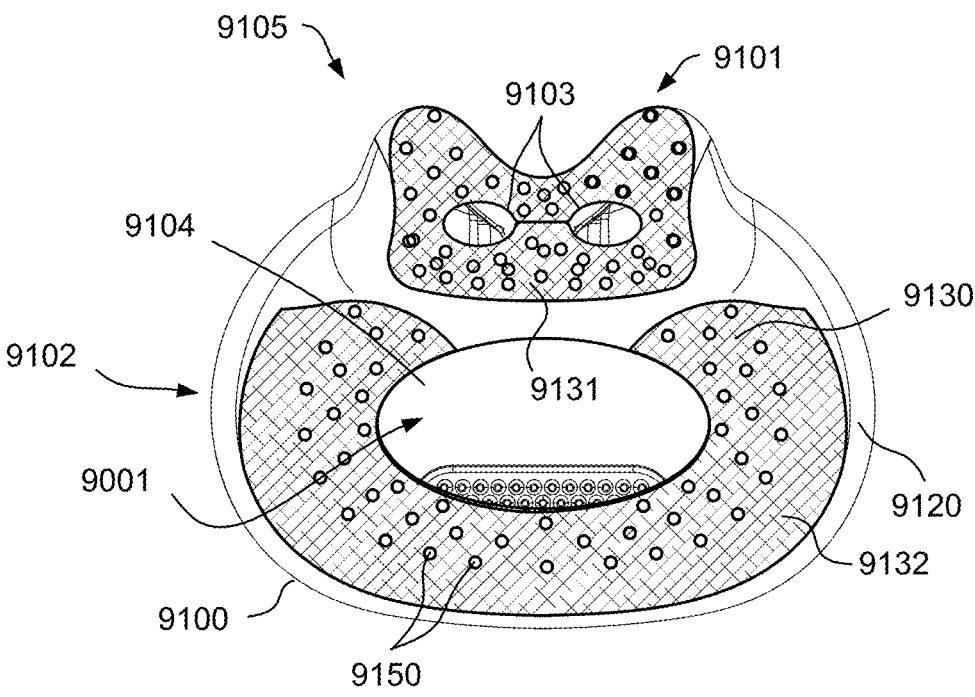

FIGS. 37-39 are front perspective views of cushion assemblies having grip pads disposed on the textile membrane according examples of the present technology.

Figure 40:
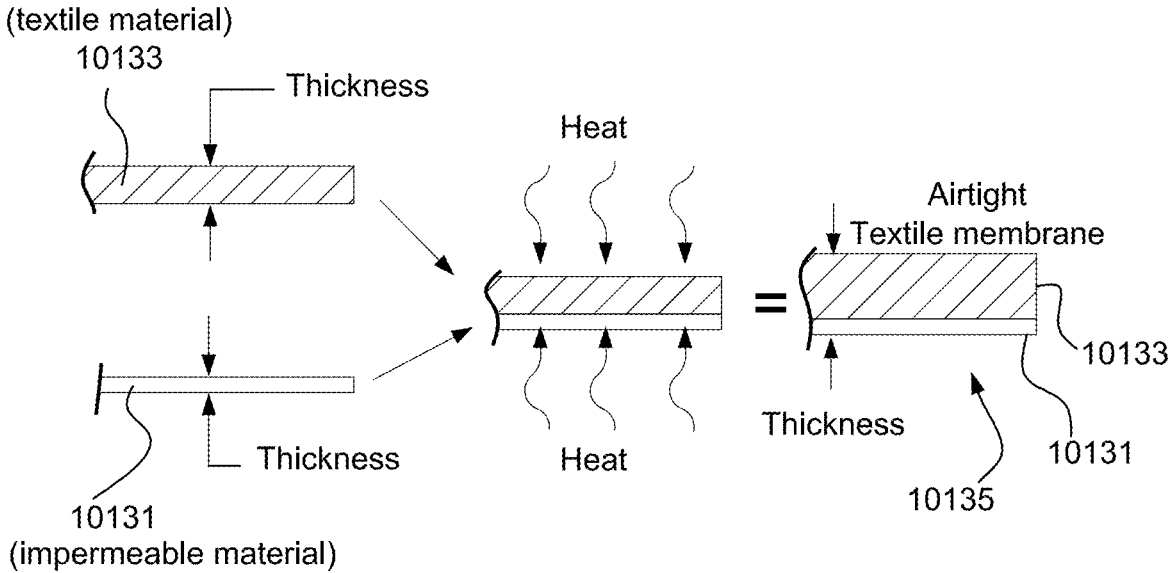
Figures 1, 40:
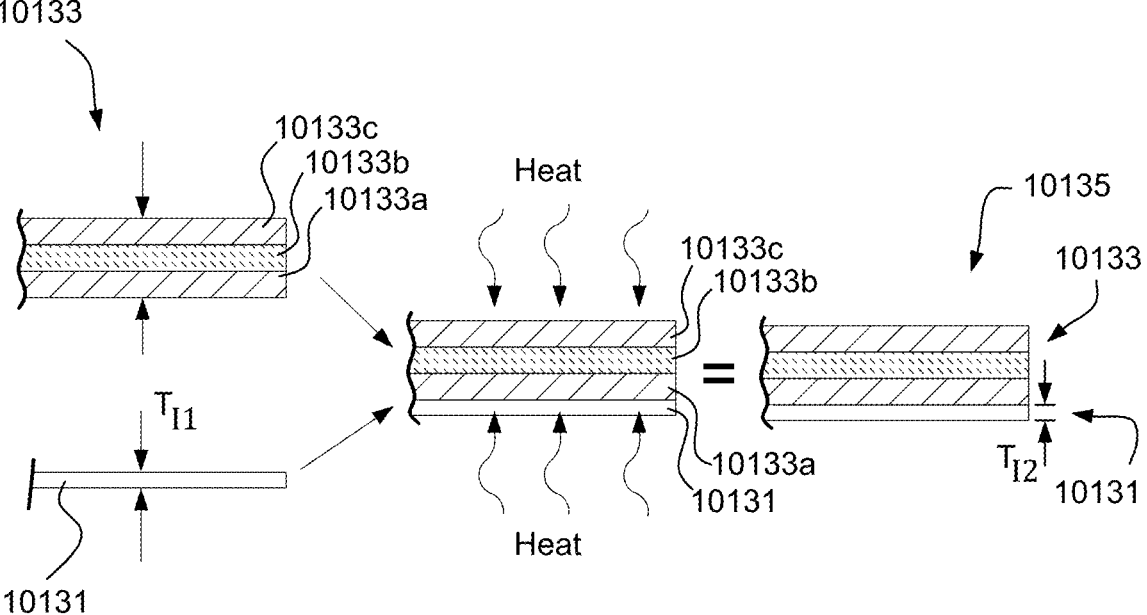

FIG. 40 is a schematic illustration of a process of providing an air impermeable layer to a textile material according to an example of the present technology.

FIG. 40-1 is a schematic illustration a process of providing an air impermeable layer to a textile material according to another example of the present technology.

Figure 41:
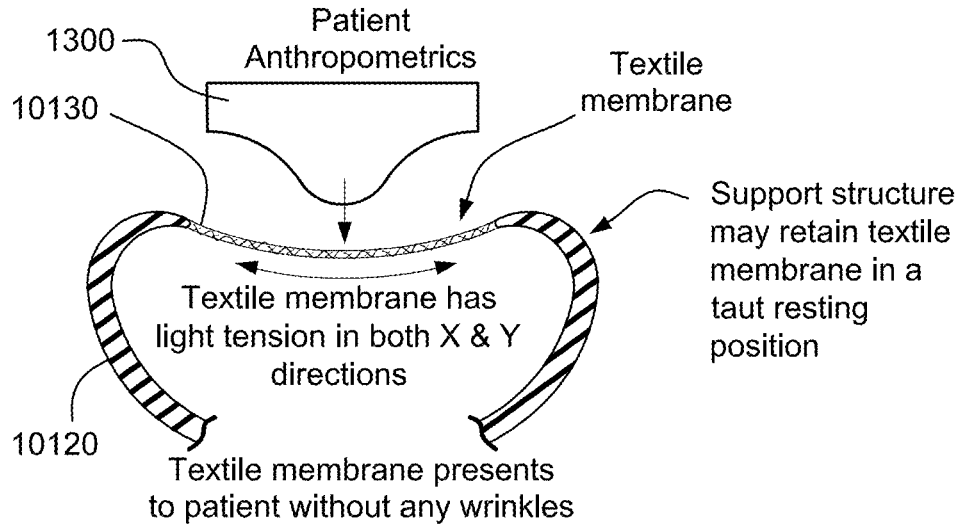

FIG. 41 is a schematic illustration depicting a patient's face being presented to a textile membrane in light tension prior to use.

FIG. 42 is a schematic illustration showing a resulting force exerted by the textile membrane on the patient's face due to tensile stress in the textile membrane.

FIG. 43 is a schematic illustration of tension forces exerted on the sealing portion of a cushion assembly according to an example of the present technology.

FIG. 44 is a schematic illustration of a force exerted by the textile membrane on the patient's face due to air pressure within the cavity formed by the cushion assembly.

Figure 45:
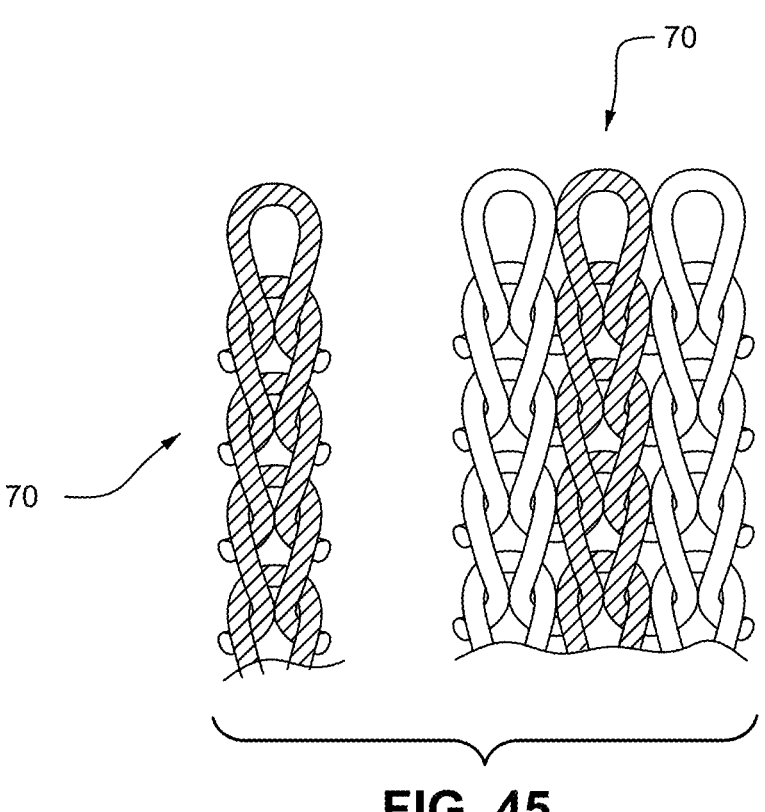
Figure 46:
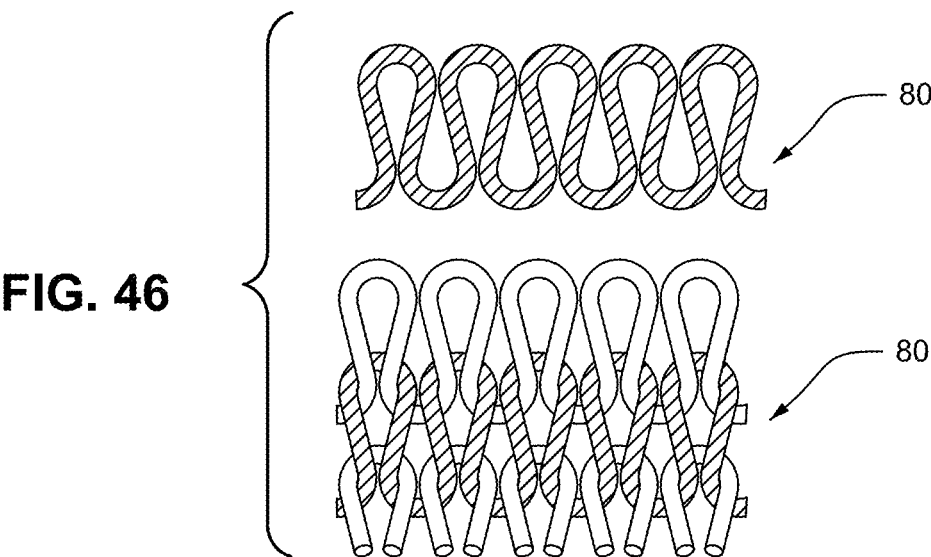

FIGS. 45 and 46 depict a knitting process.

Figure 47:
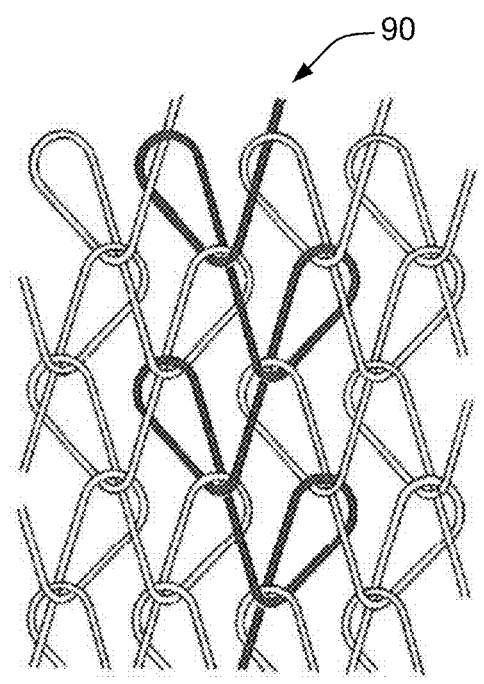

FIG. 47 illustrates a warp knitted textile according to an example of the present technology.

Figure 48:
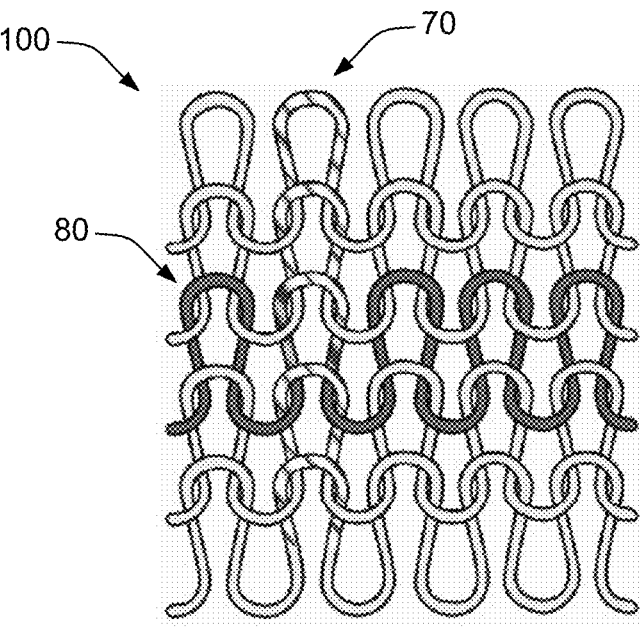

FIG. 48 illustrates a weft knitted textile according to an example of the present technology.

Figure 49:
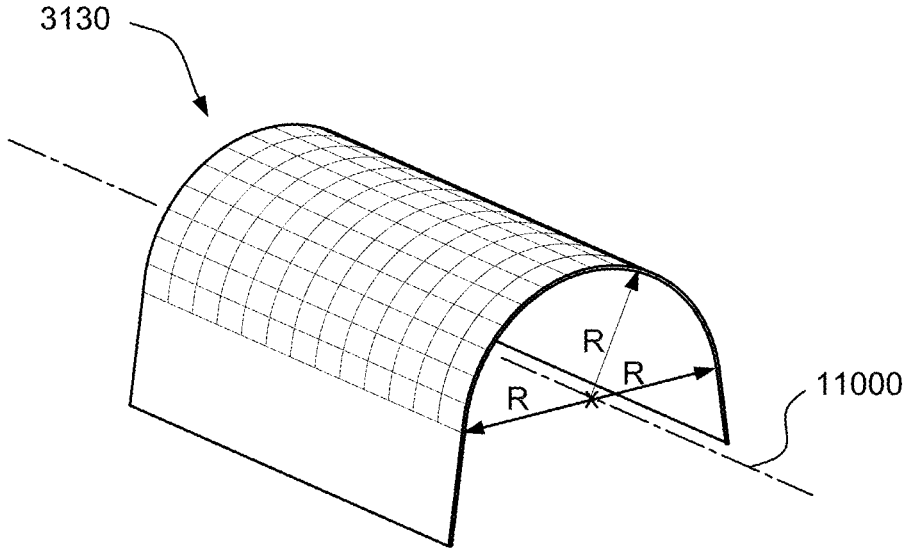

FIG. 49 is a perspective view of a textile material folded about a first axis.

Figure 50:
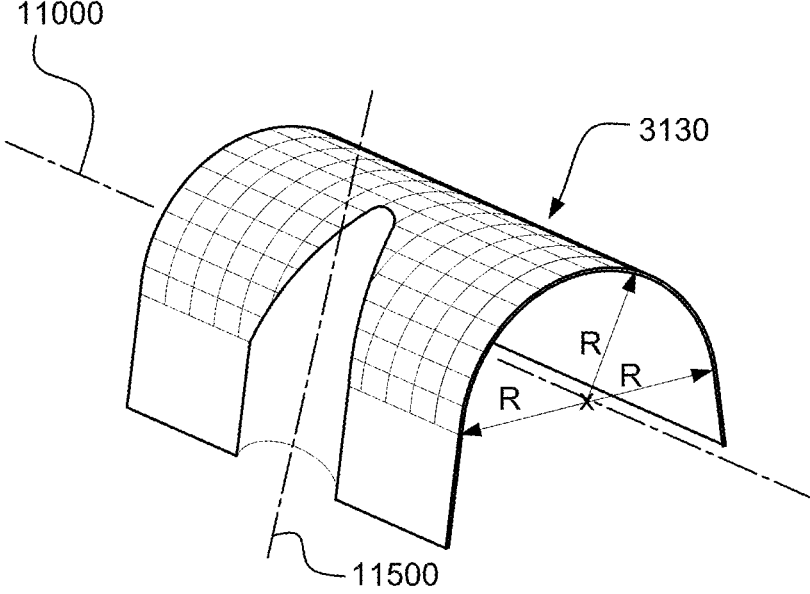

FIG. 50 is a perspective view of the textile material of FIG. 49, folded about the first axis and a second axis. The second axis is non-parallel to the first axis, and a fold about the second axis creates a crease and/or wrinkle in the textile material.

Figure 51:
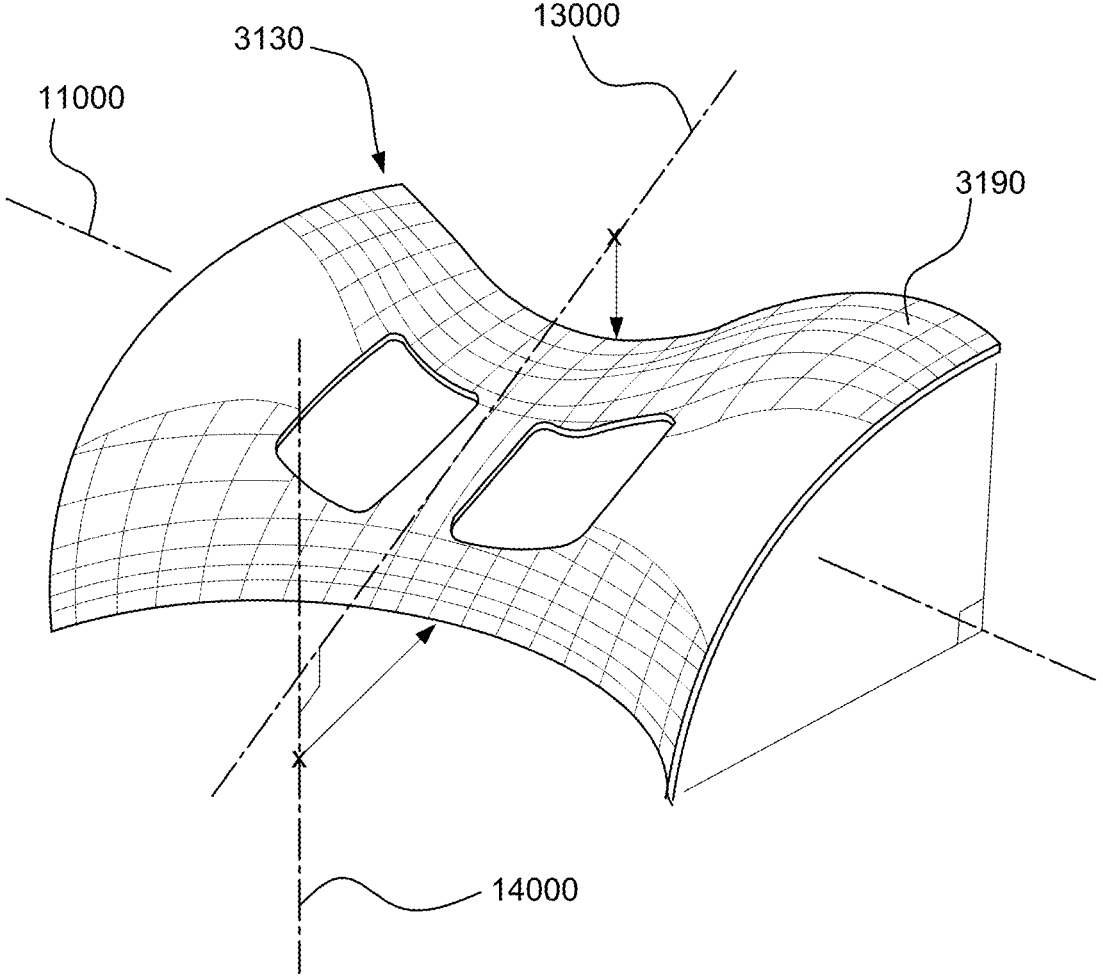

FIG. 51 is a perspective view of a textile material for use as a seal-forming structure. The textile material is folded about three, non-parallel axes and treated in order to limit the creation of creases and/or wrinkles.

FIG. 52 is a perspective view of the textile material of FIG. 49, with a pair of openings cut into the material, and a bridge portion positioned between the two openings.

FIG. 53 is a perspective view of the textile material of FIG. 52, illustrating the bridge portion flipped about a second axis, parallel to the first axis.

FIG. 54 is a perspective view of the textile material of FIG. 53, illustrating the bridge portion under tension via a crimping process.

Figures 55, 56:
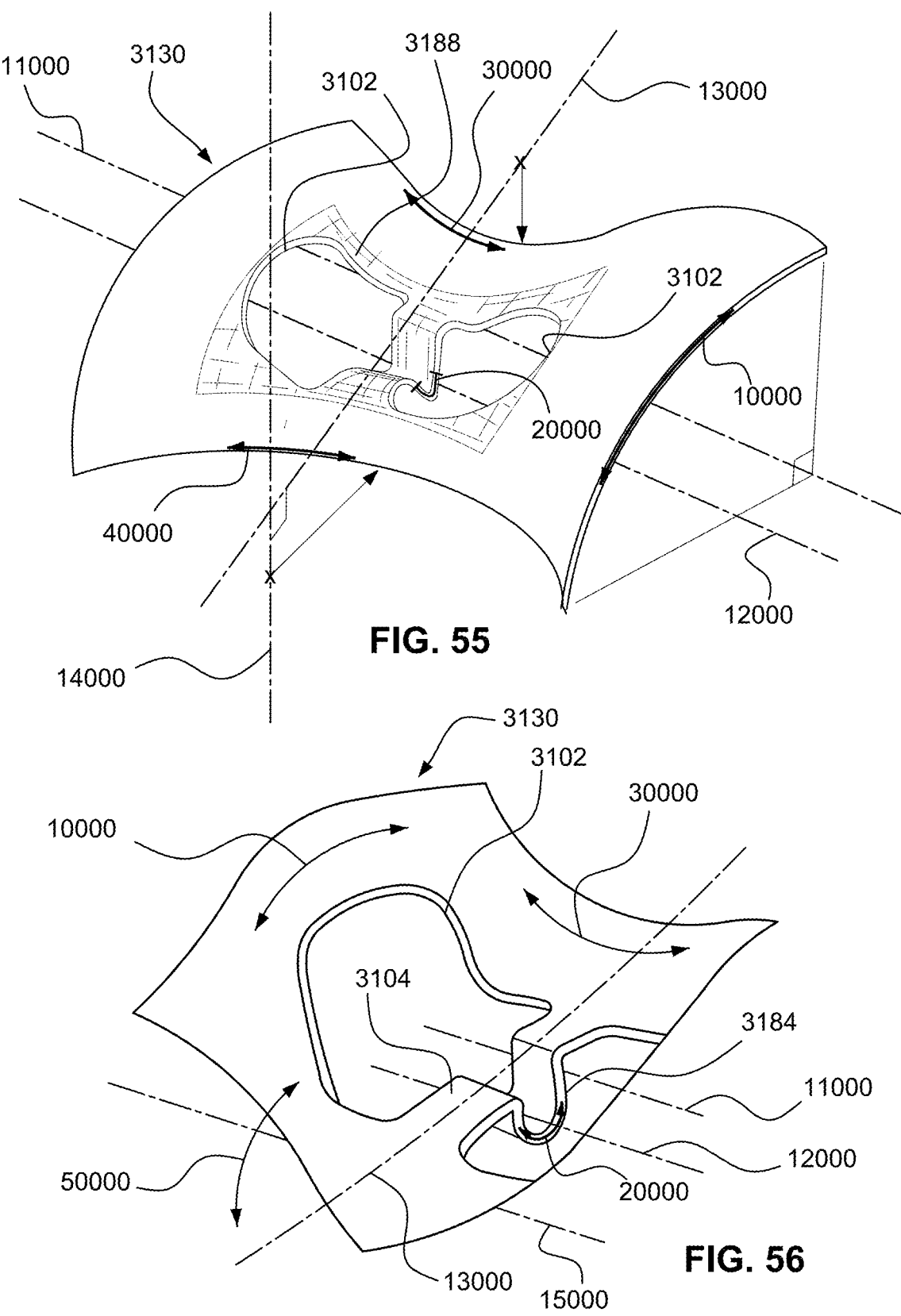

FIG. 55 is a perspective view of the textile material of FIG. 53, folded about non-parallel axes. Folding the bridge portion limits the creation of creases and/or wrinkles in the textile material.

FIG. 56 is a detail view of the textile material of FIG. 55, illustrating the curvatures about different axes.

Figure 57:
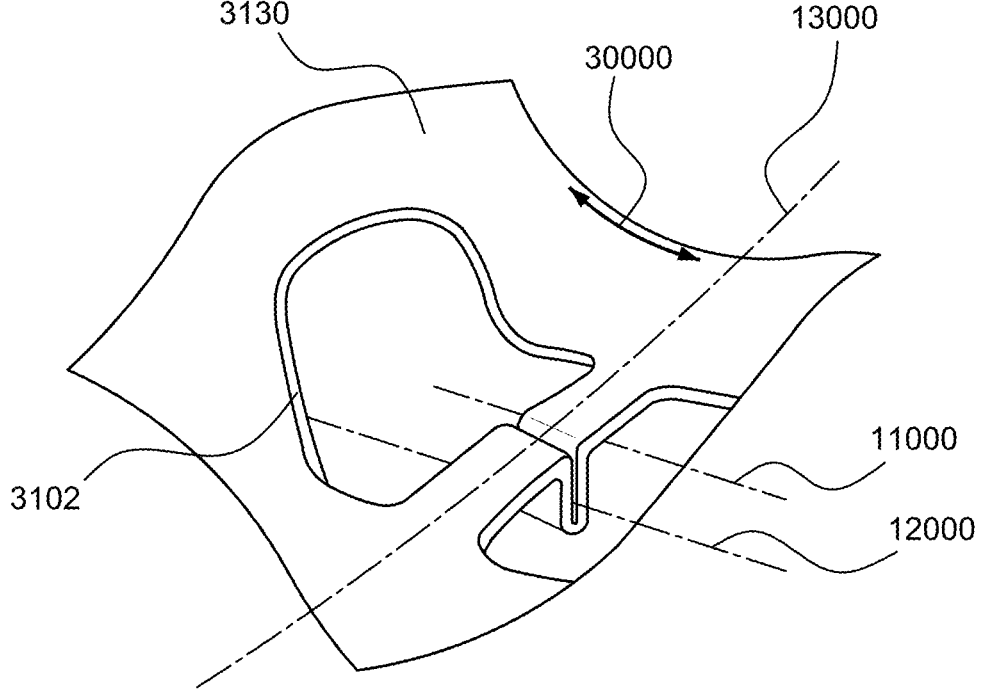

FIG. 57 is a detail view of a textile material illustrating a circumference of the opening, which may be changed depending on the length of the bridge portion that is crimped.

Figure 58:
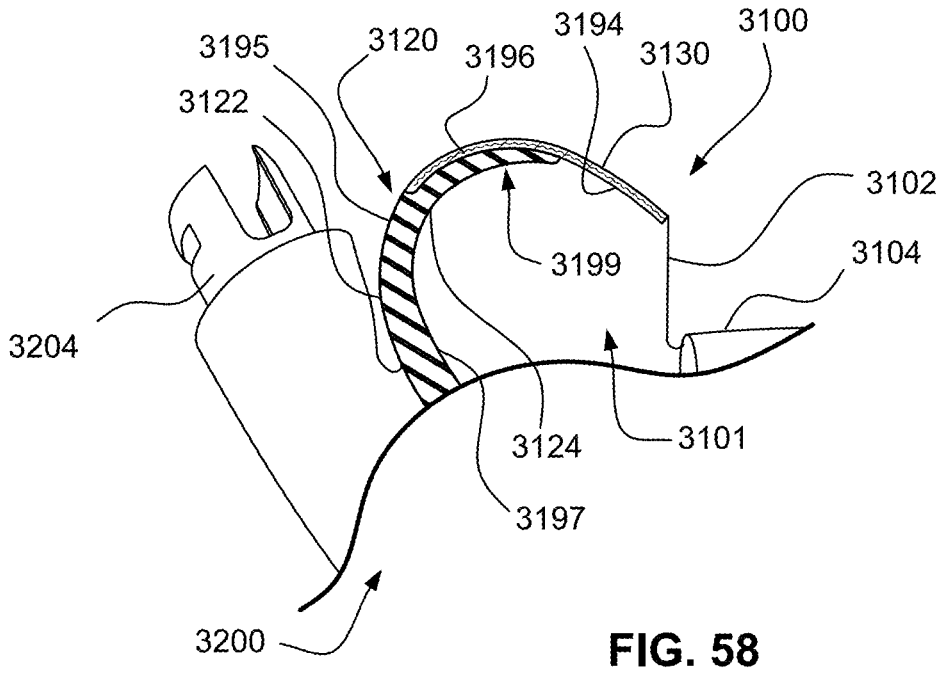

FIG. 58 is a cross-sectional view of a cushion assembly formed with the textile material of FIG. 54. A flexible support structure contacts the textile material in order to form a single wall.

Figure 59:
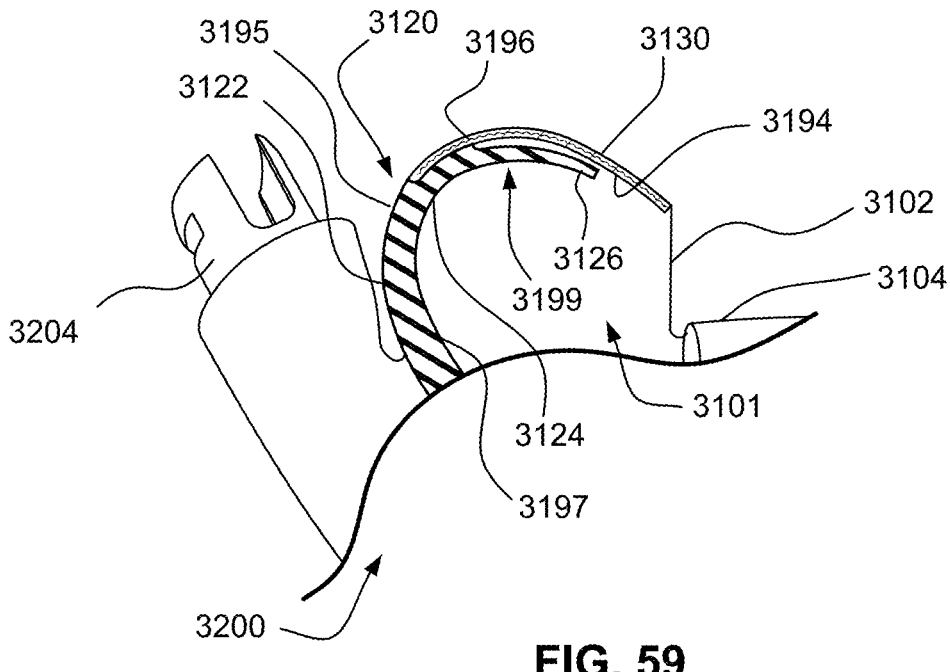

FIG. 59 is a cross-sectional view of a cushion assembly formed with the textile material of FIG. 54. A portion of a flexible support structure is spaced apart from the textile material in order to form two walls.

Figure 60:
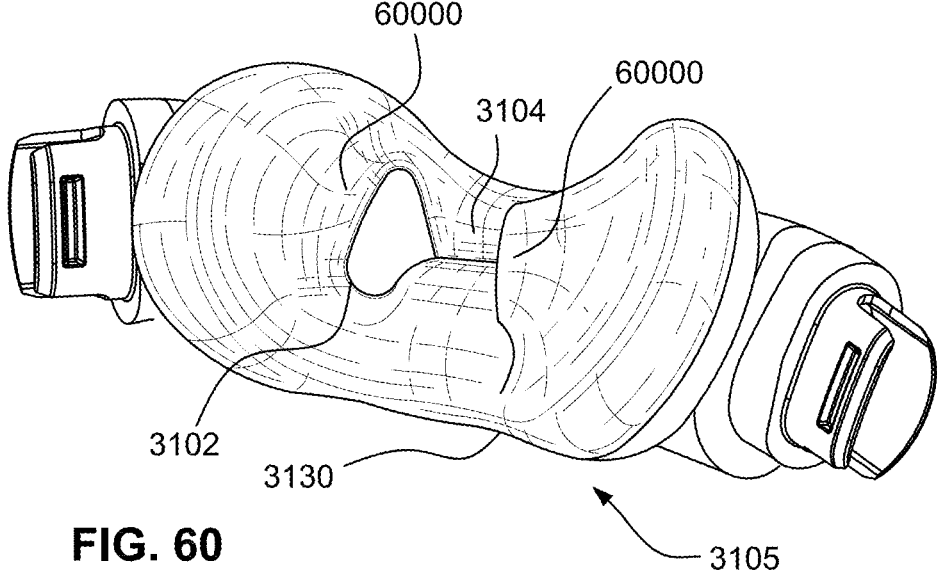

FIG. 60 is a perspective view of a cushion assembly formed with the textile material of FIG. 54. The textile material includes an arched portion partially surrounding the opening.

Figure 61:
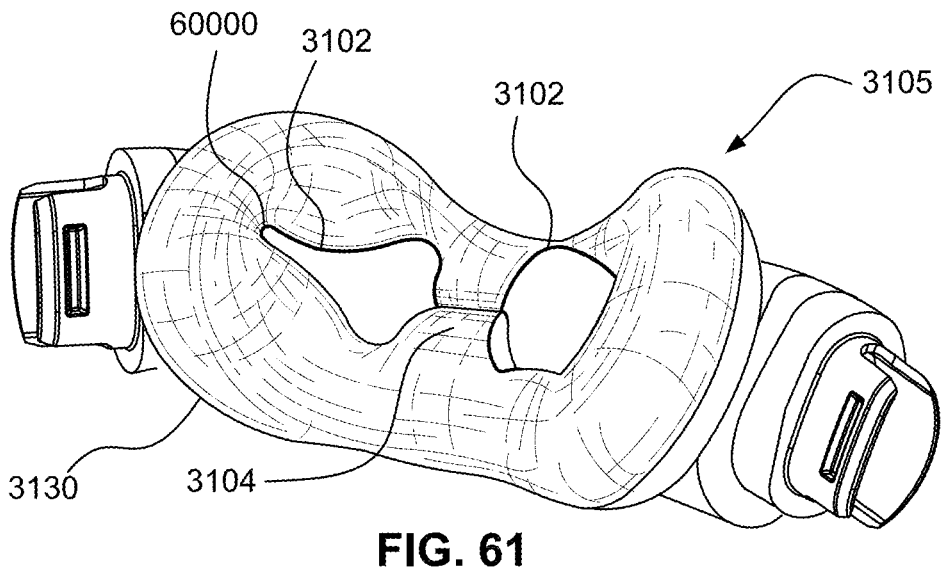

FIG. 61 is a perspective view of the cushion assembly of FIG. 60, illustrating the arched portion flipped inwardly so that the opening includes a substantially tear-dropped shape.

5. DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs the actual sealing surface may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In some forms, such as those illustrated in FIGS. 6 to 39, the seal-forming structure 3100, 6100, 9100 has a sealing portion that comprises a textile material, which may cover the entirety or a portion of the seal-forming structure 3100, 6100, 9100. In some forms, the textile may comprise a material formed of a network of fibres and be adapted such that it is air impermeable. For example, the textile may have an air impermeable film on at least one surface thereof thereby forming a textile membrane or textile sealing portion.

In some forms, the textile membrane may be constructed so as to stretch elastically in at least one dimension. For example, when a textile membrane is constructed from a network of fibres, the textile membrane may be capable of elongating in a longitudinal warp direction and/or a lateral weft direction across the textile membrane. In some forms, a textile membrane is constructed so as to elongate elastically to an extent greater than that achievable by conventional silicone seal-forming structures.

In some forms, the textile membrane is constructed so as to be substantially inelastic in at least one dimension. For example, when a textile membrane is constructed from a woven textile material, the textile membrane may be capable of substantially resisting elongation in either, or both of, a longitudinal warp direction or a lateral weft direction across the textile membrane.

The textile membrane may comprise a single layer or a plurality of layers. In forms where a plurality of layers are utilised, the individual layers can be formed using the same material, or a variety of different materials each with unique material properties.

In some forms, the textile membrane may comprise at least one layer that exhibits substantially air-impermeable characteristics, while maintaining the material characteristics necessary for providing comfort and minimal pressure points to the patient. For example, as illustrated in FIG. 40, in some forms a textile membrane may comprise an air impermeable material 10131 (e.g., a silicone layer) formed on one surface of a textile material 10133. The air impermeable material 10131 can in some forms be laminated onto the textile material 10133. The air impermeable material 10131 and textile material 10133 can, in some forms, be selected such that the resulting textile membrane 10135 can exhibit a predetermined overall elasticity, or a resistance to elasticity, as required. For example, the addition of the air impermeable material 10131 (or membrane layer) may add elasticity (or stretchiness) to the textile material 10133 such that the resulting textile membrane 10135 has increased stretchability. The air impermeable material 10131 may also have a low durometer characteristic so as not to impede on the elasticity of the textile material 10133. In other words, the textile membrane 10135 will have substantially the same elasticity as the textile material 10133 does alone, so that the addition of the air impermeable material 10131 will not substantially reduce the elasticity (or stretchiness) of the textile material 10133.

The air impermeable material 10131 may have a thickness substantially less than the thickness of the textile material 10133. This may assist in maintaining a substantially light weight textile membrane 10135, because the relatively small thickness of air impermeable material 10131 may not significantly add weight to the textile material 10133. The patient interface with a textile membrane 10135 that includes the air impermeable material 10131 may not feel noticeably heavier than a patient interface that includes only the textile material 10133.

In some examples, the thickness of the textile membrane 10135 is between approximately 0.25 mm and approximately 0.55 mm. In some examples, the thickness of the textile membrane 10135 is between approximately 0.30 mm and approximately 0.50 mm. In some examples, the thickness of the textile membrane 10135 is between approximately 0.35 mm and approximately 0.45 mm. In some examples, the thickness of the textile membrane 10135 is approximately 0.40 mm.

In some examples, the thickness of the air impermeable membrane 10131 is between approximately 0.01 mm and approximately 0.10 mm. In some examples, the thickness of the air impermeable membrane 10131 is between approximately 0.02 mm and approximately 0.08 mm. In some examples, the thickness of the air impermeable membrane 10131 is between approximately 0.03 mm and approximately 0.07 mm. In some examples, the thickness of the air impermeable membrane 10131 is between approximately 0.04 mm and approximately 0.06 mm. In some examples, the thickness of the air impermeable membrane 10131 is approximately 0.05 mm.

In some forms, the textile material 10133 may be formed as a multiple layered textile. In other words, multiple pieces of textiles may be combined together in order to form the overall textile material 10133. As shown in FIG. 40-1, the textile material 10133 may be constructed from three layers (although any number of layers may be used). A second layer 10133*b* of the textile material 10133 may be sandwiched between a first layer 10133*a* and a third layer 10133*c*. In the illustrated example, the second layer 10133*b* (i.e., the middle layer) is constructed from spandex, and the first and third layers 10133*a*, 10133*c* (i.e., inner and outer layers) are constructed from nylon. However, other materials may be used without departing from the scope and spirit of these forms. Additionally, the first and third layers 10133*a*, 10133*c* may be formed from different materials (i.e., non-identical materials).

In some forms, the overall composition of the textile material 10133 may be at least 50% nylon and at most 50% spandex. In some forms, the overall composition of the textile material 10133 may be between approximately 60% to approximately 90% nylon and between approximately 10% to approximately 40% spandex. In some forms, the overall composition of the textile material 10133 may be between approximately 70% to approximately 85% nylon and between approximately 15% to approximately 30% spandex. In some forms, the overall composition of the textile material 10133 may be approximately 82% nylon and approximately 18% spandex (e.g., JCD4018 produced by WeiMei Fabrics Limited).

In some forms, the layered structure may provide the textile material 10133 with a spongy feel. In other words, the textile material 10133 may be compliant and may deform as it comes in contact with the patient's face. Specifically, the thickness of the textile material 10133 may be capable of decreasing when a force is applied, and returning to its original shape when the force is removed. Thus, the textile material 10133 may act like a sponge because it is capable of at least partially absorbing an applied force. Specifically, the spandex layer 10133*b* of the textile material 10133 may provide the spongy feel (e.g., because of its elastic properties). The spongy feel of the textile material 10133 may help to improve comfort against a patient's skin (e.g., because the textile material 10133 is able to conform to a variety of facial contours). The spongy feel of the textile material 10133 may also assist in improving the seal against the patient's face. Particularly, the textile material 10133 may be able to deform into crevices on the patient's face (e.g., the region between the nasal ala and the nasolabial sulcus) as a result of an applied force (e.g., via a positioning and stabilizing structure 3300), but will not crease and form locations where air could leak out. This may assist the patient in establishing a seal between their skin and the textile membrane 10135, without needing the textile membrane 10135 to contact the exact same location (e.g., which may make donning the seal-forming structure 3100 easier). This may also allow the seal-forming structure 3100, 6100, 9100 to move and/or shift while it is worn without creating a leak, because the spongy properties assist in maintaining the necessary contact against the patient's skin.

In some forms, the textile material 10133 is coated (e.g., laminated) with an air impermeable layer 10131 (e.g., liquid silicone rubber) in order to form a textile membrane 10135 with impermeable properties. In the illustrated example, the air impermeable layer 10131 is applied to a single side of the textile material 10133. In other words, the air impermeable layer 10131 may be applied to the first layer 10133*a*, but not to the second or third layers 10133*b*, 10133*c*. When the textile membrane 10135 is constructed as a seal-forming structure 3100, 6100, 9100, the first layer 10133*a* is configured to be positioned within a cavity 3101, 6001, 9001, so that the third layer 10133$c$ is configured to face and contact the patient.

In one form, the textile material 10133 is formed from a fine knit textile. Specifically, the first and third layers 10133$a$, 10133$c$ are constructed with a fine knit. This may be a textile that is less than approximately 100 denier. This may be a textile that is less than approximately 50 denier. This may be a textile that is approximately denier. The fine knit of the textile, particularly in the third layer 10133$c$, provides a smooth feeling to the patient's skin, which may promote patient compliance (e.g., because of added comfort). The fine knit of the textile may also prevent seepage of the air impermeable layer 10131 through the textile layer 10133 (e.g., during a manufacturing process). For example, the fine knit of the first layer 10133$a$ may limit all seepage, or may allow some seepage, but may substantially limit seepage into the other layers 10133$b$, 10133$c$. In other words, the first layer 10133$a$ acts as a barrier and substantially limits the air impermeable layer 10131 from contacting and/or coating the second layer 10133$b$ or the third layer 10133$c$. Since the first layer 10133$a$ does not contact the patient, some seepage may be permitted since the relative stiffness of the first layer 10133$a$ is less important to patient comfort than that of the third layer 10133$c$ (i.e., which directly contacts the patient's skin). Thus, the spandex may not lose its elasticity as a result of contacting the air impermeable layer 10131. Additionally, the third layer 10133$c$ may not lose its smooth texture as a result of becoming impregnated with the air impermeable layer 10131. And since only one surface of the textile material 10133 needs to be coated with the air impermeable material 10131 (i.e., for the textile membrane 10135 to have impermeable properties), an impermeable membrane 10135 may be constructed that does not substantially limit patient comfort.

In some embodiments, coating the textile material 10133 with the air impermeable material does not substantially affect the material properties of the textile membrane 10133. For example, since the air impermeable material 10131 is substantially blocked from reaching the second layer 10133$b$, the spandex that forms the second layer 10133$b$ does not experience a substantial decrease in elasticity. This enables the textile membrane 10135 as a whole to continue to stretch as a result of an applied force. Additionally, the third layer 10133$c$ may lose its ability to drape, and instead become stiff, if impregnated with the air impermeable layer 10131. This may reduce the ability for the third layer 10133$c$ to seal against a patient's face. Thus, in addition to comfort, blocking the air impermeable layer 10131 from the third layer 10133$c$ keeps the third layer 10133$c$ substantially loose, and capable of sealing against a patient's face.

In some embodiments, the air impermeable layer 10131 includes a thickness $T_{f1}$ of no more than approximately 500 microns. In some embodiments, the air impermeable layer 10131 includes a thickness $T_{f1}$ of between approximately 4 microns to approximately 400 microns. In some embodiments, the air impermeable layer 10131 includes a thickness $T_{f1}$ of between approximately 8 microns to approximately 300 microns. In some embodiments, the air impermeable layer 10131 includes a thickness $T_{f1}$ of between approximately 12 microns to approximately 200 microns. In some embodiments, the air impermeable layer 10131 includes a thickness $T_{f1}$ of between approximately 16 microns to approximately 100 microns. In some embodiments, the air impermeable layer 10131 includes a thickness $T_{f1}$ of between approximately 20 microns to approximately 70 microns. In some embodiments, the air impermeable layer 10131 includes a thickness $T_{f1}$ of approximately 40 microns.

In some embodiments, the actual thickness $TI_2$ of the air impermeable layer 10131 in the textile membrane 10135 may be less than the thickness $T_{f1}$ of the air impermeable layer 10131 prior to being coated to the textile material 10133 (although this is not always the case). In other words, if the air impermeable material 10131 seeps into the first layer 10133$a$, then the thickness $T_{f1}$ of the air impermeable layer 10131 partially overlaps with the thickness of the first layer 10133$a$, so that a thickness $T_{f2}$ measured from an outer surface (i.e., surface facing the cavity) of the first layer 10133$a$ to an exposed surface (i.e., surface facing the cavity) of the air impermeable layer 10131 is less than the total thickness $T_{f1}$ of the air impermeable layer 10131.

Even if the thickness $T_{f2}$ of the air impermeable layer 10131 is less (e.g., because of seepage), the density remains substantially the same. In some embodiments, the air impermeable layer 10131 includes a density of no more than approximately 500 grams per meter squared (GSM). In some embodiments, the air impermeable layer 10131 includes a density of between approximately 5 GSM to approximately 400 GSM. In some embodiments, the air impermeable layer 10131 includes a density of between approximately 50 GSM to approximately 300 GSM. In some embodiments, the air impermeable layer 10131 includes a density of between approximately 100 GSM to approximately 200 GSM. In some embodiments, the air impermeable layer 10131 includes a density of between approximately 110 GSM to approximately 130 GSM. In some embodiments, the air impermeable layer 10131 includes a density of approximately 120 GSM.

The textile membrane 10135 includes a variety of benefits as a result of maintaining separation between the air impermeable layer 10131 and the second and third layers 10133$b$ (i.e., the middle layer), 10133$c$ (i.e., the patient contacting layer). As described above, the material properties of the textile material 10133 is not substantially sacrificed in order to achieve an impermeable membrane 10135. The third layer in particular 10133 maintains a smooth surface texture in order to provide comfort to the patient, and the second layer 10133$b$ does not substantially lose its elasticity. The first layer 10133$a$, the third layer 10133$c$, and the air impermeable layer 10131 may all also have elastic properties, so that they can stretch with the second layer 10133$b$. In particular, the air impermeable layer may have a low durometer (e.g., between approximately 20 to approximately 40), which may provide it with more stretchiness (e.g., it does not substantially limit the ability of the textile material 10133 to stretch) as compared to an air impermeable layer 10131 with a greater durometer.

In other examples, the textile membrane 10135 in constructed entirely from a textile material 10133. The textile material 10133 may include air impermeable threads that impart impermeability onto the textile membrane 10135. The additional layer of air impermeable material 10131 may not be needed, which may allow the textile membrane 10135 to be thinner (i.e., just the thickness of the textile material). The air impermeable threads may have similar elastic properties to non-air impermeable threads, so that the textile membrane 10135 with the air impermeable threads does not lose stretchiness.

In some forms, the textile membrane 10135 can exhibit a low spring constant (i.e. high compliance) in both warp and weft. In such forms, unlike conventional designs where a fixed cushion may cause the skin of a patient's face 1300 to distort in order to form an effective seal, the textile material 10133 and/or the resulting textile membrane 10135 may have a material spring constant and spring length such that the textile membrane 10135 is more compliant than the patient's skin that engages the textile membrane 10135. This may advantageously improve the comfort of the mask, and reduce the formation of localized pressure "hot spots," or locations likely to result in irritation because of contact with the seal-forming structure 3100, 6100, 9100.

In some forms, the surface of the textile material 10133 that contacts the patient's face 1300 can have low friction characteristics. This may advantageously improve the comfort of the surface texture of the textile membrane 10135 and reduce friction relative to the patient's face 1300. The textile material 10133 may have a surface (e.g., herringbone) that may have a first coefficient of friction in a first direction that is different (e.g., greater or less) than a coefficient of friction in a second direction. In contrast, higher friction textiles may cause the textile membrane 10135 to grip or rub against contacted regions of the patient's face, in use. Such rubbing or gripping may cause the textile membrane 10135 to be distorted or deformed thereby reducing the effectiveness of the seal and allowing air to leak undesirably from the device.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

It is noted that although the specification may refer (e.g., by reference character) to a particular illustrated example or a feature of a particular illustrated example (e.g., seal-forming structure 3100), such discussion may be applicable to other examples and/or features (e.g., seal-forming structure 6100, 9100).

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, a textile membrane 3130 (e.g., comprising nylon, polyester, nylon and polyester mix, microfiber or polyurethane) is used as the face-contacting portion of the seal-forming structure 3100 for the CPAP mask. The textile membrane 3130 may be bio-compliant, and may provide a substantially smooth and comfortable surface for the patient, which may improve patient compliance (e.g., because they are not wearing an irritating device). The textile membrane 3130 may have properties such that it is capable of elongating in at least one dimension. Prior to use, the textile membrane 3130 can be either permanently attached (e.g., molded) or attached as a removable module to a support structure (e.g., a flexible support structure 3120).

In one form, the textile membrane 3130 can be formed as a complex three-dimensional pre-determined shape such that it is untensioned (e.g., loose, slack and/or unwrinkled) prior to and/or during use, but there are no substantial leak causing wrinkles. The textile membrane 3130 may include one or more curvatures when attached to a support structure 3120, which may assist in conforming to various contours of a patient's face. Before the patient's face (e.g., a nose) approaches and depresses the textile membrane 3130, the textile membrane 3130 is adapted to form a constant surface without interruptions such as creases, folds or wrinkles. In some forms, this can be accomplished by molding the textile membrane 3130 such that it is substantially free of any leak causing wrinkles. This can be advantageous in ensuring that the textile membrane 3130 forms a smooth and continuous seal on and around the patient's face. This may provide improved respiratory pressure therapy by reducing occurrences of folded or wrinkled sections of the seal-forming structure 3100 through which treatment air may leak.

In some forms, regions of the textile membrane 3130 can be pre-tensioned (e.g., under tension before being contacted by the patient's face) and lightly stretched while other regions of the textile membrane 3130 can remain slack. In other words, the entire textile membrane 3130 may not be pre-tensioned. Having a textile membrane 3130 with various tensions may advantageously improve the seal efficiency while reducing pressure (i.e. "hot spots") on regions where the facial anthropometrics protrude a greater distance into or towards the cavity 3101. In some examples, the side of nose region (e.g., lateral side 3250 and/or corner regions 3252) may remain untensioned and/or slack prior to use, in order to provide additional material to accommodate the facial contours of these sensitive facial areas. In some examples, a bridge portion 3104 may extend between two naris openings 3102, and may be tensioned, as shown for example in FIG. 12-21. The tension applied to the bridge portion 3104 may allow for one possible way for the textile membrane 3130 to include complex shapes (e.g., multiple curvatures) in order to better contour to a patient's face, while including significantly less tension throughout the remainder of the textile membrane 3130 (e.g., as compared to the bridge portion 3104). Having a wide expanse of untensioned textile membrane 3130 may be more comfortable in some arrangements, as the untensioned textile may apply less pressure on the patient's face.

By retaining the textile membrane 3130 in an unwrinkled state continuously prior to and during use, the textile membrane 3130 can conform to the patient's facial profile while minimizing wrinkles and/or blow-out of the seal-forming structure. In some forms, this may also improve seal performance by maximising the contact area of the textile membrane 3130 on the patient's face. In some forms, this may also improve the performance of the CPAP device when it is impacted by external lateral or longitudinal forces (e.g., tube drag).

In some forms, when the plenum chamber 3200 is pulled a small distance away from the patient's face, the applied loading of the air pressure from within the plenum chamber 3200 can assist the textile membrane 3130 in retaining an effective seal. The applied loading of the air pressure can be sufficient so as to elastically stretch the textile membrane 3130 in at least one dimension such that it forms a "hover-craft" like balloon effect over the anthropometric contours of a patient's face 1300 thus retaining an effective seal thereon.

In some forms, the textile membrane 3130 may be held by a relatively stiffer support structure 3120. In various forms, the support structure 3120 can be formed from for example, any of silicone, PU foam, PU solid material or another suitable materials. While the support structure 3120 is stiffer than the textile membrane 3130, it may still be described as flexible, and may be capable of flexing or bending as a result of an applied tension. In some forms, the support structure 3120 may be relatively less stiff than a shell or frame of the plenum chamber 3200 (e.g., that is formed from hard plastic). In other forms, the plenum chamber 3200 does not include a shell or frame, and is constructed entirely from the textile membrane 3130 and the support structure 3120.

In some forms, a magnitude of the tensile stress can vary across the textile membrane 3130 of the seal-forming structure 3100 as required. The bridge portion 3104 may be held in tension, and the remainder of the textile membrane 3130 may be understood to be unstretched, as compared to the bridge portion 3104. The bridge portion 3104 is illustrated as being in a central portion of the textile membrane 3130, however the bridge portion 3104 (or any similar feature where tension is selectively applied), may be at any location throughout the textile membrane 3130. However, different locations on the textile membrane 3130 may include different degrees of tension (i.e., but all less than the bridge portion 3104). For example, there may be a region of stress concentration proximal to one or more holes (e.g., naris openings 3102) in the textile membrane 3130 through which treatment is administered or in wider stretches of material. In some examples, the region of the textile membrane 3130 (e.g., outer periphery) directly connected to the support structure 3120 may be held in greater tension than the radially inner portions of the textile membrane 3130, except for the bridge portion 3104, which may include the highest tension.

In some forms, the seal-forming structure 3100 can utilize a number of different cushion configurations including a single air assisted textile membrane 3130, a double air assisted textile membrane 3130, a textile membrane 3130 with compression support, or a textile membrane 3130 with TPU/TPE/Si support. In some forms, the cushion configuration of the seal-forming structure 3100 may be formed such that it can advantageously provide a "one-size-fits-most" solution.

In examples, the seal-forming structure 3100 and plenum chamber 3200 can be applied to nasal cushions, nasal cradles, oronasal cushions, ultra-compact full-face masks, full-face masks and other suitable cushion arrangements.

In some forms, the textile membrane 3130 may be configured to generate an effective seal against the subnasale portion of the patients nose such that the textile membrane 3130 does not engage the pronasale, as shown for example in FIG. 23. In some forms, the textile membrane may be configured to generate an effective seal across the patient's pronasale (not shown).

In some forms, the air pressure within the cavity 3101 may apply a load against the inside surface of the textile membrane (e.g., an air impermeable layer 10131) to create further tensile stress such that the textile membrane 3130 substantially fills the depressed contours of a patient's face 1300 (e.g. around the nasal ala, adjacent to the alar rim, etc.). In some forms, the elasticity of the textile membrane 3130, when combined with the applied load of the internal air pressure, can elastically stretch the textile membrane 3130 such that it forms a larger seal contact area on the patient's face. This may in some forms also be advantageous in providing a continuous seal, even when the mask is partially displaced from an optimal interface with the patient's face, as the textile membrane 3130 may partially inflate (i.e. a "hovercraft effect") due to the counter-force from the internal air pressure.

In some forms, such as illustrated in FIGS. 19-21 and 37-39, the textile membrane 3130, 9130 may have one or more grip pads 3150, 9150 arranged thereon. In an example, the grip pads 3150, 9150 may be configured to be either substantially flat along the patient facing surface of the textile membrane 3130, 9130. In other examples, the grip pads 3150, 9150 may be embossed such that the grip pad 3150, 9150 may form a bead or rim that protrudes slightly above the surface of the textile membrane 3130, 9130. In some forms, the grip pads 3150, 9150 may have a high coefficient of friction. In some forms, the grip pads 3150, 9150 may have a determined shape (e.g., ovular (see FIGS. 19, 21, 37, and 39), circular, square, etc.). In some forms, the grip pads 3150, 9150 may be elongate (see FIGS. 19 and 37). In some forms, the grip pads 3150, 9150 may be linear. In some forms, the grip pads 3150, 9150 may be arranged in a pattern across the surface of the seal-forming structure 3100, 9100. In some forms, the grip pads 3150, 9150 may be arranged sporadically across the surface of the seal-forming structure 3100, 9100 (see FIGS. 21 and 39). In some forms, the grip pads 3150, 9150 may be arranged to form a perimeter proximal to the peripheral edges of the textile membrane 3130, 9130 (see FIGS. 19, 20, 37, and 38). In some forms, the grip pads 3150, 9150 that form a perimeter can be in the form of a dotted line (see FIGS. 19 and 37). In some forms, the grip pads 3150, 9150 that form a perimeter can be in the form of a solid line (see FIGS. 20 and 38). In some forms, the grip pads 3150, 9150 that form a perimeter can be in the form of a plurality of lines, dotted or solid or a combination thereof. In some forms, the grip pads 3150, 9150 may assist a textile membrane 3130, 9130 in gripping a patient's face. In an example, the grip pads 3150, 9150 are formed as a relatively thin layer of silicone applied to the surface of the textile membrane 3130, 9130. In any of the above configurations, the grip pads 3150, 9150 may provide an additional material (e.g., textile and silicone) that contacts the patient's face. While it may not provide the level of comfort that an entirely textile surface could provide (e.g., where only the textile material of the textile membrane contacts the patient's nose), including grip pads 3150, 9150 on the textile membrane 3130, 9130 may provide benefits of helping to ensure that the seal-forming structure 3100, 9100 remains in a proper position (e.g., in order to deliver therapeutic pressure to a patient). Additionally, having only a small area covered with silicone (or other gripping material) as compared to the relatively large area of textile (or being entirely silicone), may be more comfortable to a patient than an entire seal-forming structure 3100, 9100 formed from silicone (or other similar material).

In some forms, the textile membrane 3130 may be integrated to the support structure 3120 by attaching (e.g., molding) an outer edge (e.g., outer perimeter) of the textile membrane 3130 around a lip of the curved edges (i.e., inner edge) of the support structure 3120. In an example, the textile membrane 3130 is attached so as to provide a front face of the seal-forming structure 3100. The textile membrane 3130 also extends in the anterior direction, so that the textile membrane 3130 curves away from the front face. In other words, the textile membrane 3130 is curved so as to extend beyond the front face, and provides additional surface area of textile material exposed to the patient. This arrangement may be advantageous because substantially all of the patient's face in contact with the seal-forming structure 3100 is in contact with the textile membrane 3130. This may be beneficial in improving patient compliance, because contact with the textile membrane 3130 may be more comfortable for a patient, and therefore the patient may be more likely to wear a patient interface 3000 that incorporates the textile membrane 3130, than a patient interface 3000 that includes at least some other material (e.g., silicone) in a face contacting region.

In an example, the textile membrane 3130 is attached to the support structure 3120 by a specific process (as will be described later) that may form the curved portions without creating folds, creases, wrinkles, or buckles in the textile membrane surface 3130. As can be seen, in some examples, at a transition portion 36, the support structure 3120 and the textile membrane 3130 may both have a radius of curvature (e.g., the same or similar radius of curvature) along the curve 35 in a direction from the anterior side of the seal-forming structure 3100 to the posterior side of the seal-forming structure (see FIGS. 16-18). The textile membrane 3130 may have a predefined curvature imparted thereto such that a portion of the textile membrane 3130 not directly supported by the support structure 3120 extends along the curve 35 (FIGS. 16-18). The textile membrane 3130 may be held in slight tension against the support structure 3120, but the textile membrane 3130 not directly supported by (e.g., not in direct contact with) the support structure 3120 may be considered to be substantially slack (e.g., and under less tension than the bridge portion 3104). This may help create a dome shape (e.g., convex dome) in certain regions (e.g., lateral side 3250 and/or corner regions 3252) of the textile membrane 3130 which may help the textile membrane 3130 seal against the contours of the patient's face (e.g., the subnasale region of the patient's face (i.e., the corner of nose regions, i.e., the region where the ala terminate at the lip superior proximate the nasolabial sulcus)), as shown for example in FIG. 12. The dome shape may help prevent creases, wrinkles, folds, and buckles from forming in the textile membrane 3130 which may help avoid the creation of leak paths. Also, the dome shape may help the textile membrane 3130 reach into hard to seal areas of the patient's face, such as the corner of nose regions. The textile membrane 3130 may have a saddle shape at a medial subnasale region 3260 configured to seal against the patient's subnasale thereby matching the saddle shape formed by the patient's nasolabial angle and lip superior, as shown in FIG. 12. Similarly, a pronasale region 3270 may also have a saddle shape configured to seal against the matching profile presented at or below the patient's pronasale. The curvature (e.g., magnitude of curvature and/or radius of curvature) of the textile membrane 3130 in the direction of the curve 35 may vary in different regions of the cushion assembly along an outer perimeter of the textile membrane 3130. For example, as shown in FIG. 16, the textile membrane 3130 in the medial pronasale region 3270 may have different curvature in the direction of the curve 35 than the textile membrane 3130 in the medial subnasale region 3260. In an example, the curvature (e.g., magnitude of curvature and/or radius of curvature) at a lateral side 3250 of the textile membrane 3130 may be different that the curvature at the medial pronasale region 3270 and/or medial subnasale region 3260.

In some forms, the textile membrane 3130 may be slightly angled or curved inwardly toward the mask interior (e.g., positive domed curvature in a left-right direction), as shown for example in FIGS. 12-21. In some forms, the textile membrane 3130 may form a dome shape over the support structure 3120, as shown for example in FIGS. 26-33. It is noted that any of the cushion assemblies 6105, 9105 disclosed herein may have the textile membrane 6130, 9130 attached to an outer edge of the support structure 6120, 9120 such that the textile membrane 6130, 9130 forms part of the portion of the seal-forming structure 6100, 9100 that extends along the curve 35 from the anterior side of the seal-forming structure to the posterior face-contacting side as discussed above with reference to FIG. 12, such that, for example, the textile membrane 6130 of cushion assembly 6105 may have more of a dome shape by virtue of a negative curvature from one lateral side to the other lateral side. In other words, the textile membrane 6130 can be formed with both an inward curve and a dome shape, because the textile membrane 6130 is attached to the support structure 6120 with curvatures in different directions and/or about different axes. In one example, the majority of the textile membrane 6130 includes a positive (e.g., inward) curvature that may cradle a portion of the patient's face, and only the peripheries (e.g., regions proximate to the support structure) are dome shaped (e.g., include a negative curvature).

In some forms, a central portion of the textile membrane 3130 has a saddle shape. In other words, the peripheries of the textile membrane 3130 may be shaped with a negatively domed curvature (e.g., relative to the patient's face in use), and the central portion includes a positively domed curvature (e.g., about the bridge portion 3104), so that the central portion (e.g., proximate to the bridge portion 3104) may be considered a minimax point (e.g., relative to the patient's face in use), and thus a saddle.

In some forms where the textile membrane 3130 is not under continuous tension (prior to and/or during use) or is non-elastic, the textile membrane 3130 may form an improved air-assisted seal on a patient's face that conforms dynamically to alterations/movement (i.e. "hovercraft effect"), for example due to the textile membrane 3130 being thinner and having a lower structural stiffness than support structure 3120 (e.g., silicone membrane).

In some forms, the textile membrane 3130 may be supported by a secondary or tertiary support structure that may act as a cushion support. A cushion support can provide additional flexibility and may be suitable for use by most patient's faces (one-size-fits-most). The second or third support layer can be formed using a membrane of a textile, a textile with PU/Si membrane, laminated open cell foam, a laminated PU foam, PU molding, TPU/TPE or silicone. In some forms, additional support layers can themselves be supported by a structural/rigid plastic such as PP/PC/PA/PET or other suitable materials.

In some forms, 3D printing of the textile membrane and/or cushion support sections as a "skeleton" can reduce the thickness and as a consequence, may reduce the weight of the mask.

In some forms, multiple different layers of the mask layers could be printed with different rigidity, hardness, or thicknesses. For example, "skeleton" sections may be formed using Si, PU Foam, PU solid material or any suitable plastic material.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. The tension portion may be located at any number of discrete locations throughout the seal-forming structure. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Nasal Cushion

Referring to FIGS. 6-21 a patient interface 3000 with a cushion assembly 3105 including a seal-forming structure 3100 and a plenum chamber 3200 is shown in accordance with a first example of the present technology.

The examples of seal-forming structure 3100 described in the preceding paragraph may be considered nasal cradle cushions and are intended to provide a flow of pressurised gas to the patient's nares by sealing against at least the underside of the patient's nose. The exemplary seal-forming structure 3100 may engage the patient's face below the bridge of the nose and some examples, depending on the size and shape of the patient's nose, may engage the patient's nose below the pronasale. The exemplary seal-forming structure 3100 may also engage the patient's face at least above the upper vermillion. Thus, the exemplary seal-forming structure 3100 may seal against the patient's lip superior in use. Furthermore, the patient's mouth may remain uncovered by the seal-forming structure 3100 of the depicted examples such that the patient may breathe freely, i.e., directly to atmosphere, without interference from the seal-forming structure 3100. The under-the-nose nasal cradles may be configured such that they do not have an aperture sized to receive the patient's nose within the cavity. Further, a height of the cushion 3105 from an inferior edge of the textile membrane at a medial subnasale region to a superior edge of the textile membrane 3130 at a medial pronasale region may be less than a width of the cushion 3105 in a left-right direction from a lateral edge of the textile membrane 3130 to the other lateral edge of the textile membrane 3130 (see e.g., FIG. 12).

Examples of a nasal cradle cushion 3105, e.g., the exemplary seal-forming structures 3100 disclosed herein, may include a superior saddle or concave region that has positive curvature across the cushion. Also, a nasal cradle cushion 3105 may be understood to have a single target seal forming region or surface, whereas a pillows cushion may have two target seal forming regions (one for each naris). Cradle cushions 3105 may also have a posterior wall that contacts the patient's lip superior and an upper, central, surface contacts the underside of the patient's nose (e.g., the patient's subnasale and/or columella). These two surfaces on the patient's face may form a nasolabial angle between them (see FIG. 2E). A cradle cushion 3105 may be shaped to have a nasolabial angle within the range of 90 degrees to 120 degrees.

Furthermore, the exemplary seal-forming structure 3100 may also be shaped and dimensioned such that no portion of the seal-forming structure 3100 substantially enters into the patient's nares during use. In other words, a portion of the seal-forming structure 3100 may contact the alar rim and extend slightly inside in some orientations, but the seal-forming structure 3100 is not substantially sealing within the nasal passages (e.g., as opposed to a nasal pillow style mask).

5.3.2.1 Plenum Chamber

Referring to FIGS. 6-21, the plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about any portion of the perimeter of the plenum chamber 3200 (e.g., about the entire perimeter, about a majority of the perimeter, etc.).

In certain forms of the present technology, the plenum chamber 3200 may be constructed from a flexible material (e.g., silicone) and may be formed as a one-piece structure with the support structure 3120 (e.g., from any of the materials described herein as suitable for the support structure 3120 and/or plenum chamber 3200). In some examples, the seal-forming structure 3100 may be an extension of the plenum chamber 3200 or formed as a part of the plenum chamber 3200 such that the plenum chamber 3200 encompasses the seal-forming structure 3100. In such an example, the support structure 3120 and textile membrane 3130 may be considered part of the plenum chamber 3200 (e.g., the seal-forming structure 3100 at least partially forms the internal volume of the plenum chamber 3200). In some examples, the plenum chamber 3200 may be constructed from a transparent material (e.g. a transparent silicone). The use of a transparent material can reduce the obtrusiveness of the patient interface 3000, and help improve compliance with therapy. The use of a transparent material can aid a clinician (or patient) in observing how the patient interface is located and functioning (e.g., to ensure a proper seal), and in observing the cleanliness of the patient interface 3000. A transparent material may allow a clinician or patient to observe a build-up of debris (e.g., dirt, mold, etc.) within the plenum chamber 3200, so that the patient interface 3000 can be cleaned or replaced. This may give the patient a sense of cleanliness when wearing the patient interface and may assist in ensuring that the patient is not inhaling harmful materials, both of which may improve patient compliance. A translucent material may be used instead of or in addition to a transparent material, and may provide the patient with similar benefits. Alternatively, the plenum chamber 3200 is constructed from a relatively rigid material (e.g., polycarbonate) as compared to the seal-forming structure 3100. The rigid material may also be constructed from a transparent and/or translucent material (e.g., a transparent polycarbonate, etc.), in order to achieve the similar benefits of flexible transparent material (e.g., to allow for observation).

In some forms, the seal-forming structure 3100 may include a plenum chamber 3200 connection opening where the seal-forming structure 3100 is sealingly joined to the plenum chamber 3200. The seal-forming structure 3100 and the plenum chamber 3200 may at least partly form a cavity 3101 that is pressurized by the flow of air. In the illustrated example, the seal-forming structure 3100 and the plenum chamber 3200 together form the cavity 3101. At least one opening (e.g., a pair of nasal openings 3102) in the seal-forming structure may allow for fluid communication between the cavity 3101 and the patient's nares. However, the nasal openings 3102 are not large enough to allow the patient's nose (e.g., the pronasale) into the cavity 3101.

The connection between the seal-forming structure 3100 and the plenum chamber 3200 at the plenum chamber connection opening 3106 may be a permanent bond. The connection between the seal-forming structure 3100 and the plenum chamber 3200 at the plenum chamber connection opening 3106 may be a chemical bond. The seal-forming structure 3100 may be joined to the plenum chamber 3200 at the plenum chamber 3200 connection opening without a mechanical connection. Alternatively, the seal-forming structure 3100 may be joined to the plenum chamber 3200 at the plenum chamber connection opening by a mechanical removably detachable connection.

At each lateral side of the plenum chamber 3200 there may be a plenum chamber lateral end 3202 in the form of a hollow passageway forming a plenum chamber inlet port sized and structured to receive a flow of air. A plenum chamber connector 3204 may also be provided at each lateral side of the plenum chamber 3200 laterally outward of the plenum chamber lateral end 3202. The plenum chamber connectors 3204 may connect to respective ends 3314 of the positioning and stabilising structure 3300. The connection between the plenum chamber connectors 3204 and respective ends 3314 of the positioning and stabilising structure 3300 may be releasable at both sides. In other examples, one side may have a permanent connection while the other side has a releasable connection. In still further examples, both connections between the plenum chamber connectors 3204 and respective ends 3314 of the positioning and stabilising structure 3300 may be permanent.

The plenum chamber lateral ends 3202 may receive the flow of pressurised gas from the positioning and stabilising structure 3300 (e.g., conduit headgear). The flow of pressurised gas may then pass through the plenum chamber 3200, then through the seal-forming structure 3100, and into the patient's airways for inhalation.

The ends 3314 of the positioning and stabilising structure 3300 (e.g., openings in the respective conduits) may be connected to the plenum chamber lateral ends 3202. Each plenum chamber connector 3204 in these examples may include a slot 3209, a chamfered edge 3208, and a notch 3206 that may be removably connected to a clip of the positioning and stabilizing structure with a snap-fit.

5.3.2.2 Seal-forming Structure of the Present Technology

The seal-forming structure 3100 may each include a support structure 3120 that provides support to a sealing portion 29130 (e.g., a textile membrane) that creates a seal with the patient's face. The sealing portion 29130 is configured to sealingly engage the patient's face (e.g., when pressurized air is supplied to the plenum chamber 3200).

In one example, the seal-forming structure 3100 may include a support structure having at least two regions (e.g., two, three, four, etc. regions) of different thickness (e.g., seal-forming structure 3100 comprises support structure 3120 which has a wall structure having lateral support regions 3122 of an increased thickness with respect to other portions of the wall structure). For example, as shown in FIGS. 58 and 59, some portions 3123 of the support structure 3120 may be thicker than other portions 3124, 3126 of the support structure 3120. For example, the thicker portions 3123 may be adjacent to or connecting to the plenum chamber 3200 and portions 3124, 3126 may be adjacent to or connecting to the textile membrane 3130 so as to provide structural stability at the connection with the plenum chamber 3200 and flexibility at the interface with the patient. Alternatively, the thicker lateral support regions 3122 may be located, for example, at the corner of nose region of the seal-forming structure (and e.g., may connect directly to the textile membrane), to ensure adequate sealing in the subalare region of the patient's face.

Further, in the depicted examples, each textile membrane (e.g., sealing portion) may have two separate naris openings 3102 corresponding respectively to one of the patient's nares to provide the flow of air to both of the patient's nares. There may also be a bridge portion 3104 positioned between the naris openings 3102. The bridge portion 3104 may assist in maintaining a desired shape of the textile membrane prior to and/or during use.

The sealing portion 3130 may be less rigid than the support structure 3120 and may be constructed from a textile material such as nylon, polyester, nylon and polyester mix, microfiber or polyurethane, for example, as will be described in more detail later. The sealing portion 3130 described in any of the examples of this disclosure may be referred to as a textile sealing portion or textile membrane and may comprise a textile material having an air impermeable property (e.g., a material layered, coated or otherwise applied thereon).

The support structure 3120 may have an aperture formed therein providing an inner edge of the support structure 3120 along which the sealing portion 3130 (e.g., an outer perimeter of the sealing portion 3130) may be attached to the support structure 3120 such that the sealing portion 3130 extends radially inwardly of the seal-forming structure 3100 beyond or to a further extent than the support structure, as shown for example in FIGS. 12-21. For example, the sealing portion 3130 may be molded around the inner edge of the support structure 3120 or connected to the support structure 3120 in other suitable ways, as will be described later.

Referring to FIGS. 12-15, the seal-forming portion 3100 has a wall structure that may include lateral support regions 3122 having an increased thickness as compared to other portions of the wall structure of the support structure 3120. At each lateral most side of the seal-forming structure 3100, a lateral support region 3122 may be provided. The seal-forming structure 3100 may include two lateral support regions 3122, each spaced distal from a plane bisecting the seal-forming structure 3100 that would be parallel to the patient's sagittal plane, in use. The lateral support regions 3122 may be the thickest portions of the seal-forming structure 3100 to provide resistance to lateral displacement (e.g., caused by the patient sleeping on the side of their head such that the pillow pushes laterally against the seal-forming structure) and to provide robust engagement against the patient's ala. The lateral support regions 3122 may have a thickness of approximately 0.9 mm to approximately 1.5 mm, or approximately 1.3 mm to approximately 1.4 mm, or approximately 1.3 mm, or approximately 1 mm to approximately 1.5 mm Due to the lateral support regions 3122 being the thickest regions of the seal-forming structure 3100 in the depicted examples, the lateral support regions 3122 may also provide the greatest resistance to deformation.

The textile membrane 3130 may be formed such that the textile membrane 3130 forms part of the portion of the seal-forming structure 3100 that curves from the anterior side of the seal-forming structure 3100 to the posterior face-contacting side, as described earlier. That is, the textile membrane 3130 is in contact with the support structure 3120 in the transition portion 36 such that the textile membrane portion 3130 may be configured to engage the subalare region of the patient's face (i.e., the region where the ala terminate at the lip superior proximate the nasolabial sulcus), which is a region of particularly complex geometry. The subalare region of a patient's face presents particularly complex geometry because at least three facial surfaces—the ala, the lip superior, and the cheek—converge at this region. As a result, the seal-forming structure 3100 may be more flexible and compliant (e.g., not under tension proximate the outer periphery of the textile membrane 3130) so as to more readily conform to the patient's facial contours.

As described earlier, FIGS. 19-21 show grip pads 3150 on the surface of the textile membrane 3130.

5.3.2.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure 3100 into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.2.3.1 Positioning and Stabilising Structure of the Present Technology

FIG. 6 depicts an example of the present technology, including a positioning and stabilising structure 3300. In this example, the positioning and stabilising structure 3300 includes lateral portions 3302 and superior portions 3304 in the form of conduits that direct a flow pressurised gas from a hub 3306 to ends 3314. The positioning and stabilising structure 3300 may be arranged such that the hub 3306 and the decoupling structure 3500 are positioned superior to the patient's head in use. As described below, the decoupling structure 3500 may be rotatable within the hub 3306 and when the patient is wearing the patient interface 3000, e.g., during therapy, the location of the hub 3306 and the decoupling structure 3500 superior to the patient's head allows the patient to move more freely without becoming entangled with the air circuit 4170.

The positioning and stabilising structure 3300 may be constructed of silicone. For example, the lateral portions 3302, the superior portions 3304, the hub 3306, and the lateral ends 3314 may able constructed or molded from a single piece of silicone.

The superior portions 3304 of the positioning and stabilising structure 3300 have ridges and valleys (or concertina sections) that allow the superior portions 3304 to conform to the shape of the corresponding portion of the patient's head in use. The ridges and valleys of the superior portions 3304 allow the superior portions 3304 to be extended and contracted along the longitudinal axis to accommodate larger or smaller heads. The ridges and valleys of the superior portions 3304 allow the superior portions 3304 to be flexed to different radii of curvature to accommodate patient heads of different shapes and sizes.

The lateral portions 3302 of the positioning and stabilising structure 3300 may not be formed with the ridges and valleys of the superior portions 3304. Therefore, the lateral portions 3302 may be less extensible and flexible than the superior portions 3304, which may be advantageous because there is less variability in the shape and size of the lateral sides of a patient's head.

The ends 3314 may connect to respective plenum chamber lateral ends 3202. As described above, the plenum chamber lateral ends 3202 receive the flow of pressurised gas from the positioning and stabilising structure 3300, which passes through the plenum chamber 3200, through the seal-forming structure 3100, and on to the patient's airways. As described above, the ends 3314 may connect to the plenum chamber connectors 3204 of a respective plenum chamber lateral end 3202.

The positioning and stabilising structure 3300 may be structured and arranged to direct a force/tension provided by the lateral portions 3302 into a partially superior and partially posterior force vector applied to the plenum chamber 3200. The partially superior and partially posterior force vector urges, in particular, the textile membrane of the seal forming structure 3100 into sealing contact with an underside of the patient's nose contacting, e.g., at or below the pronasale and at least above the upper vermillion.

The lateral portions 3302 may also each include a tab 3308 that receives a posterior strap end portion 3311 of a posterior strap 3310. The posterior strap 3310 may be length-adjustable, e.g., with a hook and loop material arrangement whereby one of the posterior strap end portion 3311 and the remainder of the posterior strap 3310 includes hook material on its exterior while the other includes loop material on its exterior. The length adjustability of the posterior strap 3310 allows tension on the lateral portions 3302 to be increased to pull the seal-forming structure 3100 into sealing engagement with the patient's face at a desired amount of pressure (i.e., sufficiently tight to avoid leaks while not so tight as to cause discomfort).

The lateral portions 3302 may also be provided with sleeves 3312 that cushion the patient's face against the lateral portions 3302. The sleeves 3312 may be constructed of a breathable textile material that has a soft feel. The sleeves 3312 may be removable from the lateral portions 3302 after the ends 3314 are removed from the plenum chamber lateral ends 3202.

In some forms (see e.g., FIG. 7), a positioning and stabilizing structure 6300 may include a textile tube 6350 with a left arm 6305 and a right arm 6307. The textile tube 6350 may be formed with a first side that is configured to contact the patient. This may be referred to as the inner layer 6352. The textile conduit may also include a second side that is attached to the inner layer 6352, but faces away from the patient that may be referred to as the outer layer 6354. The inner layer 6352 and the outer layer 6354 may each be secured to each other along the edges of the inner layer 6352 and the outer layer 6354 such that a channel or passageway is formed between the seams of the inner layer 6352 and the outer layer 6354. That is, the space between the seams remains unattached and forms an air passage 6372. The inner layer 6352 and the outer layer 6354 may be joined using various techniques that impart particular properties to the seam or joint. For example, in some forms, the seams are formed using ultrasonic welding, radio frequency welding, as well as cut and weld techniques. Heat may be applied in particular areas that activates a thermoset or thermoplastic material used in tube 6350. This heat may not only be used to join the layers together, but may also be used to thermoform the layers, such as outer layer 6354. Further, in some forms stitching or an adhesive such as a glue may be utilized to join the layers together. In some forms, stitching is not used. In still further forms, material beyond what is located within the layers is not utilized to join the inner and outer layers 6352, 6354 of tube. For example, in some forms the inner and outer layers 6352, 6354 may be formed such that no additional material such as glue or stitching, is necessary to join the inner and outer layers 6352, 6354 together.

Each of the inner layer 6352 and the outer layer 6354 may include an interior surface and an exterior surface. The interior surface of the inner layer 6352 is the surface that faces the exterior layer 6354. The interior surface of the exterior layer 6354 is the surface that faces the inner layer 6352. Likewise, the exterior surface of the outer layer 6354 faces away from the inner layer 6352 and the exterior surface of the inner layer 6352 faces away from the outer layer 6354. Further, in forms that include a single sheet, the interior surface is the surface of the sheet that faces inwards and towards itself.

In some forms, the sheet or sheets of the tube may include an air impermeable layer or membrane. In some forms, the interior surface of both of the layers includes a membrane that is configured to restrict or restrain air from passing through the layer from the interior surface to the exterior surface. The impermeable layer may be a thin layer that is less than the thickness of the textile sheets of the inner layer or outer layer. In other forms, the impermeable layer may be greater than the thickness of the sheets of textiles of either of the layers. The impermeable layer or membrane or film may be completely impermeable to air transfer or may be formed to allow a predetermined rate or air transfer and particular pressures.

The membrane may be formed of thermoplastic or thermoset materials such that when exposed to a particular temperature membrane material may be able to be molded or shaped into a particular form and then cures or solidifies or sets upon cooling. In some forms the membrane may be formed of silicone or polyurethane. In some forms, outer layer 6354 may be pre-formed such that in an unpressurized or supported state, outer layer 6354 is pre-positioned and pre-formed to extend away from inner layer 6352 between the opposing joints 6312. That is, outer layer 6354 may support its own weight such that when not supported by pressurized air or other support mechanism, outer layer 6354 remains spaced from inner layer 6352 between joints 6312.

In contrast, inner layer 6352 may be a floppy component. Inner layer 6352 may be attached and secured to the edges of outer layer 6354 such that inner layer 6352 is a substantially planar layer.

As shown in FIG. 8, and in particular FIG. 9, inner layer 6352 comprises a textile sheet 6360 along with membrane 6362. Textile sheet 6360 may be formed of felt, foam, woven, knit, or non-woven material or other network of fibers.

Outer layer 6354 includes tube sheet 6364 and outer covering 6366. In some forms, both sides of tube sheet 6364 may be covered with a membrane. As shown in FIG. 10, tube sheet 6364 includes membrane 6368 exposed to the chamber of tube 6350 and membrane 6370 along an opposite surface of tube sheet 6364. membrane 6368 may assist in providing a seal between inner layer 6352 and outer layer 6354 as well as forming an air tight tube. Membrane 6370 may assist in joining tube sheet 6364 to outer covering 6366.

5.3.2.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. The vent 3400 may comprise a plurality of holes, as described above. The holes of the vent 3400 may be divided into two groups spaced apart laterally. The axis of the flow path through each of the holes of the vent 3400 may be parallel such that cross-flow is avoided to prevent generation of additional noise. The vent holes may be circular.

The holes of the vent 3400 may decrease in radius from the interior of the plenum chamber 3200 to the exterior. Each vent hole is provided with a draft angle. Each hole has a smaller diameter at its anterior end than at its posterior end. The draft angle means that the holes do not have a small cross section across the entire chassis thickness, which helps to provide effective carbon dioxide wash out at high levels of humidification. Additionally, a larger draft angle may result in a plenum chamber 3200 that is easier to manufacture, especially when the plenum chamber 3200 is formed from an injection moulded plastics material. The draft angle enables relatively thick vent pins to be used in the mould and easier ejection.

The holes of the vent 3400 may be provided in two sets towards the middle of the plenum chamber 3200 and the sets may be symmetrical across the centreline of the plenum chamber 3200. Providing a pattern of multiple vent holes may reduce noise and diffuse the flow concentration.

The holes of the vent 3400 may be placed at an optimum distance away from the centreline of the plenum chamber 3200. Placing the holes of the vent 3400 towards the centreline may advantageously reduce the chance that the vent holes are blocked when the patient is sleeping on their side. However, placing the vent holes too close to the middle of the plenum chamber 3200 may result in excessive weakening of the plenum chamber 3200 at the center, especially since the cross-section of the plenum chamber 3200 in the depicted examples is smallest at the center due to the overall shape of the plenum chamber 3200. The location of the holes of the vent 3400 may avoid hole blockage during side sleep while leaving the middle section of the chassis sufficiently strong.

The size of each vent hole and the number of vent holes may be optimised to achieve a balance between noise reduction while achieving the necessary carbon dioxide washout, even at extreme humidification. In the depicted examples, the vent holes of the vent 3400 may not provide the total amount of venting for the system. The decoupling structure 3500 may include a decoupling structure vent 3402. The decoupling structure vent 3402 may include one hole or a plurality of holes through the decoupling structure 3500. The decoupling structure vent 3402 may function to bleed off excess pressure generated by the RPT device 4000 before reaching the patient, while the vent 3400 may function to washout carbon dioxide exhaled by the patient during therapy.

In some examples, a vent insert (not shown) attaches, removably or permanently, to the plenum chamber 3200 at a vent insert opening. The vent insert may be constructed from a material that is more flexible than the material of the plenum chamber 3200. In one example, heat and moisture exchanging (HME) material (e.g., a foam) is housed in the removable vent, in order to humidify air the patient inhales, without the need for a separate humidifier. The vent insert may be removable in order to allow the patient to replace the HME material after a certain time period as past, with a fresh, clean sheet of HME material. In addition, the entire vent structure could be replaceable (e.g., as opposed to the HME material alone).

5.3.2.5 Decoupling Structure(s)

In one form the patient interface 3000 includes at least one decoupling structure, for example, a swivel or a ball and socket.

The hub 3306, described above, is connected to a decoupling structure 3500, which is a rotatable elbow in these examples. The decoupling structure 3500 may be rotatable 360° within the hub 3306 in use. The decoupling structure

3500 may be removable from the hub 3306 by manually depressing buttons 3504 to release catches (not shown) from within the hub 3306.

The decoupling structure 3500 may also include a swivel 3502 that allows for rotatable connection to an air circuit 4170.

The rotatability of the decoupling structure 3500, the decoupling structure 3500 being in the form of an elbow, and the rotatability of the swivel 3502 on the decoupling structure 3500 may all increased the degrees of freedom, which in turn reduce tube drag and torque on the patient interface 3000 caused by the connection to the air circuit 4170.

5.3.2.6 Connection Port

Connection port 3600 allows for connection to the air circuit 4170.

5.3.2.7 Forehead Support

In one form, the patient interface 3000 includes a forehead support 3700.

5.3.2.8 Anti-Asphyxia Valve

In one form, the patient interface 3000 includes an anti-asphyxia valve.

5.3.2.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.3.3 Full Face Cushion

Referring to FIGS. 26-33, patient interface 6000 includes cushion assembly 6105 having a seal-forming structure 6100 that is configured to seal separately around the patient's nares and mouth (e.g., an oro-nasal cushion assembly or ultra-compact full face mask). The cushion assembly 6105 is at least partially formed by a plenum chamber 6200 and a seal-forming structure 6100 that is attached to the plenum chamber in accordance with an example of the present technology.

Referring to FIGS. 22-25 and 34-39, a cushion assembly 9105 is shown. Cushion assembly 9105 is similar to cushion assembly 6105 and has a seal-forming structure 9100 that is configured to seal separately around the patient's nares and mouth (e.g., an oro-nasal cushion assembly or ultra-compact full face mask). The cushion assembly 9105 is at least partially formed by a plenum chamber 9200 and a seal-forming structure 9100 that is attached to the plenum chamber in accordance with an example of the present technology.

The cushion assembly 9105 includes nasal portion 9101, nasal portion holes 9103, oral portion 9102, oral portion hole 9104, cavity 9001, support structure 9120, sealing portion 9130, and vent 9400 which are similar to the features described in FIG. 26-33. The description of FIGS. 26-33 may generally apply to FIGS. 22-25 and 34-39, and many similarities and differences not discussed separately. A pair of plenum chamber holes are configured to receive a flow of air.

The cushion assembly 9105 (e.g., specifically the nasal portion 9101) may include at least one curved surface as a result of the connection to the support structure 9120. This curved surface may extend from an anterior to a posterior side of the cushion assembly 9105 (see e.g., FIG. 24). A similar curvature may be present on the cushion assembly 6105 (see e.g., FIGS. 30 and 31). However, unlike the cushion assembly 6105, the cushion assembly 9105 (e.g., specifically the nasal portion 9101) may include at least one curved surface, which may be the result of a crimp in the nasal portion 9101, which is described in more detail below. The curved surface of the cushion assembly 9105 resulting from the crimp may extend along a lateral direction of the patient's face (e.g., in the left-right direction) while the cushion assembly 9105 is in use. For example, the curved surface of the cushion assembly 9105 that results from the crimp may curve about an axis perpendicular to an axis through section line 36-36 (see e.g., FIG. 34), and/or about a third axis 13000 (described in detail below). The curved surface resulting from the crimp may also have a positive curvature relative to the patient's face.

As described earlier, FIGS. 37-39 show grip pads 9150 on the surface of the textile membrane. The grip pads 9150 may be on the first sealing portion 9131 and/or the second sealing portion 9132. Although illustrated with the cushion assembly 9105, the grip pads 9150 may also be incorporated into the cushion assembly 6105.

Referring to FIG. 33-1, patient interface 21000 includes a cushion assembly 21105 with a seal-forming structure 21100 that is configured to seal around the patient's nares and mouth (e.g., an oro-nasal cushion assembly or ultra-compact full face mask). The cushion assembly 21105 is similar to the cushion assemblies 6105 and 9105. The cushion assembly 21105 is at least partially formed by a plenum chamber 21200 and the seal-forming structure 21100 that is attached to the plenum chamber in accordance with an example of the present technology. The seal-forming structure 21100 may also include a curved surface like the nasal portion 9101.

Referring to FIG. 33-2, patient interface 23000 includes a cushion assembly 23105 with a seal-forming structure 23100 that is configured to seal around the patient's nares and mouth (e.g., an oro-nasal cushion assembly or ultra-compact full face mask). The cushion assembly 23105 is similar to the cushion assemblies 6105 and 9105. The cushion assembly 23105 is at least partially formed by a plenum chamber 23200 and the seal-forming structure 23100 that is attached to the plenum chamber in accordance with an example of the present technology. The seal-forming structure 23100 may also include a curved surface like the nasal portion 9101.

Referring to FIGS. 33-3 to 33-11, patient interface 25000 includes a cushion assembly 25105 with a seal-forming structure 25100 that is configured to seal around the patient's nares and mouth (e.g., an oro-nasal cushion assembly or ultra-compact full face mask). The cushion assembly 25105 is similar to the cushion assemblies 6105 and 9105. The cushion assembly 25105 is at least partially formed by a plenum chamber 25200 and the seal-forming structure 25100 that is attached to the plenum chamber in accordance with an example of the present technology. The seal-forming structure 25100 may also include a curved surface like the nasal portion 9101.

The full face cushions of FIGS. 22-39 may have some similarities to the nasal cushion 3000 described above. For example, the seal-forming structures described in more detail below, may have tension selectively applied in order to assist in forming a resulting shape (e.g., a two-dimensional shape or a three-dimensional shape). Various similarities and differences between the full face cushions and the nasal cushion 3000 are described below.

5.3.3.1 Plenum Chamber

The plenum chamber 6200 has a perimeter that is shaped to be complementary to the surface contour of the face of an average person in the region where a seal will form in use. In use, a marginal edge of the plenum chamber 6200 is positioned in close proximity to an adjacent surface of the face. Actual contact with the face is provided by the seal-forming structure 6100. The seal-forming structure 6100 may extend in use about the entire perimeter of the plenum chamber 6200.

In certain forms of the present technology, the plenum chamber 6200 is constructed from a relatively rigid material (e.g., polycarbonate) as compared to the seal-forming structure 6100. In another example, the plenum chamber 6200 is constructed from a flexible material (e.g., silicone, textile, etc.), and may have a similar rigidity as compared to the seal-forming structure 6100. In another example, the plenum chamber 6200 may be constructed from a transparent material, e.g. a transparent polycarbonate. The use of a transparent material can reduce the obtrusiveness of the patient interface 6000, and help improve compliance with therapy. The use of a transparent material can aid a clinician in observing how the patient interface 6000 is located and functioning and/or in observing any build-up of debris (e.g., dirt, mold, etc.).

In certain forms of the present technology, the plenum chamber 6200 is constructed from a translucent material. The use of a translucent material can reduce the obtrusiveness of the patient interface 6000, and help improve compliance with therapy.

The plenum chamber 6200 according to examples of the present technology may include a plenum chamber hole on each lateral side. The plenum chamber hole may provide pneumatic communication between the conduit connectors 6800, which are described in greater detail below, and the cavity 6001. A connection rim portion around each plenum chamber hole may facilitate a mechanical connection, e.g., snap-fit or friction fit, with the respective conduit connector. The plenum chamber 6200 may be constructed of a sufficiently rigid material to provide audible and/or tactile feedback to the patient when the conduit connectors 6800 are connected to or removed from the plenum chamber 6200.

The seal-forming structure 6100 may be sealingly connected to the plenum chamber 6200. The connection may be permanent or the seal-forming structure 6100 may be removable from the plenum chamber 6200. The seal-forming structure 6100 may be molded (e.g., overmoulded, injection molded, etc.) to the plenum chamber 6200. The seal-forming structure 6100 and the plenum chamber 6200 may be joined by a mechanical connection in which no chemical bond is formed between the plenum chamber 6200 and the seal-forming structure 6100.

5.3.3.2 Seal-Forming Structure

Referring to FIGS. 26-33, the seal-forming structure 6100 may include a nasal portion 6101 that has at least one hole (e.g., a pair of nasal portion holes 6103) to seal with, and convey pressurized air to, the patient's nares. The depicted examples provide two separate holes 6103 that each corresponds to one of the patient's nares to provide the flow of air to both of the patient's nares. There may also be a bridge portion 6106 positioned between the naris openings 6103. In an alternative example, a single hole may be used to provide the flow of air to both of the patient's nares. A further alternative may include three or more holes. Unlike the bridge portion 3104, the bridge portion 6106 may not be selectively tensioned. For example, the bridge portion 6106 and the surrounding material of the nasal portion 6101 may be held under tension together, instead of tension being applied only to the bridge portion 6106.

Referring briefly to FIGS. 22-25 and 34-39, the bridge portion 9106 may be selectively tensioned in a similar manner as the bridge portion 3104. For example, the bridge portion 9106 may be tauter than the surrounding first sealing portion 9131.

With continued reference to FIGS. 26-33, the seal-forming structure 6100 may include an oral portion 6102 having an oral portion hole 6104 to seal with the patient's mouth. In some examples, the oral portion 6102 is held at least partially in tension (e.g., at any number of discrete locations) when not in use (i.e., when not contacting the patient's face). For example, the oral portion may be in tension at a join with the support structure 6120, but relaxed on an exposed sealing edge (e.g., an inner edge proximate to an opening of the cavity 6001). In some examples, the oral portion 6102 is entirely in a relaxed state when not in use. In any of the examples, contact with the patient's face may stretch the oral portion 6102, so that it is under tension while in use.

The seal-forming structure 6100 may at least partly form a cavity 6001 that is pressurized by the flow of air. The plenum chamber 6200 may be joined to the seal-forming structure 6100 to further form the cavity 6001.

The seal-forming structure 6100 may include a support structure 6120 that provides support to a sealing portion 6130 (e.g., a textile membrane). The sealing portion is configured to sealingly engage the patient's face. The sealing portion 6130 is large enough (e.g., curves in the anterior direction a sufficient amount) so that only the sealing portion 6130 (e.g., only the textile membrane) may contact and sealingly engage a patient's face. Alternatively, the support structure 6120 may also be constructed from a textile material.

In one example, the seal-forming structure 6100 may include a support structure 6120 having at least two regions (e.g., two, three, or four regions) of different thickness (e.g., seal-forming structure 6100 comprises support structure 6120 which has a wall structure having lateral support regions (see e.g., 3122 in FIGS. 58 and 59) of an increased thickness with respect to other portions of the wall structure). For example, as shown in FIGS. 58 and 59, some portions 3123 of the support structure 3120 may be thicker than other portions 3124, 3126 of the support structure 3120. For example, thicker portions 3123 may be adjacent to or connecting to the plenum chamber and portions 3124, 3126 may be adjacent to or connecting to the textile membrane 3130 so as to provide structural stability at the connection with the plenum chamber 3200 and flexibility at the interface with the patient. Alternatively, the thicker portions of the lateral support regions 3122 may be located, for example, at the corner of nose region of the seal-forming structure (and e.g., may connect directly to the textile membrane), to ensure adequate sealing in the subalare region of the patient's face.

As described above, the seal-forming structure 6100 may be sealingly connected to the plenum chamber 6200. The support structure 6120 may be less rigid than the plenum chamber 6200 and may be constructed from silicone, foam (e.g., polyurethane foam), polyurethane solid material, thermoplastic elastomers (e.g., thermoplastic polyurethane), suitable plastics, or other suitable materials, as will be described later. Further, the sealing portion 6130 may be less rigid than the support structure 6120 and may be constructed from a textile material 6130 such as nylon, polyester, nylon and polyester mix, microfiber or polyurethane, for example, as will be described in more detail later.

In the example of FIG. 32, the support structure 6120 may extend into the cavity 6001 forming an underlying cushion 6121 to provide support to the sealing portion 14130. The underlying cushion 6121 and the sealing portion 6130 may form a dual wall structure around the perimeter of sealing portion. In alternative examples, a second or third underlying cushion layer may be provided to form a triple or quadruple wall structure. In the example of FIG. 32, the underlying cushion is constructed of a foam material (e.g., polyurethane foam). In an alternative example, the underlying cushion 6122 may be constructed of silicone, as shown in FIG. 33. However, it will be recognized that the underlying cushion may be constructed from other suitable materials (e.g., textile).

The sealing portion 6130 may be constructed from two different pieces of a textile membrane. For example, one piece 6131 may be used to seal around the patient's nose, while a separate piece 6132 may be used to seal around the patient's mouth. The sealing portions 6131, 6132 may be used to independently seal around the respective orifice. In other words, the first or upper sealing portion 6131 may not contact the area around the patient's mouth, and the second or lower sealing portion 6132 may not contact the area around the patient's nose.

As shown in FIGS. 26-33, the first sealing portion 6131 is disposed in a superior portion (i.e., when in use) of the patient interface 6000 as compared to the second sealing portion 6132. The first sealing portion 6131 forms a round (e.g., generally tri-oval) perimeter that seals around the patient's nares while in use.

In some forms, the first sealing portion 6131 may contact a region between the nasal ala and the lip superior, while leaving the pronasale exposed (see e.g., FIGS. 23-25 illustrating the similar first sealing portion 9131). The textile membrane of the first sealing portion 6131 may be the only material of the seal-forming structure 6100 to contact the patient in this region. In other words, the second sealing portion 6132 and the support structure 6120 do not contact the patient in this region. This may assist in improving patient compliance because the patient may only contact a textile layer in this region of their face, which they may more closely associate with bedclothes, instead of a medical device.

The second sealing portion 6132 is disposed in an inferior portion (i.e., when in use and as compared to the first sealing portion 6131) of the patient interface 6000. In the illustrated example, the second sealing portion 6132 forms a generally U-shape, and seals around a portion of the patient's mouth. The textile membrane that forms the second sealing portion 6132 does not extend completely around the patient's mouth. In other words, a material other than the textile membrane may contact the patient in order to form a seal around the patient's mouth. In this example, the support structure 6120 (e.g., a silicone material) is molded between free ends of the second sealing portion 6132 in order to complete an oral portion hole 6104. The textile membrane of the second sealing portion 6132 may contact the patient's lip inferior, a region outside the patient's cheillion, and a portion of the patient's lip superior, and may not contact the central portion of the patient's lip superior (e.g., proximate to the patient's philtrum). The support structure 6120 extends across the patient's philtrum, between the ends of the second sealing portion 6132. A combination of the textile membrane of the sealing portion 6130 and the silicone material of the support structure 6120 may be responsible for creating a seal around the patient's mouth.

The support structure 6120 extends from a lower surface of the first sealing portion 6131 to an opening of the cavity 6001. In other words, the first sealing portion 6131 is separated from the second sealing portion 6132 by the support structure 6120. The material (e.g., silicone) of the support structure 6120 also assists in coupling the first sealing portion 6131 and the second sealing portion 6132 to each other during the manufacturing process.

As shown in FIG. 33-1, the second sealing portion 21130b extends completely around the patient's mouth. In other words, textile membrane contacts the philtrum as opposed to the support structure 21120. The support structure 21120 (e.g., silicone material) is disposed in the inferior/superior direction between the first and second sealing portions 21130a, 21130b (e.g., first and second sub-sections). The support structure 21120 may slightly contact the patient's lip superior, although sealing is accomplished primarily or exclusively via the textile membrane in the first and second sealing portions 21130a, 21130b. In other words, a location where support structure 21120 contacts the patient's skin may be unpressurized and/or exposed to ambient during therapy. Having the second support structure 21130b extend all the way around the patient's mouth may provide the patient with more comfort as compared with the U-shaped second sealing structure 21130b (e.g., because the patient may find the textile membrane more comfortable than the silicone), which may increase the patient's compliance with the therapy.

In another example of the patient interface 23000, as shown in FIG. 33-2, the second sealing portion 23130b is U-shaped. However, the philtrum and central portion of the lip superior are contacted by textile membrane. In this example, the first sealing portion 23130a extends down to an edge of the oral portion hole 23104. In other words, the first sealing portion 23130a is responsible for forming the seal around the patient's nose, and is also partially responsible for forming the seal around the patient's mouth. The U-shaped second sealing portion 23130b extends substantially around the remainder of the patient's mouth (although a small portion of the support structure 23120 is disposed laterally between the first and second sealing portions 23130a, 23130b in the left/right direction). This example may provide similar comfort benefits as described above with respect to FIG. 33-1 (e.g., because substantially all of the patient's nose and mouth contact by the patient interface 23000 is contacted by the textile membrane). However, the example of FIG. 33-2 may be easier to manufacture because the support material 23120 between the first and second seal portions 23130a, 23130b is removed in the superior/inferior direction. The small portions of the support structure 23120 between the sealing portions 23130a, 23130b may assist in forming the pressurized volume around the patient's mouth.

In other example of the patient interface 25000, as shown in FIG. 33-3, the sealing portion 25130 is formed from a single piece of textile material. In other words, the first and second sealing portions 25130a, 25130b are not constructed from separate pieces of material. The single piece of material that forms the sealing portion 25130 is responsible for forming a seal around both the patient's nose and the patient's mouth. The sealing portion 25130 may have a similar outer perimeter as described above (e.g., in examples of the patient interface 25000 having first and second sealing portions 25130). In some examples, the sealing portion 25130 may only seal around its outer perimeter, since not sealing against the patient's lip superior may not allow air to leak out of the seal-forming structure 25100. However, the sealing portion 25130 may still seal against the patient's lip superior so that pressurized air is more directly delivered to the patient's airways. By using a single piece of textile membrane to form the sealing portion 25130, the support structure 25120 may not contact the patient's upper lip. Additionally, manufacturing the patient interface may be easier because the thin strip of support structure 25120 no longer needs to be formed between two pieces of textile membrane to connect them together. Thus, the molding process may be simplified so that small amounts of a material like silicone do not need to flow between, but not cover a textile layer 10133.

As shown in FIGS. 22 to 25 and 31-1 to 39, the respective seal forming structures may all have a three-dimensional shape. Specifically, the respective first sealing portions may have a curved surface (e.g., in left-right direction), as opposed to the flat surface (e.g., in the left-right direction) shown in FIGS. 26-33. The three-dimensional shape may be formed, at least in part, by selectively applying tension to the bridge portion of the respective first sealing portion. Tension may not be applied to the material of the first sealing portion surrounding the bridge portion on the respective seal forming structures so that the first sealing portion may include a curved shape.

In any of these embodiments (e.g., FIGS. 22-39), the strength of the seal against the patient's face is substantially the same. For example, having textile material alone, or a combination of textile and silicone material does not substantially effect the quality of the seal (i.e., increase or decrease areas of leak). Different patients (e.g., different facial geometries) may be better suited for one of the particular examples over the others (e.g., because of comfort, fit, etc.). Additionally, while examples with more textile coverage may provide additional comfort to the patient, the added comfort may be minimal (e.g., since the support structure 6120 provides minimal contact in examples with both the first and second sealing portions 6131, 6132).

5.3.3.3 Positioning and Stabilising Structure

The seal-forming structure 9100 of the patient interface 9000 of the present technology may be held in sealing position in use by the positioning and stabilising structure 9300. While the positioning and stabilizing structure 9300 is specifically shown with the patient interface 9000, it may be used with any of the full face cushions (e.g., any example in FIGS. 22-39). The positioning and stabilizing structure 9300 may also be similar to the positioning and stabilizing structure 3300.

In one form the positioning and stabilising structure 9300 provides a retention force at least sufficient to overcome the effect of the positive pressure in the cavity 9001 to lift off the face.

In one form the positioning and stabilising structure 9300 provides a retention force to overcome the effect of the gravitational force on the patient interface 9000.

In one form the positioning and stabilising structure 9300 provides a retention force as a safety margin to overcome the potential effect of disrupting forces on the patient interface 9000, such as from tube drag, or accidental interference with the patient interface.

In one form of the present technology, a positioning and stabilising structure 9300 is provided that is configured in a manner consistent with being worn by a patient while sleeping. In one example the positioning and stabilising structure 9300 has a low profile, or cross-sectional thickness, to reduce the perceived or actual bulk of the apparatus. In one example, the positioning and stabilising structure 9300 comprises at least one strap having a rectangular cross-section. In one example the positioning and stabilising structure 9300 comprises at least one flat strap.

In one form of the present technology, a positioning and stabilising structure 9300 is provided that is configured so as not to be too large and bulky to prevent the patient from lying in a supine sleeping position with a back region of the patient's head on a pillow.

In one form of the present technology, a positioning and stabilising structure 9300 is provided that is configured so as not to be too large and bulky to prevent the patient from lying in a side sleeping position with a side region of the patient's head on a pillow.

In one form of the present technology, a positioning and stabilising structure 9300 is provided with a decoupling portion located between an anterior portion of the positioning and stabilising structure 9300, and a posterior portion of the positioning and stabilising structure 9300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 9300 and disrupting the seal.

In one form of the present technology, a positioning and stabilising structure 9300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion. In one form, conduits 9900 for delivering air to the cushion assembly 9105 may also make up the positioning and stabilizing structure 9100.

In certain forms of the present technology, a positioning and stabilising structure 9300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure may include a first tie (e.g., upper strap 9302 (FIG. 24)), the first tie being constructed and arranged so that in use at least a portion of an inferior edge thereof passes superior to an otobasion superior of the patient's head.

In one form of the present technology suitable for a full-face mask, the positioning and stabilising structure includes a second tie (e.g., lower strap 9303 (FIG. 24)), the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie (e.g., strap connector 9304 (FIG. 22)) that is constructed and arranged to interconnect the first tie and the second tie to reduce a tendency of the first tie and the second tie to move apart from one another.

In certain forms of the present technology, a positioning and stabilising structure 9300 comprises a strap that is bendable and e.g. non-rigid. An advantage of this aspect is that the strap is more comfortable for a patient to lie upon while the patient is sleeping.

In certain forms of the present technology, a positioning and stabilising structure 9300 comprises a strap constructed to be breathable to allow moisture vapour to be transmitted through the strap, In certain forms of the present technology, a system is provided comprising more than one positioning and stabilizing structure 9300, each being configured to provide a retaining force to correspond to a different size and/or shape range. For example, the system may comprise one form of positioning and stabilizing structure 9300 suitable for a large sized head, but not a small sized head, and another suitable for a small sized head, but not a large sized head.

The positioning and stabilising structure 9300 may include a clip 9301 to secure respective ties, e.g., to the conduit connectors 9800 as shown in FIG. 22. The clip 9301 and the conduit connector 9800 may each include a magnet arranged with opposing polarities to facilitate a connection therebetween.

5.3.3.4 Vent

In one form, the patient interface 6000 includes a vent 6400 constructed and arranged to allow for the washout of exhaled gases, e.g. carbon dioxide, as shown in FIG. 30.

In certain forms, the vent 6400 is configured to allow a continuous vent flow from an interior of the plenum chamber 6200 to ambient whilst the pressure within the plenum chamber is positive with respect to ambient. The vent 6400 is configured such that the vent flow rate has a magnitude sufficient to reduce rebreathing of exhaled $CO_2$ by the patient while maintaining the therapeutic pressure in the plenum chamber in use.

One form of vent 6400 in accordance with the present technology comprises a plurality of holes, for example, about 20 to about 80 holes, or about 40 to about 60 holes, or about 45 to about 55 holes.

A vent 6400 may be located in the plenum chamber 6200. Alternatively, a vent 9404 is located in a decoupling structure, e.g., a swivel (see e.g., FIG. 22).

The conduit connectors 6800, which are described in greater detail below, may also include vent features.

5.3.3.5 Decoupling Structure(s)

In one form, the patient interface 9000 includes at least one decoupling structure, for example, a swivel or a ball and socket.

5.3.3.6 Connection Port

Connection port 6600 allows for connection to the tube 6348 of air circuit 4170 (see e.g., FIG. 7). The connection port 9600 according to an example of the present technology may be connected to the connection port housing 9903 (see e.g., FIG. 22). The connection port 9600 may be swivelable relative to the connection port housing 9903 and the connection to the air circuit 4170 may also be swivelable.

The connection port 9600 and the connection port housing 9903 may be positioned superior to the patient's head in use.

5.3.3.7 Forehead Support

Examples of the patient interfaces of the present technology shown in FIGS. 22-39 do not include a forehead support. Variations of the patient interface of the present technology may include a forehead support.

5.3.3.8 Conduits

The patient interface 9000 according to examples of the present technology may include conduits 9900 to provide the flow of pressurized air from the connection port 9600 to the cavity 9001 in the plenum chamber 9200. The conduits 9900 may be similar to the lateral portions 3302 and superior portions 3304 of FIG. 6, and to the tube 6350 of FIG. 7. The conduits 9900 may be joined superior to the patient's head at the connection port housing 9903 and may pass along lateral sides of the patient's head between corresponding ones of the patient's eyes and ears. The conduits 9900 may be connected to the cushion assembly 9105 (e.g., plenum chamber 9200) via conduit connectors 9800, as described below, to provide the flow of pressurized air to the cavity 9001.

The conduits 9900 may also stabilize and position the seal-forming structure 9100 on the patient's face. Thus, the conduits 9900 may function similarly to the ties of the positioning and stabilising structure 9300. Accordingly, the mechanical connection of the conduits 9900 to the conduit connectors 9800 may be sufficient for tension forces in the conduits 9900 to be transmitted to the seal-forming structure 9100 through the conduit connectors 9800.

The conduits 9900 may include features of similar conduits disclosed in International Application Publication No. WO 2017/124155 A1, which is hereby incorporated by reference herein in its entirety. For example, the conduits 9900 of the present technology may include features of the headgear tubes 3350 depicted in FIGS. 3A-3L of this document, as well as the associated written description.

The conduits 9900 may also be provided with sleeves 9901 to cushion the patient's face against the conduits 9900. The sleeves 9901 may be removable. The sleeves 9901 may be made from a breathable material.

The conduits 9900 may also include tie connectors 9902 to facilitate connection with ties of the positioning and stabilising structure 9300.

5.3.3.9 Conduit Connectors

As shown in FIGS. 26-33, the patient interface 6000 may include several views of conduit connectors 6800 of the patient interface 6000, according to examples of the present technology. The conduit connectors may connect the conduits to the cushion assembly 6105 to provide the flow of pressurized air to the cavity 6001. These conduit connectors 6800 may be similar to the conduit connectors 9800 (see e.g., FIGS. 22-25), and the following description may equally apply to the conduit connectors 9800.

The conduit connectors 6800 may each be formed with a conduit connector housing 6801. The conduit connectors 6800 may provide other functions, as described below, such as venting of the plenum chamber 6200, connection to the positioning and stabilising structure, and asphyxia prevention by inclusion of an anti-asphyxia valve 6850.

In FIGS. 26-33, the conduit connectors 6800 are shown attached to the plenum chamber 6200 at the plenum chamber holes (see e.g., similar plenum chamber holes 9210). As can be seen, there is one conduit connector 6800 on each lateral side of the cushion assembly 6105, and each conduit connector 6800 is connected to a plenum chamber hole on each corresponding lateral side of the cushion assembly 6105. The conduit connectors 6800 may each include a conduit connector attachment structure to connect each of the conduit connectors 6800 to a respective plenum chamber hole at the connection rim (not shown). The connection may be mechanical, e.g., snap-fit or friction fit. The connection may also be removable. The material of the conduit connectors 6800 and the material of the plenum chamber 6200 may each be selected to facilitate the desired connection features. For example, the material of the conduit connectors 6800 and the material of the plenum chamber 6200 may each be relatively rigid to permit the audible and/or tactile feedback associated with a snap-fit. The material of the conduit connectors 6800 and the material of the plenum chamber 6200 may be different in at least one aspect or the materials may be the same. The conduit connectors 6800 may also be permanently connected to the plenum chamber at the plenum chamber holes. For example, the conduit connectors 6800 may be ultrasonically welded to the plenum chamber 6200. The connection between the conduit connectors 6800 and the plenum chamber 6200, whether removable or permanent, may also be designed to be sufficiently strong such that tension from the conduits can be transferred to the plenum chamber 6200 without disrupting the connection because, as explained above, the conduit connectors 6800 may facilitate positioning and stabilising of the seal-forming structure 6100 on the patient's head.

The conduit connectors 6800 may also be attached to lateral sides of the plenum chamber 6200 to improve aesthetics of the patient interface 6000. As explained above, the plenum chamber 6200 may be constructed of a transparent or translucent material, which may allow visibility of the patient's facial features. By locating the conduit connectors 6800 laterally on the plenum chamber, e.g., as shown in the depicted examples, more of the patient's face is visible, and that arrangement can improve aesthetics of the patient interface 6000. This contrasts with alternative designs where an elbow and air circuit may be joined to the center of the plenum chamber 6200, thereby obstructing the view of the patient's face.

The conduit connectors 6800 may also each include a conduit connection end 6802 that connects to a respective conduit (e.g., similar to the conduit 9900 in FIG. 22). The connection between the conduits and the conduit connectors 6800 at the conduit connection ends 6802 may be removable or permanent. A conduit connector inlet hole 6803 may be formed in the conduit connector housing 6801 at the conduit connection end 6802 to receive the flow of pressurized air. The conduit connectors 6800 may include structure, e.g., an undercut, to facilitate a removable, snap-fit connection with corresponding conduits, and each conduit may include a relatively rigid structure at the end that connects to the conduit connectors 6800 to facilitate such a connection. The conduit connectors 6800 may also be joined to the conduits with a friction fit, a snap-fit, or any similar fit. Again, as explained above, the conduits may provide a positioning and stabilising function to locate the seal-forming structure in a therapeutically effective sealing position on the patient's face, and therefore the connection between the conduits and the conduit connectors 6800 at the conduit connection ends 6802 may be sufficiently secure to permit tension forces from the conduits to be transmitted to the conduit connectors 6800 without disrupting the connection between the conduits and the conduit connectors 6800 at the conduit connection ends 6802.

As shown in FIG. 29, the conduit connectors 6800 may also provide a venting function for the patient interface 6000. The conduit connector housing 6801 may include a vent inlet that is in pneumatic communication with the cavity 6001 when the patient interface 6000 is assembled. The conduit connector housing 6801 may also include at least one conduit connector vent hole 6831. As can be seen in the depicted examples, each conduit connector housing 6801 includes a plurality of conduit connector vent holes 6831. This ensures adequate mixing of newly introduced air and air already present in the plenum chamber 6200, which can enhance carbon dioxide washout and increase the amount of fresh air provided to the patient for respiration.

As shown in FIG. 22-24, the similar conduit connectors 9800 may also provide a connection to ties of the positioning and stabilising structure 9300. The inferior ties may be joined to the conduit connectors 9800 with clips 9301. The clips 9301 and the conduit connectors 9800 may include magnets with opposing polarities to facilitate the connection. The connection between the ties of the positioning and stabilising structure 9300 and the conduit connectors 9800 may be releasable. The tension from the inferior ties of the positioning and stabilising structure 9300 may urge inferior portions of the seal-forming structure 9100 into sealing engagement with the patient's face, e.g., around the mouth. Alternatively, structure to connect to the clips 9301 may be formed directly on a conduit connector housing.

5.3.3.10 Anti-Asphyxia Valve

In one form, the patient interface 6000 includes an anti-asphyxia valve. As best shown in FIGS. 30 and 31, each of the conduit connectors 6800 may include an anti-asphyxia valve assembly 6850. Accordingly, the patient interface 6000 may include two anti-asphyxia valve assemblies 6850. Each of the anti-asphyxia valve assemblies 6850 may operate independent of the other, i.e., in response to a cessation of the flow of pressurized air. For example, if the patient is sleeping on his or her side when there is a cessation of the flow of pressurized air and one of the anti-asphyxia valve assemblies 6850 is occluded, e.g., by a pillow, the other of the anti-asphyxia valve assemblies 6850 can function to prevent the patient from being asphyxiated. Although not explicitly shown, the patient interfaces of FIGS. 22 to 25 and 33-1 to 39 may also include at least one anti-asphyxia valve.

5.3.3.11 Ports

In one form of the present technology, a patient interface 6000 includes one or more ports that allow access to the volume within the plenum chamber 6200. In one form this allows a clinician to supply supplemental oxygen. In one form, this allows for the direct measurement of a property of gases within the plenum chamber 6200, such as the pressure. Although not explicitly shown, the patient interfaces of FIGS. 22 to 25 and 33-1 to 39 may also include at least one port.

5.3.4 Support Structure and Sealing Portion Arrangements

The support structures and sealing portions in the examples described above may have a number of different configurations and arrangements.

In use, the sealing portion 3130 (e.g., textile membrane) may be maintained in sealing contact with the patient's face by 1) a reactive stress of the support structure 3120; 2) a pre-formed state of the textile membrane 3130 formed as a non-tensioned, yet substantially constant surface, without leak causing interruptions such as creases, folds, buckles or wrinkles in the textile membrane 3130; and/or 3) air pressure within the cavity against an inside surface of the sealing portion 3130. Each of these factors may contribute to the sealing portion 3130 complying with the anthropometric contours of the patient's face, thereby minimizing wrinkles or blow-out and maximizing the contact area of the sealing portion 3130. Tension in the sealing portion 3130 may increase as a result of any of these factors, but the sealing portion 3130 may return to a relaxed state with the removal of the associated factor.

In some examples, the sealing portion 3130 may comprise a relatively thin, compliant, stretchable, elastic material, such as a textile membrane comprising a suitable textile material (e.g., nylon, polyester, nylon and polyester mix, microfiber or polyurethane). The sealing portion 3130 may be molded or otherwise attached (e.g., adhered, glued) to the support structure 3120 so that there are no wrinkles in the material of the sealing portion 3130. This may be advantageous in ensuring that the sealing portion forms a smooth and continuous seal on the patient's face without any folded sections through which air may leak. Further, the sealing portion 3130 may be shaped or have curvature imparted thereto. The support structure 3120 may also impart curvature to the sealing portion 3130. In the illustrated examples, the sealing portion 3130 may include curvatures about multiple axes. This may assist the sealing portion 3130 in contouring to the complex facial structure of different patients.

For example, as shown in FIGS. 12-21 the sealing portion 3130 may have a concave curved profile from one lateral side (right) to an opposing lateral side (left) (e.g., positive domed curvature in a left-right direction) in order to cradle the patient's nose while the patient interface 3000 is being worn. In other words, the curvature of the sealing portion 3130 is positive relative to a location where the patient's columella and/or subnasale contact the sealing portion 3130.

In some forms, as shown for example in FIGS. 11-39, the patient's nose is not intended to be received in the cavity 3101 formed by the plenum chamber 3200 and the seal-forming structure 3100. Instead, unlike conventional masks, the patient's nose is intended to press against the textile membrane 3130 which in turn accommodates the contours of the patient's face to comfortably form a reliable seal with the patient's airways. The textile membrane 3130 may stretch to accommodate the patient's face. Specifically, the textile membrane 3130 in FIGS. 11-21 and the textile membranes in FIGS. 31-1 to 39 may be held in a relatively relaxed (i.e., un-tensioned) state prior to contact with the patient. As the patient contacts the textile membrane 3130 (e.g., via their nose), the seal-forming structure 3100 forms to the patient's face (e.g., their nose) as a result of the compliant, stretchy nature. In other words, contact with the patient's face applies tension to the textile membrane 3130, and causes it to form a complimentary shape to the patient's nose. The slack in the initial form of the seal-forming structure 3100 may allow better contouring to a patient's face than if the seal-forming structure 3100 was initially under tension, because there are fewer locations resistant to changing shape. Some examples include the bridge portion 3104 that may function to help provide, by eliminating a central opening in the textile membrane 3130, a sealing portion that presses against the patient's nose rather than receives the patient's nose in the cavity 3101. The bridge portion 3104 may create a location where the patient may apply tension to the textile membrane 3130 so that the seal-forming structure 3100 is snug and/or tight against the patient's facial features (e.g., in order to limit and/or prevent leaks). This also creates a different sealing experience as compared to conventional masks. This sealing experience may provide enhanced comfort due to contact with a compliant textile membrane 3130 rather than the more rigid materials of conventional masks or conventional sealing arrangements where the sealing portion 3130 has a smaller contact area around a perimeter of the nose and/or mouth. The bridge portion 3104 (or any area selectively tensioned) may create a location where the patient may apply tension to the textile membrane 3130 regardless of whether the bridge portion 3104 is located near at least one hole.

The textile membranes 6130 (e.g., the first sealing portion 6131) may be held in a relatively tensed state prior to contact with the patient (e.g., the first sealing portion 6131 may be under continuous tension). As the patient contacts the textile membrane 6130 (e.g., via their nose), the seal-forming structure 6100 forms to the patient's face (e.g., their nose) as a result of the compliant, stretchy nature. In other words, contact with the patient's face applies additional tension to the textile membrane 6130, and causes it to form a complimentary shape to the patient's nose. The entire first sealing portion 6131 may act in a manner similar to the bridge portion 3104 described above, because it may create a location where the patient may apply tension to the textile membrane 6130 so that the seal-forming structure 6100 is snug and/or tight against the patient's facial features (e.g., in order to limit and/or prevent leaks). While the textile membrane 6130 is taut, the material may be sufficiently compliant or stretchy so that the material can conform to the patient's facial features with the application of additional tension. The pre-tension in the first sealing portion 6131, combined with the pressurized seal resulting from the flow of pressurized air, may create a more robust seal in comparison having only pressurized seal resulting from the flow of pressurized air (e.g., as in the patient interfaces 3000, 9000, 21000, 23000, 25000).

Compared to conventional silicone membranes and compression foam seals, the sealing portion 3130 in some of the present examples has a more flexible structural stiffness and therefore has a dynamic spring back characteristic that enables the sealing portion 3130 to recover more quickly when disturbed by an external force. Further, due to the lower structural stiffness a smaller seal force is required allowing the sealing portion 3130 to be more comfortable and create less facial marks during use.

The textile membrane 3130 may exhibit variable tension forces across the material (e.g., less tension forces proximal to the naris openings 3102 or in wider stretches of material). The textile membrane 6130 may also be under less tension proximal to the naris openings 6103 since the central portion of the textile membrane 6130 may be unsupported and slightly slacked compared to the perimeter of the textile membrane 6130. In some forms, the surface of the material of the sealing portion (e.g., 3130) that contacts the patient's face may have low friction characteristics (e.g., a low friction finish), which may advantageously improve compliance of the material with the patient's face while also improving patient comfort.

The textile membrane 3130 may exhibit variable tension forces across the material (e.g., greater tension forces proximal to the bridge portion 3104). The textile membranes 9130, 21130, 23130, 21530 may exhibit similar variable tension forces. In some forms, the surface of the material of the textile membrane 3130 that contacts the patient's face may have low friction characteristics (e.g., a low friction finish), which may advantageously improve compliance of the material with the patient's face while also improving patient comfort.

In some examples, underlying cushion layer(s) (e.g., portion or second wall 3126) may assist in optimizing the sealing portion 3130 contact surface area with the patient's face. Further, in examples where the sealing portion 3130 is constructed from a breathable material (e.g., a breathable textile), the underlying cushion layer(s) may provide sufficient contact area behind the sealing portion to adequately seal the sealing portion against the patient's face and prevent leakage.

The underlying cushion layer(s) may provide additional flexibility and allow the cushion to be suitable for use by most patient faces (e.g., one size fits most). For example, the sealing portion may be structured as a double air assisted sealing portion (e.g., dual textile membranes), a sealing portion with compression support layer(s) (e.g., open cell foam, polyurethane foam, gel), a sealing portion with TPU, TPE or silicone support layer(s), or a double air assisted sealing portion with additional support layer(s) (e.g., dual textile membranes wherein the inner membrane has a foam laminate layer (e.g., open cell, polyurethane) or a TPU, TPE, polyurethane or silicone molded layer thereon).

In use, engagement of the patient's face 1000 with the sealing portion 10130 will create a temporary strain force that attempts to pull the walls of the support structure 10120 toward one another, as shown in FIG. 43. The support structure 10120 will respond to the strain force with an outwardly pulling reaction force. The reaction force transfers more tension to the sealing portion 10130 by preferentially stretching the more compliant sealing portion which creates a resultant spring force in the sealing portion that is exerted on the patient's face.

The sealing portion 10130 may be integrated with the support structure by molding or otherwise attaching the sealing portion 10130 to the inner edge of the support structure 10120. Thus, for example, an outer perimeter of the sealing portion 10130 may be attached to the inner edge of the support structure 10120 such that the sealing portion 10130 extends radially inwardly of the seal-forming structure beyond or to a further extent than the support structure 10120. The inner edge of the support structure 10120 may be curved such that the sealing portion 10130 may be slightly angled inwardly toward the mask interior. By attaching the sealing portion 10130 along the inner edge of the support structure 10120, the sealing portion 10130 does not need to be folded or cut to blend around the corners of the support structure 10120. This may advantageously reduce the occurrence of protruding folds or wrinkles in the sealing portion 10130, which may cause leakage, thereby improving the performance of the seal.

5.3.4.1 Textile Membrane

In accordance with an example of the disclosed technology, the sealing-forming structure 3100 may include a textile membrane 3130 comprising a textile material (see e.g., 10133). The textile material may have an airtight membrane/film or layer coated or otherwise applied thereto to create an air-holding textile composite. The textile composite may be cut (e.g., die cut, ultrasonic, laser, or RF) to a desired shape and then attached to the support structure 3120. The resulting textile sealing portion 3130 (or textile membrane) may be attached to the support structure 3120 (e.g., silicone, TPE), for example, by overmolding or injection molding. In another example, the textile sealing portion 3130 may be thermo-welded at its edges (outer perimeter) onto the material of the support structure 3120 (e.g., silicone, TPE). In another example, the textile sealing portion 3130 may not be coupled to a support structure 3120, and the cushion interface 3105 may be constructed substantially from a textile material.

In an example, the textile material 10133 is a stretch textile. This may include a knitted material, a woven material, or any other suitable material. A knitted material may be preferable as it provides the textile with elasticity (e.g., stretchiness), particularly in comparison with woven materials. This may be advantageous in providing comfort to the patient, as described below. The elasticity may be in all directions (e.g., four-way stretch/elasticity, e.g., substantially equal elasticity in all directions), and at least in the lateral left-right direction of the textile membrane. The textile material may have a weft knit structure or a warp knit structure, for example. The textile material 10133 may also be any other suitable knit structure. A weft knit structure may be more desirable as the elasticity of weft knit textiles is higher than the elasticity of warp knit textiles.

FIG. 45 illustrates the wale 70 of a weft knit fabric, or the direction that the loops of one thread join to a loop of another thread. The course 80, or the direction of the loops from a single thread is shown in FIG. 46. FIG. 47 illustrates a basic closed loop warp knit 90 in which the wales and courses running parallel to one another. FIG. 48 illustrates a weft knit 100 in which the wales 70 run perpendicular to the course 80.

5.3.4.1.1 Manufacturing

The human face includes a variety of contours, which may be described as either positive or negative curvatures, and either dome or saddle regions. In order to provide increased comfort to a patient, the seal-forming structure 3100 ideally matches or substantially matches the contours. As described above however, the seal-forming structure 3100 should be smooth and continuous on the patient's face without any folded sections through which air may leak. Thus, a complex geometry of the seal-forming structure 3100 needs to be formed with multiple curvatures to compliment the patient's face, without creating a surface that is susceptible to leaks.

As shown in FIG. 49, a textile material (e.g., the textile membrane 3130) can be folded about a single axis 11000 (e.g., a horizontal axis as viewed in FIG. 49). In this state, the textile material 3130 has a negative domed curvature (e.g., is substantially convex) as viewed in FIG. 49. The textile material 3130 is substantially smooth in this orientation (e.g., the curvature has a constant radius R). In other words, the textile material 3130 is substantially free of wrinkles and/or creases while oriented with a fold about a single axis 11000. This would remain true regardless of which axis the textile material 3130 was folded about, or in which direction. In other words, the textile material 3130 could be folded about a vertical axis (i.e., instead of a horizontal axis) and/or could have a positive domed curvature (i.e., instead of a negative curvature), and the surface of the textile material 3130 would remain substantially free from wrinkles and/or creases. Additionally, altering the magnitude of curvature would not create wrinkles and/or creases in the textile material. In other words, the singular fold in the textile material can include either a large radius of curvature or a small radius of curvature without creating wrinkles and/or creases in the textile material. Thus, different positive and negative curvatures (e.g., as illustrated in FIGS. 3B-3C and 3E-3F) could be applied to a textile material without creating wrinkles and/or creases.

In order to compliment the complex surface orientations of a patient (and the differences between individual patients), a seal-forming structure 3100 with multiple folds is more desirable in order to provide more contact with the patient's face. These curves are ideally about different, non-parallel axes, since the curvatures on a patient's face are about a variety of axes oriented in multiple directions. However, as shown in FIG. 50, providing an additional (e.g., a second, third, fourth, etc.) fold to the textile material may create a wrinkle and/or crease. The creases and/or wrinkles may arise when two or more folds are produced along non-parallel axes 11000, 11500. In other words, multiple folds all along parallel axes may not produce wrinkles and/or creases, but would also not produce a three-dimensional shape optimal for sealing with a patient's face (e.g., because it would not match the patient's facial contours). By including curvatures along non-parallel axes, the surface may no longer be maintained as smooth and continuous. Thus, any seal-forming structure 3100 created from a textile with two or more folds would be unlikely to effectively seal against a patient's face.

One way to effectively create curvatures in a material along multiple, non-parallel axes is to apply tension to at least a portion of the textile material 3130. The application of tension may assist in maintaining the shapes of the various curvatures, while also limiting and/or preventing the formation of creases and/or wrinkles.

One way to apply the tension is to stretch the textile material 3130, and impart multiple curvatures (e.g., along multiple, non-parallel axes) on the textile material while it is under tension. Then, the textile material 3130 can undergo a process (e.g., thermoforming), so that the textile material 3130 can be permanently held in its distorted state (i.e., with its multiple curvatures). As shown in FIG. 51, the textile material 3130 includes multiple curvatures, and its surface remains relatively smooth. Thus, this textile material 3130 could be incorporated into a patient interface 3000 as a seal-forming structure 3100, and provide a seal with a patient's face, without substantially any leaks of pressurized air from the plenum chamber 3200 to the ambient. In this example, substantially the entire textile material 3130 is under tension.

However, once the textile material 3130 is stretched and thermoformed (or a similar process is applied), the textile material 3130 substantially loses its free-state properties. For example, the elasticity that the textile material 3130 may naturally have, would be substantially lost after the thermoforming was completed. A once stretchy textile material 3130 would become relatively stiff while including multiple curvature. A textile material's 3130 free-state (i.e., before being thermoformed) properties (e.g., drape, flexibility, elasticity, etc.) are also important in determining the sealing capabilities of the eventual textile seal-forming structure 3100. Thus, if the textile material 3130 is no longer in its free-state, the quality of the seal produced by the textile material 3130 may also be reduced for some patients. In other words, while the curved textile material 3130 formed using thermoforming may be more comfortable in conforming to a patient's face (e.g., as compared to a textile membrane 3130 formed with only a single bend), the loss of its free state properties may disrupt the ability for the patient interface 3000 to effectively seal with some patient's faces. Even though there may be no wrinkles and/or creases, a seal-forming structure 3100 formed in this way may still allow leaks (e.g., because the textile membrane 3130 is too stiff to conform to some patient's faces). Other patients may experience a seal sufficient to prevent leaks.

This is not the case in the textile material 6130 of FIGS. 26-33 because the material may still include its free-state properties. Since the first sealing portion 6131 is intended to be substantially flat prior to use, the material does not need to be thermoformed in order to keep its shape. The material may still stretch and conform to a patient's face. Thus, the textile material 6130 may be able to limit leaks, unlike the example described above. The patient interface 6000 may also be easier to manufacture since the textile material 6130 may not include complex curvatures.

FIGS. 52-61 show another way to apply tension to only a portion of the textile membrane 3130. For example, less than half of the textile membrane 3130 may be under tension, while the remained of the textile membrane 3130 may be loose or slack. Thus, the tension is selectively applied to discrete locations of the textile membrane 3130. Different locations (e.g., a central portion, side portions, etc.) of the textile membrane 3130 may be tensioned in order to assist in imparting differently shaped curvatures. Additionally, more than one location may be under tension in a single textile membrane 3130. Tension may be selectively applied to the textile membrane 3130 using any number of techniques, some of which are described below.

One example technique of selectively applying tension to only a portion of the textile membrane 3130 may be accomplished by applying a crimp to a portion of the textile membrane 3130. The crimp may apply localized tension without causing the entire textile membrane 3130 to be under tension. The crimp may be applied to any portion or portions of the textile membrane 3130. In some examples, the majority of the textile membrane 3130 is not imparted with a crimp. In other words, the area of the textile membrane 3130 that is crimped is less than the area of the textile membrane 3130 that is not crimped. In some examples, sections of the textile material 3130 may be removed on at least one side of the crimped portion. In some examples, holes or other discontinuities are not needed in order to form the crimped portion.

In some examples, the crimp may be applied to a central portion of the textile membrane 3130. Applying the crimp may be accomplished by removing sections of the textile material 3130 (e.g., in order to form holes 3102) while the textile is in its free state (i.e., has not be thermoformed). The textile material 3130 can then be manipulated around the created holes 3102 in order to limit the formation of any wrinkles and/or creases. These holes 3102 may be used later as the naris openings, through which pressurized air may be delivered to the patient's nares.

As shown in FIG. 52, a textile material 3130 for use in a nasal only patient interface 3000 is shown. Two holes 3102 cut into the textile material (e.g., by hand, with a laser, etc.), with each hole 3102 corresponding to a single naris of a patient. However, any number of holes 3102 may be cut depending on the final use of the textile material (e.g., a single opening for both nares, an additional opening for the mouth, etc.). These holes 3102 may be cut into the textile material 3130 either before the first fold is made or after the first fold is made. The order of forming a single (i.e., first) fold and cutting will not substantially effect the presence of creases and/or wrinkles.

With specific reference to the textile material for use in a nasal only mask as shown in FIG. 52, each of the holes 3102 is elongated, and formed as a generally rectangular shape, although other shapes (e.g., circular, triangular, etc.) may be used in other examples. The holes 3102 may be separated by a strip of material that may be formed as a bridge portion 3104. Although the bridge portion 3104 may also be formed independently of the holes 3102. If more than two holes 3102 are cut into the textile material 3130, there may be multiple bridge portions 3104. Creating more bridge portions 3104 may be useful when additional holes are needed, and/or if the textile material 3130 is larger (e.g., so that it does not buckle despite a single bridge portion 3104). As described above, the patient's nose (e.g., their pronasale) may contact the bridge portion 3104, and the bridge portion 3104 may limit the patient's nose from extending into the plenum chamber 3200.

As shown in FIG. 53, once the initial fold is made about a first axis 11000 (e.g., a horizontal axis as shown in FIG. 53) and the holes 3102 have been cut, the bridge portion 3104 may be folded (e.g., a second fold) about a second axis 12000 that is parallel to (or collinear with) the first axis 11000. In the illustrated example, the bridge portion 3104 is flipped into a downward direction (as viewed in FIG. 53) in order to clear a space between the pair of holes 3102. In other words, a positive domed curvature (e.g., as viewed in FIG. 53) is imparted on the bridge portion 3104, while the first fold was a negative domed curvature.

In some forms, once the bridge portion 3104 is folded, a space 3180 is created between the holes 3102. Specifically, the holes 3102 may be vertically oriented (e.g., as viewed in FIG. 53) and the space 3180 is oriented along the first axis 11000. In other words, each of the holes 3102 are substantially perpendicular to the first axis 11000, and the space 3180 exists between openings to each of the holes 3102. A width of the space 3180 substantially corresponds to a width between the nasal alas or alar ridges of the patient. In other word, the width of the space 3180 is large enough to receive a patient's nose, and have the patient's nares approximately aligned with the holes. Apexes of the textile material 3130

(i.e., created by the first fold) would contact the patient proximate to the nasolabial sulcus when the nose is positioned within the space.

As shown in FIG. 54, once the bridge portion 3104 has been folded about the second axis 12000, the material may be crimped in order to maintain its "flipped" orientation. Crimping may be one way to selectively apply tension to a portion of the textile membrane 3130, without applying tension to the entire textile membrane 3130. Other techniques of selectively applying tension may similarly be incorporated either with or instead of crimping. The bridge portion 3104 is maintained so as to no longer have the first curvature 10000 about the first axis 11000. For example, the bridge portion 3104 may not have an explicitly positive domed curvature (e.g., the bridge portion 3104 may have a smaller magnitude of curvature in FIG. 54 than in FIG. 53, the bridge portion 3104 may have a zero curvature, etc.), but would not have a negative dome curvature along with the remainder of the textile material 3130 (e.g., while the cushion assembly 3105 is in use). In other words, after the crimping occurs, the curvature in the bridge portion 3104 is different (e.g., in magnitude and/or direction) than the rest of the textile material 3130.

In some examples, the bridge portion 3104 is crimped so that the material forming the bridge portion alone is taut (i.e., crimping may not apply tension to the rest of the textile membrane 3130). Specifically, a length of the bridge portion 3104 is folded against itself in order to reduce a total exposed length. The tension in the textile that comprises the crimped bridge portion 3104 is greater than the tension in the surrounding textile, which has not been crimped. Thus, a surface of the bridge portion 3104 may be substantially flat and/or may have minimal curvature (e.g., while the curvature about the first axis 11000 remains through the rest of the textile material 3130). The fold in the bridge portion 3104 may be substantially in the center, so that a length of material on either side of the fold line is substantially equal, although one side may be longer than the other. Although the crimp creates tension, the bridge portion 3104 may still be able to flex relative to the holes 3102 (e.g., as a result of the free-state properties of the textile). The crimped bridge portion 3104 may be similar to the un-crimped bridge portion 6106 since both are under tension, but also retain their free-state material properties.

In other examples, other ways of applying tension may be used to create a taut bridge portion 3104, and/or tension may be applied to other locations of the textile membrane 3130.

In some examples, the resulting length of the bridge portion 3104 after being crimped affects the size of the holes 3102. For example, if the usable length remains large (i.e., the crimped length is small), the holes 3102 remain large. Said another way, there is a direct relationship between the length of the bridge portion 3104 that is crimped and the size of the holes 3102. When the length of the bridge portion 3104 decreases (i.e., because the crimped length increases), the tension in the crimped bridge portion reduces the size (e.g., the circumference) of each hole 3102. The length of the bridge portion 3104 may be adjusted based on a size of the patient's nose (e.g., the bridge portion 3104 may be crimped with small, medium, and large sizes in order to accommodate different sized nares).

In some examples, the bridge portion 3104 is maintained in its crimped state as a result of ultrasonic welding and/or applying an adhesive (e.g., glue), although any suitable method may be used. Any of these methods may be applied to the non-usable length 3184 of the bridge portion 3104. For example, an adhesive may be applied to a selected portion of the textile layer of textile membrane 3130, and the selected portions are folded against one another. In other words, the useable length of the bridge portion 3104 may be substantially free from any substance that was applied. The crimped region of the bridge portion 3104 may still have the positive domed curvature described above, even after one of the securing methods has been applied.

In one example, a portion of the non-usable portion 3184 of the bridge portion 3104 may be trimmed or cut after the securing method is applied. Once the textile membrane 3130 is completely assembled as a seal-forming structure 3100, the non-usable portion 3184 would be positioned within the plenum chamber 3200, and may cause a disruption to airflow (e.g., and create noise). Thus, trimming the non-usable portion 3184 may reduce or eliminate any disturbances.

As shown in FIGS. 55-57, once the crimping is complete, additional curvatures about different axes may be applied to the textile material 3130. Crimping the bridge portion 3104 may reduce the total area 3188 that is affected by additional curvatures. Said another way, the affected area 3188 (i.e., shown in hatching) with the bridge portion 3104 crimped in FIG. 55 is less than the affected area 3190 in FIG. 51 where crimping has not occurred. The affected area 3188, 3190 relates to the area where creases and/or wrinkles are likely to appear as a result of introducing multiple curvatures to the textile material 3130. When the bridge portion 3104 is crimped, the affected area 3188 is substantially close to the holes 3102. For example, the affected area 3188 may form a substantially rectangular shape, with edges substantially tangent to the holes 3102. The close proximity of the affected area 3188 to the holes 3102 substantially prevents creases and/or wrinkles from forming when additional curvatures are applied to the textile material 3130.

In some examples, a third curvature 30000 is formed in the textile material 3130 about a third axis 13000. The third axis may extend along a direction substantially perpendicular to the first and second axes 11000, 12000 (although it could also be oblique or skew). In other words, the third axis 13000 may be a substantially horizontal axis (e.g., as viewed in FIGS. 55-57). In the illustrated example, the third axis 13000 is centered on the textile material 3130, and extends along the bridge portion 3104. The third curvature 30000 may have a substantially saddle region (e.g., as viewed in FIGS. 55-57). In other words, the third curvature 30000 may be positively curved and may cradle the patient's nose after the patient dons the patient interface 3000. This means that the textile layer 10133 specifically is a saddle region about the third axis 13000 when the patient interface 3000 is worn. Thus, the second and third curvatures 20000, 30000 may curve in the same direction (e.g., both positive curvatures), although about substantially perpendicular axes and may define different regions (e.g., the second curvature 20000 is a dome and the third curvature 30000 is a saddle). While the third curvature 30000 is applied, the first and second curvatures 10000, 20000 remain in their previously curved position. In other words, the application of the third curvature 30000 (or additional curvatures) may not substantially affect the magnitude and/or direction of the previous curvatures.

In some examples, a fourth curvature 40000 may be formed in the textile material 3130 about a fourth axis 14000, which may extend along a direction substantially perpendicular to the first, second, and third axes 11000, 12000, 13000 (although the fourth axis 14000 may have any relationship to the other axes). In other words, the fourth axis 14000 may be a substantially vertical axis (e.g., as viewed in FIG. 55). In the illustrated example, the fourth axis 14000 does not intersect the bridge portion 3104. The fourth curvature 40000 may extend toward a center of the textile material 3130, and may be a saddle region as viewed in FIG. 55. In other words, the fourth curvature 40000 may cradle the patient's face (e.g., their lip superior) after the patient dons the patient interface 3000.

In some examples, the fifth curvature 50000 may be formed in the textile material 3130 about a fifth axis 15000, which extends along a direction substantially parallel to, and offset from, the first and second axes 11000, 12000 (although the fifth axis 15000 may have any orientation). In other words, the fifth axis 15000 is a substantially horizontal axis (e.g., as viewed in FIG. 56). In the illustrated example, the fifth axis 15000 does not intersect the bridge portion 3104. The fifth curvature 50000 includes a similar orientation as the first curvature 10000, and may be a negative dome curvature (e.g., as viewed in FIG. 56). The first and fifth curvatures 10000, 50000 may have different magnitudes of curvature (e.g., the magnitude of the first curvature 10000 may be more negative than that of the fifth curvature 50000). The fifth curvature 50000 may have a variable curvature, in that its radius of curvature may not be constant along the length of the axis 15000. For example, since the fifth curvature 50000 and the first curvature 10000 are along substantially parallel axes, changing the radius of curvature of the fifth curvature 50000 may bring the two curvatures 10000, 50000 together (e.g., blend them into one curvature). The fifth curvature 50000 may have a smaller radius of curvature proximate its center (e.g., proximate to an intersection with the third axis 13000), and has a larger radius of curvature proximate an edge of the textile material 3130. Here, the larger radius of curvature of the fifth curvature 50000 may blend into the first curvature 10000 (e.g., proximate to an edge of the textile material 3130). In other words, fifth curvature 50000 may extend into the first curvature 10000 as the radius of curvature in the fifth curvature 50000 increases. Blending the curvatures may assist in providing a smooth surface, and limiting the potential of forming creases and/or wrinkles in the bent textile material 3130.

In some examples, the fourth and fifth curvatures 40000, 50000 are both included on the textile material 3130. In other words, the medial subnasale region 3260 of the eventual seal-forming structure 3100 constructed from the textile material 3130 may include both the fourth curvature 40000 and the fifth curvature 50000. These curvatures 40000, 50000 may work together to seal against the compound curvature (e.g., multiple curvatures in multiple directions) on a patient's lip superior. In the illustrated example, the fourth curvature 40000 is the dominate curvature of the medial subnasale region 3260 when both the fourth and fifth curvatures 40000, 50000 are included on the textile material 3130. For example, the human head has a natural curvature toward either lateral side. In other words, the lip superior curves to the left and right sides of the patient's face, from the philtrum and toward the cheilion. The lip superior may also include a curvature about a substantially horizontal axis, which runs perpendicular to the sagittal plane. However, this curvature is over a smaller distance (i.e., the distance between the subnasale and the upper vermillion is less than the mouth width), and may have more variance among different patients (e.g., some may have a larger, more defined curve than others).

The fourth curvature 40000 would be the larger curvature, as compared to the fifth curvature 50000. This may include the textile material 3130 extending around the fourth axis 14000, and a lower edge of the textile material 3130 being folded about the fifth axis 15000, so that the fourth curvature

40000 includes more total area on the textile material 3130. However, the crimped bridge portion 3104 allows both curvatures 40000, 50000 to be maintained in an overlapping region without forming creases and/or wrinkles. Thus, in some examples, the fifth curvature 50000 may not be entirely along the fifth axis 15000, and may instead extend along a curved path as it follows the length of the fourth curvature 40000.

Some patients may have a substantially vertical lip superior between the subnasale and the upper vermillion, and thus there may be substantially no curvature along the substantially horizontal axis perpendicular to the sagittal plane. In these patients, the fifth curvature 50000 may not include a curved lip region to seal against. However, the material of the fifth curvature 50000 may deform into the substantially vertical (e.g., flat) region, and is still capable of maintaining an effective seal against the patient's face. Additionally, the height between the subnasale and the upper vermillion may be different on different patients. For example, this distance may be very small. In this example, the textile material of the fifth curvature 50000 may be able to deform into the tight region and work as a lead in, in order to effectively seal against any height. In other examples, the textile material may be customizable for individual patients, and the curvatures, as well as radii of curvature, are selected based on a particular patient's facial geometry (e.g., which may be identified using scanning).

Any number of these curvatures may be applied to a single seal-forming structure 3100 in order to assist in enhancing the fit of the patient interface 3000 against the patient's face. For example, all five of these curvatures may be applied to a single seal-forming structure 3100. In other examples, only some of the curvatures may be applied to the seal-forming structure 3100. In other examples, more than five curvatures may be applied to the seal-forming structure 3100. The magnitude and/or directions of the curvatures may be variable across individual cushion assemblies 3105 (e.g., the textile membrane 3130 may be custom made for an individual patient).

In some examples, the shape of the textile membrane 3130 may be formed, and the textile membrane 3130 may be connected to the lateral support region 3122. In the illustrated example, the textile membrane 3130 and the lateral support region 3122 are connected using injection molding so that they are formed integrally with one another. In other examples, the textile membrane 3130 and the lateral support region 3122 may be coupled together in a different way (e.g., by overmolding). In still other examples, the textile membrane 3130 may not be coupled to a lateral support region 3122.

In some examples, the three-dimensional shape (i.e., resulting from the multiple curvatures) of the textile membrane 3130 may assist an injection molding tool in forming the flexible support structure 3120 and/or the plenum chamber 3200. For example, the bridge portion 3104 folded about the second axis 12000 (e.g., and crimped) may be useful when loading the textile membrane 3130 into the injection molding tool. Specifically, the crimped bridge portion 3104 may be used as a spigot when placing the textile membrane 3130 in the injection molding tool. In other examples, the textile material 3130 may be curved in order to completely form the plenum chamber 3200, such that an injection molded material is not needed in the patient interface 3000. In other words, the plenum chamber 3200 and seal-forming structure 3100 may be constructed from the textile material 3130, and not from silicone, or other flexible, molded material.

As shown in FIGS. 58 and 59, a material (e.g., silicone) may be molded onto the textile membrane 3130. The material may be applied to the inner layer 3194 of the textile membrane 3130 (e.g., the layer coated with an air impermeable material 10131), so as to avoid covering a portion of the textile on the posterior surface (and potentially contact the patient's face, in use). Although, in other examples, the material may be applied to the outer layer 3196 of the textile membrane 3130. The material may extend beyond an end of the textile membrane 3130 and toward the plenum chamber 3200 (e.g., the material may be molded so that some of the lateral support region 3122 does not contact the textile membrane 3130). As the material is molded to the textile membrane 3130, the resulting support structure 3120 may have substantially the same curvature (i.e., magnitude and direction) as the adjacent textile membrane 3130 (e.g., in order to create a substantially smooth, and uninterrupted surface). The thickness of the material (i.e., the lateral support region) may change along its length. For example, the lateral support region 3122 may be thicker distal to the textile membrane 3130. Additionally, a total thickness of the overlapping textile membrane and material may also be thinner than the adjacent region containing only the molded material (i.e., the lateral support region 3122).

As shown in FIG. 58, some examples of the patient interface 3000 may include a single wall lateral support region coupled to the textile membrane 3130. A single wall of silicone material may be molded to the textile membrane 3130, in order to form the support structure 3120 that connects the seal-forming structure 3100 to the plenum chamber 3200. An outer surface 3195 of the support structure 3120 substantially matches the outer surface 3196 of the textile membrane 3130 (i.e., the textile layer), in order to form a smooth, continuous surface. The inner surface 3197 may have a different thickness as described above. The silicone material overlaps a portion of the textile membrane 3130 in order to form a sturdy connection, but not add unnecessary weight to the patient interface 3000. The silicone material may taper to its smallest thickness at an end of the overlap region 3199 (e.g., proximate to end 3124). The end of the overlap region 3199 is spaced apart from the naris opening 3102 in order to avoid potential interference (e.g., that creates noise) of pressurized air into the patient's nares. The overlap region 4000 substantially on the first curvature 10000, and may provide additional support for maintaining the appropriate magnitude for the first curvature 10000.

As shown in FIG. 59, some examples of the patient interface may include a dual walled support structure 3120 coupled to the textile membrane 3130. A single wall of silicone material may be molded to the textile membrane 3130, in order to connect the seal-forming structure 3100 to the plenum chamber 3200. As described above, the outer surface 3195 substantially matches the outer surface 3196 of the textile membrane 3130, and the inner surface 3197 includes varying thicknesses along its length. However, the overlap region 3199 may extend a different length along the inner surface 3194 of the textile membrane 3130. Specifically, the overlap region 3199 may contact a length of the textile membrane 3130 that is less than in the single wall support structure 3120, described above. Instead, a portion of the silicone wall 3126 may continue to extend along a length of the textile membrane 3130, but spaced apart from the inner surface 3194. This second wall 3126 of the support structure 3120 may extend in a cantilevered manner from the remainder of the lateral support region (i.e., from end 3124). The support structure 3120, with the inclusion of the second wall 3126, may extend along a similar total overlapped length as the support structure 3120 in the single wall example. The second wall 3126 may particular be disposed proximate to an apex of the first curvature 10000, in order to provide additional support. The second wall 3126 is stiffer than the textile membrane 3130, and may assist in maintaining the shape of first curvature 10000 when the textile membrane 3130 contacts the patient's face. If additional force is applied, the textile membrane 3130 and the second wall 3126 may deform together.

After assembling the textile membrane 3130 to the support structure 3120, the resulting cushion assembly 3105 may be used in a patient interface 3000. Specifically, the patient's face (e.g., the patient's nose) may be positioned within the space 3180 so that the naris openings 3102 are positioned proximate to the respective nares.

When positioning the cushion assembly 3105, the patient may align the bridge portion 3104 with their nose. Specifically, the bridge portion 3104 may be directed in the anterior/posterior direction as the cushion assembly 3105 is donned (e.g., the textile membrane 3130 may be substantially facing the superior direction). The patient moves the bridge portion 3104 into contact with their nose, where the taut material of the bridge portion 3104 presses against the patient's nose (e.g., in the subnasale region and may contact the columella). The bridge portion 3104 limits the patient's nose from moving into the cavity 3101, but as the patient's nose presses against the taut material, tension may be applied to the surrounding regions on the textile membrane 3130. In other examples, the patient may move their face toward a separate area of the textile membrane 3130 that is under tension (e.g., if the entire area of the textile membrane is under tension like in FIGS. 26-33).

While the patient contacts the bridge portion 3104, the patient may also contact the lateral side 3250 and/or corner regions 3252 of the textile membrane. The lateral side 3250 and the corner region are disposed on a region of the third curvature 30000 proximate to an apex of the first curvature 10000. In other words, the lateral side 3250 and corner region 3252 are disposed on a surface having a saddle region, and face toward a center of the cushion assembly 3105. A positive curvature may be between the opposing lateral sides 3250. The lateral side 3250 and corner regions 3252 are also positioned proximate to where the textile membrane transitions to a negative dome curvature (i.e., formed by the first curvature 10000), and may be understood to be at a posterior portion of the cushion assembly 3105. This transition region may be understood to be a domed region of the sealing portion 3130. The lateral side 3250 and/or the corner regions 3252 contact the outer surface of the patient's nose (e.g., proximate to the patient's nasal ala), and may terminate proximate to the alar crest points on either side of the patient's nose. In this orientation, the naris openings 3102 are aligned with the patient's nares, and may effectively deliver pressurized air to the patient's airways. The lateral side 3250 and/or corner regions 3252 are generally loose, which allows these regions of the textile membrane 3130 to better form to the various contours of the patient's face. For example, the lateral side 3250 and/or corner regions 3252 may be able to adjust in shape in order to better conform to the region surrounding the patient's nares in order to develop a tight seal. As the patient's nose engages the bridge portion 3104, the lateral side 3250 and/or corner regions 3252 may experience tension, in order to maintain the appropriate shape from the patient.

As shown in FIG. 60, the textile membrane 3130 may include an arch 60000 adjacent each of the naris openings

3102. The arches 60000 are also disposed proximate to the lateral side 3250 and/or corner regions 3252. The arches 60000 have a saddle region in the same direction as the first curvature 10000 (and may also be about the first axis 11000). The arches 60000 extend into the space 3180 so that a distance between the arches 60000 may be the narrowest distance between opposing lateral sides 3250 and/or corner regions 3252.

When the patient dons the cushion assembly 3105, the naris openings 3102 may have a generally vertical alignment (as described above), and an inner surface of each nostril contacts the respective arch 60000. In other words, the each arch 60000 is configured to contact an inner surface of the each respective nasal ala. Since the patient's nose is also contacting the bridge portion 3104 of the textile membrane 3130, each naris opening 3102 fully surrounds each respective naris.

As shown in FIG. 61, once each of the arches 60000 contacts the inner surface of the respective naris, the arch 60000 flips to a concave orientation (i.e., a positive dome curvature relative to the inner surface of the respective naris). This is similar to what occurred with the bridge portion 3104, although a curvature of the arches 60000 may be directed in a different direction. For example, each arch 60000 may move along the first axis 11000 toward the respective plenum chamber connector 3204. In this orientation, each naris opening may have a substantially tear-drop shape.

When the arch 60000 flips (i.e., from a negative dome curvature to a positive dome curvature), the arch 60000 may wrap around an alar rim of the respective naris. In other words, each arch 60000 wraps around the outer periphery of the respective naris. The compliant nature of the textile membrane 3130 allows the arches 60000 to adjust to the shape of the patient's alar rim in order to form a seal sufficient to maintain the therapeutic pressure within the plenum chamber 3200.

Once the cushion assembly 3105 is properly positioned, the patient may supply pressurized air. The compliant nature of the textile membrane 3130, and the fact that the outer portions are initial loose (e.g., as opposed to taut like the bridge portion), allows the seal-forming structure 3100 to form a dynamic seal as pressurized air fills the cavity 3101. The dynamic seal allows the cushion assembly to shift slightly on the patient's nose, while still maintaining a pressurized cavity 3101, and delivering pressurized air to the patient's airways. For example, the arches 60000 may be able to slightly move against the alar rims without losing their seal.

Additionally, the third, fourth, and/or fifth curvatures 30000, 40000, 50000 may provide additional assistance in maintaining the position of the seal-forming structure 3100, and enhancing comfort for the patient. For example, the third curvature 30000 may have a saddle region relative to the patient, and may contact the subnasale region of the patient along the columella (e.g., via a positive curvature). The third curvature 30000 may not extend to the patient's pronasale, leaving it exposed. The third curvature 30000 may be disposed in the pronasale region 3270 of the textile membrane 3130. The fourth curvature 40000 may have a saddle region relative to the patient, and may contact the patient's lip superior (e.g., via a positive curvature). Thus, the fourth curvature 40000 extends in the lateral (left/right) direction while worn by the patient, and may also extend substantially along the mouth width. The fifth curvature 50000 may have a negative dome curvature relative to the patient's lip superior. In other words, the fifth curvature

50000 curves away from, and does not cradle, the patient's lip superior. The fourth and fifth curvatures 40000, 50000 may contact substantially the same region of the patient's face, and one or both may be included on a given textile membrane 3130. The fourth and/or fifth curvatures 40000, 50000 may be disposed in the medial subnasale region 3260 of the textile membrane 3130. The fifth curvature 50000 may create a "pillow" and/or "airbag" effect on the patient. In other words, the negative dome curvature of the fifth curvature, relative to the patient's lip superior in use, may provide additional cushioning and/or comfort to the patient as a result of the pressurized air inflating the textile membrane 3130.

While the above description was specifically directed toward a nasal cradle, it is equally applicable to the patient interfaces 9000, 21000, 23000, 25000 described above. Additional description specific to the full face cushion is described below.

5.3.4.1.1.1 Full Face Cushion

In addition to the steps described above, manufacturing and assembling the full face cushion differs from the nasal cushion because of the additional area that the full face cushion is required to seal around (i.e., both the patient's nares and mouth). Accordingly, additional surface area of textile membrane 10135 is required, and additional surface area of the support structure 6120 (e.g., silicone material) is required, since the overall size of the full face cushion is larger than the nasal cushion.

The patient interfaces, illustrated in FIGS. 22 to 39, are assembled by placing two pieces of textile membrane 10135 into a molding tool, and molding a flexible material (e.g., silicone) onto the textile membranes 10135 in order to form the patient interface 6000, 9000, 21000, 23000, 25000. In these examples, the two textile membranes 10135 are different shapes, in order to seal with a specific region on the patient's face (although a single textile membrane 10135 could be used). As described above, the first textile membrane 10135 (i.e., used to form the first sealing portion 6131) has a rounded shape, and the second textile membrane 10135 includes a U-shape or a C-shape (see e.g., FIG. 33), or a ring or annular shape (see e.g., FIG. 33-1). The textile membranes 10135 are substantially flat (e.g., having a two-dimensional shape) prior to being placed into the mold. Once they are positioned in the mold, the two textile membranes 10135 are spaced slightly apart from one another (e.g., via a gap 21190). In some examples, the mold maintains the textile membrane 10135 in a partially flat position as the flexible material (e.g., silicone) is introduced into the mold (e.g., the patient interface 6000). In some examples, the mold introduces curvatures to the textile membranes 10135 and holds the textile membranes 10135 in their curved shape as flexible material (e.g., silicone) is introduced into the mold (e.g., the patient interface 9000, 21000, 23000, 25000). The curvatures introduced to the textile membranes 10135 by the mold may cause the bridge portion (e.g., 9106) to fold on itself. As the flexible material is introduced into the mold and hardens, it secures the two flexible textile membranes 10135 together. After the molding process is complete, the bridge portion 9106 can be crimped in order to remove slack from the textile membrane 10135. Alternatively, the bridge portion 9106 can be crimped prior to positioning the textile membranes 10135 in the mold. This may impart a pre-deformation onto the textile membranes 10135 (e.g., the textile membranes 10135 deform prior to being positioned within the mold and having additional curvatures imparted on the remainder of the textile membranes 10135). The bridge portion 6106 may not need to be crimped since the textile membrane 10135 was held in taut position by the mold, and may be generally flat along the lateral direction. The bridge portion 6106 may be under tension without a crimp, and may apply substantially the same benefits as the bridge portions with a crimp. As noted previously, it may be easier to manufacture the textile membrane 10135 into the first sealing structure 6131 as opposed to the first sealing structure on another patient interface (e.g., 9000) since the first sealing structure 6131 may not include complex curvatures.

By using two separate pieces of textile membrane 10135 to form the patient interface (e.g., 9000, 21000, etc.), overlap of the textile material 10135 can be avoided. Particularly, overlap may be an issue when attempting to impart complex curvatures onto a large piece of textile membrane 10135, because longer curvatures may be possible, which may lead to more opportunities for the textile membrane 10135 to fold on itself. Since the patient interface 6000 does not include complex curvatures, overlap of the textile material 10135 may be less likely. However, using two separate pieces of textile material 10135 may allow the patient interface 6000 to include a substantially planar surface of the first sealing structure 6131 oriented in a first direction, and a substantially planar surface of the second sealing structure 6132 in a second direction. In other words, the separate pieces of textile membranes 10135 may be disposed in different orientations in order to better conform to a patient's face as a result of the patient interface 6000 being constructed from separate textile membranes 10135.

One way to solve the issue of overlap was to stack multiple pieces of the textile membrane 10135 on top of one another to produce complex curvatures (e.g., by creating an overlap of a few millimeters with two or more textile membranes 10135), while reducing the stress experienced in each textile membrane 10135 (e.g., as compared to a single textile membrane 10135). However, leaks could occur in the overlapped region, which could degrade the quality of the seal in the eventual patient interface 9000, 21000, etc.

If two separate pieces of the textile membrane 10135 are used but not overlapped, the likelihood that a single piece of textile membrane 10135 will fold on itself is reduced because the length of each individual curve is reduced. Additionally, the likelihood of leaks occurring may be reduced from an example where the textile membranes 10135 overlap, since the overlapping interface of textile membranes 10135 has been removed.

Two spaced apart pieces of textile membrane 10135 are used, and the flexible material may be molded in the space between the two textile membranes 10135. As illustrated, this space may be relatively small (e.g., in order to reduce contact between the patient's skin and the support structure 9120, 21120, etc.). As a result, this may make molding this section of the patient interface (e.g., 9000, 21000, etc.) difficult (e.g., because the textile membranes 10135 have to be accurately positioned, the flexible material has to fill the space without covering the textile layer 10133, etc.), but may increase the likelihood that the resulting patient interface (e.g., 9000, 21000, etc.) will not include creases formed as a result of the complex curvatures imparted on the textile membrane 10135. A similar principle may be true for the patient interface 6000, even though there are no complex curvatures in the first sealing portion 6131.

In this example, there is a direct trade-off between ease of manufacturing, and full textile contact. For example, the patient interface 9000 shown in FIG. 35 (or the patient interface 6000 in FIG. 33) may be easier to manufacture than the patient interface 21000 shown in FIG. 33-1 (e.g., because the liquid material may not be molded into as small of spaces). However, the patient's lip superior (e.g., proximate to the philtrum) will contact a larger surface area of the support structure 9120 (i.e., not the textile layer 10133) in the example shown in FIG. 35, potentially having a lower comfort level for the patient than the patient interface 21000 of FIG. 33-1.

The example of the patient interface 23000 shown in FIG. 33-2 may attempt to balance the issues observed in the patient interface 9000 of FIG. 34 (or 6000 of FIG. 33) and the patient interface 21000 of 33-1. In other words, the patient interface 23000 of FIG. 33-2 may attempt to reduce the manufacturing complexity, without sacrificing patient comfort. To do this, the second textile membrane 10133 may include a U-shape or C-shape (e.g., similar to the example shown in FIGS. 33 and 35). The U-shaped textile membrane 10135 includes an outer edge 23180 that forms a portion of the outer periphery of the lower sealing portion 23130b, and an inner edge 23182 that forms a portion of the oral portion hole 23104. The first textile membrane 10135, which forms the upper sealing portion 23130a of FIG. 33-2, may be larger than the first textile membrane 10135 that forms the upper sealing portion 21130a of FIG. 33-1, so that a lower edge 23184 of the first textile membrane 10135 may be aligned with the inner edge 23182 of the second textile membrane 10135. In other words, substantially all of the perimeter of the oral portion hole 23104 includes the textile membrane 10135, as opposed to the support structure 23120. Since the textile membranes 10135 are separate pieces, gaps 23190 filled with the flexible material may still exist between the individual pieces (i.e., between the upper and lower sealing portions 23130a, 23130b). These gaps 23190 are generally in the longitudinal (e.g., left/right) direction, and extend at least between the outer and inner edges 23180, 23182. The gaps 23190 may be small enough that the patient's comfort is not effected by their presence (e.g., the patient may not feel the support structure 23120 between the sealing portions 23130a, 23130b, and may instead feel as though only textile material contacts the region around their mouth). In some examples, the gap 23190 may be substantially small, so that the patient may be unable to detect its presence.

In the mold, the textile membranes 10135 are arranged in the manner described above, and the flexible material is introduced into the mold to form the patient interface 23000. Since the lower edge 23184 of the first textile membrane 10135 extends to the inner edge 23182 of the second textile membrane, the flexible material is not introduced into the mold in an area that will be between the naris opening 23103 and the oral portion hole 23104. In other words, the textile membrane 11035 is the only material that is configured to contact the lip superior in this region (e.g., against the philtrum). Even though the flexible material is able to bend and move, the combination of textile membrane 10135 with the flexible material may reduce the resiliency of the patient interface 23000. For example, during the molding process, the flexible material may solidify on an interior surface (i.e., within the cavity 23001) of the textile membrane 10135, which increases the thickness of this region. In use, the patient interface 23000 may have more difficulty flexing when the patient's lip superior contacts this region, which may result in an imperfect seal (i.e., allow for leaks). By removing the need for the support region between the naris openings 23103 and the oral portion hole 23104, the flexible material does not need to flow into this region, and the thickness of the textile membrane 10135 may not substantially increase. Without the flexible material substantially backing the textile membranes 10135 (e.g., as in FIG. 33-1), the textile membrane 10135 may be able to stretch as much as a patient interface made entirely from silicone (e.g., 0.3 mm thick silicone), so that the textile membrane 10135 can achieve substantially the same or similar quality of seal against the patient's face as with the entirely silicone membrane.

In order to manufacture this patient interface 23000, the textile membranes 10135 may be substantially flat (e.g., have a two-dimensional shape) prior to being placed into the mold, and may receive complex curvatures as a result of being placed into the mold. The liquid flexible material may be applied in order to form the three-dimensional patient interface 23000 (e.g., maintain the complex curvatures in the textile membranes 10135 after being removed from the mold). As described above, any crimp may be applied either before or after the textile membrane 10135 is placed into the mold.

As shown in FIG. 33-3, the patient interface 25000 may be formed using a single textile membrane 10135 when constructing the sealing portion 25130. In other words, one sheet of textile membrane 10135 is used to seal around both the patient's nares and the patient's mouth. The sealing portion 25000 includes an upper sealing portion 25130*a* and a lower sealing portion 25130*b*. The outer perimeter of the sealing portion 25130 is substantially the same as the examples mentioned above. However, in this example, the support structure 25120 is not needed to be formed between first and second textile membranes 10135 in order to space them apart and connect them together. Thus, manufacturing may be easier since textile membranes do not have to be properly spaced and filled with the liquid mold material. Additionally, the entire area of the patient interface 25000 that contacts the patient proximate to the mouth and/or nose is constructed from the textile layer 10133. This may help to improve patient comfort, since the support structure 25120 will not contact the patient proximate to their lip superior.

Using the crimp method described above, the likelihood of the single textile membrane 10135 folding onto itself may be reduced or eliminated, even while using a larger piece of textile membrane 10135 (e.g., as compared to the examples shown in FIGS. 33-1 and 33-2). Particularly, the crimp may reduce or eliminate overlap from occurring in the nasal region, where more curvatures are applied.

Additionally, there may not be a significant drop off in the quality of the seal in the resulting patient interface (e.g., as compared to the patient interfaces 21000, 23000 of FIGS. 33-1 and 33-2). The textile membrane 10135 in FIG. 33-3 may include the textile layer 10133 backed with the impermeable layer 10131, but the overall textile membrane 10135 may be unbacked (e.g., may not be backed with the flexible material of the support structure 25120). The textile membrane 10135 may be able to stretch a similar amount as silicone alone (e.g., the impermeable layer 10131 may not significantly reduce the stretchability of the textile membrane 10135), and thus may be able to accommodate various contours along the patient's face (e.g., proximate to the patient's nasal ala), which may assist in forming the seal.

In order to reduce and/or eliminate leaks from occurring while the patient interface 25000 is worn, the shape of the textile membrane 10135 may be modified in order to better accommodate a wider range of patient's faces, and limit leaks from occurring (see e.g., FIGS. 33-4 to 33-5). In one example, the modifications to the textile membrane 10135 may include reducing the radius of curvature in the upper sealing portion 25130*a*. Reducing the radius of curvature creates a deeper pocket or nasal radii to receive the patient's face. For example, the portion of the upper sealing portion

25130*a* that receives the patient's nose may be narrower, so that when the patient's nose contacts the textile layer 10133 of the sealing portion 25130, the textile membrane 10135 is tighter against the patient's nose. This may be particularly beneficial for patients with smaller and/or narrower noses, who found the sealing portion 25130 with a larger radius of curvature to fit too loosely. Since the textile membrane 10135 are able to flex and deform, patient's with slightly larger noses may still use the patient interface 25000, and experience the tight fit (e.g., in order to reduce leaks).

Additionally, reducing the radius of curvature of the upper sealing portion 25130*a* may impart a similar shape on the join between the sealing portion 25130 and the support structure 25120. Since the upper sealing portion 25130*a* and the support structure 25120 are connected, the support structure 25120 may be pulled in the direction of the deep pocket formed in the upper sealing portion 25130*a*.

Reducing the radius of curvature of the upper sealing portion 25130*a* may impart a similar shape on the lower sealing portion 25130*b*, since the upper and lower sealing portions 25130*a*, 25130*b* are formed from one piece of the same textile membrane 10135. This may specifically reduce the curvature at the inferior end of the lower sealing portion 25130*b* (e.g., region configured to contact the patient's chin), and provide similar benefits of the deeper pocket described above.

In some examples, the radius of curvature may be adjusted about the third axis 13000. In other words, lateral sides 25250 and/or corner regions 25252 of the patient interface 25000 may be closer together and the patient may have to put their nose further into the cushion assembly 25105 in order to contact the bridge portion 25106. Additionally, the radius of curvature about the fifth axis 15000 may be increased, so that the curvature is reduced. Increasing the radius of curvature about the fifth axis 15000 helps to maintain the deep curvature about the third axis 13000 because the fifth curvature 50000 does not flatten out the third curvature 30000 (e.g., as a result of the third curvature 30000 and the fifth curvature 50000 being about non-parallel axes).

In some examples, the radius of curvature about the third axis may be less than approximately 40 mm. In some examples, the radius of curvature about the third axis may be less than approximately 30 mm. In some examples, the radius of curvature about the third axis may be between approximately 25 mm and approximately 15 mm. In some examples, the radius of curvature about the third axis may be approximately 20 mm. This radius of curvature may be in the textile membrane 10135 only. By reducing the radius of curvature, the patient's nose is secured within the sealing portion with a tighter fit, and leaking may be reduced. Reducing the radius of curvature also assists the patient to more accurately position their nose against the patient interface 25000 (e.g., to more accurately align their nares with the respective naris openings 25103) because there is less room for the patient's nose to move laterally (e.g., slide and/or shift) against the patient interface 25000.

Leaks may also be prevented and/or reduced by reinforcing the sealing portion 25130 and/or the support structure 25120. As shown in FIG. 33-6, support ribs 25186 may be added within the cavity 25001 in order to increase the localized stiffness of the patient interface, and improve the quality of the seal against the patient's skin. In some examples, a support rib 25186 may be included and/or enlarged in order to increase the localized stiffness. In some examples, the support rib 25186 is enlarged by adding a secondary rib 25188. In some examples, the support rib 25186 is enlarged by increasing its width. In some examples, the support rib 25186 is enlarged by increasing its length.

In one example, the support rib 25186 is molded to the patient interface 25000 within the cavity 25001, and the secondary rib 25188 is molded to an end of the support rib 25186. One end of the support rib 25186 may contact the impermeable layer 10131 of the sealing portion 25130, and the secondary rib 25188 may be molded to the other end of the support rib 25186. Together, the support rib 25186 and the secondary rib 25188 may form an L-shape. The support rib 25816 may intersect the secondary rib in approximately a perpendicular relationship. The secondary rib 25188 may be parallel to at least a section of the sealing portion 25130. In the illustrated example, the patient interface may include two support ribs 25186 (although any number is acceptable), which each connect to the sealing portion 25130. An inner end of each support rib 25186 may extend between approximately 2 mm to approximately 8 mm from an inner edge of the sealing portion 25130 (e.g., a free end proximate an opening to the cavity 25001). Each secondary rib 25188 may not extend further so as to not block airflow through the naris openings 25103. The single secondary rib 25188 may extend between the two support ribs 25186. The ends of the secondary rib 25188 may connect to the impermeable layer 10131 of the sealing portion 25130 so that the secondary rib 25186 follows an arcuate pattern. In other examples, the secondary rib 25188 may not extend beyond the furthest support ribs 25186. In other words, the distance between the support ribs 25186 may be approximately the length of the secondary rib 25188.

Including the secondary rib 25188 may improve the sealing of the patient interface 25000 when worn by the patient. Specifically, the stiffness of the sealing portion 25130 may increase. For example, the portion of the sealing portion 25130 configured to contact the lip superior may increase in stiffness as a result of the support ribs 25186 and/or the secondary rib 25188. The distance between the support ribs 25186, as well as the number of support ribs 25186, may affect the total increase in stiffness. In other words, increasing the number of support ribs 25186 and/or decreasing the distance between adjacent support ribs 25186 will increase the stiffness of the sealing portion 25130. The secondary rib 25188 may act as a backstop, and help limit the compression of the support ribs 25186 (e.g., because of contact with the patient's face). Increasing the stiffness may help to maintain the shape of the different curvatures, and allow for an ideal fit for the patient. For example, the ribs 25186, 25188 assist in maintaining the various radii of curvature of the sealing portion 25130, and limit creasing or folding from occurring, in order to limiting leaking from occurring.

In one example (see e.g., FIG. 33-7), the support ribs 25186 are molded to the patient interface 25000 within the cavity 25001, with a length that is longer than the length shown in FIG. 33-6. The support ribs 25186 that have the larger width may be molded with or without the secondary rib 25188. Increasing the width of the support ribs 25186 decreases the likelihood that the support ribs 25186 will buckle when the patient dons the patient interface 25000. Thus, the stiffness of the support ribs 25186 will be greater, so there will be a decreased likelihood that the sealing portion 25130 will crease and/or fold. Providing the secondary rib 25188 in conjunction with the wider support ribs 25186 may increase the stiffness of the sealing portion 25130 more than if only one of these modifications were included. However, increasing the thickness of the support ribs 25186 may specifically increase the stiffness in locations where they are attached to the sealing portion 25130 (i.e., a localized increase in stiffness), as opposed to the secondary rib 25188 increasing the stiffness around a larger area of the sealing portion 25130.

In one example, the support ribs 25186 are molded to the patient interface 25000 within the cavity 25001, with a length that is longer than the length shown in FIG. 33-7. The longer support ribs 25186 may be molded with or without the secondary rib 25188, and/or with or without the wider support ribs 25186. In some examples the length of each of the support ribs 25186 may increase by between approximately 0.1 mm to approximately 8 mm. In some examples the length of each of the support ribs 25186 may increase by between approximately 0.5 mm to approximately 5 mm. In some examples the length of each of the support ribs 25186 may increase by between approximately 1 mm to approximately 3 mm. In some examples the length of each of the support ribs 25186 may increase by approximately 2.5 mm. Lengthening the support ribs 25186 may provide additional support for the portion of the sealing portion 25130 along the third curvature 30000 that may contact the patient's lip superior.

Leaks may also be prevented and/or reduced by changing a shape of the patient interface 25000 (see e.g., FIGS. 33-8 and 33-9). For example, the shape and/or contour of the lateral side 25250 and/or the corner regions 25252 of the sealing portion 25130 may be adjusted in order to better conform to the patient's face (e.g., proximate the corner of nose or nasal ala region). The shape change to the sealing portion 25130 may be caused by changing the shape of the support structure 25120. Since the support structure 25120 helps to determine where the sealing portion 25130 sits, the shape of the support structure 25120 will change with the shape of the sealing portion 25130.

In some examples, the first curvature 10000 may be adjusted in order to assist in providing an improved seal for the patient. Specifically, the magnitude of the first curvature 10000 may be more negative (i.e., than in previously described examples) about the first axis 11000. As described above, the lateral side 25250 and/or the corner regions 25252 are disposed on the sealing portion 25130 proximate a transition between the positive curvature about the third axis 13000 (i.e., the third curvature) and the first curvature 10000. By increasing the magnitude of the first curvature 10000, the positive dome shape may become more pronounced (e.g., the curvature is steeper). This may decrease the width between the opposing lateral sides 25250, which may provide a tighter fit for the patient wearing the patient interface 25000, which in turn could limit the patient's nose from shifting against the sealing portion 25130.

The shape of the support structure 25120 may also be adjusted in order to limit and/or prevent leaks. Changing the shape of the support structure 25120 (e.g., molding a negative curvature with a larger magnitude) may also impart a shape change on the sealing portion 25130, since the support structure 25120 is molded to the sealing portion 25130. This may be specifically shown in FIG. 33-9, which shows the sealing portion 25130-1 after the shape change, and the sealing portion 25130 before the shape change. Creating a larger positive dome shape in the support structure 25120 creates a similar affect as described above with respect to the sealing portion 25130.

As shown in FIG. 33-10, leaks may be prevented and/or limited by raising the top vector of the patient interface 25000. Similar to the patient interface 9000 shown in FIG. 24, the positioning and stabilizing structure 9300 may engage the patient interface 25000 at four points of contact (i.e., two on either side) with the plenum chamber 25200 and/or the seal-forming structure 25100. For example, a clip 9301 and a conduit 9900 (see e.g., FIG. 24) connect on the left side and on the right side of the cushion assembly 25105. When worn, the patient may adjust a length of the upper strap 9302 and/or the conduits 9900 may stretch (e.g., because of the elastomeric material, because of concertinas, etc.) in order to pull the cushion assembly 25105 against the patient's face. The tensile force from the positioning and stabilizing structure 9300 assists in forming a seal between the sealing portion 25130 (see e.g., FIG. 33-3) and the patient's face.

The sealing force from the tensile force may be improved by changing the position that the clips 9301 and/or the conduits 9900 connect to the cushion assembly 25105. For example, changing the location of the vectors may allow the patient to achieve a tighter seal against their face. This may be achieved by spacing the connection points of clip 9301 and of the conduit 9900 further apart (i.e., on either lateral side). In one example, the connection points for the conduits 9900 are raised from the position the example illustrated in FIG. 24 (e.g., and are closer to the pronasale when worn). Raising where the conduits 9900 connect to the cushion assembly 25105 allows the force supplied by the conduits 9900 to act more directly on the nasal portion (e.g., proximate to the naris openings 25103) of the cushion assembly 25105. Raising the conduit connection point may also cause the forces applied by the conduits to be more localized about the naris openings 25103 (e.g., so that a larger component of the force is applied at that location). Since the patient's nose includes a variety of contours, concentrating a greater portion of the force from the conduits 9900 may allow the sealing portion 25130 to more accurately compliment the patient's facial geometry.

As shown in FIG. 33-10, the upper vector may be raised from a first height $H_1$ to a second height $H_2$. The second height $H_2$ is closer to the naris openings 25103 than the first height $H_1$. In some examples the distance between the first height $H_1$ and the second height $H_2$ is at least approximately 0.5 mm. In some examples the distance between the first height $H_1$ and the second height $H_2$ is between approximately 1 mm and approximately 10 mm. In some examples the distance between the first height $H_1$ and the second height $H_2$ is between approximately 2 mm and approximately 8 mm In some examples the distance between the first height $H_1$ and the second height $H_2$ is between approximately 3 mm and approximately 5 mm. In some examples the distance between the first height $H_1$ and the second height $H_2$ is approximately 4 mm.

As shown in FIG. 33-11, leaks may be prevented and/or limited by applying inserts 25194 to a surface of the cushion assembly 25105. In some examples, the inserts 25194 may be constructed from a foam material, and may be disposed on an outer surface of the sealing portion 25130 (e.g., in contact with the textile layer 10133). The inserts 25194 may also be disposed on a surface of the support structure 25120 in addition to and/or instead of being disposed on the sealing portion 25130.

The inserts 25194 may be disposed at any location along the cushion assembly 25105. In the illustrated example, the inserts 25194 are disposed at discrete locations throughout the cushion assembly 25105, and may specifically be disposed at locations susceptible to leaks. For example, this may be proximate to the lateral side 25150 and/or corner regions 25252, which is configured to contact the nasal alar region of the patient's face. The inserts may be able to deform into the complex facial geometry of the patient, in order to form a tighter seal, and reduce gaps through which air can escape. In some examples, the foam is not exposed to the ambient when the cushion assembly 25105 is donned by the patient. Thus, the insert 25194 provides additional material to tighten the fit at some areas, but does not provide passages through itself where air can leak.

In some examples, the inserts 25194 are permanently fixed to the cushion assembly 25105. For example, the inserts 25194 may be glue, or otherwise fixed, to a surface of the cushion assembly 25105 so that a patient is unable to remove the inserts 25194 without potentially damaging the cushion assembly 25105. In other examples, the inserts 25194 may be removable so that the patient can position them in a variety of locations, or remove the inserts 25194 entirely.

Any combination of the leak prevention and/or reduction examples described above and in FIGS. 33-1 to 33-11 may be used in a single cushion assembly 25105. Including several of the above described examples may offer further improvements in preventing and/or limiting leaks from occurring. However, some patients may experience substantially no leaks of pressurized air, and may not require a cushion assembly 25105 with any of these examples. For example, patients with larger noses may have a more secure fit against an unmodified cushion assembly 6105, 9105, or their nose may be too tight against the modified cushion assembly 25105.

5.3.4.1.2 Textile Membrane Examples

Below are example properties and structural arrangements of the textile composite used as the material for the textile membrane.

5.3.4.1.2.1 Textile Composite Structure

Various combinations of textile materials and membrane/film layers may be used. In an example, a three-layer arrangement including a thermoplastic polyurethane (TPU) film disposed between two textile layers (e.g., nylon, nylon and polyester mix, nylon and spandex mix, polyester and spandex mix, or nylon/polyester/spandex mix) is used. The additional textile layer is needed to protect the TPU film from breaking (e.g., during cleaning).

In another example, a two-layer arrangement including a textile (e.g., nylon, nylon and polyester mix, nylon and spandex mix, polyester and spandex mix, or nylon/polyester/spandex mix) having a silicone layer (e.g., coated thereon) is used. This composite material may be less expensive than the three-layer arrangement discussed above, since only one layer of textile is needed.

In another example, a textile material (e.g., a microfiber or polyurethane material) may be coated with a polyurethane film to form a two-layer arrangement.

5.3.4.1.2.2 Textile Material

As described above, a number of textile materials maybe used to form the sealing portion, such as nylon, polyester, spandex, nylon and polyester mix, nylon and spandex mix, polyester and spandex mix, nylon/polyester/spandex mix, microfiber or polyurethane.

In an example, a nylon material is used. Nylon may provide comfort benefits to the patient as it is softer than polyester. Nylon is also more durable than polyester and therefore provides enhancements in life span and durability. Further, as compared to polyester, nylon has a higher melt temperature and therefore is able to withstand higher temperature manufacturing conditions.

In another example, a nylon and polyester mix material is used. This material may be more desirable as it absorbs moisture less readily due to the addition of polyester and therefore reduces irritation to the patient. The nylon and polyester mix is also less expensive than nylon.

5.3.4.1.2.3 Textile Composite Total Thickness

Thicker textile membrane thicknesses (e.g., 0.5 mm) may be sturdier and provide a less flimsy impress. These textile membranes may be easier to handle during manufacturing as they are less likely to flop around.

A middle range thickness (e.g., 0.35 mm to 0.45 mm) may provide a flexible, lightweight structure that is relatively easy to handle during manufacturing and may provide more comfort to the patient than a thicker textile membranes.

A thinner textile membrane may provide a very light-weight structure that provides a soft comfortable touch to the patient, but may provide less durability than thicker textile membranes.

5.3.4.1.2.4 Knit Structure

The textile material of the textile membrane may have a weft knit structure or, alternatively, a warp knit structure, for example. A textile material with a weft and/or warp knit structure may be considered a stretch textile. A weft knit textile may be more desirable as this may provide the material with higher elasticity as compared to a warp knit textiles. This may be advantageous as it may provide more comfort to the patient by stretching as the patient's face engages the textile membrane thereby reducing the force applied to the patient's face by the textile membrane.

In an example, the weft direction (direction of the course 80) may extend in the nose width direction of the textile membrane, since the weft direction may have greater elasticity or stretch. Alternatively, the weft direction may extend in the nose length direction (superior-inferior direction).

Additionally, weft knitting is more suitable for producing relatively thin materials, such as discloses herein. Also, weft knitting is generally less cost prohibitive than warp knitting.

However, in some examples, warp knitting may be desirable as it provides less shrinkage than weft knit materials.

In some examples, the textile membrane may include any knit structure that allows the textile membrane to stretch.

In other examples, the textile membrane may include a different structure (e.g., woven), but may still be considered a stretch textile.

5.3.4.1.2.5 Knitting Machine

A weft knit textile material may have a single jersey knit structure which provides a technical face and a technical back that have different appearances. A single jersey knit may be formed by one set of needles and may provide knit stitches on the technical face (front) and purl stitches on the technical back. In an example, the technical face may form the outer surface of the textile membrane and the air impermeable membrane may be attached to the technical back. Alternatively, the technical face could be oriented towards an inner surface of the textile membrane and have the membrane attached thereto.

In an example where the textile membrane includes an air impermeable membrane sandwiched between two textile layers, the technical face of each textile material may form the exposed surfaces of the textile membrane.

5.3.4.1.2.6 Textile Weight

The textile material may have a weight in the range of 95 grams per square meter (gsm) to 130 gsm (e.g., 105 gsm to 120 gsm, or 110 gsm to 115 gsm, or 105 gsm, or 110 gsm, or 120 gsm). A heavier weight textile (e.g., 120 gsm) may provide a desirable comfortable textile feel even after being coated with a laminate layer due to the weightiness/thickness of the textile. A lighter weight textile (e.g., 105 gsm) may be desirable as it provides a lighter product.

5.3.4.1.2.7 Machine Gauge

The machine gauge (i.e., the number of stitches per inch) of the textile material may vary. For example, the machine gauge may be in the range of 35GG to (e.g., 44GG to 60GG, or 50GG to 55GG, or 55GG to 60GG, or 44GG, or or 55GG, or 60GG).

Using relatively larger gauge materials (e.g., 44GG) may be desirable as this provides greater options for melange materials. However, a finer gauge materials (e.g., 60GG) may be desirable as this softer materials which may enhance patient comfort.

5.3.4.1.2.8 Aesthetic

The textile material may have a solid color aesthetic or a melange aesthetic. A melange material may be considered a material that has been made with more than one color of fabric/textile/yarn, either by using different color fabrics/textiles/yarns or made with different fabrics/textiles/yarns which are then individually dyed. A melange material may be desirable as it may have a greater ability to hide dirt or grime thereby more easily improving the sense of cleanliness of the product. A melange material may also provide benefits during manufacturing as it is easier to visually align the textile knit structure correctly during cutting and/or overmolding.

However, a solid color material may be desirable as it provides greater options for finer gauge materials (e.g., 55GG+) which are softer and therefore more comfortable to the patient.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a pressure generator 4140, and transducers 4270. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH₂O to about 20 cmH₂O, or in other forms up to about 30 cmH₂O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to a central controller.

In one form, the input device 4220 may be constructed and arranged to allow a person to select a value and/or a menu option.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube (see e.g., 6348 in FIG. 7). In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000.

5.6 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

5.7 Breathing Waveforms

FIG. 5 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak L/s, exhalation time Te 2.4 s, peak expiratory flow rate Qpeak –0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Portable Oxygen Concentrator (POC)

Portable oxygen concentrators may take advantage of pressure swing adsorption (PSA). Pressure swing adsorption may involve using one or more compressors to increase gas pressure inside a canister that contains particles of a gas separation adsorbent arranged in a "sieve bed". As the pressure increases, certain molecules in the gas may become adsorbed onto the gas separation adsorbent. Removal of a portion of the gas in the canister under the pressurized conditions allows separation of the non-adsorbed molecules from the adsorbed molecules. The gas separation adsorbent may be regenerated by reducing the pressure, which reverses the adsorption of molecules from the adsorbent. Further details regarding oxygen concentrators may be found, for example, in U.S. Published Patent Application No. 2009-0065007, published Mar. 12, 2009, and entitled "Oxygen Concentrator Apparatus and Method", which is incorporated herein by reference.

Ambient air usually includes approximately 78% nitrogen and 21% oxygen with the balance comprised of argon, carbon dioxide, water vapor and other trace gases. If a gas mixture such as air, for example, is passed under pressure through a canister containing a gas separation adsorbent bed that attracts nitrogen more strongly than it does oxygen, part or all of the nitrogen will stay in the bed, and the gas coming out of the canister will be enriched in oxygen. When the bed reaches the end of its capacity to adsorb nitrogen, it can be regenerated by reducing the pressure, thereby releasing the adsorbed nitrogen. It is then ready for another cycle of producing oxygen enriched air. By alternating canisters in a two-canister system, one canister can be separating oxygen while the other canister is being purged (resulting in a continuous separation of the oxygen from the nitrogen). In this manner, oxygen enriched air can be accumulated, such as in a storage container or other pressurizable vessel or conduit coupled to the canisters, for a variety of uses including providing supplemental oxygen to patients.

5.9 Glossary

For the purposes of the present technology disclosure, in certain forms of the present technology, one or more of the following definitions may apply. In other forms of the present technology, alternative definitions may apply.

88

5.9.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including cmH$_2$O, g-f/cm 2 and hectopascal. 1 cmH$_2$O is equal to 1 g-f/cm 2 and is approximately 0.98 hectopascal (1 hectopascal=100 Pa=100 N/m 2=1 millibar 0.001 atm). In this specification, unless otherwise stated, pressure is given in units of cmH$_2$O.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.9.1.1 Materials

Fiber: A filament (mono or poly), a strand, a yarn, a thread or twine that is significantly longer than it is wide. A fiber may include animal-based material such as wool or silk, plant-based material such as linen and cotton, and synthetic material such as polyester and rayon. A fiber may specifically refer to a material that can be interwoven and/or interlaced (e.g., in a network) with other fibers of the same or different material.

Polycarbonate: a thermoplastic polymer of Bisphenol-A Carbonate.

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Textile: A material including at least one natural or artificial fiber. In this specification, a textile may refer to any material that is formed as a network of interwoven and/or interlaced fibers. A type of textile may include a fabric, which is constructed by interlacing the fibers using specific techniques. These include weaving, knitting, crocheting, knotting, tatting, tufting, or braiding. Cloth may be used synonymously with fabric, although may specifically refer to a processed piece of fabric. Other types of textiles may be constructed using bonding (chemical, mechanical, heat, etc.), felting, or other nonwoven processes. Textiles created through one of these processes are fabric-like, and may be considered synonymous with fabric for the purposes of this application.

5.9.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.9.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi))=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP–EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other respiratory therapy device such as an RPT device or portable oxygen concentrator, delivers a volume of breathable gas to a spontaneously breathing patient, it is said to be triggered to do so. Triggering usually takes place at or near the initiation of the respiratory portion of the breathing cycle by the patient's efforts.

5.9.4 Anatomy 5.9.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius): A point on the face between the mouth and supramenton, lying in the median sagittal plane.

Lip, upper (labrale superius): A point on the face between the mouth and nose, lying in the median sagittal plane.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronas ale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.9.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.9.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.9.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.9.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.9.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.9.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.9.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 30).

Osculating plane: The plane containing the unit tangent vector and the unit principal normal vector. See FIGS. 30 and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 30), a space curve turning towards the direction of the left-hand binormal may be considered as having a left-hand positive torsion (e.g. a left-hand helix). Hence left-hand positive is equivalent to right-hand negative. See FIG. 3T.

5.9.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections there-through in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.10 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means +/−5 to +/−10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured together or separately, and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.11 Reference Signs List

| | |
|---|---|
| curve | 35 |
| transition portion | 36 |
| wale | 70 |
| course | 80 |
| basic closed loop warp knit | 90 |
| weft knit | 100 |
| patient | 1000 |
| bed partner | 1100 |
| face | 1300 |
| patient interface | 3000 |

| | |
|---|---|
| seal-forming structure | 3100 |
| cavity | 3101 |
| naris openings | 3102 |
| bridge portion | 3104 |
| cushion assembly | 3105 |
| plenum chamber connection opening | 3106 |
| support structure | 3120 |
| lateral support region | 3122 |
| proximate end | 3124 |
| second wall | 3126 |
| textile membrane | 3130 |
| grip pad | 3150 |
| space | 3180 |
| non-usable portion | 3184 |
| area | 3188 |
| area | 3190 |
| inner surface | 3194 |
| outer surface | 3195 |
| outer surface | 3196 |
| inner surface | 3197 |
| plenum chamber | 3200 |
| plenum chamber lateral ends | 3202 |
| plenum chamber connector | 3204 |
| notch | 3206 |
| edge | 3208 |
| slot | 3209 |
| chord | 3210 |
| superior point | 3220 |
| inferior point | 3230 |
| lateral side | 3250 |
| corner regions | 3252 |
| medial subnasale region | 3260 |
| pronasale region | 3270 |
| positioning and stabilizing structure | 3300 |
| lateral portions | 3302 |
| superior portions | 3304 |
| hub | 3306 |
| tab | 3308 |
| posterior strap | 3310 |
| end portion | 3311 |
| sleeves | 3312 |
| lateral end | 3314 |
| headgear tubes | 3350 |
| vent | 3400 |
| structure vent | 3402 |
| structure | 3500 |
| swivel | 3502 |
| depressing buttons | 3504 |
| connection port | 3600 |
| forehead support | 3700 |
| ISO | 3744 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| air circuit | 4171 |
| supplementary gas | 4180 |
| electrical components | 4200 |
| single Printed Circuit Board Assembly | 4202 |
| power supply | 4210 |
| input device | 4220 |
| transducer | 4270 |
| humidifier | 5000 |
| patient interface | 6000 |

| | |
|---|---|
| cavity | 6001 |
| seal-forming structure | 6100 |
| nasal portion | 6101 |
| oral portion | 6102 |
| naris openings | 6103 |
| oral portion hole | 6104 |
| cushion assembly | 6105 |
| bridge portion | 6106 |
| support structure | 6120 |
| cushion | 6121 |
| cushion | 6122 |
| textile membrane | 6130 |
| sealing portion | 6130 |
| first sealing portion | 6131 |
| second sealing portion | 6132 |
| plenum chamber | 6200 |
| positioning and stabilizing structure | 6300 |
| left arm | 6305 |
| right arm | 6307 |
| joints | 6312 |
| tube | 6348 |
| tube | 6350 |
| inner layer | 6352 |
| outer layer | 6354 |
| textile sheet | 6360 |
| membrane | 6362 |
| tube sheet | 6364 |
| outer covering | 6366 |
| membrane | 6368 |
| membrane | 6370 |
| air passage | 6372 |
| vent | 6400 |
| connection port | 6600 |
| conduit connector | 6800 |
| conduit connector housing | 6801 |
| conduit connection end | 6802 |
| conduit connector inlet hole | 6803 |
| one conduit connector vent hole | 6831 |
| anti-asphyxia valve | 6850 |
| cavity | 9001 |
| seal-forming structure | 9100 |
| nasal portion | 9101 |
| oral portion | 9102 |
| nasal portion holes | 9103 |
| oral portion hole | 9104 |
| cushion assembly | 9105 |
| bridge portion | 9106 |
| support structure | 9120 |
| textile membrane | 9130 |
| first sealing portion | 9131 |
| second sealing portion | 9132 |
| grip pad | 9150 |
| plenum chamber | 9200 |
| plenum chamber hole | 9210 |
| positioning and stabilizing strucutre | 9300 |
| clip | 9301 |
| upper strap | 9302 |
| lower strap | 9303 |
| connector | 9304 |
| vent | 9400 |
| vent | 9404 |
| connection port | 9600 |
| conduit connector | 9800 |
| conduit | 9900 |
| sleeve | 9901 |
| tie connectors | 9902 |
| connection port housing | 9903 |
| first curvature | 10000 |
| support structure | 10120 |
| sealing portion | 10130 |
| air impermeable material | 10131 |
| textile material | 10133 |
| first layer | 10133a |
| second layer | 10133b |
| third layer | 10133c |
| textile membrane | 10135 |
| first axis | 11000 |
| axis | 11500 |
| second axis | 12000 |

-continued

| | |
|---|---|
| third axis | 13000 |
| fourth axis | 14000 |
| fifth axis | 15000 |
| second curvature | 20000 |
| patient interface | 21000 |
| cavity | 21001 |
| seal-forming structure | 21100 |
| nasal portion | 21101 |
| oral portion | 21102 |
| naris openings | 21103 |
| oral portion hole | 21104 |
| cushion assembly | 21105 |
| bridge portion | 21106 |
| support structure | 21120 |
| sealing portion | 21130 |
| first sealing portion | 21131 |
| second sealing portion | 21132 |
| plenum chamber | 21200 |
| gap | 21190 |
| patient interface | 23000 |
| cavity | 23001 |
| seal-forming structure | 23100 |
| nasal portion | 23101 |
| oral portion | 23102 |
| naris openings | 23103 |
| oral portion hole | 23104 |
| cushion assembly | 23105 |
| bridge portion | 23106 |
| support structure | 23120 |
| sealing portion | 23130 |
| first sealing portion | 23131 |
| second sealing portion | 23132 |
| inner edge | 23182 |
| lower edge | 23184 |
| gap | 23190 |
| plenum chamber | 23200 |
| patient interface | 25000 |
| cavity | 25001 |
| seal-forming structure | 25100 |
| nasal portion | 25101 |
| oral portion | 25102 |
| naris openings | 25103 |
| oral portion hole | 25104 |
| cushion assembly | 25105 |
| bridge portion | 25106 |
| support structure | 25120 |
| sealing portion | 25130 |
| sealing portion | 25130-1 |
| first sealing portion | 25131 |
| second sealing portion | 25132 |
| support rib | 25186 |
| secondary rib | 25188 |
| insert | 25194 |
| plenum chamber | 25200 |
| lateral side | 25250 |
| corner region | 25252 |
| third curvature | 30000 |
| fourth curvature | 40000 |
| fifth curvature | 50000 |
| arch | 60000 |
| first height | $H_1$ |
| second height | $H_2$ |
| first impermeable thickness | $T_{I1}$ |
| second impermeable thickness | $T_{I2}$ |

The invention claimed is:

1. A cushion assembly for delivery of a flow of air at a continuously positive pressure with respect to ambient air pressure to an entrance to a patient's nares and to an entrance to the patient's mouth, the cushion assembly comprising:

a plenum chamber at least partially forming a cavity pressurisable to a therapeutic pressure of at least 6 cmH2O above ambient air pressure, said plenum chamber including at least one plenum chamber inlet port sized and structured to receive a flow of air at the therapeutic pressure for breathing by the patient; and a seal-forming structure comprising a silicone support structure and a textile membrane, the textile membrane being constructed and arranged to, in use, form a seal with the patient's face, the textile membrane comprising:

a nasal portion configured to, in use, form a seal with an underside of the patient's nose, the nasal portion including two naris openings and a bridge portion positioned between the naris openings, the two naris openings being arranged to deliver the flow of air to the entrance to the patient's nares in use, and an oral portion configured to, in use, form a seal with a region of the patient's face around the entrance to the patient's mouth, the oral portion including an oral portion hole formed therein such that the oral portion encircles the oral portion hole, the oral portion hole being arranged to deliver the flow of air to the entrance to the patient's mouth in use, wherein the textile membrane includes a textile material configured to contact the patient's face in use, the textile material being a single, continuous piece of material, wherein the textile membrane is connected to the support structure at an overlapping region, the textile membrane being connected directly to the support structure to form a layered arrangement in the overlapping region with no additional layers between the textile membrane and the support structure, wherein at least the nasal portion of the textile membrane extends radially inwardly beyond the support structure, the nasal portion of the textile membrane being configured to press against the patient's face in use such that the patient's nose is not received in the cavity, and wherein the nasal portion of the textile membrane includes a three-dimensional shape having multiple curvatures.

2. The cushion assembly of claim 1, wherein the nasal portion is configured to, in use, form the seal only on portions of the patient's face inferior to a nasal bridge region of the patient.

3. The cushion assembly of claim 2, wherein the nasal portion is configured to form the seal with an underside of the patient's nose at or below the patient's pronasale in use.

4. The cushion assembly according to claim 1, wherein the bridge portion limits the patient's nose from entering into the cavity during use.

5. The cushion assembly according to claim 1, wherein the textile membrane is air impermeable.

6. The cushion assembly according to claim 1, wherein the textile membrane including a textile material that overlaps with an edge portion of the support structure.

7. The cushion assembly according to claim 6, wherein the plenum chamber comprises silicone and is formed with the support structure as a one-piece silicone structure.

8. The cushion assembly according to claim 1, wherein the textile membrane includes an air impermeable layer layered onto the textile material.

9. The cushion assembly according to claim 1, wherein the at least one plenum chamber inlet port comprises two plenum chamber inlet ports formed in respective lateral sides of the plenum chamber.

10. The cushion assembly according to claim 1, wherein each of the naris openings is configured to be positioned adjacent to one of the patient's nares in use.

11. The cushion assembly according to claim 1, wherein the textile membrane includes a first portion held in a relaxed state and a second portion held in a taut state, the taut state of the second portion causing the textile membrane to have the three-dimensional shape with multiple curvatures.

12. The cushion assembly of claim 11, wherein the bridge portion is the second portion and is held in a taut state.

13. The cushion assembly according to claim 11, wherein the bridge portion is crimped.

14. The cushion assembly according to claim 11, wherein the first portion is at least partially comprised of the oral portion.

15. The cushion assembly according to claim 11, wherein the textile membrane is curved about at least two non-parallel axes as a result of the taut state of the second portion in order to form the three-dimensional shape.

16. The cushion assembly according to claim 11, wherein the support structure is configured to hold the textile membrane in the three-dimensional shape.

17. The cushion assembly according to claim 1, wherein the textile membrane includes an air impermeable layer layered onto the textile material, and wherein the seal-forming structure includes a pair of ribs projecting inwardly into the cavity from an inner surface of the support structure on respective lateral sides of the plenum chamber, the ribs being configured to increase stiffness of the cushion assembly.

18. The cushion assembly according to claim 1, wherein the nasal portion of the textile membrane is configured to form the seal at or below the patient's pronasale and in contact with the patient's subnasale and/or columella in use.

19. The cushion assembly according to claim 1, wherein only the textile membrane of the cushion assembly seals with the patient's face.

20. A patient interface for delivering a flow of air at positive pressure to a patient for treatment of sleep disordered breathing, the patient interface comprising:

the cushion assembly of claim 1; and a positioning and stabilising structure to provide a force to hold the seal-forming structure in a therapeutically effective position on the patient's head.

21. The patient interface of claim 20, wherein the positioning and stabilising structure comprising a pair of conduits for delivering the flow of air to the cushion assembly in use, the pair of conduits being configured to extend along respective sides of the patient's head when the patient interface is worn.

22. The patient interface of claim 21, wherein the at least one plenum chamber inlet port comprises two plenum chamber inlet ports formed in respective lateral sides of the plenum chamber, and wherein the conduits are configured to respectively connect to the plenum chamber inlet ports.

* * * * *